United States Patent [19]

Koyama et al.

[11] Patent Number: 5,489,613
[45] Date of Patent: Feb. 6, 1996

[54] CARBACYCLIN DERIVATIVES, PROCESS FOR THEIR PREPARATION AND COMPOSITIONS CONTAINING THEM

[75] Inventors: Kazuo Koyama; Shigeo Amemiya; Koichi Kojima; Shinsaku Kobayashi, all of Hiromachi, Japan

[73] Assignee: Sankyo Company, Limited, Tokyo, Japan

[21] Appl. No.: 824,696

[22] Filed: Jan. 21, 1992

Related U.S. Application Data

[63] Continuation of Ser. No. 711,513, Jun. 3, 1991, abandoned, which is a continuation of Ser. No. 587,520, Sep. 24, 1990, abandoned, which is a continuation of Ser. No. 481,665, Feb. 14, 1990, abandoned, which is a continuation of Ser. No. 298,770, Jan. 17, 1989, abandoned, which is a continuation of Ser. No. 157,113, Feb. 10, 1988, abandoned, which is a continuation of Ser. No. 930,020, Nov. 7, 1986, abandoned, which is a continuation of Ser. No. 634,351, Jul. 25, 1984, abandoned.

[30] Foreign Application Priority Data

| Jul. 26, 1983 | [JP] | Japan | 58-136625 |
| Feb. 16, 1984 | [JP] | Japan | 59-27810 |
| Feb. 29, 1984 | [JP] | Japan | 59-38151 |

[51] Int. Cl.$^6$ .................. A61K 31/557; C07C 405/00
[52] U.S. Cl. .................. 514/573; 560/119; 562/501
[58] Field of Search .................. 562/501; 514/573

[56] References Cited

U.S. PATENT DOCUMENTS

| 4,736,058 | 4/1988 | Ikesami | 560/119 |
| 4,774,341 | 9/1988 | Shibasaki | 549/214 |
| 4,777,184 | 10/1988 | Kojima | 560/119 |

FOREIGN PATENT DOCUMENTS

| 0011591 | 5/1980 | European Pat. Off. . | |
| 0055208 | 6/1982 | European Pat. Off. . | |
| 0134246 | 3/1985 | European Pat. Off. | 560/121 |
| 8402902 | 8/1984 | WIPO | 560/119 |

OTHER PUBLICATIONS

Torisawa, Chem. Letters, 1984 p. 1069.

Shibasaki, Tet Letters, 3493, 1983.

*Primary Examiner*—Robert Gerstl
*Attorney, Agent, or Firm*—Frishauf, Holtz, Goodman, Langer & Chick

[57] ABSTRACT

Compounds of formula (I):

$$(CH_2)_n\text{—}R^1 \qquad \text{(I)}$$

[structure with $OR^2$, $OR^3$, $B\text{—}CH\text{—}R^4$]

have valuable platelet-aggregation inhibitory activities and may be used for the prophylaxis and treatment of such diseases as thrombosis.

6 Claims, No Drawings

CARBACYCLIN DERIVATIVES, PROCESS FOR THEIR PREPARATION AND COMPOSITIONS CONTAINING THEM

This application is a continuation of application Ser. No. 07/711,513 filed Jun. 3, 1991 (abandoned); which is a continuation of application Ser. No. 07/587,520 filed Sep. 24, 1990 (abandoned); which is a continuation of application Ser. No. 07/481,665 filed Feb. 14, 1990 (abandoned); which is a continuation of application Ser. No. 07/298,770 filed Jan. 17, 1989 (abandoned); which is a continuation of application Ser. No. 07/157,113 filed Feb. 10, 1988 (abandoned); which is a continuation of application Ser. No. 06/930,020 filed Nov. 7, 1986 (abandoned); which is a continuation of application Ser. No. 06/634,351 filed Jul. 25, 1984 (abandoned).

BACKGROUND TO THE INVENTION

The present invention relates to a series of new carbacyclin derivatives and describes processes for their preparation and compositions containing them.

The compound known by the trivial name "carbacyclin" is described, for example, in United Kingdom Patent Specification No. 2,012,265, which describes and claims a series of compounds which may be represented by the general formula:

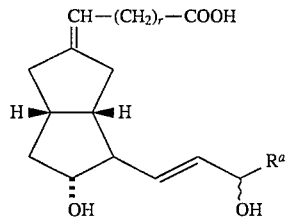

and various salts and esters thereof. Carbacyclin is one of the isomers of the compound having this formula in which r is 4 and $R^a$ represents a pentyl group. The compounds of United Kingdom Patent Specification No. 2,012,265 have strong platelet aggregation inhibitory activity, comparable with that of the known prostaglandin $E_1$, but are much more stable than prostaglandin $E_1$.

Another related compound has been briefly described in a lecture entitled "Preparation of new prostacyclin-carbon analogs" by Y. Torizawa, M. Shibazaki and S. Ikegami and reported as an abstract in the reports of The $103^{rd}$ Annual Meeting of the Pharmaceutical Society of Japan, April 1983, page 156. The relevant compound has the formula:

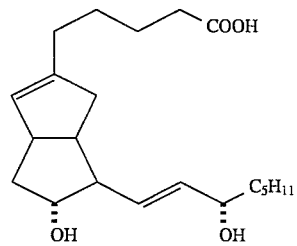

and a method of producing this compound is described. The compound is said to have biological activity, although the nature of this activity is not defined in the published abstract. We have shown that the compound has the ability to inhibit aggregation blood platelets.

We have now discovered a series of novel carbacyclin derivatives which surprisingly have an ability to inhibit the aggregation of blood platelets which is significantly better than that of certain well-known compounds, for example, prostaglandin $E_1$ and the prostacyclin derivatives of United Kingdom Patent Specification No. 2,012,265 (including carbacyclin), and which is also better than that of the compound disclosed in the aforementioned lecture. Moreover, the activity of the compounds in vivo is of much greater duration, which means that the compounds can be given less frequently and/or in lower doses.

BRIEF SUMMARY OF INVENTION

It is, accordingly, an object of the present invention to provide a series of new carbacyclin derivatives having the ability to inhibit the aggregation of blood platelets as well as various other valuable biological activities.

The compounds of the invention may be represented by the formula (I):

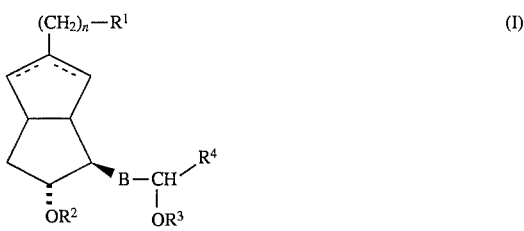

in which:

$R^1$ represents a hydroxymethyl group, a protected hydroxymethyl group, a formyl group, a protected formyl group, a carboxy group, a protected carboxy group, a group of formula $—CO.NR_2$ (in which each R represents a hydrogen atom, a $C_1$–$C_6$ alkyl group, an aryl group, a carboxylic acyl group or a sulfonyl group and the two groups or atoms represented by R may be the same or different) or a group of formula $—A(CH_2)_m—R^5$ (in which A represents the $—O—CH_2—$, $—S—CH_2—$ or $—CH=CH—$ group $R^5$, represents a hydroxymethyl group, a protected hydroxymethyl group, a formyl group, a protected formyl group, a carboxy group, a protected carboxy group or said group of formula $—CO.NR_2$, and m is 0 or an integer from 1 to 4);

$R^2$ and $R^3$ are the same or different and each represents a hydrogen atom or a hydroxy-protecting group;

$R^4$ represents a $C_1$–$C_{12}$ alkyl group, a $C_3$–$C_{12}$ alkenyl group, a $C_3$–$C_{12}$ alkynyl group (said alkyl alkenyl and alkynyl groups being unsubstituted or having one or more substituents selected from halogen atoms, $C_1$–$C_6$ alkoxy groups, hydroxy groups and $C_1$–$C_6$ aliphatic acyl groups), a $C_3$–$C_7$ cycloalkyl group (said cycloalkyl group being unsubstituted or having at least one substituent selected from $C_1$–$C_6$ alkyl groups, $C_1$–$C_6$ haloalkyl groups, halogen atoms, $C_1$–$C_6$ alkoxy groups, hydroxy groups and $C_1$–$C_6$ aliphatic acyl groups) or a group of formula $—CH_2—Q_p—R^6$ [in which: p is 0 or 1; Q represents an oxygen atom, a sulphur atom or a $—CH_2—$ group; and $R^6$ represents a $C_3$–$C_7$ cycloalkyl group (which is unsubstituted or has at least one substituent selected from $C_1$–$C_6$ alkyl groups, $C_1$–$C_6$ haloalkyl groups, halogen atoms, $C_1$–$C_6$ alkoxy groups, hydroxy groups and $C_1$–$C_6$ aliphatic acyl groups), a phenyl group (which is unsubstituted or has at least one substituent selected from $C_1$–$C_6$ alkyl groups, $C_1$–$C_6$ haloalkyl groups, halogen atoms and $C_1$–$C_6$ alkoxy groups) or a 5- or 6- membered heterocyclic group containing an oxygen or sulphur hereto-atom (which group is unsubstituted or has at least one substituent selected from $C_1$–$C_6$ alkyl groups, $C_1$–$C_6$ haloalkyl groups, halogen atoms and $C_1$–$C_6$ alkoxy groups)], provided that, when $R^4$ represents said substituted or unsubstituted alkyl group, $R^1$ represents a group of formula —A(CH$_2$)$_m$—R$^5$;

B represents the —CH$_2$CH$_2$—, —CH=CH— or —C≡C—] group;

n is an integer from 1 to 6; and the dotted line represents a double bond between the 2- and 3- positions or between the 3- and 4- positions and a single bond between the other of said positions and pharmaceutically acceptable salts and esters thereof.

The invention also provides a pharmaceutical composition comprising at least one compound of the invention in admixture with a pharmaceutically acceptable carrier or diluent.

The invention still further provides a method of treating a mammal, which may be human or non-human, by administering thereto an effective amount of at least one compound according to the present invention.

DETAILED DESCRIPTION OF INVENTION

For the avoidance of doubt, the compounds of the present invention are hereinafter named as bicyclo-[ 3,3,0]octane derivatives, in which the numbering scheme employed on the bicyclo[3,3,0]octane system is as follows:

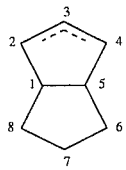

The configuration of the carbon atoms common to the cyclopentane and cyclopentene rings, that is the carbon atoms in the 1- and 5- positions is cis.

One preferred class of compounds of the present invention are those compounds of formula (Ia):

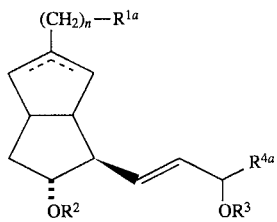

(wherein:

$R^2$, $R^3$, n and the dotted line are as defined above;

$R^{1a}$ represents a hydroxymethyl group, a protected hydroxymethyl group, a formyl group, a carboxy group or a protected carboxy group; and $R^{4a}$ represents an alkenyl group or a cycloalkyl group) and pharmaceutically acceptable salts and esters thereof.

A further preferred class of compounds of the present invention may be represented by the formula (Ib):

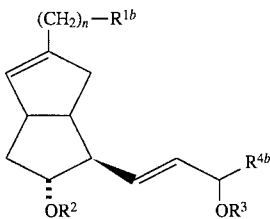

[wherein:

$R^2$, $R^3$ and n are as defined above;

$R^{1b}$ represents a hydroxymethyl group, a protected hydroxymethyl group, a formyl group, a protected formyl group, a carboxy group, a protected carboxy group or a group of formula —CO.NR$_2$ (wherein R is as defined above); and $R^{4b}$ represents a $C_3$–$C_{12}$ alkenyl group, a $C_3$–$C_{12}$ alkynyl group, a $C_3$–$C_7$ cycloalkyl group (which is unsubstituted or has at least one substituent selected from $C_1$–$C_6$ alkyl groups, $C_1$–$C_6$ haloalkyl groups, halogen atoms, $C_1$–$C_6$ alkoxy groups, hydroxy groups and $C_1$–$C_6$ aliphatic acyl groups) or a group of formula —CH$_2$—Q$_p$—R$^{6b}$ (wherein Q and p are as defined above and R$^{6b}$ represents a $C_3$–$C_7$ cycloalkyl group which is unsubstituted or has at least one substituent selected from $C_1$–$C_6$ alkyl groups, $C_1$–$C_6$ haloalkyl groups, halogen atoms, $C_1$–$C_6$ alkoxy groups, hydroxy groups and $C_1$–$C_6$ aliphatic acyl groups, or a phenyl group which is unsubstituted or has at least one substituent selected from $C_1$–$C_6$ alkyl groups, $C_1$–$C_6$ haloalkyl groups, halogen atoms and $C_1$–$C_6$ alkoxy groups)]

and pharmaceutically acceptable salts and esters thereof.

Another preferred class of compounds of the present invention may be represented by the formula (Ic):

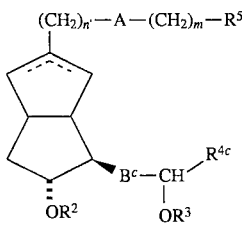

[wherein:

$R^2$, $R^3$, $R^5$, A, m and the dotted line are as defined above;

n' represents an integer from 2 to 4;

$B^c$ represents the —CH$_2$CH$_2$—, trans —CH=CH— or —C≡C— group;

$R^{4c}$ represents the substituted or unsubstituted alkyl, alkenyl, alkynyl or cycloalkyl groups hereinbefore defined for $R^4$ or a group of formula —CH$_2$—Q$_p$—R$^{6c}$ (in which Q and p are as defined above and R$^{6c}$ represents any one of the groups defined for $R^6$ other than said heterocyclic group)];

and pharmaceutically acceptable salts and esters thereof.

In the compounds of the above formulae, where $R^1$, $R^{1a}$, $R^{1b}$ or $R^5$ represents a protected hydroxymethyl group or $R^2$ or $R^3$ represents a hydroxy-protecting group, the nature of the protecting group is not particularly critical and any group conventionally used for the protection of hydroxy groups may equally be employed in the present invention. Suitable protecting groups include, for example: $C_1$–$C_6$ aliphatic acyl groups, such as the acetyl, propionyl, butyryl, isobutyryl, valeryl, isovaleryl, pivaloyl or hexanoyl groups; aromatic acyl groups, such as the benzoyl, toluoyl or naphthoyl groups; aralkyl groups, such as the benzyl, p-nitrobenzyl or p-methoxybenzyl groups: 5- or 6- membered heterocyclic groups containing at least one oxygen and/or sulphur heteroatom and optionally having at least one alkoxy substituent, for example the 2-tetrahydropyranyl, 2-tetrahydrofuranyl, 4-methoxytetrahydropyran-4-yl or 2-tetrahydrothiopyranyl groups; methyl groups having at least one alkoxy or aralkoxy substituent, for example the methoxymethyl, ethoxymethyl or benzyloxymethyl groups; 1-alkoxyethyl groups, for example the 1-methoxyethyl or 1-ethoxyethyl groups; tri($C_1$–$C_6$ alkyl)silyl groups or diaryl($C_1$–$C_6$ alkyl)silyl groups, for example the trimethylsilyl, triethylsilyl, tripropylsilyl, t-butyldimethylsilyl or diphenyl-t-butylsilyl groups. Of these, the preferred hydroxy-protecting groups for use in the group $R^1$, $R^{1a}$, $R^{1b}$ or $R^5$ are the aralkyl groups (particularly the benzyl or p-methoxybenzyl groups) and the preferred hydroxy-protecting groups represented by $R^2$ and $R^3$ are the 2-tetrahydropyranyl and 2-tetrahydrofuranyl groups.

Where $R^1$, $R^{1a}$, $R^{1b}$ or $R^5$ represents a protected formyl group, the nature of the protecting group is not particularly critical and any groups commonly used for protecting formyl groups may be employed. Suitable groups include those of formulae

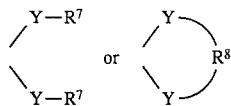

wherein:

Y represents an oxygen atom or a sulphur atom;

$R^7$ represents a $C_1$–$C_6$ alkyl group, for example a methyl, ethyl, propyl, isopropyl or butyl group; and $R^8$ represents a $C_2$–$C_5$ alkylene group, for example an ethylene, propylene, trimethylene, butylene, tetramethylene or 2,2-dimethyltrimethylene group.

Where $R^1$, $R^{1a}$, $R^{1b}$ or $R^5$ represents a protected carboxy group, the nature of the protecting group is not particularly critical and any carboxy-protecting group conventionally used may be employed. Preferred examples of such protecting groups include: the $C_1$–$C_6$ alkyl groups, such as the methyl, ethyl, propyl, isopropyl, butyl, t-butyl, pentyl, isopentyl, neopentyl, t-pentyl, hexyl or isohexyl groups; the aralkyl groups, such as the benzyl or p-bromobenzyl groups; the aryl groups, such as the phenyl, tolyl or 4-benzoylaminophenyl groups; the benzhydryl group; or the phenacyl group. Of these, the $C_1$–$C_6$ alkyl, particularly $C_1$–$C_4$ alkyl, groups are preferred.

Where $R^1$, $R^{1b}$ or $R^5$ represents the optionally substituted carbamoyl group of formula —$CO.NR_2$, the two groups represented by R may be the same or different. The groups represented by R are: hydrogen atoms; $C_1$–$C_6$ alkyl groups, particularly the methyl, ethyl, propyl, isopropyl and butyl groups; aryl groups, particularly the phenyl and tolyl groups; carboxylic acyl groups, which may be aliphatic or aromatic, particularly the acetyl, trifluoroacetyl or benzoyl groups; and sulfonyl groups, such as the methanesulfonyl, benzenesulfonyl or p-toluenesulfonyl groups. Of these optionally substituted carbamoyl groups, the preferred groups are the carbamoyl group and the methanesulfonylcarbamoyl group, of which the methanesulfonylcarbamoyl group is most preferred.

Where $R^4$ represents an alkyl group, this may be substituted or unsubstituted and may be a branched or straight-chain group having from 1 to 12 carbon atoms. Examples of such alkyl groups include the methyl, ethyl, propyl, isopropyl, butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl, nonyl, 2-methylnonyl, 2-ethyloctyl, decyl, 2-methyldecyl or 2-ethyldecyl groups. Of these, we prefer the alkyl groups having from 4 to 10 carbon atoms, particularly the butyl, isobutyl, pentyl, isopentyl, 1-methylpentyl, 2-methylpentyl, hexyl, heptyl, 1,1-dimethylpentyl, 1-methylhexyl, 2-methylhexyl, 2-ethylpentyl, octyl, 2-methyloctyl and 2-ethyloctyl groups, most preferably the pentyl, 1-methylpentyl, hexyl, 1,1-dimethylpentyl, 1-methylhexyl and 2-methylhexyl groups.

Where the alkyl group represented by $R^4$ is substituted, the parent alkyl group may be any one of those exemplified above and the substituent may be a halogen atom (e.g. a fluorine, chlorine or bromine atom), a $C_1$–$C_6$ alkoxy group (e.g. a methoxy, ethoxy, propoxy, isopropoxy, butoxy, t-butoxy, pentyloxy, isopentyloxy, neopentyloxy, t-pentyloxy, hexyloxy or isohexyloxy group), a hydroxy group or a $C_1$–$C_6$ aliphatic acyl group (e.g. a formyl, acetyl, propionyl, butyryl, isobutyryl, valeryl, isovaleryl, pivaloyl or hexanoyl group). Of these, the halogen atoms, particularly those exemplified above, and $C_1$–$C_4$ alkoxy groups, particularly those exemplified above, are preferred and fluorine atoms, chlorine atoms and methoxy groups are most preferred.

Where $R^4$ represents an alkenyl group, this may be a straight or branched chain alkenyl group having from 3 to 12 carbon atoms and having one or more carbon-carbon double bonds. Examples of such groups include the 1-butylvinyl, allyl, 2-propylallyl, 2-butenyl, 2-pentenyl, 4-pentenyl, 2-methyl-3-pentenyl, 4-methyl-3-pentenyl, 1-methyl-4-pentenyl, 4-hexenyl, 5-hexenyl, 1,4-dimethyl-3-pentenyl, 5-heptenyl, 1-methyl-5-hexenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl, 2,6-diethyl-5-octenyl or 1,4,8-trimethylnona-3,7-dienyl groups. Of these, we prefer alkenyl groups having from to 9 carbon atoms, particularly the 1-butylvinyl, 2-propylallyl, 2-pentenyl, 4-pentenyl, 2-methyl-3-pentenyl, 4-methyl-3-pentenyl, 1-methyl-4-pentenyl, 4-hexenyl, 5-hexenyl, 1,4-dimethyl-3-pentenyl, 5-heptenyl, 1-methyl-5-hexenyl, 6-methyl-5-heptenyl and 2,6-dimethyl-5-heptenyl groups.

Where $R^4$ represents a substituted alkenyl group, the preferred, more preferred and most preferred substituents are as outlined above in relation to substituted alkyl groups represented by $R^4$.

Where $R^4$ represents an alkynyl group, this may be a straight or branched chain alkynyl group having from 3 to 12, preferably from 3 to 8, carbon atoms. Of such groups, preferred groups are the propargyl, 2-butynyl, 2-pentynyl, 3-pentynyl, 1-methyl-2-butynyl, 2-hexynyl, 1-methyl-2-pentynyl, 1-methyl-3-pentynyl, 1,1-dimethyl-2-pentynyl, 1,1-dimethyl-3-pentynyl and 1,1-dimethyl-2-hexynyl groups, more preferably the 2-butynyl, 2-pentynyl, 3-pentynyl, 1-methyl-2-pentynyl and 1-methyl-3-pentynyl groups, most preferably the 1-methyl-3-pentynyl group.

Where $R^4$ represents a substituted alkynyl group, the preferred, more preferred and most preferred substituents are as outlined above in relation to substituted alkyl groups represented by $R^4$.

Where $R^4$ or $R^6$ represents a cycloalkyl group, this has from 3 to 7 ring carbon atoms and may be unsubstituted or may have one or more $C_1$–$C_6$ alkyl, $C_1$–$C_6$ haloalkyl, $C_1$–$C_6$ alkoxy, halogen, hydroxy or $C_1$–$C_6$ aliphatic acyl substituents. Examples of such unsubstituted cycloalkyl groups include the cyclopropyl, cyclobutyl, cyclopentyl, cyclohexyl and cycloheptyl groups. Where the cycloalkyl group is substituted by one or more $C_1$–$C_6$ alkyl groups, these may be straight or branched chain groups and preferred examples are given in relation to the groups represented by R above. Preferred halogen, $C_1$–$C_6$ alkoxy and $C_1$–$C_6$ aliphatic acyl substituents are as given in relation to the substituted alkyl groups represented by $R^4$ above. Preferred $C_1$–$C_6$ haloalkyl groups, which may be straight or branched chain groups, are groups having from 1 to 3 halogen (e.g. fluorine, chlorine, bromine or iodine, preferably fluorine or chlorine) substituents and are preferably the fluoromethyl, chloromethyl, trifluoromethyl, trichloromethyl or 2,2,2-trichloroethyl groups. Most preferably, the substituent is a $C_1$–$C_6$, particularly $C_1$–$C_4$ alkyl group and preferred substituted cycloalkyl groups are the 3-methylcyclopentyl, 3-ethylcyclopentyl, 3-methylcyclohexyl, 4-methylcyclohexyl and 4-ethylcyclohexyl groups. The most preferred of the substituted or unsubstituted cycloalkyl groups represented by $R^4$ and $R^6$ are the cyclopentyl and cyclohexyl groups.

Where $R^6$ represents a phenyl group, this may be unsubstituted or may have one or more, preferably 1 or 2, substituents. The substituents may be $C_1$–$C_6$ alkyl groups (preferred examples of which are given in relation to the groups represented by R), $C_1$–$C_6$ haloalkyl groups (preferred examples of which are given in relation to the substituents on the cycloalkyl groups represented by $R^5$ and $R^6$), halogen atoms or $C_1$–$C_6$ alkoxy groups (preferred examples of both of which are given in relation to the substituents on the alkyl groups represented by $R_4$). Particularly preferred such substituted or unsubstituted phenyl groups are the phenyl, o-tolyl, m-tolyl, p-tolyl, p-ethylphenyl, m-propylphenyl, m-methoxyphenyl, p-methoxyphenyl, o-ethoxyphenyl, o-fluorophenyl, m-fluorophenyl, p-fluorophenyl, m-chlorophenyl, p-chlorophenyl, p-bromophenyl, p-trifluoromethylphenyl, 3,4-dimethylphenyl, 3-fluoro-4-methylphenyl and 2,4-dichlorophenyl groups, of which the phenyl group or the phenyl group having a methyl, fluorine, chlorine or trifluoromethyl substituent are preferred, the unsubstituted phenyl group being most preferred.

In the group of formula —$CH_2$—$Q_p$—$R^6$ or —$CH_2$—$Q_p$—$R^{6c}$, where p is 0, a direct bond exists between the —$CH_2$— and $R^6$ or $R^{6c}$ groups. Where p is 1, Q represents an oxygen or sulphur atom or a —$CH_2$— group, of which the oxygen atom or —$CH_2$— group is preferred. We particularly prefer that p should be 0 or that p should be 1 and that Q should represent an oxygen atom.

Particularly preferred groups which may be represented by the formula —$CH_2$—$Q_p$—$R^6$ or —$CH_2$—$Q_p$—$R^{6c}$ are the cyclopentylmethyl, cyclohexylmethyl, 4-methylcyclohexylmethyl, benzyl, p-methylbenzyl, m-trifluoromethylbenzyl, 2-cyclopentylethyl, 2-(3-methylcyclopentyl)ethyl, 2-cyclohexylethyl, 2-phenylethyl, 2-(p-fluorophenyl)ethyl, cyclopentyloxymethyl, cyclohexyloxymethyl, phenoxymethyl, m-tolyloxymethyl, p-chlorophenoxymethyl and phenylthiomethyl groups.

A in the group of formula —$A(CH_2)_m$—$R^5$ or in the compound of formula (Ic) may represent an oxymethylene (—O—$CH_2$—), thiomethylene (—S—$CH_2$—) or vinylene (—CH=CH—) group and is preferably an oxymethylene group or a thiomethylene group.

B is preferably a trans-vinylene group or a —C≡C— group, more preferably a trans-vinylene group.

Where $R^1$ represents an optionally protected hydroxymethyl, formyl or carboxy group or the optionally substituted carbamoyl group of formula —CO.NH—, n is preferably an integer from 1 to 4. Where $R^1$ represents the aforementioned group of formula —$A(CH_2)_m$—$R^5$, n [in formula (I) or n' [in formula (Ic)] is preferably 2 and m is preferably 0 or 2, more preferably 0.

The dotted line in formulae (I), (Ia) and (Ic) represents one carbon-carbon double bond and one carbon-carbon single bond, the double bond being in the 2- position (i.e. between the 2- and 3- carbon atoms) or in the 3- position (i.e. between the 3- and 4- carbon atoms) and the single bond correspondingly being in the 3- position or the 2- position. Preferably, the double bond is in the 2- position.

Compounds of the invention in which $R^1$ represents a carboxy group can, of course, form salts, and pharmaceutically acceptable salts of such compounds also form part of the present invention. There is no particular criticality as to the salt-forming cation, provided that it is pharmaceutically acceptable in the sense that it does not, or does not to an unacceptable degree, adversely affect the pharmacological activity of the compound and provided that it does not, or does not to an unacceptable degree, increase or add to the toxicity of the compound. Within these constraints, which are well-recognized in the art, any conventional salt-forming cation may be employed. Examples of suitable salts include: salts of alkali metals such as sodium or potassium; salts of alkaline earth and other related metals, such as magnesium or calcium: the ammonium salt; quaternary ammonium salts, such as the tetramethylammonium, tetraethylammonium, benzyltrimethylammonium or phenyltriethylammonium salts; salts with amines of formula $N(R^9)_3$, in which the three symbols $R^9$ may be same or different and each represents a hydrogen atom, a $C_1$–$C_6$ aliphatic group, an araliphatic group, a $C_3$–$C_7$ alicyclic group or an aromatic group (provided that no more than two of the symbols $R^9$ may represent hydrogen atoms) and related diamines, for example methylamine, ethylamine, dimethylamine, diethylamine, trimethylamine, triethylamine, N-methylhexylamine, cyclopentylamine, dicyclohexylamine, benzylamine, dibenzylamine, α-phenylethylamine or ethylenediamine; a salt with a heterocyclic amine or a $C_1$–$C_6$ alkyl derivative thereof, such as piperidine, morpholine, pyrrolidine, piperazine, pyridine, 1-methylpiperazine or 4-ethylmorpholine; or a salt with an amine containing a hydrophilic group, such as monoethanolamine, ethyldiethanolamine or 2-amino-1-butanolamine.

The compounds of the present invention can also form clathrates with various compounds, particularly α-, β- or γ-cyclodextrin.

The compounds of the invention can exist in the form of various stereoisomers, depending upon the asymmetric carbon atoms, for example the configuration of the hydroxy group in the side chain on the cyclopentane ring and the double bond in the alkenyl group represented by $R^4$, B and others. Also, positional isomers are possible as a result of the double bond in the cyclopentene ring. The compounds of the invention will often be obtained in the form of mixtures of such isomers, in which case each individual isomer may be obtained by conventional isolation and resolution techniques. Although all of the isomers are represented herein by a single formula, it will be understood that all of the possible isomers are included within the scope of the present invention.

Particularly preferred compounds of formula (I) are those in which: $R^1$ represents a carboxy, hydroxymethyl, ($C_1$–$C_6$ alkoxy)carbonyl or N-methanesulfonylcarbamoyl group or a group of formula —$A(CH_2)_m$—$R^5$, in which $R^5$ represents an optionally protected hydroxymethyl group, an optionally protected carboxy group or the aforementioned carbamoyl group of formula —$CO.NR_2$; $R^2$ and $R^3$ both represent hydrogen atoms; $R^4$ represents a $C_4$–$C_{10}$ alkyl group optionally having one or more halogen or $C_1$–$C_6$ alkoxy substituents, an alkenyl group having from 5 to 9 carbon atoms, a $C_4$–$C_6$ alkynyl group, a 5- or 6-membered cycloalkyl group (optionally substituted by one or more of the aforementioned substituents), or a group of formula —$CH_2$—$Q_p$—$R^6$ (in which p is 0 or p is 1 and Q represents an oxygen atom or a methylene group and $R^6$ represents a cyclopentyl, cyclohexyl or phenyl group optionally having one or more $C_1$–$C_6$ alkyl, halogen or $C_1$–$C_6$ alkoxy substituents); and n is an integer from 1 to 4.

Particularly preferred compounds of formula (Ia) are those compounds in which:

(A) $R^{1a}$ represents a carboxy group, a hydroxymethyl group or a ($C_1$–$C_6$ alkoxy)carbonyl group $R^2$ and $R^3$ both represent hydrogen atoms; $R^{4a}$ represents a $C_5$–$C_9$ alkenyl group or a 5- or 6-membered cycloalkyl group (optionally having one or more of the aforementioned substituents); and n is an integer from 1 to 4;

(B) $R^{1a}$ represents a carboxy group, a hydroxymethyl group or a methoxycarbonyl group; $R^2$ and $R^3$ both represent hydrogen atoms; $R^{4a}$ represents a $C_5$–$C_9$ alkenyl group, a cyclopentyl group or a cyclohexyl group; and n is 4.

Particularly preferred compounds of formula (Ib) are those compounds in which:

(C) $R^{1b}$ represents a carboxy group, a hydroxymethyl group, a $C_2$–$C_7$ alkoxycarbonyl group or a N-methanesulfonylcarbamoyl group; $R^2$ and $R^3$ both represent hydrogen atoms; $R^{4b}$ represents a $C_5$–$C_9$ alkenyl group, a $C_4$–$C_7$ alkynyl group, a 5- or 6-membered cycloalkyl group (optionally having one or more of the aforementioned substituents) or a group of formula —$CH_2$—$Q_p$—$R^6$ (in which p is 0 or p is 1 and Q represents an oxygen atom, and $R^6$ represents a cyclopentyl group, a cyclohexyl group or a phenyl group); and n is integer from 1 to 4;

(D) $R^{1b}$ represents a carboxy group, a hydroxymethyl group or a methoxycarbonyl group; $R^2$ and $R^3$ both represent hydrogen atoms; $R^{4b}$ represents a $C_5$–$C_9$ alkenyl group, a 1-methyl-3-pentynyl group, a cyclopentyl group or a cyclohexyl group; and n is 4; and (E) $R^{1b}$ represents a carboxy group or a methoxycarbonyl group; $R^2$ and $R^3$ both represent hydrogen atoms; $R^{4b}$ represents a $C_5$–$C_9$ alkenyl group, a 1-methyl-3-pentynyl group, a cyclopentyl group or a cyclohexyl group; and n is 4.

Particularly preferred compounds of formula (Ic) are those compounds in which:

(F) R represents a hydroxymethyl group, a protected hydroxymethyl group, a carboxy group, a protected carboxy group or the aforementioned group of formula —$CO.NR_2$ (particularly a hydroxymethyl group, a carboxy group, a protected carboxy group or an N-methanesulfonylcarbamoyl group): $R^2$ and $R^3$ both represent hydrogen atoms; $R^{4c}$ represents a $C_4$–$C_{10}$ alkyl group (optionally having one or more halogen or $C_1$–$C_6$ alkoxy substituents), a $C_3$–$C_{12}$ alkenyl group, a $C_4$–$C_7$ alkynyl group, a 5- or 6- membered cycloalkyl group (optionally having one or more of the aforementioned substituents) or a group of formula —$CH_2$—$Q_p$—$R^{6c}$ [in which p is 0 or p is 1 and Q represents an oxygen atom or a methylene group and $R^{6c}$ represents a 5- or 6- membered cycloalkyl group or a phenyl group (said cycloalkyl or phenyl group optionally having one or more $C_1$–$C_6$ alkyl, halogen or $C_1$–$C_6$ alkoxy substituents)]; A represents an oxymethylene group or a thiomethylene group;

(G) $R^5$ represents a hydroxymethyl group, a carboxy group, a protected carboxy group or an N-methanesulfonylcarbamoyl group; $R^2$ and $R^3$ both represent hydrogen atoms; $R^{4c}$ represents a $C_4$–$C_{10}$ alkyl group (optionally having one or more halogen or $C_1$–$C_6$ alkoxy substituents), a $C_3$–$C_{12}$ alkenyl group, a $C_4$–$C_7$ alkynyl group, a 5- or 6- membered cycloalkyl group (optionally having one or more of the aforementioned substituents) or a group of formula —$CH_2$—$Q_p$—$R^{6c}$ (in which p is 0 or p is 1 and Q represents an oxygen atom or a methylene group, and $R^{6c}$ represents a 5- or 6- membered cycloalkyl or phenyl group, said cycloalkyl or phenyl group optionally having one or more $C_1$–$C_6$ alkyl, halogen or $C_1$–$C_6$ alkoxy substituents); A represents an oxymethylene group, a thiomethylene group or a vinylene group; and $B^c$ represents a trans-vinylene group;

(H) $R^5$ represents a hydroxymethyl group, a carboxy group or a protected carboxy group; $R^2$ and $R^3$ both represent hydrogen atoms; $R^{4c}$ represents a $C_4$–$C_{10}$ alkyl group (optionally having one or more fluorine, chlorine or methoxy substituents), a $C_3$–$C_{12}$ alkenyl group, a $C_4$–$C_7$ alkynyl group, a 5- or 6-membered cycloalkyl group (optionally having one or more of the aforementioned substituents) or a group of formula —$CH_2$—$Q_p$—$R^{6c}$ (in which p is 0 or p is 1 and Q represents an oxygen atom, and $R^{6c}$ represents a 5- or 6- membered cycloalkyl group or a phenyl group, said cycloalkyl or phenyl group optionally having one or more methyl, fluorine, chlorine or methoxy substituents); A represents an oxymethylene group or a thiomethylene group; $B^c$ represents a trans-vinylene group; and n is an integer from 2 to 4;

(J) $R^5$ represents a hydroxymethyl group, a carboxy group or a methoxycarbonyl group; $R^2$ and $R^3$ both represent hydrogen atoms; $R^{4c}$ represents a $C_4$–$C_{10}$ alkyl group, a $C_3$–$C_{12}$ alkenyl group, a $C_4$–$C_7$ alkynyl group, a cyclopentyl group, a cyclohexyl group or a group of formula —$CH_2$—$Q_p$—R6c (in which p is 0, or p is 1 and Q represents an oxygen atom, and $R^{6c}$ represents a cyclopentyl group, a cyclohexyl group or a phenyl group); A represents an oxymethylene group or a thiomethylene group; $B^c$ represents a trans-vinylene group; and n is 2.

In the above classes of compound (F)–(J), m' is also preferably 0. In the above classes of compound (A), (B) and (F)–(J), the double bond is preferably at the 2-position.

The salts and esters (particularly those salts discussed above) of the above preferred classes of compound are also preferred.

Examples of compounds of the present invention are listed below; the expression "oct-2/3-ene" means "oct-2-ene, oct-3-ene or oct-2(3)-ene (i.e. a mixture of the 2- and 3-isomers)". The numbers appended to the compounds in the following list are, where appropriate, hereafter used to identify them.

1. 3-(2-Hydroxyethyl)-6β-(3α-hydroxy-4-methylnona-1,8-dienyl)-7α-hydroxy-cis-bicyclo[3,3,0]oct- 2/3-ene 2. 3-Carboxymethyl-6β-(3α-hydroxy-4-methylnona-1,8-dienyl)- 7α-hydroxy-cis-bicyclo[3,3,0]oct-2/3-ene 3. 3-Carboxymethyl-6β-(3α-hydroxy-5,9-dimethyldeca-1,8-dienyl)-7α-hydroxy-cis.-bicyclo[3,3,0]oct-2/3-ene 4. 3-Methoxycarbonylmethyl-6β-[3α-(2-tetrahydropyranyloxy)- 5,9-dimethyldeca-1,8-dienyl]-7α-(2-tetrahydropyranyloxy)-cis-bicyclo[ 3,3,0]oct-2/3-ene 5. 3-(2-Carboxyethyl)-6β-(3α-hydroxy-4-methylnona-1,8-dienyl)-7α-hydroxy-cis-bicyclo[3,3,0]oct-2/3-ene 6. 3-(4-Carboxybutyl)-6β-(3α-hydroxyocta-1,7-dienyl)-7α-hydroxy-cis-bicyclo[3,3,0]oct-2/3-ene 7. 3-(4-Methoxycarbonylbutyl)-6β-[3α-(2-tetrahydrofuranyloxy)octa- 1,6-dienyl]-7α-(2-tetrahydrofuranyloxy)-cis-bicyclo[ 3,3,0]oct-2/3-ene 8. 3-(4-Carboxybutyl)-6β-[3α-(t-butyldimethylsilyloxy)octa- 1,5-dienyl]-7α-(t-butyldimethylsilyloxy)-cis-bicyclo[ 3,3,0]oct-2/3-ene 9. 3-(5-Hydroxypentyl)-6β-(3α-hydroxynona-1,8-dienyl)- 7α-hydroxy-cis-bicyclo[3,3,0]oct-2/3-ene 10. 3-(5-Benzyloxypentyl)-6β-[3α-(2-tetrahydropyranyloxy)nona- 1,7-dienyl]-7α-(2-tetrahydropyranyloxy)-cis-bicyclo[ 3,3,0]oct-2/3-ene 11. 3-(4-Benzyloxybutyl)-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 12. 3-(5-Hydroxypentyl)-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 13. 3-(5-Hydroxypentyl)-6β-(3α-hydroxy-4,4-dimethylnona- 1,8-dienyl)-7α-hydroxy-cis-bicyclo[3,3,0]-oct- 2/3-ene 14. 3-(4-Carboxybutyl)-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 15. 3-(4-Carboxybutyl)-6β-[3α-(t-butyldimethylsilyloxy)- 4-methylnona-1,8-dienyl]-7α-(t-butyldimethylsilyloxy)-cis-bicyclo[ 3,3,0]oct-2/3-ene 16. 3-(4-Carboxybutyl)-6β-(3α-hydroxy-4-methylnona-1,8-dienyl)-7α-hydroxy-cis-bicyclo[3,3,0]oct-2/3-ene 17. 3-(4-Methoxycarbonylbutyl)-6β-(3α-hydroxy-4-methylnona- 1,8-dienyl)-7α-hydroxy-cis-bicyclo[3,3,0]oct- 2/3-ene 18. 3-(4-Carboxybutyl)-6β-(3α-hydroxy-4,7-dimethylocta- 1,6-dienyl)-7α-hydroxy-cis-bicyclo[3,3,0]-oct- 2/3-ene 19. 3-(5-Hydroxypentyl)-6β-(3α-hydroxy-9-methyldeca-1,8-dienyl)-7α-hydroxy-cis-bicyclo[3,3,0]oct-2/3-ene 20. 3-(4-Formylbutyl)-6β-[3α-(2-tetrahydropyranyloxy)-9-methyldeca-1,8-dienyl]-7α-(2-tetrahydropyranyloxy)-cis-bicyclo[ 3,3,0]oct-2/3-ene 21. 3-(5-Benzyloxypentyl)-6β-[3α-(2-tetrahydropyranyloxy)- 4,8-dimethylnona-1,7-dienyl]-7α-(2-tetrahydropyranyloxy)-cis-bicyclo[ 3,3,0]oct-2/3-ene 22. 3-(4-Carboxybutyl)-6β-(3α-hydroxy-4,8-dimethylnona- 1,7-dienyl)-7α-hydroxy-cis-bicyclo[3,3,0]oct-2/3-ene 23. 3-(5-Hydroxypentyl)-6β-(3α-hydroxy-10-methylundeca- 1,9-dienyl)-7α-hydroxy-cis-bicyclo[3,3,0]oct-2/3-ene 24. 3-(4-Methoxycarbonylbutyl)-6β-(3α-hydroxy-10-methylundeca-1,9-dienyl)-7α-hydroxy-cis-bicyclo-[ 3,3,0]oct-2/3-ene 25. 3-(5-Benzyloxypentyl)-6β-[3α-(2-tetrahydropyranyloxy)- 4,9-dimethyldeca-1,8-dienyl]-7α-(2-tetrahydropyranyloxy)-cis-bicyclo[ 3,3,0]oct-2/3-ene 26. 3-(5-Benzyloxypentyl)-6β-(3α-hydroxy-4,9-dimethyldeca- 1,8-dienyl)-7α-hydroxy-cis-bicyclo[3,3,0]-oct-2/3-ene 27. 3-(5-Hydroxypentyl)-6β-(3α-hydroxy-4,9-dimethyldeca- 1,8-dienyl)-7α-hydroxy-cis-bicyclo[3,3,0]-oct-2/3-ene 28. 3-(4-Carboxybutyl)-6β-[3α-(t-butyldimethylsilyloxy)- 4.9-dimethyldeca-1,8-dienyl]-7α-(t-butyldimethylsilyloxy)-cis-bicyclo[ 3,3,0]oct-2/3-ene 29. 3-(5-Carboxypentyl)-6β-[3α-(2-tetrahydropyranyloxy)- 4,9-dimethyldeca-1,8-dienyl]-7α-(2-tetrahydropyranyloxy)-cis-bicyclo[ 3,3,0]oct-2/3-ene 30. 3-(4-Methoxycarbonylbutyl)-6β-[3α-hydroxy- 4,4,9-trimethyldeca-1,8-dienyl]- 7α-hydroxy-cis-bicyclo-[ 3,3,0]oct-2/3-ene 31. 3-(4-Carboxybutyl)-6β-(3α-hydroxy-4,9-dimethyldeca- 1,8-dienyl)-7α-hydroxy-cis-bicyclo[3,3,0]oct-2/3-ene 32. 3-(5-Hydroxypentyl)-6β-(3α-hydroxy-9-ethylundeca- 1,8-dienyl)-7α-hydroxy-cis-bicyclo[3,3,0]oct-2/3-ene 33. 3-(4-Carboxybutyl)-6β-(3α-hydroxy-9-ethylundeca-1,8-dienyl)-7α-hydroxy-cis-bicyclo[3,3,0]oct-2/3-ene 34. 3-(2-Benzyloxyethyl)-6β-[3α-(2-tetrahydropyranyloxy)- 3-cyclopentylprop-1-enyl]-7α-(2-tetrahydropyranyloxy)-cis-bicyclo[ 3,3,0]oct-2/3-ene 35. 3-(3-Carboxypropyl)-6β-(3α-hydroxy-3-cyclopentylprop- 1-enyl)-7α-hydroxy-cis-bicyclo[3,3,0]oct-2/3-ene 36. 3-(5-Benzyloxypentyl)-6β-[3α-(2-tetrahydropyranyloxy)- 3-cyclopentylprop-1-enyl]-7α-(2-tetrahydropyranyloxy)-cis-bicyclo[3,3,0]oct-2/3-ene 37. 3-(5-Hydroxypentyl)-6β-(3α-hydroxy-3-cyclopentylprop- 1-enyl)-7α-hydroxy-cis-bicyclo[3,3,0]oct-2/3-ene 38. 3-(4-Carboxybutyl)-6β-[3α-(2-tetrahydropyranyloxy)- 3-cyclopentylprop-1-enyl]-7α-(2-tetrahydropyranyloxy)-cis-bicyclo[3,3,0]oct-2/3-ene 39. 3-(4-Methoxycarbonylbutyl)-6β-[3α-(2-tetrahydropyranyloxy)- 3-cyclopentylprop-1-enyl]-7α-(2-tetrahydropyranyloxy)-cis-bicyclo[ 3,3,0]oct-2/3-ene 40. 3-(4-Carboxybutyl)-6β-(3α-hydroxy-3-cyclopentylprop- 1-enyl)-7α-hydroxy-cis-bicyclo[3,3,0]oct-2/3-ene 41. 3-(4-Carboxybutyl)-6β-[3α-hydroxy-3-(4-methylcyclohexyl)prop- 1-enyl]-7α-hydroxy-cis-bicyclo-[ 3,3,0]oct-2/3-ene 42. 3-(5-Hydroxypentyl)-6β-(3α-hydroxy-3-cyclohexylprop- 1-enyl)-7α-hydroxy-cis-bicyclo[3,3,0]oct-2/3-ene 43. 3-(4-Carboxybutyl)-6β-(3α-hydroxy-3-cyclohexylprop- 1-enyl)-7α-hydroxy-cis-bicyclo[3,3,0]oct-2/3-ene 44. 3-(2-Hydroxyethyl)-6β-(3α-hydroxy-4-methylnona-1,8-dienyl)-7α-hydroxy-cis-bicyclo[3,3,0]oct-2-ene 45. 3-Carboxymethyl-6β-(3α-hydroxy-4-methylnona-1,8-dienyl)-7α-hydroxy-cis-bicyclo[3,3,0]oct-2-ene 46. 3-(2-Hydroxyethyl)-6β-[3α-(2-tetrahydropyranyloxy)- 5,9-dimethyldeca-1,8-dienyl]-7α-(2-tetrahydropyranyloxy)-cis-bicyclo[ 3,3,0]oct-2-ene 47. 3-Carboxymethyl-6β-(3α-hydroxy-5,9-dimethyldeca-1,8-dienyl)-7α-hydroxy-cis-bicyclo[3,3,0]oct-2-ene 48. 3-Methoxycarbonylmethyl-6β-[3α-(2-tetrahydropyranyloxy)- 5,9-dimethyldeca-1,8-dienyl]-7α-(2-tetrahydropyranyloxy)-cis-bicyclo[ 3,3,0]oct-2-ene 49. 3-(2-Carboxyethyl)-6β-(3α-hydroxy-4-methylnona-1,8-dienyl)-7α-hydroxy-cis-bicyclo[3,3,0]oct-2-ene 50. 3-(4-Carboxybutyl)-6β-(3α-hydroxyocta-1,7-dienyl)-7α-hydroxy-cis-bicyclo[3,3,0]oct-2-ene 51. 3-(4-Methoxycarbonylbutyl)-6β-[3α-(2-tetrahydrofuranyloxy)octa- 1,6-dienyl]-7α-(2-tetrahydrofuranyloxy)-cis-bicyclo[ 3,3,0]oct-2-ene 52. 3-(4-Carboxybutyl)-6β-(3α-hydroxyocta-1,5-dienyl)-7α-hydroxy-cis-bicyclo[3,3,0]oct-2-ene 53. 3-(5-Hydroxypentyl)-6β-(3α-hydroxynona-1,8-dienyl)- 7α-hydroxy-cis-bicyclo[3,3,0]oct-2-ene 54. 3-(5-Benzyloxypentyl)-6β-[3α-(2-tetrahydropyranyloxy)nona- 1,7-dienyl]-7α-(2-tetrahydropyranyloxy)-cis-bicyclo[ 3,3,0]oct-2-ene 55. 3-(4-Benzyloxybutyl)-6β-[3α-(2-tetrahydropyranyloxy)- 4-methylnona-1,8-dienyl]-7α-(2-tetrahydropyranyloxy)-cis-bicyclo[ 3,3,0]oct-2-ene 56. 3-(5-Hydroxypentyl)-6β-[3α-(2-tetrahydropyranyloxy)- 4-methylnona-1,8-dienyl]-7α-(2-tetrahydropyranyloxy)-cis-bicyclo[ 3,3,0]oct-2-ene 57. 3-(5-Hydroxypentyl)-6β-(3α-hydroxy-4,4-dimethylnona- 1,8-dienyl)-7α-hydroxy-cis-bicyclo[3,3,0]-oct- 2-ene 58. 3-(4-Carboxybutyl)-6β-[3α-(2-tetrahydropyranyloxy)- 4-methylnona-1,8-dienyl]-7α-(2-tetrahydropyranyloxy)-cis-bicyclo[ 3,3,0]oct-2-ene 59. 3-(4-Carboxybutyl)-6β-[3α-(t-butyldimethylsilyloxy)- 4-methylnona-1,8-dienyl]-7α-(t-butyldimethylsilyloxy)-cis-bicyclo[ 3,3,0]oct-2-ene 60. 3-(4-Carboxybutyl)-6β-(3α-hydroxy-4-methylnona-1,8-dienyl)-7α-hydroxy-cis-bicyclo[3,3,0]oct-2-ene 61. 3-(4-Methoxycarbonylbutyl)-6β-(3α-hydroxy-4-methylnona- 1,8-dienyl)-7α-hydroxy-cis-bicyclo[3,3,0]oct-2-ene 62. 3-(4-Carboxybutyl)-6β-(3α-hydroxy-4,7-dimethylocta- 1,6-dienyl)-7α-hydroxy-cis-bicyclo[3,3,0]-oct- 2-ene 63. 3-(5-Hydroxypentyl)-6β-(3α-hydroxy-9-methyldeca-1,8-dienyl)-7α-hydroxy-cis-bicyclo[3,3,0]oct-2-ene 64. 3-(4-Formylbutyl)-6β-[3α-(2-tetrahydropyranyloxy)-9-methyldeca-1,8-dienyl]-7α-(2-tetrahydropyranyloxy)-cis-bicyclo[ 3,3,0]oct-2-ene 65. 3-(5-Benzyloxypentyl)-6β-[3α-(2-tetrahydropyranyloxy)- 4,8-dimethylnona-1,7-dienyl]-7α-(2-tetrahydropyranyloxy)-cis-bicyclo[ 3,3,0]oct-2-ene 66. 3-(4-Carboxybutyl)-6β-(3α-hydroxy-4,8-dimethylnona- 1,7-dienyl)-7α-hydroxy-cis-bicyclo[3,3,0]oct-2-ene 67. 3-(5-Hydroxypentyl)-6β-(3α-hydroxy-10-methylundeca- 1,9-dienyl)-7α-hydroxy-cis-bicyclo[3,3,0]oct-2-ene 68. 3-(4-Methoxycarbonylbutyl)-6β-(3α-hydroxy-10-methylundeca-1,9-dienyl)-7α-hydroxy-cis-bicyclo-[ 3,3,0]oct-2-ene 69. 3-(5-Benzyloxypentyl)-6β-[3α-(2-tetrahydropyranyloxy)- 4,9-dimethyldeca-1,8-dienyl]-7α-(2-tetrahydropyranyloxy)-cis-bicyclo[ 3,3,0]oct-2-ene 70. 3- ( 5-Benzyloxypentyl ) -6β- ( 3α-hydroxy-4,9-dimethyldeca- 1,8-dienyl ) -7α-hydroxy-cis-bicyclo[ 3,3,0] -oct- 2-ene 71. 3-(5-Hydroxypentyl)-6β-(3α-hydroxy-4,9-dimethyldeca- 1,8-dienyl)-7α-hydroxy-cis-bicyclo[3,3,0]-oct- 2-ene 72. 3-(4-Carboxybutyl)-6β-[3α-(t-butyldimethylsilyloxy)- 4,9-dimethyldeca-1,8-dienyl]-7α-(t-butyldimethylsilyloxy)-cis-bicyclo[ 3,3,0]oct-2-ene 73. 3-(6-Carboxyhexyl)-6β-(3α-hydroxy-5,9-dimethyldeca- 1,8-dienyl)-7α-hydroxy-cis-bicyclo[3,3,0]oct-2-ene 74. 3-(4-Methoxycarbonylbutyl)-6β-[3α-(2-tetrahydropyranyloxy)- 4,9-trimethyldeca-1,8-dienyl]-7α-( 2-tetrahydropyranyloxy)-cis-bicyclo[3,3,0]oct-2-ene 75. 3-(4-Carboxybutyl)-6β-(3α-hydroxy-4,9-dimethyldeca- 1,8-dienyl)-7α-hydroxy-cis-bicyclo[3,3,0]oct-2-ene 76. 3-(4-Carboxybutyl)-6β-(3α-hydroxy-5,5,9-trimethyldeca- 1,8-dienyl)-7α-hydroxy-cis-bicyclo[3,3,0]-oct- 2-ene 77. 3-(5-Hydroxypentyl)-6β-(3α-hydroxy-9-ethylundeca- 1,8-dienyl)-7α-hydroxy-cis-bicyclo[3,3,0]oct- 2-ene 78. 3-(4-Carboxybutyl)-6β-(3α-hydroxy-9-ethylundeca-1,8-dienyl)-7α-hydroxy-cis-bicyclo[3,3,0]oct-2-ene 79. 3-(4-Carboxybutyl)-6β-(3α-hydroxy-5-propylhex-5-enyl)-7α-hydroxy-cis-bicyclo[3,3,0]oct-2-ene 80. 3-(4-Carboxybutyl)-6β-(3α-hydroxy-4-butylpent-4-enyl)-7α-hydroxy-cis-bicyclo[3,3,0]oct-2-ene 81. 3-(2-Hydroxyethyl)-6β-[3α-(2-tetrahydropyranyloxy)- 4-methyloct-1-en-6-ynyl]-7α-(2-tetrahydropyranyloxy)-cis-bicyclo[ 3,3,0]oct-2-ene 82. 3-(5-Hydroxypentyl)-6β-(3α-hydroxyoct-1-en-5-ynyl)- 7α-hydroxy-cis-bicyclo[3,3,0]oct-2-ene 83. 3-(4-Carboxybutyl)-6β-[3α-(2-tetrahydropyranyloxy)- 4-methyloct-1-en-5-ynyl]-7α-(2-tetrahydropyranyloxy)-cis-bicyclo[ 3,3,0]oct-2-ene 84. 3-(4-Carboxybutyl)-6β-(3α-hydroxy-4-methyloct-1-en-5-ynyl)-7α-hydroxy-cis-bicyclo[3,3,0]oct-2-ene 85. 3-(4-Carboxybutyl)-6β-(3α-hydroxy-4-methyloct-1-en-6-ynyl)-7α-hydroxy-cis-bicyclo[3,3,0]oct-2-ene 86. 3-(5-Hydroxypentyl)-6β-(3α-hydroxy-4-methyloct-1-en-6-ynyl)-7α-hydroxy-cis-bicyclo[3,3,0]oct-2-ene 87. 3-(4-Carboxybutyl)-6β-(3α-hydroxy-4,4-dimethyloct- 1-en-6-ynyl)-7α-hydroxy-cis-bicyclo-[ 3,3,0]oct-2-ene 88. 3-(3-hydroxypropyl)-6β-[3α-(2-tetrahydropyranyloxy)- 3-cyclopentylprop-1-enyl]-7α-(2-tetrahydropyranyloxy)-cis-bicyclo[ 3,3,0]oct-2-ene 89. 3-(3-Carboxypropyl)-6β-(3α-hydroxy-3-cyclopentylprop- 1-enyl)-7α-hydroxy-cis-bicyclo[3,3,0]oct-2-ene 90. 3-(4-Carboxybutyl)-6β-(3α-hydroxy-3-cyclopentylprop- 1-enyl)-7α-hydroxy-cis-bicyclo[3,3,0]oct-2-ene 91. 3-(5-Hydroxypentyl)-6β-(3α-hydroxy-3-cyclopentylprop- 1-enyl)-7α-hydroxy-cis-bicyclo[3,3,0]oct-2-ene 92. 3-(5-Benzyloxypentyl)-6β-[3α-(2-tetrahydropyranyloxy)- 3-cyclohexylprop-1-enyl]-7α-(2-tetrahydropyranyloxy)-cis-bicyclo[ 3,3,0]oct-2-ene 93. 3-(3-Hydroxypropyl)-6β-[3α-(2-tetrahydropyranyloxy)- 3-cyclohexylprop-1-enyl]-7α-(2-tetrahydropyranyloxy)-cis-bicyclo[ 3,3,0]oct-2-ene 94. 3-(4-Carboxybutyl)-6β-[3α-(2-tetrahydropyranyloxy)- 3-cyclohexylprop-1-enyl]-7α-(2-tetrahydropyranyloxy)-cis-bicyclo[ 3,3,0]oct-2-ene 95. 3-(4-Methoxycarbonylbutyl)-6β-(3α-hydroxy-3-cyclohexylprop- 1-enyl)-7α-hydroxy-cis-bicyclo[3,3,0]oct-2-ene 96. 3-(4-Carboxybutyl)-6β-(3α-hydroxy-3-(4-methylcyclohexyl)prop- 1-enyl]-7α-hydroxy-cis-bicyclo-[ 3,3,0]oct-2-ene 97. 3-(5-Hydroxypentyl)-6β-(3α-hydroxy-3-cyclohexylprop- 1-enyl)-7α-hydroxy-cis-bicyclo[3,3,0]oct-2-ene 98. 3-(4-Carboxybutyl)-6β-(3α-hydroxy-3-cyclohexylprop- 1-enyl)-7α-hydroxy-cis-bicyclo[3,3,0]oct-2-ene 99. 3-(2-Hydroxyethyl)-6β-[3α-(2-tetrahydropyranyloxy)- 4-cyclopentylbut-1-enyl]-7α-(2-tetrahydropyranyloxy)-cis-bicyclo[ 3,3,0]oct-2-ene 100. 3-(4-Carboxybutyl)-6β-(3α-hydroxy-4-cyclopentylbut- 1-enyl)-7α-hydroxy-cis-bicyclo[3,3,0]oct-2-ene 101. 3-(4-Carboxybutyl)-6β-(3α-hydroxy-4-phenylthiobut- 1-enyl)-7α-hydroxy-cis-bicyclo[3,3,0]oct-2-ene 102. 3-(5-Hydroxypentyl)-6β-(3α-hydroxy-4-phenoxybut- 1-enyl)-7α-hydroxy-cis-bicyclo[3,3,0]oct-2-ene 103. 3-(4-Carboxybutyl)-6β-(3α-hydroxy-4-phenoxybut-1-enyl)-7α-hydroxy-cis-bicyclo[3,3,0]oct-2-ene 104. 3-(4-Carboxybutyl)-6β-(3α-hydroxy-4-p-fluorophenoxybut- 1-enyl)-7α-hydroxy-cis-bicyclo[3,3,0]oct-2-ene 105. 3-(4-Carboxybutyl)-6β-(3α-hydroxy-4-m-chlorophenoxybut- 1-enyl )-7α-hydroxy-cis-bicyclo[3,3,0]oct-2-ene 106. 3-(5-Hydroxypentyl)-6β-(3α-hydroxy-4-m-methoxyphenoxybut- 1-enyl)-7α-hydroxy-cis-bicyclo-[ 3,3,0]oct-2-ene 107. 3-(4-Carboxybutyl)-6β-[3α-(2-tetrahydropyranyloxy)- 4-m-trifluoromethylphenoxybut-1-enyl]-7α-(2-tetrahydropyranyloxy)-cis-bicyclo[ 3,3,0]oct-2-ene 108. 3-(4-Carboxybutyl)-6β-(3α-hydroxy-5-phenylpent-1-enyl)-7α-hydroxy-cis-bicyclo[3,3,0]oct-2-ene 109. 3-(4-Methanesulfonylcarbamoylbutyl)-6β-(3α-hydroxy- 5,9-dimethyldeca-1,8-dienyl)-7α-hydroxy-cis-bicyclo[ 3,3,0]oct-2-ene 110. 3-[2-(Carboxymethoxy)ethyl]-6β-(3α-hydroxyhept-1-enyl)-7α-hydroxy-cis-bicyclo[3,3,0]oct-2/3-ene 111. 3-[2-(Carboxymethylthio)ethyl]-6β-(3α-hydroxyhept- 1-enyl)-7α-hydroxy-cis-bicyclo[3,3,0]oct-2/3-ene 12. 3-(4-Carboxybut-3-enyl)-6β-(3α-hydroxyhept- 1-enyl)-7α-hydroxy-cis-bicyclo[3,3,0]oct-2/3-ene 113. 3-[2-(Carboxymethoxy)ethyl]-6β-(3α-hydroxyoct-1-enyl)-7α-hydroxy-cis-bicyclo[3,3,0]oct-2/3-ene 114. 3-[2-(Carboxymethylthio)ethyl]-6β-(3α-hydroxyoct- 1-enyl)-7α-hydroxy-cis-bicyclo[3,3,0]oct-2/3-ene 115. 3-(4-Carboxybut-3-enyl)-6β-(3α-hydroxyoct-1-enyl)-7α-hydroxy-cis-bicyclo[3,3,0]oct-2/3-ene 116. 3-[2-(3-Carboxypropoxy)ethyl]-6β-(3α-hydroxyoct-1-enyl)-7α-hydroxy-cis-bicyclo[3,3,0]oct-2/3-ene 117. 3-[2-(3-Carboxypropylthio)ethyl]-6β-(3α-hydroxyoct-1-enyl)-7α-hydroxy-cis-bicyclo[3,3,0]oct-2/3-ene 118. 3-[2-(Carboxymethoxy)ethyl]-6β-[3α-(2-tetrahydropyranyloxy)oct-1-enyl]-7α-(2-tetrahydropyranyloxy)-cis-bicyclo[3,3,0]oct-2/3-ene 119. 3-[2-(Carboxymethylthio)ethyl]-6β-[3α-(2-tetrahydropyranyloxy)oct-1-enyl]-7α-(2-tetrahydropyranyloxy)-cis-bicyclo[3,3,0]oct-2/3-ene 120. 3-(4-Carboxybut-3-enyl)-6β-[3α-(2-tetrahydropyranyloxy)oct-1-enyl]-7α-(2-tetrahydropyranyloxy)-cis-bicyclo[3,3,0]oct-2/3-ene 121. 3-[2-(2-Hydroxyethoxy)ethyl]-6β-(3α-hydroxy-oct-1-enyl)-7α-hydroxy-cis-bicyclo[3,3,0]oct-2/3-ene 122. 3-[2-(2-Hydroxyethylthio)ethyl]-6β-(3α-hydroxyoct-1-enyl)-7α-hydroxy-cis-bicyclo[3,3,0]oct-2/3-ene 123. 3-(5-Hydroxypent-3-enyl)-6β-(3α-hydroxyoct-1-enyl)-7α-hydroxy-cis-bicyclo[3,3,0]oct-2/3-ene 124. 3-[2-(2-Hydroxyethoxy)ethyl]-6β-(3α-hydroxyoctyl)-7α-hydroxy-cis-bicyclo[3,3,0]oct-2/3-ene 125. 3-[2-(2-Hydroxyethylthio)ethyl]-6β-(3α-hydroxyoctyl)-7α-hydroxy-cis-bicyclo[3,3,0]oct-2/3-ene 126. 3-(5-Hydroxypent-3-enyl)-6β-(3α-hydroxyoctyl)-7α-hydroxy-cis-bicyclo[3,3,0]oct-2/3-ene 127. 3-[2-(Carboxymethoxy)ethyl]-6β-(3α-hydroxy-5-methylhept-1-enyl)-7α-hydroxy-cis bicyclo[3,3,0]oct-3-ene 128. 3-[2-(Carboxymethylthio)ethyl]-6β-(3α-hydroxy-5-methylhept-1-enyl)-7α-hydroxy-cis-bicyclo[3,3,0]oct-3-ene 129. 3-(4-Carboxybut-3-enyl)-6β-(3α-hydroxy-5-methylhept-1-enyl)-7α-hydroxy-cis-bicyclo[3,3,0]oct-3-ene 130. 3-[2-(Carboxymethoxy)ethyl]-6β-(3α-hydroxynon-1-enyl)-7α-hydroxy-cis-bicyclo[3,3,0]oct-2/3-ene 131. 3-[2-(Carboxymethylthio)ethyl]-6β-(3α-hydroxynon-1-enyl)-7α-hydroxy-cis-bicyclo[3,3,0]oct-2/3-ene 132. 3-(4-Carboxybut-3-enyl)-6β-(3α-hydroxynon-1-enyl)-7α-hydroxy-cis-bicyclo[3,3,0]oct-2/3-ene 133. 3-[2-(Carboxymethoxy)ethyl]-6β-(3α-hydroxy-5-methyloct-1-enyl)-7α-hydroxy-cis-bicyclo[3,3,0]oct-3-ene 134. 3-[2-(Carboxymethylthio)ethyl]-6β-(3α-hydroxy-5-methyloct-1-enyl)-7α-hydroxy-cis-bicyclo[3,3,0]oct-3-ene 135. 3-(4-Carboxybut-3-enyl)-6β-(3α-hydroxy-5-methyloct-1-enyl)-7α-hydroxy-cis-bicyclo[3,3,0]oct-2/3-ene 136. 3-[2-(3-Carboxypropoxy)ethyl]-6β-(3α-hydroxy-5-methyloct-1-enyl)-7α-hydroxy-cis-bicyclo[3,3,0]oct-2/3-ene 137. 3-[2-(3-Carboxypropylthio)ethyl]-6β-(3α-hydroxy-5-methyloct-1-enyl)-7α-hydroxy-cis-bicyclo-[3,3,0]oct-2/3-ene 138. 3-[3-(Carboxymethoxy)propyl]-6β-[3α-(2-tetrahydrofuranyloxy)-6-methyloct-1-enyl]-7α-(2-tetrahydrofuranyloxy)-cis-bicyclo[3,3,0]oct-2/3-ene 139. 3-[3-(Carboxymethylthio)propyl]-6β-[3α-(2-tetrahydrofuranyloxy)-6-methyloct-1-enyl]-7α-(2-tetrahydrofuranyloxy)-cis-bicyclo[3,3,0]oct-2/3-ene 140. 3-(5-Carboxypent-4-enyl)-6β-[3α-(2-tetrahydrofuranyloxy)-6-methyloct-1-enyl]-7α-(2-tetrahydrofuranyloxy)-cis-bicyclo[3,3,0]oct-2/3-ene 141. 3-[2-(Methoxycarbonylmethoxy)ethyl]-6β-(3α-hydroxydec-1-enyl)-7α-hydroxy-cis-bicyclo[3,3,0]oct-2/3-ene 142. 3-[2-(Methoxycarbonylmethylthio)ethyl[-6β-(3α-hydroxydec-1-enyl)-7α-hydroxy-cis-bicyclo[3,3,0]oct-2/3-ene 143. 3-[4-(Methoxycarbonyl)but-3-enyl]-6β-(3α-hydroxydec-1-enyl)-7α-hydroxy-cis-bicyclo[3,3,0]oct-2/3-ene 144. 3-[2-(Carboxymethoxy)ethyl]-6β-(3α-hydroxy-5-methylnon-1-enyl)-7α-hydroxy-cis-bicyclo[3,3,0]oct-3-ene 145. 3-[2-(Carboxymethylthio)ethyl]-6β-(3α-hydroxy-5-methylnon-1-enyl)-7α-hydroxy-cis-bicyclo[3,3,0]oct-3-ene 146. 3-(4-Carboxybut-3-enyl)-6β-(3α-hydroxy-5-methylnon-1-enyl)-7α-hydroxy-cis-bicyclo[3,3,0]oct-2/3-ene 147. 3-[2-(3-Carboxypropoxy)ethyl]-6β-(3α-hydroxy-5-methylnon-1-enyl)-7α-hydroxy-cis-bicyclo[3,3,0]oct-2/3-ene 148. 3-[2-(3-Carboxypropylthio)ethyl]-6β-(3α-hydroxy-5-methylnon-1-enyl)-7α-hydroxy-cis-bicyclo-[3,3,0]oct-2/3-ene 149. 3-[2-(Carboxymethoxy)ethyl]-6β-[3α-(t-butyldimethylsilyloxy)-5-methylnon-1-enyl]-7α-(t-butyldimethylsilyloxy)-cis-bicyclo[3,3,0]oct-2/3-ene 150. 3-[2-(Carboxymethylthio)ethyl]-6β-[3α-(t-butyldimethylsilyloxy)-5-methylnon-1-enyl]-7α-(t-butyldimethylsilyloxy)-cis-bicyclo[3,3,0]oct-2/3-ene 151. 3-(4-Carboxybut-3-enyl)-6β-[3α-(t-butyldimethylsilyloxy)-5-methylnon-1-enyl]-7α-(t-butyldimethylsilyloxy)-cis-bicyclo[3,3,0]oct-2/3-ene 152. 3-[2-(Carboxymethoxy)ethyl]-6β-(3α-hydroxy-4,4-dimethyloct-1-enyl)-7α-hydroxy-cis-bicyclo[3,3,0]-oct-2/3-ene 153. 3-[2-(Carboxymethylthio)ethyl]-6β-(3α-hydroxy-4,4-dimethyloct-1-enyl)-7α-hydroxy-cis-bicyclo[3,3,0]-oct-2/3-ene 154. 3-(4-Carboxybut-3-enyl)-6β-(3α-hydroxy-4,4-dimethyloct-1-enyl)-7α-hydroxy-cis-bicyclo[3,3,0]oct-2/3-ene 155. 3-[4-(Carboxymethoxy)butyl]-6β-(3α-hydroxy-4,4-dimethyloct-1-enyl)-7α-hydroxy-cis-bicyclo[3,3,0]-oct-2/3-ene 156. 3-[4-(Carboxymethylthio)butyl]-6β-(3α-hydroxy-4,4-dimethyloct-1-enyl)-7α-hydroxy-cis-bicyclo[3,3,0]-oct-2/3-ene 157. 3-(6-Carboxyhex-5-enyl)-6β-(3α-hydroxy-4,4-dimethyloct-1-enyl)-7α-hydroxy-cis-bicyclo[3,3,0]-oct-2/3-ene 158. 3-[2-(Carboxymethoxy)ethyl]-6β-(3α-hydroxy-4-fluorooct-1-enyl)-7α-hydroxy-cis-bicyclo[3,3,0]oct-2/3-ene 159. 3-[2-(Carboxymethylthio)ethyl]-6β-(3α-hydroxy-4-fluorooct-1-enyl)-7α-hydroxy-cis-bicyclo[3,3,0]oct-2/3-ene 160. 3-(4-Carboxybut-3-enyl)-6β-(3α-hydroxy-4-fluorooct-enyl)-7α-hydroxy-cis-bicyclo[3,3,0]oct-2/3-ene 161. 3-[2-(2-Hydroxyethoxy)ethyl]-6β-(3α-hydroxy-8-methoxyoct-1-enyl)-7α-hydroxy-cis-bicyclo[3,3,0]oct-3-ene 162. 3-[2-(2-Hydroxyethylthio)ethyl]-6β-(3α-hydroxy-8-methoxyoct-1-enyl)-7α-hydroxy-cis-bicyclo-[3,3,0]oct-2/3-ene 163. 3-(5-Hydroxypent-3-enyl)-6β-(3α-hydroxy-8-methoxyoct-1-enyl)-7α-hydroxy-cis-bicyclo[3,3,0]oct-3-ene 164. 3-[2-(Carboxymethoxy)ethyl]-6β-(3α-hydroxy-8-methoxyoct-1-enyl)-7α-hydroxy-cis-bicyclo[3,3,0]oct-3-ene 165. 3-[2-(Carboxymethylthio)ethyl]-6β-(3α-hydroxy-8-methoxyoct-1-enyl)-7α-hydroxy-cis-bicyclo[3,3,0]oct-3-ene 166. 3-(4-Carboxybut-3-enyl)-6β-(3α-hydroxy- 8-methoxyoct-1-enyl)-7α-hydroxy-cis-bicyclo[3,3,0]oct- 3-ene 167. 3-[2-(Carboxymethoxy)ethyl]-6β-(3α-acetoxy-4-methyl-7-methoxyhept-1-enyl)-7α-acetoxy-cis-bicyclo[3,3,0]oct-2/3-ene 168. 3-[2-(Carboxymethylthio)ethyl]-6β-(3α-acetoxy-4-methyl-7-methoxyhept-1-enyl)-7α-acetoxy-cis-bicyclo[3,3,0]oct-2/3-ene 169. 3-(4-Carboxybut-3-enyl)-6β-(3α-acetoxy- 4-methyl-7-methoxyhept-1-enyl)-7α-acetoxy-cis-bicyclo[ 3,3,0]oct-2/3-ene 170. 3-[2-(Carboxymethoxy)ethyl]-6β-(3α-hydroxy-4-methyl-7-methoxyhept-1-enyl)-7α-hydroxy-cis-bicyclo-[3,3,0]oct-2/3-ene 171. 3-[2-(Carboxymethylthio)ethyl]-6β-(3α-hydroxy-4-methyl-7-methoxyhept-1-enyl)-7α-hydroxy-cis-bicyclo-[3,3,0]oct-2/3-ene 172. 3-(4-Carboxybut-3-enyl)-6β-(3α-hydroxy- 4-methyl-7-methoxyhept-1-enyl)-7α-hydroxy-cis-bicyclo-[ 3,3,0]oct-2/3-ene 173. 3-[2-(Carboxymethoxy)ethyl]-6β-(3α-hydroxy- 4,4-dimethyl-5-ethoxypent-1-enyl)-7α-hydroxy-cis-bicyclo[3,3,0]oct-2/3-ene 174. 3-[2-(Carboxymethylthio)ethyl]-6β-(3α-hydroxy-4,4-dimethyl-5-ethoxypent-1-enyl)-7α-hydroxy-cis-bicyclo[3,3,0]oct-2/3-ene 175. 3-(4-Carboxybut-3-enyl)-6β-(3α-hydroxy- 4,4-dimethyl-5-ethoxypent-1-enyl)-7α-hydroxy-cis-bicyclo[ 3,3,0]oct-2/3-ene 176. 3-[2-(Carboxymethoxy)ethyl]-6β-(3α-hydroxy- 4,4-dimethyl-5-ethoxypent-1-ynyl)-7α-hydroxy-cis-bicyclo[3,3,0]oct-2/3-ene 177. 3-[2-(Carboxymethylthio)ethyl]-6β-(3α-hydroxy-4,4-dimethyl-5-ethoxypent-1-ynyl)-7α-hydroxy-cis-bicyclo[ 3,3,0]oct-2/3-ene 178. 3-(4-Carboxybut-3-enyl)-6β-(3α-hydroxy- 4,4-dimethyl-5-ethoxypent-1-ynyl)-7α-hydroxy-cis-bicyclo[ 3,3,0]oct-2/3-ene 179. 3-[2-(2-Hydroxyethoxy)ethyl]-6β-(3α-hydroxy-4-methylnona-1,8-dienyl)-7α-hydroxy-cis-bicyclo[3,3,0]-oct- 2/3-ene 180. 3-[2-(2-Hydroxyethylthio)ethyl]-6β-(3α-hydroxy-4-methylnona-1,8-dienyl)-7α-hydroxy-cis-bicyclo-[ 3,3,0]oct-2/3-ene 181. 3-(5-Hydroxypent-3-enyl)-6β-(3α-hydroxy- 4-methylnona-1,8-dienyl)-7α-hydroxy-cis-bicyclo[3,3,0]oct- 2/3-ene 182. 3-[2-(2-Hydroxyethoxy)ethyl]-6β-(3α-hydroxy-5,9-dimethyldeca-1,8-dienyl)-7α-hydroxy-cis-bicyclo-[ 3,3,0]oct-2/3-ene 183. 3-[2-(2-Hydroxyethylthio)ethyl]-6β-(3α-hydroxy-5,9-dimethyldeca-1,8-dienyl)-7α-hydroxy-cis-bicyclo[ 3,3,0]oct-2/3-ene 184. 3-(5-Hydroxypent-3-enyl)-6β-(3α-hydroxy- 5,9-dimethyldeca-1,8-dienyl)-7α-hydroxy-cis-bicyclo-[ 3,3,0]oct-2/3-ene 185. 3-[3-(Methoxycarbonylmethoxy)propyl]-6β-[ 3α-(2-tetrahydropyranyloxy)-5,9-dimethyldec-8-enyl]-7α-(2-tetrahydropyranyloxy)-cis-bicyclo[3,3,0]oct-2/3-ene 186. 3-[3-(Methoxycarbonylmethylthio)propyl]-6β-[ 3α-(2-tetrahydropyranyloxy)-5,9-dimethyldec-8-enyl]-7α-(2-tetrahydropyranyloxy)-cis-bicyclo[3,3,0]oct-2/3-ene 187. 3-[5-(Methoxycarbonyl)pent-4-enyl]-6β-[ 3α-(2-tetrahydropyranyloxy)-5,9-dimethyldec-8-enyl]- 7α-(2-tetrahydropyranyloxy)-cis-bicyclo[3,3,0]oct-2/3-ene 188. 3-[2-(Carboxymethoxy)ethyl]-6β-(3α-hydroxy-octa- 1,7-dienyl)-7α-hydroxy-cis-bicyclo[3,3,0]-oct- 2/3-ene 189. 3-[2-(Carboxymethylthio)ethyl]-6β-(3α-hydroxy-octa- 1,7-dienyl)-7α-hydroxy-cis-bicyclo[3,3,0]-oct- 2/3-ene 190. 3-(4-Carboxybut-3-enyl)-6β-(3α-hydroxy-octa- 1,7-dienyl)-7α-hydroxy-cis-bicyclo[3,3,0]-oct- 2/3-ene 191. 3-[4-(Methoxycarbonylmethoxy)butyl]-6β-[3α-( 2-tetrahydrofuranyloxy)octa-1,6-dienyl]-7α-(2-tetrahydrofuranyloxy)-cis-bicyclo[ 3,3,0]oct-2/3-ene 192. 3-[4-(Methoxycarbonylmethylthio)butyl]-6β-[3α-( 2-tetrahydrofuranyloxy)octa-1,6-dienyl]-7α-(2-tetrahydrofuranyloxy)-cis-bicyclo[ 3,3,0]oct-2/3-ene 193. 3-[6-(Methoxycarbonyl)hex-5-enyl]-6β-[3α-( 2-tetrahydrofuranyloxy)octa-1,6-dienyl]-7α-(2-tetrahydrofuranyloxy)-cis-bicyclo[ 3,3,0]oct-2/3-ene 194. 3-[2-(Carboxymethoxy)ethyl]-6β-(3α-hydroxyoct-5-en-1-ynyl)-7α-hydroxy-cis-bicyclo[3,3,0]-oct- 2/3-ene 195. 3-[2-(Carboxymethylthio)ethyl]-6β-(3α-hydroxyoct- 5-en-1-ynyl)-7α-hydroxy-cis-bicyclo[3,3,0]-oct- 2/3-ene 196. 3-(4-Carboxybut-3-enyl)-6β-(3α-hydroxyoct- 5-en-1-ynyl)-7α-hydroxy-cis-bicyclo[3,3,0]-oct- 2/3-ene 197. 3-[2-(2-Hydroxyethoxy)ethyl]-6β-(3α-hydroxynona- 1,8-dienyl)-7α-hydroxy-cis-bicyclo[3,3,0]oct-2/3-ene 198. 3-[2-(2-Hydroxyethylthio)ethyl]-6β-(3α-hydroxynona- 1,8-dienyl)-7α-hydroxy-cis-bicyclo[3,3,0]-oct- 2/3-ene 199. 3-(5-Hydroxypent-3-enyl)-6β-(3α-hydroxynona-1,8-dienyl)-7α-hydroxy-cis-bicyclo[3,3,0]oct-2/3-ene 200. 3-[2-(2-Benzyloxyethoxy)ethyl]-6β-[3α-(2-tetrahydropyranyloxy)nona- 1,7-dienyl]-7α-(2-tetrahydropyranyloxy)-cis-bicyclo[ 3,3,0]oct-2/3-ene 201. 3-[2-(2-Benzyloxyethylthio)ethyl]-6β-[3α-(2-tetrahydropyranyloxy)nona- 1,7-dienyl]-7α-(2-tetrahydropyranyloxy)-cis-bicyclo[ 3,3,0]oct-2/3-ene 202. 3-(5-Benzyloxypent-3-enyl)-6β-[3α-(2-tetrahydropyranyloxy)nona- 1,7-dienyl]-7α-(2-tetrahydropyranyloxy)-cis-bicyclo[ 3,3,0]oct-2/3-ene 203. 3-[3-(2-Benzyloxyethoxy)propyl]-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 204. 3-[3-(2-Benzyloxyethylthio)propyl]-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 205. 3-(6-Benzyloxyhex-4-enyl)-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 206. 3-[2-(2-Hydroxyethoxy)ethyl]-6β-[3α-(2-tetrahydropyranyloxy)- 4-methylnon-8-enyl]-7α-(2-tetrahydropyranyloxy)-cis-bicyclo[ 3,3,0]oct-2/3-ene 207. 3-[2-(2-Hydroxyethylthio)ethyl]-6β-[3α-(2-tetrahydropyranyloxy)- 4-methylnon-8-enyl]-7α-(2-tetrahydropyranyloxy)-cis-bicyclo[ 3,3,0]oct-2/3-ene 208. 3-(5-Hydroxypent-3-enyl)-6β-[3α-(2-tetrahydropyranyloxy)- 4-methylnon-8-enyl]-7α-(2-tetrahydropyranyloxy)-cis-bicyclo[ 3,3,0]oct-2/3-ene 209. 3-[2-(2-hydroxyethoxy)ethyl]-6β-(3α-hydroxy- 4,4-dimethylnona-1,8-dienyl)-7α-hydroxy-cis-bicyclo-[ 3,3,0]oct-2/3-ene 210. 3-[2-(2-Hydroxyethylthio)ethyl]-6β-(3α-hydroxy-4,4-dimethylnona-1,8-dienyl)-7α-hydroxy-cis-bicyclo[ 3,3,0]oct-2/3-ene 211. 3-(5-hydroxypent-3-enyl)-6β-(3α-hydroxy- 4,4-dimethylnona-1,8-dienyl)-7α-hydroxy-cis-bicyclo-[ 3,3,0]oct-2/3-ene 212. 3-[4-(Carboxymethoxy)butyl]-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 213. 3-[4-(Carboxymethylthio)butyl]-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 214. 3-(6-Carboxyhex-5-enyl)-6β-[3α-(2-tetrahydropyranyloxy)- 4-methylnona-1,8-dienyl]-7α-(2-tetrahydropyranyloxy)-cis-bicyclo[ 3,3,0]oct-2/3-ene 215. 3-[2-(Carboxymethoxy)ethyl]-6β-[3α-(t-butyldimethylsilyloxy)- 4-methylnon-8-en-1-ynyl]-7α-(t-butyldimethylsilyloxy)-cis-bicyclo[ 3,3,0]oct-2/3-ene 216. 3-[2-(Carboxymethylthio)ethyl]-6β-[3α-(t-butyldimethylsilyloxy)- 4-methylnon-8-en-1-ynyl]-7α-(t-butyldimethylsilyloxy)-cis-bicyclo[ 3,3,0]oct-2/3-ene 217. 3-(4-Carboxybut-3-enyl)-6β-[3α-(t-butyldimethylsilyloxy)- 4-methylnon-8-en-1-ynyl]-7α-(t-butyldimethylsilyloxy)-cis-bicyclo[ 3,3,0]oct-2/3-ene 218. 3-[2-(Carboxymethoxy)ethyl]-6β-(3α-hydroxy- 4-methylnona-1,8-dienyl)-7α-hydroxy-cis-bicyclo[3,3,0]-oct- 2/3-ene 219. 3-[2-(Carboxymethylthio)ethyl]-6β-(3α-hydroxy- 4-methylnona-1,8-dienyl)-7α-hydroxy-cis-bicyclo[3,3,0]-oct- 2/3-ene 220. 3-(4-Carboxybut-3-enyl)-6β-(3α-hydroxy- 4-methylnona-1,8-dienyl)-7α-hydroxy-cis-bicyclo[3,3,0]-oct- 2/3-ene 221. 3-[2-(3-Carboxypropoxy)ethyl]-6β-(3α-hydroxy- 4-methylnona-1,8-dienyl)-7α-hydroxy-cis-bicyclo[3,3,0]-oct- 2/3-ene 222. 3-[2-(3-Carboxypropylthio)ethyl]-6β-(3α-hydroxy- 4-methylnona-1,8-dienyl)-7α-hydroxy-cis-bicyclo-[ 3,3,0]oct-2/3-ene 223. 3-[2-(Methoxycarbonylmethoxy)ethyl]-6β-(3α-hydroxy- 4-methylnona-1,8-dienyl )-7α-hydroxy-cis-bicyclo-[ 3,3,0]oct-2/3-ene 224. 3-[2-(Methoxycarbonylmethylthio)ethyl]-6β-(3α-hydroxy- 4-methylnona-1,8-dienyl)-7α-hydroxy-cis-bicyclo-[ 3,3,0]oct-2/3-ene 225. 3-[4-(Methoxycarbonyl)but-3-enyl]-6β-(3α-hydroxy- 4-methylnona-1,8-dienyl)-7α-hydroxy-cis-bicyclo-[ 3,3,0]oct-2/3-ene 226. 3-[2-(Carboxymethoxy)ethyl]-6β-(3α-hydroxy- 4,7-dimethylocta-1,6-dienyl)-7α-hydroxy-cis-bicyclo-[ 3,3,0] oct-2/3-ene 227. 3-[2-(Carboxymethylthio)ethyl]-6β-(3α-hydroxy- 4,7-dimethylocta-1,6-dienyl)-7α-hydroxy-cis-bicyclo-[ 3,3, 0]oct-2/3-ene 228. 3-(4-Carboxybut-3-enyl)-6β-(3α-hydroxy- 4,7-dimethylocta-1,6-dienyl)-7α-hydroxy-cis-bicyclo-[ 3,3,0]oct-2/3-ene 229. 3-[2-(3-Carboxypropoxy)ethyl]-6β-(3α-hydroxy- 4,7-dimethylocta-1,6-dienyl)-7α-hydroxy-cis-bicyclo-[ 3,3, 0]oct-2/3-ene 230. 3-[2-(3-Carboxypropylthio)ethyl]-6β-(3α-hydroxy- 4,7-dimethylocta-1,6-dienyl)-7α-hydroxy-cis-bicyclo[ 3,3, 0]oct-2/3-ene 231. 3-[2-(Carboxymethoxy)ethyl]-6β-(3α-hydroxy- 9-methyldeca-1,8-dienyl)-7α-hydroxy-cis-bicyclo[3,3,0]-oct- 2/3-ene 232. 3-[2-(Carboxymethylthio)ethyl]-6β-(3α-hydroxy- 9-methyldeca-1,8-dienyl)-7α-hydroxy-cis-bicyclo[3,3,0]-oct- 2/3-ene 233. 3-(4-Carboxybut-3-enyl)-6β-(3α-hydroxy- 9-methyldeca-1,8-dienyl)-7α-hydroxy-cis-bicyclo[3,3,0]-oct- 2/3-ene 234. 3-[2-(3-Carboxypropoxy)ethyl]-6β-(3α-hydroxy- 9-methyldeca-1,8-dienyl)-7α-hydroxy-cis-bicyclo[3,3,0]-oct- 2/3-ene 235. 3-[2-(3-Carboxypropylthio)ethyl]-6β-(3α-hydroxy- 9-methyldeca-1,8-dienyl)-7α-hydroxy-cis-bicyclo-[ 3,3,0] oct-2/3-ene 236. 3-[2-(Formylmethoxy)ethyl]-6β-[3α-(2-tetrahydropyranyloxy)- 9-methyldeca-1,8-dienyl]-7α-(2-tetrahydropyranyloxy)-cis-bicyclo[ 3,3,0]oct-2/3-ene 237. 3-[2-(Formylmethylthio)ethyl]-6β-[3α-(2-tetrahydropyranyloxy)- 9-methyldeca-1,8-dienyl]-7α-(2-tetrahydropyranyloxy)-cis-bicyclo[ 3,3,0]oct-2/3-ene 238. 3-(4-Formylbut-3-enyl)-6β-[3α-(2-tetrahydropyranyloxy)- 9-methyldeca-1,8-dienyl]-7α-(2-tetrahydropyranyloxy)-cis-bicyclo[ 3,3,0]oct-2/3-ene 239. 3-[3-(2-Benzyloxyethoxy)propyl]-6β-[3α-(2-tetrahydropyranyloxy)- 4,8-dimethylnon-7-enyl]-7α-(2-tetrahydropyranyloxy)-cis-bicyclo[ 3,3,0]oct-2/3-ene 240. 3-[3-(2-Benzyloxyethylthio)propyl]-6β-[3α-(2-tetrahydropyranyloxy)- 4,8-dimethylnon-7-enyl]-7α-(2-tetrahydropyranyloxy)-cis-bicyclo[ 3,3,0]oct-2/3-ene 241. 3-(6-Benzyloxyhex-4-enyl)-6β-[3α-(2-tetrahydropyranyloxy)- 4,8-dimethylnon-7-enyl]-7α-(2-tetrahydropyranyloxy)-cis-bicyclo[ 3,3,0]oct-2/3-ene 242. 3-[2-(Carboxymethoxy)ethyl]-6β-(3α-hydroxy- 4,8-dimethylnona-1,7-dienyl)-7α-hydroxy-cis-bicyclo-[ 3,3,0] oct-2/3-ene 243. 3-[2-(Carboxymethylthio)ethyl]-6β-(3α-hydroxy- 4,8-dimethylnona-1,7-dienyl)-7α-hydroxy-cis-bicyclo-[ 3,3,0]oct-2/3-ene 244. 3-(4-Carboxybut-3-enyl)-6β-(3α-hydroxy- 4,8-dimethylnona-1,7-dienyl)-7α-hydroxy-cis-bicyclo-[ 3,3,0]oct-2/3-ene 245. 3-[2-(2-Hydroxyethoxy)ethyl]-6β-(3α-hydroxy- 10-methylundeca-1,9-dienyl)-7α-hydroxy-cis-bicyclo-[ 3,3, 0]oct-2/3-ene 246. 3-[2-(2-Hydroxyethylthio)ethyl]-6β-(3α-hydroxy- 10-methylundeca-1,9-dienyl)-7α-hydroxy-cis-bicyclo[ 3,3, 0]oct-2/3-ene 247. 3-(5-Hydroxypent-3-enyl)-6β-(3α-hydroxy- 10-methylundeca-1,9-dienyl)-7α-hydroxy-cis-bicyclo-[ 3,3,0]oct-2/3-ene 248. 3-[4-(Methoxycarbonylmethoxy)butyl]-6β-(3α-hydroxy- 10-methylundeca-1,9-dienyl)-7α-hydroxy-cis-bicyclo[ 3,3,0]oct-2/3-ene 249. 3-[4-(Methoxycarbonylmethylthio)butyl]-6β-(3α-hydroxy- 10-methylundeca-1,9-dienyl)-7α-hydroxy-cis-bicyclo[ 3,3,0]oct-2/3-ene 250. 3-[6-(Methoxycarbonyl)hex-5-enyl]-6β-(3α-hydroxy- 10-methylundeca-1,9-dienyl)-7α-hydroxy-cis-bicyclo[ 3,3,0]oct-2/3-ene 251. 3-[3-(2-Benzyloxyethoxy)propyl]-6β-[3α-(2-tetrahydropyranyloxy)- 4,9-dimethyldeca-1,8-dienyl]-7α-( 2-tetrahydropyranyloxy)-cis-bicyclo[3,3,0]oct-2/3-ene 252. 3-[3-(2-Benzyloxyethylthio)propyl]-6β-[3α-(2-tetrahydropyranyloxy)- 4,9-dimethyldeca-1,8-dienyl]-7α-( 2-tetrahydropyranyloxy)-cis-bicyclo[3,3,0]oct-2/3-ene 253. 3-(6-Benzyloxyhex-4-enyl)-6β-[3α-(2-tetrahydropyranyloxy)- 4,9-dimethyldeca-1,8-dienyl]-7α-( 2-tetrahydropyranyloxy)-cis-bicyclo[3,3,0]oct-2/3-ene 254. 3-[2-(2-Benzyloxyethoxy)ethyl]-6β-(3α-hydroxy- 4,9-dimethyldeca-1,8-dienyl)-7α-hydroxy-cis-bicyclo-[ 3,3, 0]oct-2/3-ene 255. 3-[2-(2-Benzyloxyethylthio)ethyl]-6β-(3α-hydroxy- 4,9-dimethyldeca-1,8-dienyl)-7α-hydroxy-cis-bicyclo[ 3,3, 0]oct-2/3-ene 256. 3-(5-Benzyloxypent-3-enyl)-6β-(3α-hydroxy- 4,9-dimethyldeca-1,8-dienyl)-7α-hydroxy-cis-bicyclo-[ 3,3,0] oct-2/3-ene 257. 3-[2-(2-Hydroxyethoxy)ethyl]-6β-(3α-hydroxy- 4,9-dimethyldeca-1,8-dienyl)-7α-hydroxy-cis-bicyclo-[ 3,3, 0]oct-2/3-ene 258. 3-[2-(2-Hydroxyethylthio)ethyl]-6β-(3α-hydroxy- 4,9-dimethyldeca-1,8-dienyl)-7α-hydroxy-cis-bicyclo[ 3,3, 0]oct-2/3-ene 259. 3-(5-Hydroxypent-3-enyl)-6β-(3α-hydroxy- 4,9-dimethyldeca-1,8-dienyl)-7α-hydroxy-cis-bicyclo-[3,3,0]oct-2/3-ene 260. 3-[2-(Carboxymethoxy)ethyl]-6β-[3α-(t-butyldimethylsilyloxy)- 4,9-dimethyldeca-1,8-dienyl]-7α-(t-butyldimethylsilyloxy)-cis-bicyclo[3,3,0]oct-2/3-ene 261. 3-[2-(Carboxymethylthio)ethyl]-6β-[3α-(t-butyldimethylsilyloxy)- 4,9-dimethyldeca-1,8-dienyl]-7α-(t-butyldimethylsilyloxy)-cis-bicyclo[3,3,0]oct-2/3-ene 262. 3-(4-Carboxybut-3-enyl)-6β-[3α-(t-butyldimethylsilyloxy)- 4,9-dimethyldeca-1,8-dienyl]-7α-(t-butyldimethylsilyloxy)-cis-bicyclo[3,3,0]oct-2/3-ene 263. 3-[2-(Carboxymethoxy)ethyl]-6β-(3α-hydroxy- 5,9-dimethyldeca-1,8-dienyl)-7α-hydroxy-cis-bicyclo-[3,3,0]oct-2/3-ene 264. 3-[2-(Carboxymethylthio)ethyl]-6β-(3α-hydroxy-5,9-dimethyldeca-1,8-dienyl)-7α-hydroxy-cis-bicyclo-[3,3,0]oct-2/3-ene 265. 3-(4-Carboxybut-3-enyl)-6β-(3α-hydroxy-5,9-dimethyldeca- 1,8-dienyl)-7α-hydroxy-cis-bicyclo[3,3,0]oct-2/3-ene 266. 3-[2-(3-Carboxypropoxy)ethyl]-6β-(3α-hydroxy-5,9-dimethyldeca-1,8-dienyl)-7α-hydroxy-cis-bicyclo-[3,3,0]oct-2/3-ene 267. 3-[2-(3-Carboxypropylthio)ethyl]-6β-(3α-hydroxy-5,9-dimethyldeca-1,8-dienyl)-7α-hydroxy-cis-bicyclo[3,3,0]oct-2/3-ene 268. 3-[2-(Methoxycarbonylmethoxy)ethyl]-6β-[3α-(2-tetrahydropyranyloxy)-4,4,9-trimethyldec-8-enyl]-7α-(2-tetrahydropyranyloxy)-cis-bicyclo[3,3,0]oct-2/3-ene 269. 3-[2-(Methoxycarbonylmethylthio)ethyl]-6β-[3α-(2-tetrahydropyranyloxy)-4,4,9-trimethyldec-8-enyl]-7α-(2-tetrahydropyranyloxy)-cis-bicyclo[3,3,0]oct-2/3-ene 270. 3-[4-(Methoxycarbonyl)but-3-enyl]-6β-[3α-(2-tetrahydropyranyloxy)-4,4,9-trimethyldec-8-enyl]-7α-(2-tetrahydropyranyloxy)-cis-bicyclo[3,3,0]oct-2/3-ene 271. 3-[2-(Carboxymethoxy)ethyl]-6β-(3α-hydroxy- 4,9-dimethyldeca-1,8-dienyl)-7α-hydroxy-cis-bicyclo-[3,3,0]oct-2/3-ene 272. 3-[2-(Carboxymethylthio)ethyl]-6β-(3α-hydroxy-4,9-dimethyldeca-1,8-dienyl)-7α-hydroxy-cis-bicyclo-[3,3,0]oct-2/3-ene 273. 3-(4-Carboxybut-3-enyl)-6β-(3α-hydroxy-4,9-dimethyldeca- 1,8-dienyl)-7α-hydroxy-cis-bicyclo[3,3,0]oct-2/3-ene 274. 3-[2-(Carboxymethoxy)ethyl]-6β-(3α-hydroxy- 5,5,9-trimethyldeca-1,8-dienyl)-7α-hydroxy-cis-bicyclo-[3,3,0]oct-2/3-ene 275. 3-[2-(Carboxymethylthio)ethyl]-6β-(3α-hydroxy-5,5,9-trimethyldeca-1,8-dienyl)-7α-hydroxy-cis-bicyclo-[3,3,0]oct-2/3-ene 276. 3-(4-Carboxybut-3-enyl)-6β-(3α-hydroxy-5,5,9-trimethyldeca- 1,8-dienyl)-7α-hydroxy-cis-bicyclo[3,3,0]oct-2/3-ene 277. 3-[2-(2-Hydroxyethoxy)ethyl]-6β-(3α-hydroxy-9-ethylundeca-1,8-dienyl)-7α-hydroxy-cis-bicyclo-[3,3,0]oct-2/3-ene 278. 3-[2-(2-Hydroxyethylthio)ethyl]-6β-(3α-hydroxy-9-ethylundeca-1,8-dienyl)-7α-hydroxy-cis-bicyclo[3,3,0]oct-2/3-ene 279. 3-(5-Hydroxypent-3-enyl)-6β-(3α-hydroxy- 9-ethylundeca-1,8-dienyl)-7α-hydroxy-cis-bicyclo-[3,3,0]oct-2/3-ene 280. 3-[2-(Carboxymethoxy)ethyl]-6β-(3α-hydroxy-9-ethylundeca-1,8-dienyl)-7α-hydroxy-cis-bicyclo-[3,3,0]oct-2/3-ene 281. 3-[2-(Carboxymethylthio)ethyl]-6β-(3α-hydroxy-9-ethylundeca-1,8-dienyl)-7α-hydroxy-cis-bicyclo-[3,3,0]oct-2/3-ene 282. 3-(4-Carboxybut-3-enyl)-6β-(3α-hydroxy-9-ethylundeca- 1,8-dienyl)-7α-hydroxy-cis-bicyclo[3,3,0]oct-2/3-ene 283. 3-[2-(Carboxymethoxy)ethyl]-6β-(3α-hydroxy-5-propylhexa-1,5-dienyl)-7α-hydroxy-cis-bicyclo-[3,3,0]oct-2/3-ene 284. 3-[2-(Carboxymethylthio)ethyl]-6β-(3α-hydroxy-5-propylhexa-1,5-dienyl)-7α-hydroxy-cis-bicyclo-[3,3,0]oct-2/3-ene 285. 3-(4-Carboxybut-3-enyl)-6β-(3α-hydroxy-5-propylhexa- 1,5-dienyl)-7α-hydroxy-cis-bicyclo[3,3,0]oct- 2/3-ene 286. 3-[2-(Carboxymethoxy)ethyl]-6β-(3α-hydroxy-4-butylpenta-1,4-dienyl)-7α-hydroxy-cis-bicyclo-[3,3,0]oct-2/3-ene 287. 3-[2-(Carboxymethylthio)ethyl]-6β-(3α-hydroxy-4-butylpenta-1,4-dienyl)-7α-hydroxy-cis-bicyclo-[3,3,0]oct-2/3-ene 288. 3-(4-Carboxybut-3-enyl)-6β-(3α-hydroxy-4-butylpenta- 1,4-dienyl)-7α-hydroxy-cis-bicyclo[3,3,0]oct- 2/3-ene 289. 3-[2-(2-Hydroxyethoxy)ethyl]-6β-[3α-(2-tetrahydropyranyloxy)- 4-methylocta-1,6-diynyl]-7α-(2-tetrahydropyranyloxy)-cis-bicyclo[3,3,0]oct-2/3-ene 290. 3-[2-(2-Hydroxyethylthio)ethyl]-6β-[3α-(2-tetrahydropyranyloxy)- 4-methylocta-1,6-diynyl]-7α-(2-tetrahydropyranyloxy)-cis-bicyclo[3,3,0]oct-2/3-ene 291. 3-(5-Hydroxypent-3-enyl)-6β-[3α-(2-tetrahydropyranyloxy)- 4-methylocta-1,6-diynyl]-7α-(2-tetrahydropyranyloxy)-cis-bicyclo[3,3,0]oct-2/3-ene 292. 3-[2-(2-Hydroxyethoxy)ethyl]-6β-(3α-hydroxyoct-1-en-5-ynyl)-7α-hydroxy-cis-bicyclo[3,3,0]oct-2/3-ene 293. 3-[2-(2-Hydroxyethylthio)ethyl]-6β-(3α-hydroxyoct- 1-en-5-ynyl)-7α-hydroxy-cis-bicyclo[3,3,0]oct- 2/3-ene 294. 3-(5-Hydroxypent-3-enyl)-6β-(3α-hydroxyoct-1-en-5-ynyl)-7α-hydroxy-cis-bicyclo[3,3,0]oct-2/3-ene 295. 3-[2-(Phenacyloxycarbonylmethoxy)ethyl]-6β-(3α-hydroxy-4-methyloct-1-en-6-ynyl)-7α-hydroxy-cis-bicyclo[3,3,0]oct-2/}-ene 296. 3-[2-(Phenacyloxycarbonylmethylthio)ethyl]-6β-(3α-hydroxy-4-methyloct-1-en-6-ynyl)-7α-hydroxy-cis-bicyclo[3,3,0]oct-2/3-ene 297. 3-[4-(Phenacyloxycarbonyl)but-3-enyl]-6β-(3α-hydroxy-4-methyloct-1-en-6-ynyl)-7α-hydroxy-cis-bicyclo[3,3,0]oct-2/3-ene 298. 3-[2-(Carboxymethoxy)ethyl]-6β-(3α-hydroxy-4-methyloct-1-en-5-ynyl)-7α-hydroxy-cis-bicyclo-[3,3,0]oct-2/3-ene 299. 3-[2-(Carboxymethylthio)ethyl]-6β-(3α-hydroxy-4-methyloct-1-en-5-ynyl)-7α-hydroxy-cis-bicyclo-[3,3,0]oct-2/3-ene 300. 3-(4-Carboxybut-3-enyl)-6β-(3α-hydroxy-4-methyloct- 1-en-5-ynyl)-7α-hydroxy-cis-bicyclo[3,3,0]oct- 2/3-ene 301. 3-[2-(Carboxymethoxy)ethyl]-6β-(3α-hydroxy-4-methyloct-1-en-6-ynyl)-7α-hydroxy-cis-bicyclo-[3,3,0]oct-2/3-ene 302. 3-[2-(Carboxymethylthio)ethyl]-6β-(3α-hydroxy-4-methyloct-1-en-6-ynyl)-7α-hydroxy-cis-bicyclo-[3,3,0]oct-2/3-ene 303. 3-(4-Carboxybut-3-enyl)-6β-(3α-hydroxy-4-methyloct- 1-en-6-ynyl)-7α-hydroxy-cis-bicyclo[3,3,0]oct- 2/3-ene 304. 3-[2-(3-Carboxypropoxy)ethyl]-6β-(3α-hydroxy-4-methyloct-1-en-6-ynyl)-7α-hydroxy-cis-bicyclo[3,3,0]-oct- 2/3-ene 305. 3-[2-(3-Carboxypropylthio)ethyl]-6β-(3α-hydroxy-4-methyloct-1-en-6-ynyl)-7α-hydroxy-cis-bicyclo-[3,3,0]oct-2/3-ene 306. 3-[2-(2-Hydroxyethoxy)ethyl]-6β-(3α-hydroxy-4-methyloct-1-en-6-ynyl)-7α-hydroxy-cis-bicyclo-[3,3,0]oct-2/3-ene 307. 3-[2-(2-Hydroxyethylthio)ethyl]-6β-(3α-hydroxy-4-methyloct-1-en-6-ynyl)-7α-hydroxy-cis-bicyclo-[3,3,0]oct-2/3-ene 308. 3-(5-Hydroxypent-3-enyl)-6β-(3α-hydroxy-4-methyloct-1-en-6-ynyl)-7α-hydroxy-cis-bicyclo[3,3,0]-oct-2/3-ene 309. 3-[2-(Carboxymethoxy)ethyl]-6β-(3α-hydroxy-4,4-dimethyloct-1-en-6-ynyl)-7α-hydroxy-cis-bicyclo-[3,3,0]oct-2/3-ene 310. 3-[2-(Carboxymethylthio)ethyl]-6β-(3α-hydroxy-4,4-dimethyloct-1-en-6-ynyl)-7α-hydroxy-cis-bicyclo-[3,3,0]oct-2/3-ene 311. 3-(4-Carboxybut-3-enyl)-6β-(3α-hydroxy-4,4-dimethyloct-1-en-6-ynyl)-7α-hydroxy-cis-bicyclo[3,3,0]-oct-2/3-ene 312. 3-[2-(2-Hydroxyethoxy)ethyl]-6β-[3α-(2-tetrahydropyranyloxy)-3-cyclopentylprop-1-enyl]-7α-(2-tetrahydropyranyloxy)-cis-bicyclo[3,3,0]oct-2/3-ene 313. 3-[2-(2-Hydroxyethylthio)ethyl]-6β-[3α-(2-tetrahydropyranyloxy)-3-cyclopentylprop-1-enyl]-7α-(2-tetrahydropyranyloxy)-cis-bicyclo[3,3,0]oct-2/3-ene 314. 3-(5-Hydroxypent-3-enyl)-6β-[3α-(2-tetrahydropyranyloxy)-3-cyclopentylprop-1-enyl]-7α-(2-tetrahydropyranyloxy)-cis-bicyclo[3,3,0]oct-2/3-ene 315. 3-[2-(Carboxymethoxy)ethyl]-6β-(3α-hydroxy-3-cyclopentylprop-1-enyl)-7α-hydroxy-cis-bicyclo-[3,3,0]oct-2/3-ene 316. 3-[2-(Carboxymethylthio)ethyl]-6β-(3α-hydroxy-3-cyclopentylprop-1-enyl)-7α-hydroxy-cis-bicyclo-[3,3,0]oct-2/3-ene 317. 3-(4-Carboxybut-3-enyl)-6β-(3α-hydroxy-3-cyclopentylprop-1-enyl)-7α-hydroxy-cis-bicyclo[3,3,0]-oct-2/3-ene 318. 3-[2-(3-Carboxypropoxy)ethyl]-6β-(3α-hydroxy-3-cyclopentylprop-1-enyl)-7α-hydroxy-cis-bicyclo-[3,3,0]oct-2/3-ene 319. 3-[2-(3-Carboxypropylthio)ethyl]-6β-(3α-hydroxy-3-cyclopentylprop-1-enyl)-7α-hydroxy-cis-bicyclo[3,3,0]oct-2/3-ene 320. 3-[2-(Carboxymethoxy)ethyl]-6β-(3α-hydroxy-3-cyclopentylpropyl)-7α-hydroxy-cis-bicyclo[3,3,0]-oct-2/3-ene 321. 3-[2-(Carboxymethylthio)ethyl]-6β-(3α-hydroxy-3-cyclopentylpropyl)-7α-hydroxy-cis-bicyclo[3,3,0]-oct-2/3-ene 322. 3-(4-Carboxybut-3-enyl)-6β-(3α-hydroxy-3-cyclopentylpropyl)-7α-hydroxy-cis-bicyclo[3,3,0]-oct-2/3-ene 323. 3-[2-(2-Hydroxyethoxy)ethyl]-6β-(3α-hydroxy-3-cyclopentylprop-1-enyl)-7α-hydroxy-cis-bicyclo-[3,3,0]oct-2/3-ene 324. 3-[2-(2-Hydroxyethylthio)ethyl]-6β-(3α-hydroxy-3-cyclopentylprop-1-enyl)-7α-hydroxy-cis-bicyclo[3,3,0]oct-2/3-ene 325. 3-(5-Hydroxypent-3-enyl)-6β-(3α-hydroxy-3-cyclopentylprop-1-enyl)-7α-hydroxy-cis-bicyclo-[3,3,0]oct-2/3-ene 326. 3-[3-(2-Benzyloxyethoxy)propyl]-6β-[3α-(2-tetrahydropyranyloxy)-3-cyclohexylprop-1-enyl]-7α-(2-tetrahydropyranyloxy)-cis-bicyclo[3,3,0]oct-2/3-ene 27. 3-[3-(2-Benzyloxyethylthio)propyl]-6β-[3α-(2-tetrahydropyranyloxy)-3-cyclohexylprop-1-enyl]-7α-(2-tetrahydropyranyloxy)-cis-bicyclo[3,3,0]oct-2/3-ene 328. 3-(6-Benzyloxyhex-4-enyl)-6β-[3α-(2-tetrahydropyranyloxy)-3-cyclohexylprop-1-enyl]-7α-(2-tetrahydropyranyloxy)-cis-bicyclo[3,3,0]oct-2/3-ene 329. 3-[2-(2-Hydroxyethoxy)ethyl]-6β-[3α-(2-tetrahydropyranyloxy)-3-cyclohexylprop-1-ynyl]-7α-(2-tetrahydropyranyloxy)-cis-bicyclo[3,3,0]oct-2/3-ene 330. 3-[2-(2-Hydroxyethylthio)ethyl]-6β-[3α-(2-tetrahydropyranyloxy)-3-cyclohexylprop-1-ynyl]-7α-(2-tetrahydropyranyloxy)-cis-bicyclo[3,3,0]oct-2/3-ene 331. 3-(5-Hydroxypent-3-enyl)-6β-[3α-(2-tetrahydropyranyloxy)-3-cyclohexylprop-1-ynyl]-7α-(2-tetrahydropyranyloxy)-cis-bicyclo[3,3,0]oct-2/3-ene 332. 3-[2-(Carboxymethoxy)ethyl]-6β-[3α-(2-tetrahydropyranyloxy)-3-cyclohexylprop-1-enyl]-7α-(2-tetrahydropyranyloxy)-cis-bicyclo[3,3,0]oct-2/3-ene 333. 3-[2-(2-Carboxymethylthio)ethyl]-6β-[3α-(2-tetrahydropyranyloxy)-3-cyclohexylprop-1-enyl]-7α-(2-tetrahydropyranyloxy)-cis-bicyclo[3,3,0]oct-2/3-ene 334. 3-(4-Carboxybut-3-enyl)-6β-[3α-(2-tetrahydropyranyloxy)-3-cyclohexylprop-1-enyl]-7α-(2-tetrahydropyranyloxy)-cis-bicyclo[3,3,0]oct-2/3-ene 335. 3-[4-(Methoxycarbonylmethoxy)butyl]-6β-(3α-hydroxy-3-cyclohexylprop-1-enyl)-7α-hydroxy-cis-bicyclo[3,3,0]oct-2/3-ene 336. 3-[4-(Methoxycarbonylmethylthio)butyl]-6β-(3α-hydroxy-3-cyclohexylprop-1-enyl)-7α-hydroxy-cis-bicyclo[3,3,0]oct-2/3-ene 337. 3-[6-(Methoxycarbonyl)hex-5-enyl]-6β-(3α-hydroxy-3-cyclohexylprop-1-enyl)-7α-hydroxy-cis-bicyclo[3,3,0]oct-2/3-ene 338. 3-[2-(Carboxymethoxy)ethyl]-6β-[3α-hydroxy-3-(4-methylcyclohexyl)prop-1-enyl]-7α-hydroxy-cis-bicyclo-[3,3,0]oct-2/3-ene 339. 3-[2-(Carboxymethylthio)ethyl]-6β-[3α-hydroxy-3-(4-methylcyclohexyl)prop-1-enyl]-7α-hydroxy-cis-bicyclo[3,3,0]oct-2/3-ene 340. 3-(4-Carboxybut-3-enyl)-6β-[3α-hydroxy-3-(4-methylcyclohexyl)prop-1-enyl]-7α-hydroxy-cis-bicyclo-[3,3,0]oct-2/3-ene 341. 3-[2-(2-Hydroxyethoxy)ethyl]-6β-(3α-hydroxy-3-cyclohexylprop-1-enyl)-7α-hydroxy-cis-bicyclo-[3,3,0]oct-2/3-ene 342. 3-[2-(2-Hydroxyethylthio)ethyl]-6β-(3α-hydroxy-3-cyclohexylprop-1-enyl)-7α-hydroxy-cis-bicyclo[3,3,0]oct-2/3-ene 343. 3-(5-Hydroxypent-3-enyl)-6β-(3α-hydroxy-3-cyclohexylprop-1-enyl)-7α-hydroxy-cis-bicyclo-[3,3,0]oct-2/3-ene 344. 3-[2-(Carboxymethoxy)ethyl]-6β-(3α-hydroxy-3-cyclohexylprop-1-enyl)-7α-hydroxy-cis-bicyclo-[3,3,0]oct-2/3-ene 345. 3-[2-(Carboxymethylthio)ethyl]-6β-(3α-hydroxy-3-cyclohexylprop-1-enyl)-7α-hydroxy-cis-bicyclo-[3,3,0]oct-2/3-ene 346. 3-(4-Carboxybut-3-enyl)-6β-(3α-hydroxy-3-cyclohexylprop-1-enyl)-7α-hydroxy-cis-bicyclo[3,3,0]-oct-2/3-ene 347. 3-[2-(3-Carboxypropoxy)ethyl]-6β-(3α-hydroxy-3-cyclohexylprop-1-enyl)-7α-hydroxy-cis-bicyclo-[3,3,0]oct-2/3-ene 348. 3-[2-(3-Carboxypropylthio)ethyl]-6β-(3α-hydroxy-3-cyclohexylprop-1-enyl)-7α-hydroxy-cis-bicyclo[3,3,0]oct-2/3-ene 349. 3-[2-(2-Hydroxyethoxy)ethyl]-6β-[3α-(2-tetrahydropyranyloxy)-4-cyclopentylbut-1-enyl]-7α-(2-tetrahydropyranyloxy)-cis-bicyclo[3,3,0]oct-2/3-ene 350. 3-[2-(2-Hydroxyethylthio)ethyl]-6β-[3α-(2-tetrahydropyranyloxy)-4-cyclopentylbut-1-enyl]-7α-(2-tetrahydropyranyloxy)-cis-bicyclo[3,3,0]oct-2/3-ene 351. 3-(5-Hydroxypent-3-enyl)-6β-[3α-(2-tetrahydropyranyloxy)- 4-cyclopentylbut-1-enyl]-7α-(2-tetrahydropyranyloxy)-cis-bicyclo[ 3,3,0]oct-2/3-ene 352. 3-[2-(Carboxymethoxy)ethyl]-6β-(3α-hydroxy-4-cyclopentylbut-1-enyl)-7α-hydroxy-cis-bicyclo-[ 3,3,0] oct-2/3-ene 353. 3-[2-(Carboxymethylthio)ethyl]-6β-(3α-hydroxy-4-cyclopentylbut-1-enyl)-7α-hydroxy-cis-bicyclo-[ 3,3,0] oct-2/3-ene 54. 3-(4-Carboxybut-3-enyl)-6β-(3α-hydroxy-4-cyclopentylbut- 1-enyl)-7α-hydroxy-cis-bicyclo[3,3,0]-oct- 2/3-ene 55. 3-[2-(Carboxymethoxy)ethyl]-6β-(3α-hydroxy- 4-phenylthiobut-1-enyl)-7α-hydroxy-cis-bicyclo-3,3,0]oct-2/3-ene 356. 3-[2-(Carboxymethylthio)ethyl]-6β-(3α-hydroxy-4-phenylthiobut-1-enyl)-7α-hydroxy-cis-bicyclo-[ 3,3,0] oct-2/3-ene 357. 3-(4-Carboxybut-3-enyl)-6β-(3α-hydroxy-4-phenylthiobut- 1-enyl)-7α-hydroxy-cis-bicyclo[3,3,0]-oct- 2/3-ene 358. 3-[2-(2-Hydroxyethoxy)ethyl]-6β-(3α-hydroxy-4-phenoxybut-1-enyl)-7α-hydroxy-cis-bicyclo[3,3,0]oct-2/3-ene 359. 3-[2-(2-Hydroxyethylthio)ethyl]-6β-(3α-hydroxy-4-phenoxybut-1-enyl)-7α-hydroxy-cis-bicyclo-[ 3,3,0]oct-2/3-ene 360. 3-(5-Hydroxypent-3-enyl)-6β-(3α-hydroxy- 4-phenoxybut-1-enyl)-7α-hydroxy-cis-bicyclo[3,3,0]oct- 2/3-ene 361. 3-[2-(Carboxymethoxy)ethyl]-6β-(3α-hydroxy-4-phenoxybut-1-enyl)-7α-hydroxy-cis-bicyclo-[ 3,3,0]oct-2/3-ene 362. 3-[2-(Carboxymethylthio)ethyl]-6β-(3α-hydroxy-4-phenoxybut-1-enyl)-7α-hydroxy-cis-bicyclo-[ 3,3,0]oct-2/3-ene 363. 3-(4-Carboxybut-3-enyl)-6β-(3α-hydroxy-4-phenoxybut- 1-enyl)-7α-hydroxy-cis-bicyclo[3,3,0]-oct- 2/3-ene 364. 3-[2-(Carboxymethoxy)ethyl]-6β-(3α-hydroxy- 4-p-fluorophenoxybut-1-enyl)-7α-hydroxy-cis-bicyclo-[ 3,3,0] oct-2/3-ene 365. 3-[2-(Carboxymethylthio)ethyl]-6β-(3α-hydroxy-4-p-fluorophenoxybut-1-enyl)-7α-hydroxy-cis-bicyclo-[ 3,3,0]oct-2/3-ene 366. 3-(4-Carboxybut-3-enyl)-6β-(3α-hydroxy-4-p-fluorophenoxybut- 1-enyl)-7α-hydroxy-cis-bicyclo[3,3,0]-oct- 2/3-ene 367. 3-[2-(Carboxymethoxy)ethyl]-6β-(3α-hydroxy-4-m-chlorophenoxybut-1-enyl)-7α-hydroxy-cis-bicyclo-[ 3,3,0]oct-2/3-ene 368. 3-[2-(Carboxymethylthio)ethyl]-6β-(3α-hydroxy-4-m-chlorophenoxybut-1-enyl)-7α-.hydroxy-cis-bicyclo-[ 3,3,0]oct-2/3-ene 369. 3-(4-Carboxybut-3-enyl)-6β-(3α-hydroxy-4-m-chlorophenoxybut- 1-enyl)-7α-hydroxy-cis-bicyclo[3,3,0]-oct- 2/3-ene 370. 3-[2-(2-Hydroxyethoxy)ethyl]-6β-(3α-hydroxy-4-m-methoxyphenoxybut-1-enyl)-7α-hydroxy-cis-bicyclo-[ 3,3,0]oct-2/3-ene 371. 3-[2-(2-Hydroxyethylthio)ethyl]-6β-(3α-hydroxy-4-m-methoxyphenoxybut-1-enyl)-7α-hydroxy-cis-bicyclo[ 3,3,0]oct-2/3-ene 372. 3-(5-hydroxypent-3-enyl)-6β-(3α-hydroxy- 4-m-methoxyphenoxybut-1-enyl)-7α-hydroxy-cis-bicyclo-[ 3o3, 0]oct-2/3-ene 373. 3-[2-(Carboxymethoxy)ethyl]-6β-[3α-(2-tetrahydropyranyloxy)- 4-(m-trifluoromethylphenoxy)but-1-enyl]-7α-(2-tetrahydropyranyloxy)-cis-bicyclo[3,3,0]oct-2/3-ene 374. 3-[2-(Carboxymethylthio)ethyl]-6β-[3α-(2-tetrahydropyranyloxy)- 4-(m-trifluoromethylphenoxy)but-1-enyl]-7α-(2-tetrahydropyranyloxy)-cis-bicyclo[3,3,0]oct- 3-ene 375. 3-(4-Carboxybut-3-enyl)-6β-[3α-(2-tetrahydropyranyloxy)- 4-(m-trifluoromethylphenoxy)but-1-enyl]- 7α-(2-tetrahydropyranyloxy)-cis-bicyclo[3,3,0]oct- 3-ene 376. 3-[2-(Carboxymethoxy)ethyl]-6β-(3α-hydroxy-5-phenylpent-1-enyl)-7α-hydroxy-cis-bicyclo[3,3,0]oct-2/3-ene 377. 3-[2-(Carboxymethylthio)ethyl]-6β-(3α-hydroxy-5-phenylpent-1-enyl)-7α-hydroxy-cis-bicyclo[3,3,0]oct-2/3-ene 378. 3-(4-Carboxybut-3-enyl)-6β-(3α-hydroxy-5-phenylpent- 1-enyl)-7α-hydroxy-cis-bicyclo[3,3,0]-oct- 2/3-ene 379. 3-[2-(Methanesulfonylcarbamoylmethoxy)ethyl]-6β-(3α-hydroxy-5,9-dimethyldeca-1,8-dienyl)-7α-hydroxy-cis-bicyclo[ 3,3,0]oct-2/3-ene 380. 3-[2-(Methanesulfonylcarbamoylmethylthio)ethyl]-6β-(3α-hydroxy-5,9-dimethyldeca-1,8-dienyl)-7α-hydroxy-cis-bicyclo[ 3,3,0]oct-2/3-ene 381. 3-[4-(Methanesulfonylcarbamoyl)but-3-enyl]-6β-(3α-hydroxy-5,9-dimethyldeca-1,8-dienyl)-7α-hydroxy-cis-bicyclo[ 3,3,0]oct-2/3-ene 382. 3-(4-Carboxybutyl)-6β-(3α-hydroxy-5,9-dimethyldeca- 1,8-dienyl)-7α-hydroxy-cis-bicyclo[3,3,0]-oct- 2/3-ene 383. 3-(4-Carboxybutyl)-6β-(3α-hydroxy-5,9-dimethyldeca- 1,8-dienyl)-7α-hydroxy-cis-bicyclo[3,3,0]-oct-2-ene 384. 3-(4-Carboxybutyl)-6β-(3α-hydroxy-5,9-dimethyldeca- 1,8-dienyl) -7α-hydroxy-cis-bicyclo[3,3,0]oct-2/3-ene 385. 3-(4-Carboxybutyl)-6β-(3α-hydroxy-5,9-dimethyldeca- 1,8-dienyl)- 7oα-hydroxy-cis-bicyclo[3,3,0]oct-2-ene It will be noted that Compounds No. 1–43 and 382 above are compounds of formula (Ia); Compounds 44–109 and 383 are compounds of formula (Ib)= and Compounds 110–381 are compounds of formula (Ic).

Of the compounds listed above, the preferred compounds are Compounds Nos. 16, 18, 30, 33, 40, 41, 43, 46, 56, 60, 85, 90, 98, 99, 100, 103, 108, 113, 144, 152, 194, 218, 226, 231, 263, 301, 309, 315, 344, 352, 361, 379 384 and 385. Where the compounds referred to above contain a free carboxy group in their molecule, the sodium and potassium salts thereof are also amongst the preferred compounds of the present invention.

The compounds of the invention may be prepared by a variety of methods, as explained below.

METHOD A

Compounds of formula (I) where B represents a vinylene group, as well, of course, as compounds of formula (Ia) and (Ib), may be prepared as illustrated in the following reaction scheme:

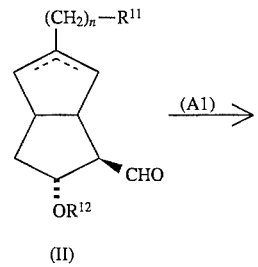

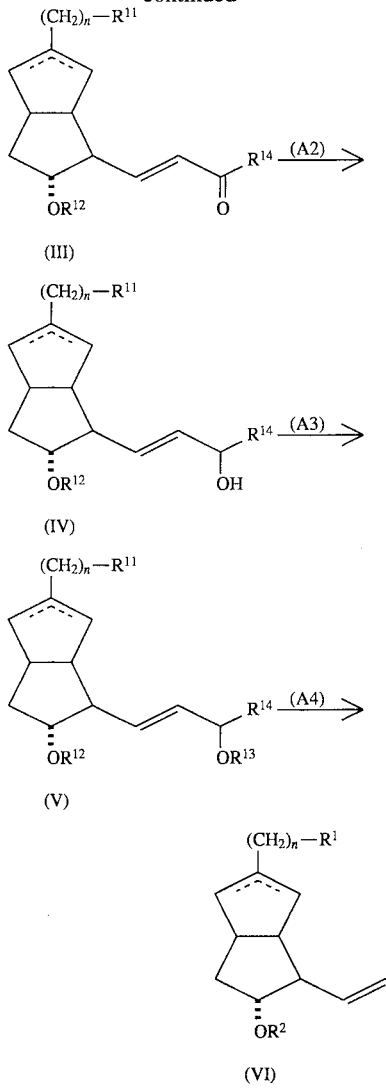

(III)

(IV)

(V)

(VI)

In the above formulae, $R^1$, $R^2$, $R^3$, $R^4$, n and the dotted line are as defined above. $R^{11}$ represents a protected hydroxymethyl group, a protected formyl group, a protected carboxy group or a group of formula $-A(CH_2)_m-R^{15}$ (in which A and m are as defined above and $R^{15}$ represents a protected hydroxymethyl group, a protected formyl group or a protected carboxy group). Examples of preferred protected hydroxymethyl, formyl and carboxy groups are given hereinabove in relation to $R^1$ and $R^5$. $R^{12}$ and $R^{13}$ both represent hydroxy-protecting groups, examples of which have been given above in relation to $R^2$ and $R^3$. $R^{14}$ represents any of the groups defined above for $R^4$, provided that any acyl or hydroxy group in said group represented by $R^4$ must be protected. Examples of hydroxy-protecting groups have been given above in relation to $R^2$ and $R^3$, whilst examples of protecting groups for acyl groups have been given above in relation to the formyl-protecting groups of $R^1$ and $R^5$.

Step (A1)

In step (A1) of the above reaction scheme, an unsaturated compound of formula (III) is prepared by reacting an aldehyde of formula (II) with a Wittig reagent of general formula (VII):

$$(R^{10})_3P^{\oplus}-^{\ominus}CH-COR^{14} \qquad (VII)$$

or with a modified Wittig reagent having the formula (VIII):

wherein: $R^{14}$ is as defined above; $R^{10}$ represents an aryl group (particularly a phenyl group) or an alkyl group (particularly a $C_1$–$C_6$ alkyl group, such as a methyl or butyl group); and M represents an alkali metal atom (for example a lithium, sodium or potassium atom).

The Wittig reagent of formula (VII) or the modified Wittig reagent of formula (VIII) may be prepared by reaction of the corresponding compound of formula (VIIa):

$$(R^{10})_3P^{\oplus}-CH_2COR^{14} \; X^{\ominus} \qquad (VIIa)$$

or (VIIIa):

(in which: $R^{14}$ and $R^{10}$ are as defined above; and X represents a halogen atom, for example a chlorine, bromine or iodine atom) with an alkali metal base, for example: an alkali metal hydride, such as sodium hydride or potassium hydride; an alkali metal alkoxide, such as sodium methoxide, sodium ethoxide or potassium t-butoxide; an alkali metal amide, such as sodium amide or potassium amide; an alkyl-alkali metal, such as butyllithium; or an alkali metal methylsulfinylcarbanion, such as sodium dimsyl. This reaction is preferably effected in the presence of a solvent under conventional conditions for the preparation of Wittig reagents and requires no further elucidation here.

The reaction of step (A1) is preferably effected in the presence of a solvent. The nature of the solvent employed is not particularly critical, provided that it has no adverse effect on the reaction and any solvent conventionally used in Wittig reagents may equally be employed in this step. Examples of suitable solvents include: ethers, such as diethyl ether, tetrahydrofuran, dioxane or ethylene glycol dimethyl ether; a cyclic sulfone, such as sulfolane; a hydrocarbon, such as benzene, toluene or hexane; a dialkyl sulfoxide, such as dimethyl sulfoxide; a dialkylamide of an aliphatic acid, such as dimethylformamide or dimethylacetamide; a halogenated hydrocarbon, such as methylene chloride or chloroform; a phosphoric triamide, such as hexamethylphosphoric triamide. The reaction is preferably carried out under an atmosphere of an inert gas, such as nitrogen, argon or helium. There is no particular limitation on the reaction temperature and the reaction may be carried out over a very wide temperature range, for example from −10° C. to the reflux temperature of the solvent employed. For convenience, we generally prefer that the reaction temperature should be about ambient temperature. The time required for the reaction will vary, depending upon various reaction conditions, notably the reaction temperature, but a period of from 6 to 50 hours will normally suffice.

After completion of the reaction, the resulting compound of formula (III) may be isolated from the reaction mixture by conventional means. For example, one suitable recovery procedure comprises: adding ice-water to the reaction mixture; acidifying the mixture, if necessary; extracting the mixture with an organic solvent, such as diethyl ether; washing the resulting organic extract with water; drying the extract; and evaporating off the solvent to leave the desired product.

Step (A2)

In this step, an alcohol derivative of formula (IV) is prepared by reducing the compound of formula (III) prepared in step (A1). This reaction is preferably carried out in the presence of an inert solvent using a reducing agent.

There is no particular limitation on the nature of the reducing agent and any such agent which is capable of converting a carbonyl group to a hydroxy group without, or without to any significant degree, adversely affecting the remainder of the molecule may be employed. Examples of suitable reducing agents include: metal hydrides, such as sodium borohydride, potassium borohydride, lithium borohydride, zinc borohydride, lithium aluminum tri-t-butoxyhydride, lithium aluminum trimethoxyhydride or sodium cyanoborohydride; or an aluminum compound, such as aluminum isopropoxide or diisobutyl(2,6-di-t-butyl-4-methylphenoxy)aluminum. Of these, we particularly prefer sodium borohydride.

In order to minimize reduction of carbon-carbon double bonds, the reaction is preferably effected in the presence of cerium chloride.

The nature of the solvent employed for this reaction is not critical, provided that it has no adverse effect on the reaction. Suitable solvents include: alcohols, such as methanol, ethanol, propanol, butanol or t-butanol; and ethers, such as diethyl ether, tetrahydrofuran or dioxane. Of these, alcohols, particularly methanol are preferred.

The reaction is preferably carried out at a temperature of from 0° C. to room temperature and the time required for the reaction, although it may vary depending upon many factors (including the nature of the reagents and the reaction temperature), is generally from 10 minutes to 2 hours.

After completion of the reaction, the desired product of formula (IV) may be isolated from the reaction mixture by conventional means. For example, one suitable recovery procedure comprises: removing the solvent by evaporation under reduced pressure; adding ice-water to the residue: extracting the resulting solution with a water-immiscible organic solvent; and finally distilling off the solvent to leave the desired product.

The reactions described above in steps (A1) and (A2) may equally be carried out employing compounds of formula (II) or (III) in which $R^{11}$ instead of having any hydroxy group protected, has the hydroxy group unprotected. In such a case, the hydroxy group may be protected following the procedure described in step (A3) below, to give a group $R^{11}$ including a protected hydroxy group which may be the same as or different from the protected hydroxy groups of $OR^{12}$ and $OR^{13}$.

Step (A3)

In this step, the hydroxy group at the 3- position of the side chain on the cyclopentane ring of the compound of formula (IV) is optionally protected to give the compound of formula (V). Introduction of the protecting group may be effected by contacting the compound of formula (IV) with a reagent which forms a protecting group by any conventional procedure and the nature of the reagent will, of course, determine the nature of the protecting group introduced. Examples of such reagents include, for example: carboxylic acids, such as acetic acid, propionic acid, burytic acid, benzoic acid or a naphthalenecarboxylic acid; a reactive derivative (such as an acid anhydride, mixed acid anhydride, acid halide, particularly the chloride, or reactive ester) of such a carboxylic acid: an aralkyl halide, such as benzyl chloride, benzyl bromide, p-nitrobenzyl bromide or p-methoxybenzyl bromide; a 5- or 6- membered heterocyclic compound, such as dihydropyran, dihydrothiopyran, dihydrothiophene or 4-methoxy-5,6-dihydro-(2H)pyran; an alkoxyalkyl or aralkoxyalkyl halide, such as methoxymethyl chloride, ethoxyethyl chloride or benzyloxymethyl chloride: an unsaturated ether, such as methyl vinyl ether or ethyl vinyl ether: a silyl compound, such as hexamethyldisilazane, trimethylsilyl chloride, tripropylsilyl chloride, t-butyldimethylsilyl chloride or t-butyldiphenylsilyl chloride.

When a carboxylic acid is employed, the reaction is preferably carried out in the presence of a condensing agent, such as dicyclohexylcarbodiimide.

Examples of suitable reactive derivatives of carboxylic acids include: acid halides, such as acetyl chloride, acetyl bromide, benzoyl chlorde, benzoyl bromide or naphthoyl chloride; or an acid anhydride, such as acetic anhydride, propionic anhydride or benzoic anhydride. When such a reactive derivative is used, the reaction is preferably carried out in the presence of an organic base, such as triethylamine, pyridine, 4-dimethylaminopyridine, quinoline or N,N-dimethylaniline.

Reaction with a carboxylic acid or reactive derivative thereof is preferably carried out in the presence of a solvent. The nature of the solvent is not critical, provided that it has no adverse effect on the reaction. Suitable solvents include: hydrocarbons, such as benzene, toluene, xylene or hexane; halogenated hydrocarbons, such as methylene chloride, chloroform, carbon tetrachloride or chlorobenzene; ethers, such as diethyl ether, tetrahydrofuran or dioxane; and ketones, such as acetone or methyl ethyl ketone. Of these, the hydrocarbons are preferred.

The reaction temperature is preferably within the range from 0° C. to 100° C. and the time required for the reaction, although varying depending upon the reagents, reaction temperature and other reaction conditions, is usually from 30 minutes to 6 hours.

When an aralkyl halide, an alkoxyalkyl halide, an aralkoxyalkyl halide or a silyl compound is used as the protecting reagent, the compound of formula (IV) is preferably first converted to its alkali metal salt, for example by treatment with an alkali metal hydride such as sodium hydride or potassium hydride. This salt is then reacted with the appropriate halide or silylating agent (such as disilazane) in an inert solvent.

The nature of the solvent employed in this reaction is not critical, provided that it has no adverse effect upon the reaction. Examples of suitable solvents include: ethers, such as diethyl ether, tetrahydrofuran and dioxane; amides, such as dimethylformamide, dimethylacetamide or hexamethylphosphoric triamide; nitriles, such as acetonitrile or benzonitrile; and sulfoxides, such as dimethyl sulfoxide. Of these, the amides are preferred.

The reaction temperature is preferably from 0° C. to 100° C., and the time required for the reaction, although varying depending upon the nature of the reagents, the reaction temperature and other reaction conditions, is usually from 10 minutes to 3 hours.

Corresponding ethers of the compound of formula (IV) may also be prepared by reacting the compound of formula (IV) with the appropriate halide in the presence of an organic base, such as triethylamine, pyridine, 4-dimethylaminopyridine or imidazole, or an inorganic base, such as sodium hydroxide, potassium hydroxide or potassium carbonate.

When a 5- or 6- membered heterocyclic compound or an unsaturated ether is employed, the reaction may be conducted in the presence or absence of an inert solvent and is preferably conducted in the presence of a small amount of an acid. Suitable acids include mineral acids (such as hydrochloric acid or hydrobromic acid) and organic acids (such as picric acid, trifluoroacetic acid, benzenesulfonic acid, p-toluenesulfonic acid or camphorsulfonic acid).

The nature of the solvent employed in this reaction is not critical, provided that it does not interfere with the reaction and examples of suitable such solvents include: ethers, such as diethyl ether, tetrahydrofuran or dioxane; halogenated hydrocarbons, such as methylene chloride, chloroform or carbon tetrachloride; and aromatic hydrocarbons, such as benzene, toluene or xylene. Of these, the halogenated hydrocarbons are preferred. Alternatively, an excess of the heterocyclic compound or of the vinyl ether may serve as a solvent in the absence of any added solvent.

The reaction temperature is preferably from 0° C. to 50° C., and the time required for the reaction, although varying depending upon the nature of the reagents, the reaction temperature and other reaction conditions, is usually from 30 minutes to 3 hours.

After completion of the reaction, the resulting compound of formula (V) in which the hydroxy groups are protected may be removed from the reaction mixture by conventional means. For example, one suitable recovery procedure comprises: pouring the reaction mixture into ice-water; separating insoluble materials, if any, by filtration; neutralizing the filtrate: extracting the desired compound with a water-immiscible organic solvent; and then removing the solvent by distillation. If required, the compound may be further purified by conventional means, for example by column chromatography, thin layer chromatography or recrystallization, or by any combination thereof.

Sometimes, in the course of the reactions outlined above, a substantial quantity of the compound of formula (IV) or (V) having the 7- hydroxy or protected hydroxy group in the 8-configuration is produced. Since the 7μ-hydroxy compound is less important, this may, if desired, be removed by conventional methods, for example recrystallization, column chromatography or a combination thereof.

Step (A4)

This step comprises any one or more of a number of optional reactions, although, of course, it may be that the compound of formula (V) obtained in step (A3) or the compound of formula (IV) obtained in step (A2) is the desired final product, in which case step (A4) may be omitted altogether. The reactions involved in this step are: removal of the hydroxy-protecting or carboxy-protecting group of $R^{11}$ removal of the hydroxy-protecting group of $R^{12}$ and/or $R^{13}$; conversion of the hydroxymethyl group represented by or included within the group represented by $R^1$ to a formyl group or to a carboxy group: esterification of the carboxy group; or conversion of the carboxy group or an esterified carboxy group to the corresponding amide.

When the hydroxy-protecting group is a $C_1$-$C_6$ aliphatic or aromatic acyl group, it may be removed by a conventional hydrolysis reagent, employing an acid or a base. The acid or base employed may be any one of those conventionally used for hydrolysis reactions of this type. However, we normally prefer to carry out the hydrolysis under basic conditions, using as the base a hydroxide of an alkali metal or of an alkaline earth metal, such as lithium hydroxide, sodium hydroxide, potassium hydroxide, calcium hydroxide or barium hydroxide. The reaction is normally carried out in a solvent, and any solvent commonly used for hydrolysis reactions may be employed, although, once again, the choice is not particularly critical. Examples of suitable solvents include: alcohols, such as methanol, ethanol, propanol or isopropanol; ethers, such as diethyl ether, tetrahydrofuran, dioxane or ethylene glycol dimethyl ether; or a mixture of one or more or these organic solvents with water.

There is no particular limitation on the reaction temperature, which may, accordingly, vary over a wide range. For convenience, the reaction is normally carried out at about room temperature or at the reflux temperature of the solvent employed or at a temperature between these. The time required for the reaction, although varying depending upon the reaction temperature and other reaction conditions, is usually from 1 to 12 hours. When the carboxy-protecting group is a $C_1$-$C_6$ alkyl group or an aryl group, this reaction to remove hydroxy-protecting groups simultaneously removes the carboxy-protecting group.

Where the hydroxy-protecting group is an aralkyl group, it may be removed by contacting the compound of formula (V) with a reducing agent in an inert solvent.

Reducing agents employed for this type of reaction are well-known and examples include: alkali metals, such as lithium, sodium or potassium; and alkali metal sulfides, such as sodium sulfide or potassium sulfide; alkali metals are preferred. Where an alkali metal is used, the solvent is preferably liquid ammonia or a mixture of liquid ammonia with an ether such as diethyl ether or tetrahydrofuran. Where the reducing agent is an alkali metal sulfide, the solvent is preferably an alcohol (such as methanol or ethanol), an ether (such as tetrahydrofuran or dioxane) or a mixture of one or more of these with water.

The reaction temperature is preferably from −78° C. to −20° C. when an alkali metal is used or from 0° C. to 100° C. when an alkali metal sulfide is used. Although the time required for the reaction will vary depending upon the reagents and reaction conditions (including the reaction temperature), a period of from 20 minutes to 6 hours will normally suffice.

When the carboxy-protecting group is an aralkyl, benzhydryl or phenacyl group, this reaction will simultaneously remove the carboxy-protecting group.

When the hydroxy-protecting group is a p-methoxybenzyl group, it may also be removed by treatment with ammonium cerium fluoride in aqueous acetone at about room temperature or by treatment with an oxidizing agent, such as dichlorodicyanoquinone or sodium persulfate.

When the hydroxy-protecting group is a heterocyclic group, a substituted methyl group (such as an alkoxymethyl group or an aralkoxymethyl group) or a 1-alkoxyethyl group, it can easily be removed by contacting the compound with an acid. Suitable acids include organic acids (such as formic acid, acetic acid, trifluoroacetic acid, propionic acid, butyric acid, oxalic acid, malonic acid, methenesulfonic acid, benzenesulfonic acid, p-toluenesulfonic acid or camphorsulfonic acid) or a mineral acid (such as hydrochloric acid, hydrobromic acid or sulfuric acid). Although this reaction may be carried out in the presence or absence of a solvent, the use of a solvent is preferred, in order to ensure that the reaction proceeds smoothly. The nature of the solvent is not critical, provided that it has no adverse effect upon the reaction. Examples of suitable solvents include: water; alcohols, such as methanol or ethanol: ethers, such as tetrahydrofuran or dioxane; ketones, such as acetone or methyl ethyl ketone; and mixtures of one or more of the aforementioned organic solvents with water. The reaction temperature is not particularly critical and, for convenience, the reaction is normally carried out at a temperature ranging from room temperature to the reflux temperature of the reaction mixture. The time required for the reaction will vary, depending upon the nature of the reagents, the reaction temperature and other reaction conditions, but a period of from 30 minutes to 10 hours will normally suffice.

Where the hydroxy-protecting group is a tri-($C_1$-$C_6$ alkyl)silyl group or a diaryl($C_1$-$C_6$ alkyl)silyl group, this may easily be removed by contacting the compound with water or with an acid or a base preferably in the presence of water. Suitable acids and bases include: organic acids, such as formic acid, acetic acid, propionic acid, butyric acid, oxalic acid or malonic acid; mineral acids, such as hydrochloric acid, hydrobromic acid or sulfuric acid; alkali metal or alkaline earth metal hydroxides, such as potassium hydroxide or calcium hydroxide; and alkali metal or alkaline earth metal carbonates, such as potassium carbonate or calcium carbonate. If water is used with the acid or base, there is no need for any other solvent. However, if another solvent is desired, the choice is not critical, provided that the solvent does not interfere with the reaction: suitable other solvents include: ethers, such as tetrahydrofuran or dioxane; and alcohols, such as methanol or ethanol; these are, in any case, preferably employed in admixture with water.

There is no particular limitation on the reaction temperature and, for convenience, the reaction is normally carried out at about room temperature. The time required for the reaction will vary, depending upon the reagents, the reaction temperature and other reaction conditions, but is usually from 30 minutes to 5 hours.

When the hydroxy-protecting group is a t-butyldimethylsilyl group, this may also be removed by treatment with tetrabutylammonium fluoride in the presence of an ether (such as dioxane) under similar reaction conditions.

After completion of the reaction, the desired product may be recovered from the reaction mixture by conventional means. For example, the compound may be obtained simply by distilling off the solvent under reduced pressure. Alternatively, it may be obtained by the following technique: pouring the reaction mixture, without distillation, into ice-water; if necessary, neutralizing the mixture; extracting the mixture with an appropriate organic solvent; washing and then drying the extract; and finally removing the solvent from the extract by distillation.

Where the hydroxy-protecting groups represented by or included within the groups represented by $R^{11}$, $R^{12}$ and $R^{13}$ are identical, they will be removed simultaneously by these reactions. Also, of course, it will be appreciated that, by appropriate selection of the protecting groups, they may be removed selectively.

Where the carboxy-protecting group is a $C_1$-$C_6$ alkyl group or an aryl group, it may be removed by a conventional hydrolysis reaction. The reagents employed and the reaction conditions are exactly the same as for the removal of a hydroxy-protecting group when the hydroxy-protecting group is an acyl group.

Where the carboxy-protecting group is an aralkyl group, a benzhydryl group or a phenacyl group, it may be removed in the same way, employing the same reagents and reaction conditions, as removal of a hydroxy-protecting group when the hydroxy-protecting group is an aralkyl group.

After completion of these reactions, the desired product may be isolated from the reaction mixture by conventional methods. For example, where the reaction was a hydrolysis reaction, a suitable recovery technique comprises: acidifying the reaction mixture; extracting the mixture with an appropriate organic salt; washing and then drying the extract; and then removing the solvent from the extract by distillation.

Conversion of the hydroxymethyl group represented by or included within the group represented by $R^1$ in the resulting compound of formula (I) to a formyl group may be carried out by employing a conventional reaction for the oxidization of a primary alcohol to an aldehyde. When carrying out this reaction, it is necessary that the hydroxy-protecting groups represented by $R^{12}$ and $R^{13}$ should not have been removed: in other words, the hydroxy groups at the 3- position of the side chain on the cyclopentane ring and at the 7 position of the bicyclooctane system should both be protected.

The reaction is carried out employing an oxidizing agent which is conventional for this type of reaction. Suitable oxidizing agents include: chromic acid compounds, such as chromic anhydride, chromic anhydride-pyridine complex (Collin's reagent), chromic anhydride-concentrated sulfuric acid-water (Jones' reagent), sodium bichromate or potassium bichromate; an organic compound containing an active halogen atom, such as N-bromoacetamide, N-bromosuccinimide, N-bromophthalimide, N-chloro-p-toluenesulfonamide or N-chlorobenzenesulfonamide; an aluminum alkoxide, such as aluminum t-butoxide or aluminum isopropoxide; dimethyl sulfoxide-dichlorocarbodiimide; or pyridine-sulfuric anhydride-dimethyl sulfoxide.

The reaction is preferably carried out in the presence of an organic solvent, the nature of which is not critical, provided that it has no adverse effect upon the reaction. Suitable solvents include: halogenated hydrocarbons, such as methylene chloride, chloroform or carbon tetrachloride; ethers, such as diethyl ether, tetrahydrofuran or dioxane; ketones, such as acetone or methyl ethyl ketone; and sulfoxides, such as dimethyl sulfoxide.

The reaction is preferably carried out at a temperature of from 0° C. to ambient temperature and the time required for the reaction, although varying depending upon the reagents, reaction temperature and other reaction conditions, is generally within the range from 30 minutes to 3 hours.

After completion of the reaction, the desired formyl compound may be isolated from the reaction mixture by conventional means. For example, one suitable recovery technique comprises: separating insoluble matter, if any, by filtration; pouring the filtrate into ice-water; if necessary, neutralizing the mixture; extracting the mixture with a water-immiscible organic solvent; if necessary, washing and drying the extract; and then removing the solvent by distillation from the extract.

This formyl group may be converted to a carboxy group by a conventional method for oxidizing an aldehyde to a carboxylic acid. When this reaction is carried out, it is necessary that $R^2$ and $R^3$ should both be hydroxy-protecting groups; in other words, the hydroxy-protecting groups represented by $R^{12}$ and $R^{13}$ should not have been removed.

Suitable oxidizing agents include chromic anhydride-concentrated sulfuric acid-water (Jones' reagent), potassium permanganate-sodium hydroxide, potassium permanganate-sodium carbonate, silver oxide or potassium bichromate-sulfuric acid.

This reaction is normally carried out in the presence of a solvent, the nature of which is not critical, provided that it has no adverse effect upon the reaction. Suitable solvents include: ketones, such as acetone; water; and mixtures of water with an alcohol, such as methanol or ethanol.

The reaction may be carried out over a wide temperature range, for example from −30° C. to 100° C. The time required for the reaction will vary, depending upon the reagents, the reaction temperature and other reaction conditions, but is usually within the range from 30 minutes to 5 hours.

This reaction may also be carried out employing as a starting material a compound in which $R^1$ represents or includes a group representing a hydroxymethyl group; in other words, the conversion of the hydroxymethyl group to a formyl group and conversion of the formyl group to a carboxy group take place in a single reaction step.

After completion of the reaction, the desired carboxy compound may be isolated from the reaction mixture by conventional means. For example, one suitable recovery technique comprises: pouring the reaction mixture into ice-water; where the mixture is alkaline, acidifying it; extracting the mixture with a water-immiscible organic solvent; if necessary, washing and drying the extract; and then removing the solvent from the extract by distillation.

Conversion of the carboxy group in the carboxy compound thus obtained to an esterified carboxy group may, of course, be effected using techniques well-known for the esterification of carboxylic acids. Any esterifying agent commonly used for esterification of a carboxy group may be employed, the nature of such agent depending upon the ester which it is desired to produce. Suitable, esterifying agents include: diazoalkanes, such as diazomethane, diazoethane, diazopropane, diazoisopropane or diazobutane; an ester group-forming alcohol, such as methanol, ethanol, propanol, isopropanol or butanol, in admixture with a mineral acid (such as hydrochloric acid, hydrobromic acid or sulfuric acid) or an organic acid (such as methanesulfonic acid, benzenesulfonic acid or p-toluenesulfonic acid): or a $C_1$-$C_6$ alkyl halide, such as methylbromide or ethylbromide, in admixture with a base (such as sodium hydroxide, potassium hydroxide or sodium carbonate).

When a diazoalkane is employed, the reaction is preferably carried out in the presence of a solvent, the nature of which is not critical, provided that it does not adversely affect the reaction. The solvent employed is preferably an ether, such as diethyl ether or dioxane. Although there is no particular limitation to the reaction temperature, the reaction is preferably carried out at a relatively low temperature, in order to inhibit side reactions and to prevent decomposition of the diazoalkane; usually, the reaction is carried out at the temperature achieved by cooling with ice.

Where the esterifying agent is an alcohol in the presence of an acid, an excess of the alcohol is preferably used as the reaction solvent. There is no particular limitation on the reaction temperature and the reaction is, for convenience, normally carried out at a temperature between ambient temperature and the reflux temperature of the alcohol. The time required for the reaction will vary, depending upon the nature of the reagents (particularly the alcohol), the reaction temperature and other reaction conditions, but a period of from 1 hour to 2 days normally suffices.

After completion of this reaction, the desired ester may be isolated from the reaction mixture by conventional means. For example, one suitable recovery procedure comprises: removing the solvent by distillation from the reaction mixture; if necessary, dissolving the resulting residue in an organic solvent; washing the resulting solution with an aqueous solution of an alkali, such as an alkali metal bicarbonate (e.g. sodium bicarbonate) or an alkali metal carbonate (e.g. sodium carbonate); drying the solution; and then distilling off the organic solvent.

Instead of converting the formyl group to a carboxy group, it may, if desired, be protected by a conventional method, for example by reacting the formyl compound with a thiol or an alcohol in the presence of an acid, such as p-toluenesulfonic acid or boron trifluoride, to convert the formyl group to the corresponding acetal or thioacetal.

Conversion of the carboxy group or of the esterified carboxy group to the corresponding amide may be effected by contacting the compound with the appropriate amine in the presence of a solvent. The nature of the amine will, of course, depend upon the amide which it is desired to produce. Suitable amines include ammonia and primary or secondary amines, such as methylamine, ethylamine, propylamine, isopropylamine, butylamine, aniline, p-methylaniline, dimethylamine, methylethylamine, diethylamine, N-methylaniline, N-ethylaniline or N,m-dimethylaniline. The nature of the solvent employed is not critical, provided that it does not interfere with the reaction and preferred solvents include water or an ether (such as diethyl ether, tetrahydrofuran or dioxane).

The reaction may be carried out over a wide range of temperatures, for example from 0° C. to 100° C., and, although the time required for the reaction will vary depending upon the nature of the reagents, the reaction temperature and other reaction conditions, a period of from 1 to 24 hours will normally suffice.

Conversion of the carboxy group to an N-acylcarbamoyl group may be effected by contacting the compound with an acyl isocyanate or benzoylisocyanate in an inert solvent, the nature of which is not critical, provided that it does not have any adverse effect upon the reaction. Suitable solvents include: hydrocarbons, such as benzene, toluene or xylene; and ethers, such as diethyl ether, tetrahydrofuran or ethylene glycol dimethyl ether. For convenience, the reaction is normally effected at ambient temperature and, although the time required for the reaction may vary, it is generally within the range from 30 minutes to 10 hours.

Conversion of the carboxy group to an N-sulfonylcarbamoyl group may be effected by converting the carboxy group to an active amide and then reacting this with a sulfonic acid amide, such as methanesulfonamide, benzenesulfonamide or p-toluenesulfonamide. The active amide can be prepared by reacting the carboxy compound with an N-hydroxylamide, such as N-hydroxysuccinimide or N-hydroxyphthalamide, in the presence of a condensing agent, such as dicyclohexylcarbodiimide, preferably at about room temperature for a period of from 30 minutes to 10 hours. Reaction of the resulting active amide with the sulfonic acid amide is preferably effected in the presence of a base (such as sodium methoxide, sodium ethoxide or potassium t-butoxide), at about room temperature for a period of from 30 minutes to 15 hours.

Both formation of the active amide and reaction of this with a sulfonic acid amide are preferably effected in the presence of an inert solvent, the nature of which is not critical, provided that it has no adverse effect upon the reaction. Suitable solvents include: aromatic hydrocarbons, such as benzene, toluene or xylene; ethers, such as diethyl ether, tetrahydrofuran or ethylene glycol dimethyl ether; amides, such as dimethylformamide or dimethylacetamide; and sulfoxides, such as dimethyl sulfoxide.

After completion of the reaction, the desired compound can be obtained from the reaction mixture by conventional means. For example, one suitable recovery procedure comprises: pouring the reaction mixture into ice-water; if necessary, neutralizing the mixture; extracting the mixture with a water-immiscible organic solvent; if necessary, washing and drying the extract; and then distilling the solvent from the extract to leave the desired compound. This compound may be further purified, if necessary, by such conventional means as silica gel column chromatography or recrystallization, or a combination thereof.

METHOD B

Any of the compounds of the invention may be prepared by the reactions outlined in the following reaction scheme:

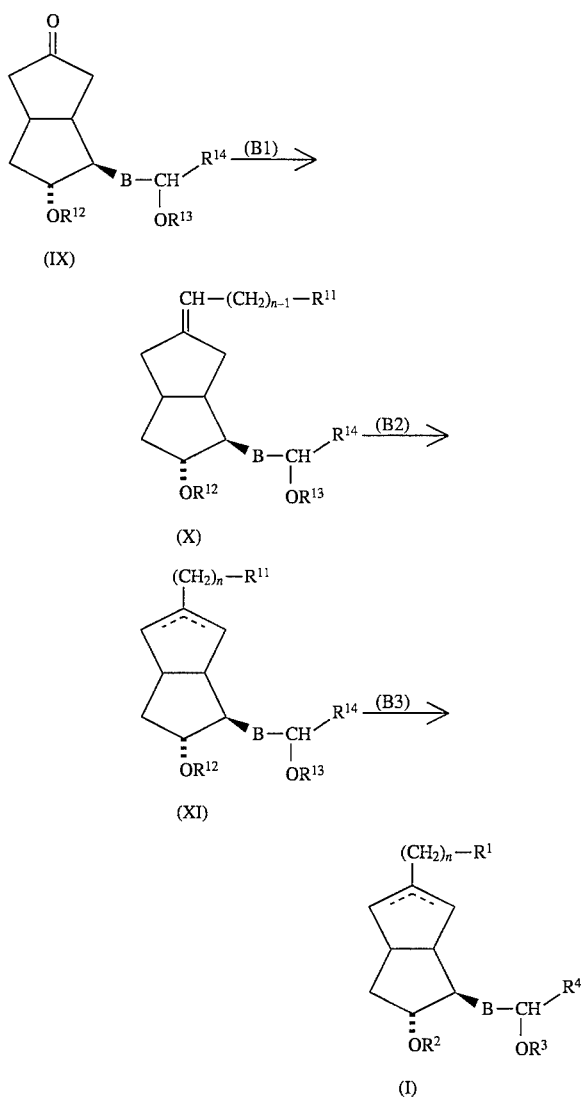

In the above scheme, $R^1$, $R^2$, $R^3$, $R^4$, $R^{11}$, $R^{12}$, $R^{13}$, $R^{14}$, n and the dotted line are as defined above.

Step (B1)

The cycloketone of formula (IX) is converted to the compound of formula (X) following essentially the same procedure as described in step (A1), but using a Wittig reagent of formula (LIV):

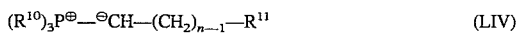

(in which $R^{10}$, $R^{11}$ and n are as defined above) or a modified Wittig reagent of formula (LV):

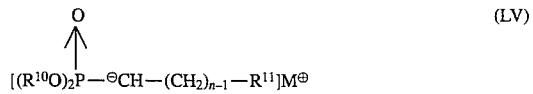

(in which $R^{10}$, $R^{11}$, n and M are as defined above). These Wittig and modified Wittig reagents may be prepared from their corresponding precursors in the same way as the similar reagents used in step (A1) and may be reacted under similar conditions. The above starting cycloketone (IX) may be prepared, for example, according to those methods as disclosed in United Kingdom Published Applications No. 2012265A, No. 2014143A and No. 2013661.

Step (B2)

In this step, the exo double bond is isomerized to an endo double bond.

This isomerization may be effected by contacting the compound of formula (X) with a base, preferably in the presence of a suitable inert solvent. The base is preferably an aminolithium compound, such as diisopropylaminolithium, isopropylcyclohexylaminolithium or dicyclohexylaminolithium. The nature of the solvent employed is not critical, provided that it has no adverse effect upon the reaction. The solvent is preferably an ether, such as diethyl ether, tetrahydrofuran or ethylene glycol dimethyl ether.

The reaction is preferably effected at a relatively low temperature, for example from −78° C. to 0° C. and the time required for the reaction, although varying depending upon the reagents, reaction temperature and other reaction conditions is generally within the range from 30 minutes to 3 hours.

Alternatively, the isomerization reaction of this step may be carried out by contacting the compound of formula (X) with an acid. A wide range of acids may be employed, for example inorganic acids (such as hydrochloride acid, nitric acid or sulfuric acid) or organic acids (such as acetic acid, trifluoroacetic acid, benzoic acid, methanesulfonic acid, benzenesulfonic acid, p-toluenesulfonic acid or camphorsulfonic acid), of which we prefer p-toluenesulfonic acid or camphorsulfonic acid. This reaction is likewise preferably carried out in the presence of an inert solvent, the nature of which is not critical, provided that it has no adverse effect upon the reaction. Suitable inert solvents include: aromatic hydrocarbons, such as benzene, toluene or xylene; ethers, such as diethyl ether, tetrahydrofuran or dioxane; halogenated hydrocarbons, such as methylene chloride, chloroform or carbon tetrachloride; ketones, such as acetone or methyl ethyl ketone; water; or a mixture of one or more of these organic solvents with water. Aromatic hydrocarbons are the preferred solvents.

The reaction is preferably effected at a temperature of from 50° C. to 150° C. and the time required for the reaction, although varying depending upon the nature of the reagents, the reaction temperature and other reaction conditions, is usually from 1 hour to 10 hours.

Where the compound of formula (X) includes a hydroxy-protecting group which is removable with an acid (for example a heterocyclic group, an alkoxymethyl group, an aralkoxymethyl group, a 1-alkoxyethyl group or a tri-substituted silyl group), isomerization by means of an acid will normally lead to the simultaneous removal of this protecting group or these protecting groups. This may be desired or undesired. If removal of the protecting groups at this stage is not desired, then isomerization may be effected by means of a base or protecting groups which are not removable by an acid may be chosen. Alternatively, where the hydroxy-protecting group has been removed, the same or a different hydroxy-protecting group may be reestablished.

After completion of the reaction, the desired compound of formula (XI) may be removed from the reaction mixture by conventional means. For example, one suitable recovery sequence comprises: pouring the reaction mixture into ice-water; extracting the mixture with a water-immiscible organic solvent; if necessary, washing and then drying the extract; and finally removing the solvent by distillation. If desired, the product may be further purified by such conventional techniques as column chromatography or recrystallization. Also, since the product is a mixture of the 2- and 3-unsaturated isomers, these isomers may, if desired, be separated similarly by chromatography or recrystallization.

Step (B3)

This comprises the series of optional reactions already described in relation to step (A4).

METHOD C

Compounds of formula (I) in which $R^1$ represents a group of formula $—A—(CH_2)_m—R^5$ and compounds of formula (Ic) in both of which A represents an oxymethylene ($—OCH_2—$) group may be prepared as illustrated in the following reaction scheme:

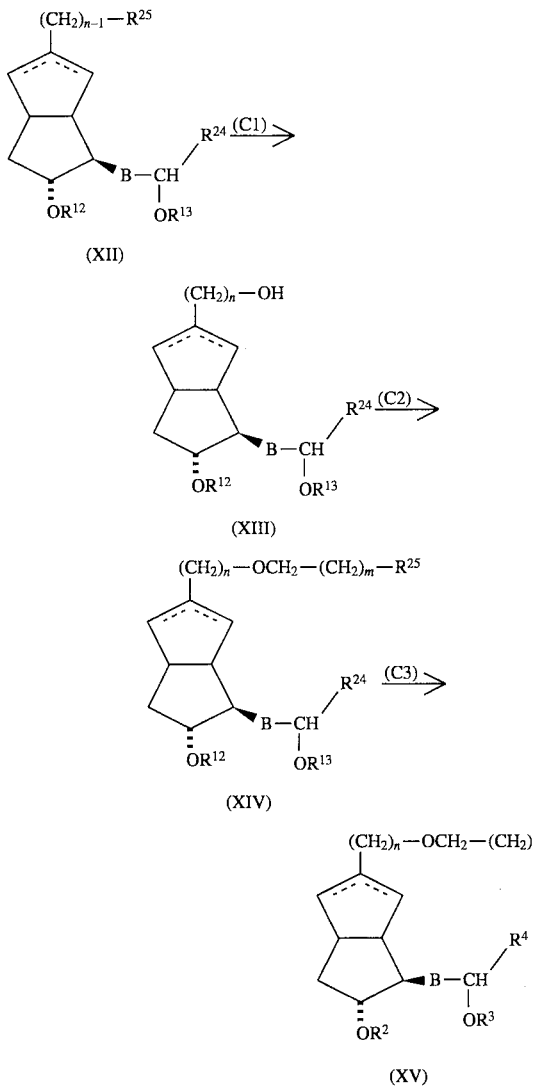

In the above formulae, $R^2$, $R^3$, $R^4$, $R^5$, B, $R^{12}$, $R^{13}$, m and the dotted line are as defined above; $R^{24}$ represents any one of the groups hereinbefore defined for $R^4$, provided that any free hydroxy group therein is protected; and $R^{25}$ represents an optionally protected carboxy group.

Step (C1)

In this step, the starting material of formula (XII) (which can have been prepared by the procedures described in Methods A and B above) is converted to a hydroxy compound of formula (XIII) by contacting the compound of formula (XII) with a reducing agent in an inert solvent.

Any reducing agent which is capable of converting a carboxy group or an esterified carboxy group to a hydroxymethyl group without, or without to an unacceptable extent, adversely affecting the remainder of the molecule may be employed in this reaction. Examples of such reducing agents include: boron compounds, such as lithium borohydride, sodium borohydride-aluminum chloride complex and boron trihydride-cyclohexylamine complex; and aluminum compounds, such as lithium aluminum hydride, lithium aluminum hydride-aluminum chloride complex and diisobutylaluminum hydride. Of these, we particularly prefer lithium aluminum hydride.

The nature of the inert solvent employed in this reaction is not critical, provided that it has no adverse effect upon the reaction. Preferred solvents are ethers, such as diethyl ether, tetrahydrofuran or dioxane.

We prefer to carry out the reaction at a temperature of from 0° C. to 50° C. The time required for the reaction will vary, depending upon the nature of the reagents, the reaction temperature and other reaction conditions, but a period of from 30 minutes to 3 hours will normally suffice.

After completion of the reaction, the desired product of formula (XIII) may be isolated from the reaction mixture by conventional means. For example, one suitable recovery procedure comprises: adding a dilute aqueous solution of sodium hydroxide or ice-water to the reaction mixture; extracting the mixture with a water-immiscible organic solvent; if necessary, washing and then drying the extract; and finally distilling off the organic solvent to give the desired product. If necessary, the product may be further purified by such conventional methods as column chromatography or recrystallization.

Step (C2) In this step, a compound of formula (XIV) is prepared from the compound of formula (XIII) by reacting the compound of formula (XIII) in an inert solvent with a base and then with a compound of formula (XVI):

$$XCH_2—(CH_2)_m—R^{25} \qquad (XVI)$$

(in which $R^{25}$ and m are as defined above and X represents a halogen atom, for example a chlorine, bromine or iodine atom) or with an alkali metal salt thereof.

A wide variety of bases can be employed in this reaction and examples include: alkali metal hydrides, such as lithium hydride, sodium hydride or potassium hydride; alkaline earth metal hydrides, such as calcium hydride or barium hydride; organic lithium compounds, such as methyllithium, butyllithium or phenyllithium; and alkali metal alkoxides, such as sodium methoxide, sodium ethoxide, sodium propoxide, potassium t-butoxide or sodium t-pentoxide. Of these, the alkali metal hydrides are preferred.

The nature of the inert solvent is not critical, provided that it has no adverse effect on the reaction. Examples of suitable solvents include: hydrocarbons, such as hexane, benzene, toluene or xylene; ethers, such as diethyl ether, tetrahydrofuran, ethylene glycol dimethyl ether or diglyme; amides, such as dimethylformamide, dimethylacetamide or hexamethylphosphoric triamide; and sulfoxides, such as dimethyl sulfoxide. Mixtures of one or more of these solvents may also be employed. We prefer to use an amide, a sulfoxide or a mixture thereof.

The temperature employed for the reaction with a base is preferably from −78° C. to 50° C. and the time required for this reaction, which may vary depending upon the nature of the reagents, the reaction temperature and other reaction conditions, is normally from 10 minutes to 1 hour. The temperature employed for the reaction with the compound of formula (XVI) is preferably from 0° C. to 50° C. and the time required for this reaction, which may vary depending upon the nature of the reagents, the reaction temperature and other reaction conditions, is generally from 1 hour to 48 hours.

After completion of the reaction, the desired product of formula (XIV) may be isolated from the reaction mixture by conventional means. For example, one suitable recovery technique comprises: pouring the reaction mixture into water; acidifying the mixture, if necessary; extracting the product from the mixture with a water-immiscible organic solvent; if necessary, washing and drying the extract; and then distilling the solvent from the extract. If desired, the resulting product may be further purified by such conventional techniques as column chromatography or recrystallization.

Step (C3)

This step involves a series of optional reactions and may, therefore, be omitted if the compound of formula (XIV) is the desired final product.

Hydroxy-protecting groups represented by $R^{12}$ and $R^{13}$ and included within the group represented by $R^{24}$ may, if desired, be removed. If desired, a single one, two or all three of the protecting groups may be removed by appropriate choice of protecting groups and removal reactions. The reactions involved, reagents and reaction conditions are all as described in step (A4).

The protected carboxy group represented by $R^{25}$ may, if desired, be converted to a free carboxy group and, again, the reactions involved, reagents and reaction conditions are described in step (A4).

This carboxy group may be esterified or it or the esterified carboxy group may be converted to an optionally substituted carbamoyl group, again employing reactions, reagents and reaction conditions illustrated in step (A4).

The protected carboxy group represented by $R^{25}$ or the group in which the carboxy-protecting group has been removed may be converted to a hydroxymethyl group following the procedures described in step (C1) above.

If desired, the resulting hydroxymethyl group may be oxidized to a formyl group and the reagents and reaction conditions involved are as described in relation to step (A4).

METHOD D

Compounds of formula (I) in which $R^1$ represents a group of formula $-A(CH_2)_m-R^5$ and compounds of formula (Ic), in both of which A represents a thiomethylene ($-SCH_2$) group may be prepared as illustrated in the following reaction scheme:

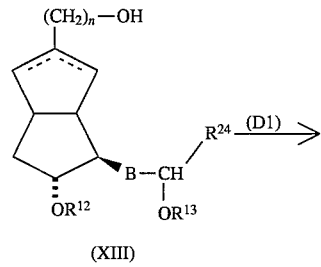

(XIII)

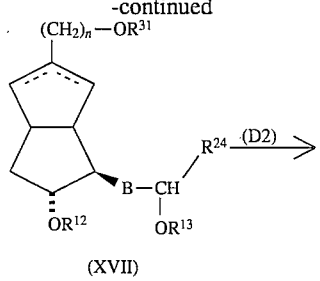

(XVII)

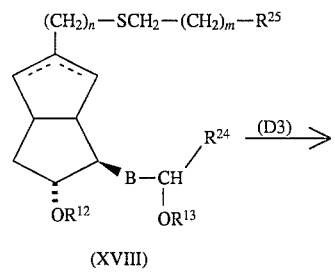

(XVIII)

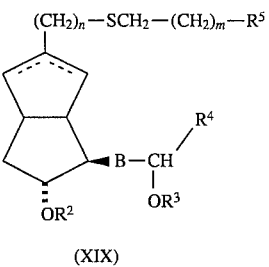

(XIX)

In the above formulae, $R^2$, $R^3$, $R^4$, $R^5$, B, n, m, $R^{12}$, $R^{13}$, $R^{24}$, $R^{25}$ and the dotted line are as defined above represents an alkanesulfonyl or arenesulfonyl group.

Step (D1)

In this step, a sulfonyloxy compound of formula (XVII) is prepared by reacting the compound of formula (XIII) [whose preparation is discussed in step (C1) above] with a sulfonyl halide of formula $R^{31}X$, in which $R^{31}$ and X are as defined above. Preferred sulfonyl halides are methanesulfonyl chloride, ethanesulfonyl chloride, benzenesulfonyl chloride, p-toluenesulfonyl bromide and p-toluenesulfonyl chloride.

This reaction is preferably effected in the presence of a base, preferably an organic amine, such as triethylamine, N,N-dimethylaniline, pyridine, 4-(dimethylamino)pyridine, 1,5-diazabicyclo-[4,3,0]non-5-ene or 1,8-diazabicyclo[5,4,0]undec-7-ene.

The reaction is preferably effected in the presence of an inert solvent, the nature of which is not critical, provided that it has no adverse effect upon the reaction. Suitable such solvents include: hydrocarbons, such as hexane, cyclohexane, benzene, toluene or xylene; ethers, such as diethyl ether, tetrahydrofuran or ethylene glycol dimethyl ether; and halogenated hydrocarbons, such as methylene chloride, chloroform or carbon tetrachloride. We particularly prefer aromatic hydrocarbons (such as benzene or toluene) or halogenated hydrocarbons.

The reaction temperature is not particularly critical and, for convenience, a temperature of about ambient is normally chosen. The time required for the reaction will vary depending upon the reagents, the reaction temperature and other reaction conditions, but a period of from 30 minutes to 10 hours will normally suffice.

43

After completion of the reaction, the desired compound of formula (XVII) may be isolated from the reaction mixture by conventional means. For example, one suitable recovery procedure comprises: pouring the reaction mixture into ice-water; if necessary, neutralizing the mixture; extracting the mixture with a water-immiscible organic solvent; if necessary, washing and then drying the extract; and distilling the solvent from the extract. If desired, the product may be further purified by conventional means, for example by silica gel column chromatography or recrystallization.

Step (D2)

In this step, a compound of formula (XVIII) is prepared by reacting the compound of formula (XVII) prepared as described in step (D1), with a compound of formula (XX):

$$HS-CH_2-(CH_2)_m-R^{25} \quad (XX)$$

(in which m and $R^{25}$ are as defined above) in the presence of a base and in an inert solvent. Bases and solvents which may be employed in this reaction are the same as those described in relation to step (C2).

The reaction is preferably effected at a temperature of from 0° C. to 100° C. and the time required for the reaction, which may vary, depending upon the nature of the reagents, the reaction temperature and other reaction conditions, is normally from 30 minutes to 5 hours.

The product of formula (XVIII) may, if desired, be recovered from the reaction mixture by conventional means. For example, one suitable recovery technique comprises: pouring the reaction mixture into ice-water; if necessary, acidifying the mixture; extracting the mixture with a water-immiscible organic solvent; if necessary, washing and then drying the extract; and removing the solvent by distillation. If necessary, the product may be further purified by conventional means, for example by column chromatography or recrystallization.

Step (D3)

This step comprises the same series of optional reactions as described in relation to step (C3).

In addition, if desired, the compound of formula (XIX) may be oxidized to the corresponding sulfoxide or sulfone by conventional oxidation procedures.

METHOD E

Compounds of formula (I) in which $R^1$ represents a group of formula $-A-(CH_2)_m-R^5$ and compounds of formula (Ic), in both of which A represents a vinylene group and m is 0 may be prepared by the procedures illustrated in the following reaction scheme:

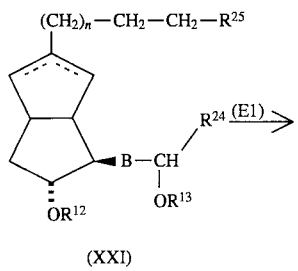

(XXI)

44

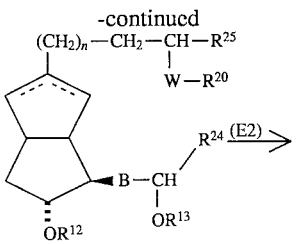

(XXII)

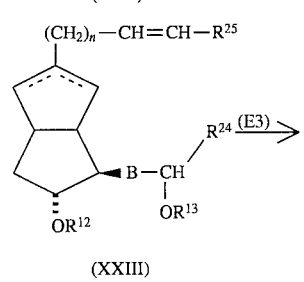

(XXIII)

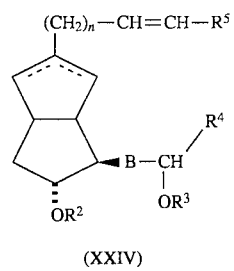

(XXIV)

In the above formulae, $R^2$, $R^3$, $R^4$, $R^5$, B, $R^{12}$, $R^{13}$, $R^{24}$, $R^{25}$, n and the dotted line have the meanings heretofor defined. W represents a sulfur atom or a selenium atom. $R^{20}$ represents an alkyl group or an aryl group.

Step (E1) In this step, a compound of formula (XXI) (which may have been prepared as described in Methods A or B) is reacted with a base and then with a compound of formula (XXV):

$$R^{20}-W-W-R^{20} \quad (XXV)$$

or a compound of formula (XXVI):

$$R^{20}-W-X \quad (XXVI)$$

(in which $R^{20}$, W and X are as defined above), in the presence of an inert solvent.

In this reaction, $R^{25}$ of the compound of formula (XXI) is preferably a protected carboxy group and $R^{20}$ of the compounds of formulae (XXV) and (XXVI) is preferably an aryl group.

Preferred bases include: organic lithium compounds, such as methyllithium, butyllithium, sec-butyllithium or phenyllithium; dialkylaminolithium compounds, such as diisopropylaminolithium, dicyclohexylaminolithium or isopropylcyclohexylaminolithium; or bis(silyl)lithium amides, such as bis(trimethylsilyl)lithium amide, bis(triethylsilyl)lithium amide or bis(diphenylmethylsilyl)lithium amide. Of these, we prefer the dialkylaminolithium compounds.

The nature of the solvent employed in these reactions is not critical, provided that it has no adverse effect upon the reaction. Suitable solvents include: ethers, such as diethyl ether, tetrahydrofuran, ethylene glycol dimethyl ether or diglyme; and aromatic hydrocarbons, such as benzene, toluene or xylene. Of these, we prefer the ethers.

For the reaction with the base, the reaction temperature may vary over a wide range, for example from −100° C. to ambient temperature, and the time required for the reaction, which will vary depending upon the nature of the reagents, the reaction temperature and other reaction conditions, will generally be from 10 minutes to 2 hours. For the reaction with the compound of formula (XXV) or (XXVI), the reaction temperature is preferably from 0° C. to 50° C. and the time required for the reaction, which may vary depending upon the nature of the reagents, the reaction temperature and other reaction conditions, is normally from 30 minutes to 5 hours.

After completion of the reaction, the desired product of formula (XXII) may be isolated from the reaction mixture by conventional means. For example, one suitable recovery procedure comprises: pouring the reaction mixture into water; extracting the mixture with a water-immiscible organic solvent; if necessary, washing and then drying the extract; and finally removing the solvent by distillation. If desired, the compound may be further purified by such conventional techniques as column chromatography or recrystallization.

Step (E2)

In this step, the compound of formula (XXII) prepared as described in step (E1) above, is converted to the compound of formula (XXIII) by oxidization in the presence of an inert solvent, followed by, if necessary, heating.

Suitable oxidizing agents for carrying out this reaction include hydrogen peroxide and such organic peracids as peracetic acid, perpropionic acid, perbenzoic acid and m-chloroperbenzoic acid. Of these, we prefer hydrogen peroxide or perbenzoic acid.

The nature of the solvent employed is not critical, provided that it has no adverse effect upon the reaction and suitable inert solvents include: aromatic hydrocarbons, such as benzene, toluene or xylene; halogenated hydrocarbons, such as methylene chloride or chloroform: ethers, such as diethyl ether, tetrahydrofuran, ethylene glycol dimethyl ether or diglyme; esters, such as ethyl acetate; alcohols, such as methanol, ethanol or propanol; water; and mixtures of any two or more of these. When the oxidizing agent is hydrogen peroxide, the preferred solvent is a mixture of water, an alcohol and an ester; on the other hand, when the oxidizing agent is an organic peracid, the preferred solvent is a halogenated hydrocarbon.

The reaction temperature may vary over a wide range, although we usually prefer to carry out the reaction at a temperature within the range from −50° C. to 50° C.; the time required for the reaction will vary depending upon the nature of the reagents, the reaction temperature and other reaction conditions, but is usually from 30 minutes to 5 hours. If desired, formation of the double bond may be promoted by further heating the reaction product at a temperature of from 50° C. to 100° C. for a period of from 1 hour to 5 hours.

After completion of the reaction, the desired product of formula (XXIII) may be isolated from the reaction mixture by conventional means. For example, one suitable recovery technique comprises: pouring the reaction mixture into water; removing insoluble matter, if any, by filtration; extracting the filtrate with a water-immiscible organic solvent; if necessary, washing and then drying the extract; and finally distilling off the solvent. If necessary, the product may be further purified by such conventional techniques as column chromatography or recrystallization.

Step (E3)

This comprises the series of optional reactions previously discussed in detail in relation to step (C3).

If desired, compounds in which m is an integer greater than 0 may be prepared by conventional techniques for lengthening carbon chains.

PREPARATION OF STARTING MATERIALS

The starting materials employed in the various Methods described above may be prepared as follows.

METHOD F

Compounds of formula (II), used as starting materials for the reactions of Method A may be prepared following the procedures illustrated in the following reaction scheme:

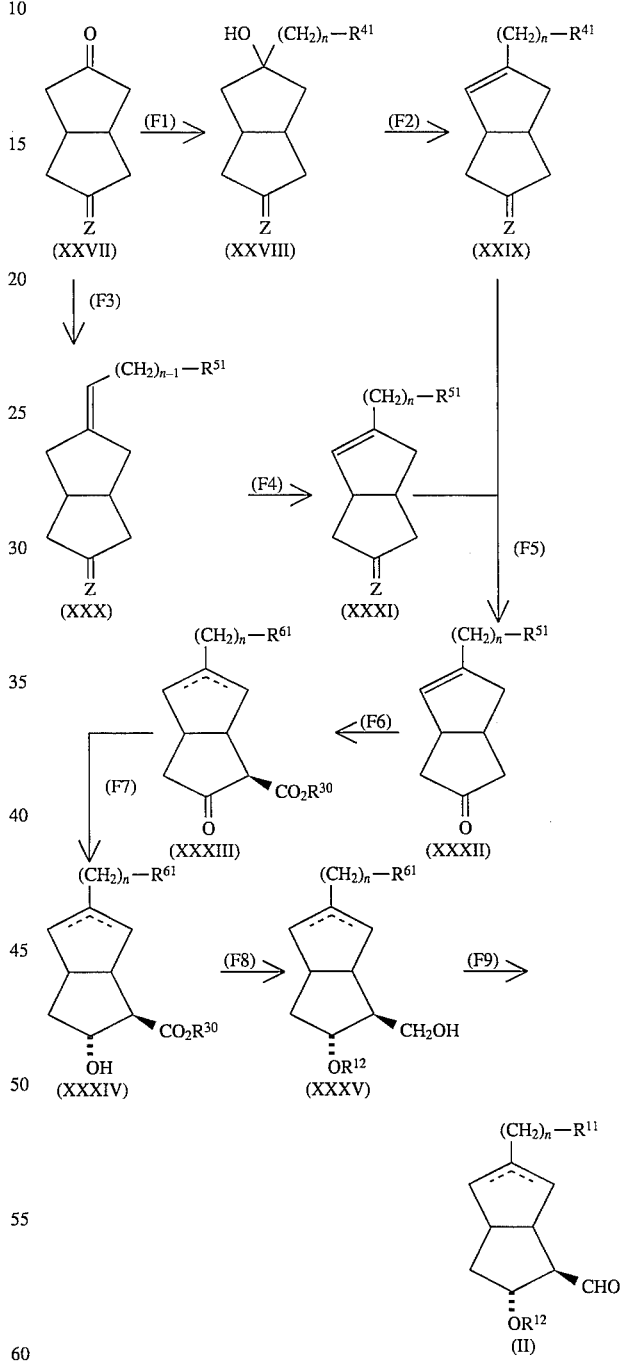

In the above formulae, $R^{11}$, $R^{12}$, n and the dotted line are as defined above. $R^{30}$ represents a hydrogen atom or a $C_1$-$C_6$ alkyl group, for example a methyl, ethyl, propyl or butyl group. $R^{41}$ represents a protected hydroxymethyl group. $R^{51}$ represents an optionally protected hydroxymethyl group or an optionally protected carboxy group. $R^{61}$ represents a protected hydroxymethyl group or an optionally protected carboxy group. Z represents a protected carbonyl group of formula:

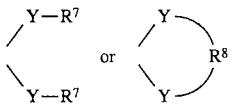

(in which Y, $R^7$ and $R^8$ are as defined above).

Step (F1)

In this step, an alcohol derivative of formula (XXVIII) is prepared from the ketone compound of formula (XXVII), by reacting the ketone compound with a Grignard reagent of formula (XXXVI);

$$X\text{---}Mg\text{---}(CH_2)_n\text{---}R^{41} \quad \text{(XXXVI)}$$

(in which $R^{41}$, n and X are as defined above). The reaction is preferably effected in the presence of an inert solvent, the nature of which is not critical, provided that it has no adverse effect upon the reaction. Preferred solvents are: ethers, such as diethyl ether, tetrahydrofuran or ethylene glycol dimethyl ether; amides, such as hexamethylphosphoric triamide; and mixtures of any two or more thereof. The reaction temperature is preferably from 0° C. to 100° C. and the time required for the reaction is normally from 30 minutes to 3 hours.

Step (F2)

In this step, a compound of formula (XXIX) is prepared by dehydrating the compound of formula (XXVIII). The reaction is carried out by contacting the compound of formula (XXVIII) with an acid in an inert solvent.

Suitable acids include: mineral acids, such as hydrochloric acid, sulfuric acid, nitric acid or phosphoric acid; organic carboxylic acids, such as acetic acid or trifluoroacetic acid, or organic sulfonic acids, such as methanesulfonic acid, benzenesulfonic acid, p-toluenesulfonic acid or camphorsulfonic acid. Of these, we prefer p-toluenesulfonic acid or camphorsulfonic acid.

The nature of the solvent is not critical, provided that it does not interfere with the reaction and preferred solvents are the aromatic hydrocarbons, such as benzene, toluene or xylene.

This acidification can result in conversion of the protected carbonyl group Z to a free carbonyl group. This can be avoided by carrying out the reaction in the presence of the alcohol used to produce the protecting group.

The preferred reaction temperature is from 50° C. to 150° C. and the time required for the reaction is normally from 1 hour to 5 hours.

Step (F3)

The sequence of steps (F3) and (F4) provides an alternative to steps (F1) and (F2).

In step (F3), the starting material of formula (XXVII) is converted to a compound of formula (XXX) having an exo double bond by reaction with a Wittig reagent of formula (XXXVII):

or with a modified Wittig reagent of general formula (XXXVIII):

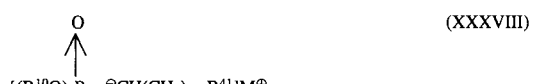

(in which $R^{10}$, $R^{41}$, n and M are as previously defined). These Wittig reagents may be prepared from compounds of formulae (XXXVIIa):

or (XXXVIIIa):

as described in step (A1). The reaction of the compound of formula (XXVII) with the Wittig reagent or the modified Wittig reagent is likewise carried out as described in step (A1).

Where $R^{41}$ represents an optionally protected carboxy group, the resulting compound may be reduced to form a compound having a free hydroxymethyl group and this may be converted, by protecting the hydroxy group, to a compound in which $R^{41}$ represents a protected hydroxymethyl group. The reduction reaction may be carried out as described in step (C1). Protection of the hydroxy group may be carried out as described in step (A3).

Step (F4)

In this step, the exo double bond of the compound of formula (XXX) is isomerized to an endo double bond in the compound of formula (XXXI). This reaction is identical with that of step (B2) and may be carried out using the same reagents and reaction conditions.

The isomerization reaction involves the presence of an acid. Where $R^{41}$ is a protected hydroxymethyl group of which the hydroxy-protecting group can be removed with an acid (for example where the hydroxy-protecting group is a heterocyclic group, an alkoxy group, an aralkoxymethyl group, a 1-alkoxyethyl group or a silyl group), this may be removed in the course of the reaction and it may, accordingly, be necessary to reinstate the group. Where Y in the protected carbonyl group represented by Z is an oxygen atom, then this protecting group will also be removed by the presence of an acid. However, removal of the carbonyl-protecting group can be avoided if the isomerization reaction is carried out in the presence of the alcohol which formed that protecting group.

Step (F5)

In this step, the carbonyl-protecting group represented by Z in the compounds of formulae (XXIX) and (XXXI) is converted to a free carbonyl group. Where Y represents an oxygen atom in the protected carbonyl group Z, then the protecting group may be removed by treating the compound of formula (XXIX) or (XXXI) with an aqueous acid at a temperature of from 0° C. to 100° C. Suitable aqueous acids are aqueous acetic acid, dilute aqueous hydrochloric acid, dilute aqueous hydrochloric acid/acetonitrile or dilute aqueous sulfuric acid/acetone. The time required for the reaction is normally from 30 minutes to 3 hours.

Once again, because the reaction involves the use of an acid, hydroxy-protecting groups may be removed: this can be avoided by appropriate choice of hydroxy-protecting group or the hydroxy-protecting group may subsequently be reinstated as described in step (A3).

When Y in the protected carbonyl group represented by Z contains a sulphur atom, the carbonyl-protecting group may be removed by contacting the compound of formula (XXIX) or (XXXI) at a temperature of from 0° C. to 60° C. with mercuric acetate, mercuric chloride or mercuric oxide (red) in a solvent such as an ether (e.g. tetrahydrofuran or diethyl ether), a halogenated hydrocarbon (e.g. methylene chloride or chloroform), an alcohol (e.g. methanol or ethanol), water or a mixture of any two or more thereof. If necessary, the reaction may be catalysed by the presence of a Lewis acid, such as boron trifluoride-diethyl ether complex.

Step (F6)

In this step, a carboxy or alkoxycarbonyl compound of formula (XXXIII) is prepared by reacting the compound of formula (XXXII), prepared as described in step (F5), with carbon dioxide (which may be gaseous or in the form of dry ice) or a carbonate derivative, such as a compound of formula (XXXIX):

(XXXIX)

(in which $R^7$ is as defined above and $R^{40}$ represents a $C_1$-$C_6$ alkoxy group or a halogen atom) in the presence of a base and in an inert solvent.

Where carbon dioxide (which may be gaseous or in the form of dry ice is used), the base employed may be, for example: an organic lithium compound, such as methyllithium, butyllithium, sec-butyllithium or phenyllithium; an organic potassium compound, such as triphenylmethylpotassium; or a metal hydride, such as sodium hydride, potassium hydride or calcium hydride. The reaction is preferably carried out in the presence of a phenol, such as di-t-butyl-p-methylphenol.

Where a carbonate derivative of formula (XXXIX) is employed, the base is preferably: an alkali metal alkoxide, such as sodium methoxide, sodium ethoxide, potassium t-butoxide or sodium t-pentoxide; or an alkali metal or alkaline earth metal hydride, such as sodium hydride, potassium hydride or calcium hydride.

The nature of the solvent employed is not critical, provided that it does not interfere with the reaction and suitable solvents are the ethers, such as diethyl ether, tetrahydrofuran, dioxane, ethylene glycol dimethyl ether or diglyme.

The reaction temperature is preferably from $-20°$ C. to $80°$ C. and the time required for the reaction is normally from 1 hour to 24 hours.

Step (F7)

In this step, the carbonyl group of the compound of formula (XXXIII), prepared as described in step (F6), is converted to a hydroxy group; this reaction involves the same reagents and reaction conditions as the similar reaction described in step (A2).

Step (F8)

In this step, the hydroxy group formed in step (F7) is protected, as described in step (A3), and then the carboxy group or alkoxycarbonyl group of the compound of formula (XXXIV), prepared as described in step (F7), is reduced to form a hydroxymethyl group.

Where R is a protected hydroxymethyl group or a protected carboxy group and R is a $C_1$-$C_6$ alkyl group, the reduction is preferably carried out in an inert solvent (such as diethyl ether, tetrahydrofuran or toluene) by contacting the corresponding compound with lithium aluminum hydride, lithium borohydride or vitride [sodium bis(2-methoxyethoxy)aluminum hydride] at a temperature of from $-40°$ C. to $70°$ C. for a period of from 30 minutes to 5 hours. The preferred reducing agent is lithium aluminum hydride and the reaction should be carried out carefully, not using an excess of reducing agent.

Where $R^{61}$ represents a protected carboxy group and $R^{30}$ represents a hydrogen atom, the reduction (hydrogenation) reaction of this step is preferably carried out in the presence of an inert solvent, which is preferably an ether (such as diethyl ether or tetrahydrofuran) by contacting the corresponding compound with diborane at a temperature from $0°$ C. to ambient temperature for a period of from 30 minutes to 3 hours.

Step (F9)

In this step, the hydroxymethyl group prepared in step (F8) is oxidized to a formyl group. This reaction is carried out in exactly the same way, using the same reagents and reaction conditions, as the corresponding reaction described in step (A4).

METHOD G

This involves the stereospecific preparation of a starting material for Method A, specifically the 2-unsaturated isomer of the compound of formula (II), here called (IIa). This is carried out as illustrated in the following reaction scheme:

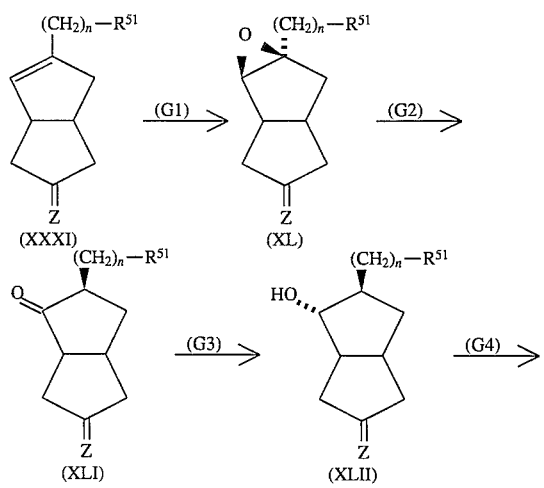

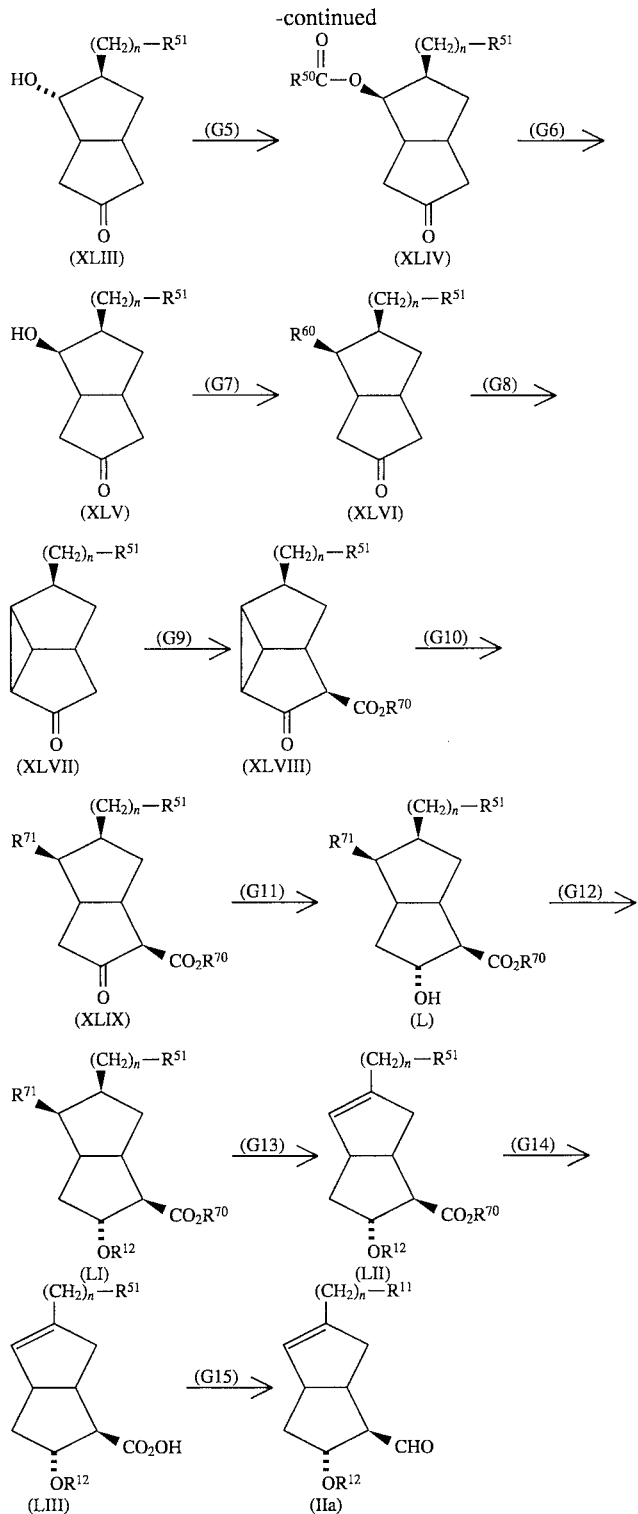

In the above formulae, $R^{11}$, $R^{12}$, $R^{51}$, Z and n are as defined above. $R^{50}$ represents a hydrogen atom, a $C_1$-$C_6$ alkyl group (for example a methyl, ethyl, propyl or butyl group) or an aryl group (for example a phenyl or tolyl group). $R^{60}$ represents a halogen atom (for example a chlorine, bromine or iodine atom) or a group of formula $R^{72}.SO_3$— (in which $R^{72}$ represents a $C_1$-$C_6$ alkyl group or an aryl group, examples of which have been given in relation to $R^{50}$). $R^{70}$ represents a hydrogen atom or a $C_1$-$C_6$ alkyl group (examples of which have been given in relation to $R^{50}$). $R^{71}$ represents a halogen atom (examples of which have been given in relation to $R^{60}$) or a group of formula $R^{50}.CO_2$— (in which $R^{50}$ is as defined above).

The starting material [the compound of formula (XXXI) (which embraces the compound of formula (XXIX)] may be prepared as described in Method F, steps (F1) and (F2) or (F3) and (F4).

Step (G1)

In this, the compound of formula (XXXI) is oxidized to produce an epoxy derivative of formula (XL). This is effected by contacting the compound of formula (XXXI) with an oxidizing agent in an inert solvent.

There is no particular limitation on the nature of the oxidizing agent employed, and any such agent capable of oxidizing a carbon-carbon double bond to an epoxide may be used in this reaction. Examples of such oxidizing agents include: hydrogen peroxide; organic peracids, such as peracetic acid, perbenzoic acid, m-chloroperbenzoic acid or perphthalic acid; organic peroxides, such as t-butyl peroxide; and alkali metal halogenares, such as sodium chlorate or potassium chlorate, together with osmium oxide. Of these, organic peracids are preferred.

There is no particular limitation on the nature of the solvent to be employed, provided that it does not interfere with the reaction. Examples of suitable solvents include: water; halogenated hydrocarbons, such as methylene chloride, chloroform or carbon tetrachloride; hydrocarbons, such as hexane, cyclohexane, benzene, toluene or xylene; ethers, such as diethyl ether, tetrahydrofuran or ethylene glycol dimethyl ether; or mixtures of any two or more thereof. Of these, halogenated hydrocarbons are preferred.

The reaction is preferably effected at a temperature of from 0° C. to 100° C., and the time required for the reaction is usually from 30 minutes to 15 hours.

Step (G2)

In this step, the epoxide is converted to a ketone of formula (XLI) by contacting the compound of formula (XL) with an acid in an inert solvent.

The acid is preferably a Lewis acid, such as zinc chloride, aluminum chloride, boron trifluoride or boron trifluoride-diethyl ether complex.

There is no particular limitation on the nature of the solvent to be employed, provided that it does not interfere with the reaction. Suitable solvents include: halogenated hydrocarbons, such as methylene chloride or chloroform: hydrocarbons, such as hexane, cyclohexane, benzene, toluene or xylene; and ethers, such as diethyl ether, tetrahydrofuran or ethylene glycol dimethyl ether. Of these, the hydrocarbons are preferred.

The reaction is preferably effected at a temperature of from −78° C. to 50° C., more preferably from 0° C. to ambient temperature, and the time required for the reaction is usually from 3 minutes to 5 hours.

Step (G3)

In this step, the ketone derivative of formula (XLI) is converted to a hydroxy compound of formula (XLII). The reaction is similar to that described in step (A2) and is carried out employing the same reagents and reaction conditions.

Step (G4)

In this step, the protected carbonyl group represented by Z is converted to a free carbonyl group. The reaction is identical with that effected in step (F5) and may be carried out using the same reagents and reaction conditions.

Step (G5)

In this step, the compound of formula (XLIII) having a free hydroxy group is converted to an ester derivative of formula (XLIV) by reaction with an organic carboxylic acid in the presence of a phosphine and an azodicarboxylate in an inert solvent.

Examples of suitable phosphines include: tri($C_1$-$C_6$alkyl)phosphines, such as trimethylphosphine, triethylphosphine or tributylphosphine; and triarylphosphines, such as triphenylphosphine, tri-p-tolylphosphine or tri-m-tolylphosphine. Of these, the triarylphosphines are preferred.

Suitable azodicarboxylates are the di($C_1$-$C_6$ alkyl) azodicarboxylates, such as dimethyl azodicarboxylate, diethyl azodicarboxylate or dipropyl azodicarboxylate.

The organic carboxylic acid may be, for example, an aliphatic carboxylic acid (such as formic acid, acetic acid, propionic acid or butyric acid) or an aromatic carboxylic acid (such as benzoic acid, p-methylbenzoic acid or m-chlorobenzoic acid), of which formic acid is preferred.

There is no particular limitation on the nature of the solvent to be employed, provided that it has no adverse effect upon the reaction and suitable solvents include, for example: hydrocarbons, such as hexane, cyclohexane, benzene, toluene or xylene; halogenated hydrocarbons, such as methylene chloride, chloroform or carbon tetrachloride: ethers, such as diethyl ether, tetrahydrofuran and ethylene glycol dimethyl ether; and ketones, such as acetone or methyl ethyl ketone. Of these, the ethers are preferred.

The reaction is preferably effected at a temperature of from −20° C. to 50° C. and the time required for the reaction is normally from 30 minutes to 10 hours.

Step (G6)

In this step, the carboxy or alkoxycarbonyl group introduced into the compound of formula (XLIV) in step (G5) is converted back to a hydroxy group and the net effect of steps (G5) and (G6) is to invert the configuration of the hydroxy group at the 2-position of the bicyclooctane ring. This is effected by treating the compound of formula (XLIV) with a base in an inert solvent. Suitable bases include, for example: alkali metal hydroxides, such as sodium hydroxide or potassium hydroxide; alkali metal bicarbonates, such as sodium bicarbonate or potassium bicarbonate; alkali metal carbonates, such as lithium carbonate, sodium carbonate or potassium carbonate; and organic amines, such as triethylamine or N,N-dimethylaniline. Of these, the alkali metal hydroxides or carbonates are preferred.

There is no particular limitation on the nature of the solvent employed, provided that it has no adverse effect upon the reaction. Suitable solvents include: alcohols, such as methanol, ethanol, propanol, isopropanol or butanol; ethers, such as tetrahydrofuran, dioxane or ethylene glycol dimethyl ether: amides, such as dimethylformamide or dimethylacetamide; sulfoxides, such as dimethyl sulfoxide; and mixtures of one or more such organic solvents with water. Of these, alcohols or aqueous alcohols are preferred.

The reaction temperature is preferably from 0° C. to 100° C. and the time required for the reaction is usually from 10 minutes to 5 hours.

When the hydroxy-protecting group represented by $R^{51}$ in the compound of formula (XLIV) is an acyl group, this may be removed simultaneously, depending upon the reaction conditions. However, the hydroxy-protecting group of $R^{51}$ can remain in the compound, provided suitable reagents and reaction conditions are employed, to take account of the difference in reactivity between primary hydroxymethyl groups and the secondary hydroxy group.

As an alternative to steps (G4), (G5) and (G6), it is possible to sulfonylate the compound of formula (XLII) and then treat the resulting product with a superoxide, such as potassium superoxide, to give the desired product of formula (XLV).

The sulfonylation reaction may be carried out in the same way as the corresponding reaction described in step (G7) below. The reaction with the superoxide is preferably effected in the presence of a crown ether in an inert solvent.

Suitable inert solvents include: sulfoxides, such as dimethyl sulfoxide; amides, such as dimethylformamide or hexamethylphosphoric triamide; ethers, such as diethyl ether, tetrahydrofuran or ethylene glycol dimethyl ether; aromatic hydrocarbons, such as benzene, toluene or xylene; or mixtures of any two or more thereof. Dimethyl sulfoxide is preferred.

There is no particular limitation on the crown ether to be employed and any common crown ether may be used, 18-crown-6 being preferred. The reaction temperature is normally about ambient and the time required for the reaction is normally from 30 minutes to 5 hours.

Step (G7)

In this step, a compound of formula (XLVI) is prepared by sulfonylating the compound of formula (XLV), prepared in step (G6) above, or halogenating the compound of formula (XLII), prepared in step (G3) above.

Sulfonylation may be effected by reacting the compound of formula (XLV) with a sulfonyl halide in an inert solvent, to give a compound in which $R^{60}$ represents an alkanesulfonyloxy group or an arene-sulfonyloxy group. Alternatively, reaction of the compound of formula (XLV) with a mixture of phosphine and a carbon tetrahalide will give a compound in which $R^{60}$ represents a halogen atom.

The sulfonyl halide employed is a compound of formula $R^{72}$—$SO_2X$ (in which $R^{72}$ and X are as defined above), methanesulfonyl chloride, ethanesulfonyl chloride, benzenesulfonyl chloride and p-toluenesulfonyl chloride being preferred. This reaction may be performed in the presence of a base, for example an organic amine, such as triethylamine, ethyldiisopropylamine, pyridine or N,N-dimethylaniline.

Where a halide is to be prepared, the phosphine employed may be any one of those described in relation to step (G5) above and the carbon tetrahalide may be, depending upon the nature of the halogen atom that it is desired to introduce, carbon tetrachloride, carbon tetrabromide or carbon tetraiodide, of which carbon tetrachloride or carbon tetrabromide are preferred.

There is no particular limitation on the nature of the solvent to be employed, provided that it does not interfere with the reaction. Suitable solvents include: hydrocarbons, such as hexane, cyclohexane, benzene, toluene or xylene; halogenated hydrocarbons, such as methylene chloride, chloroform or 1,2-dichloroethane; ethers, such as diethyl ether, tetrahydrofuran, ethylene glycol dimethyl ether or dioxane; and ketones, such as acetone or methyl ethyl ketone. Halogenated hydrocarbons are preferred for the reaction with the sulfonyl halide, whilst ethers are preferred for the reaction with the carbon tetrahalide.

The reaction temperature is preferably from −30° C. to 50° C. and the time required for the reaction is normally from 10 minutes to 10 hours.

Step (G8)

In this step, the compound of formula (XLVI) prepared in step (G7) is converted to the tricyclic compound of formula (XLVII) by treating the compound of formula (XLVI) with a base in the presence or absence of an inert solvent.

Suitable bases include: tertiary amines, such as triethylamine, ethyldiisopropylamine, N,N-dimethylaniline, 4-(dimethylamino)pyridine, 1,5-diazobicyclo[4,3,0]non-5-ene or 1,8-diazobicyclo[5,4,0]undec-7-ene; alkali metal hydroxides, such as lithium hydroxide, sodium hydroxide or potassium hydroxide; alkali metal carbonates, such as sodium carbonate or potassium carbonate; alkali metal alkoxides, such as sodium methoxide, sodium ethoxide, potassium ethoxide, sodium t-butoxide, potassium t-butoxide or sodium t-pentoxide. Of these, the tertiary amines are preferred.

Where an inert solvent is employed, its nature is not critical, provided that it does not interfere with the reaction. Suitable inert solvents include, for example: alcohols, such as methanol, ethanol, propanol or t-butanol; hydrocarbons, such as hexane, cyclohexane, benzene, toluene or xylene; and ethers, such as diethyl ether, tetrahydrofuran, dioxane or ethylene glycol dimethyl ether. Of these, the ethers are preferred. However, an excess of the above-mentioned tertiary amines, which are used as the base, can also serve as the reaction solvent and this is most preferred.

The reaction is preferably effected at a temperature in the range from 0° C. to 80° C. and the time required for the reaction is normally from 10 minutes to 5 hours.

Step (G9)

In this step, a carboxy or alkoxycarbonyl group is introduced at the 6- position of the bicyclooctane ring to give a compound of formula (XLVIII). This is achieved by reacting the compound of formula (XLVII) with carbon dioxide (which may be gaseous or in the form of dry ice) or with a carbonate derivative of formula $R^{72}.CO_2R^{70}$ (in which $R^{70}$ is as defined above and $R^{72}$ represents a $C_1$-$C_6$ alkoxy group or a halogen atom) in the presence of a base and in an inert solvent. This reaction is precisely the same as that in the aforementioned step (F6) and reagents and reaction conditions are identical.

Step (G10)

In this, a group represented by R (defined above) is introduced at the 2-position of the bicyclooctane ring by reacting the compound of formula (XLVIII) with a compound of formula $HR^{71}$, i.e. a carboxylic acid or a hydrogen halide, in the presence of an inert solvent.

The carboxylic acid employed for this reaction has the formula $R^{50}.COOH$ (in which R is as defined above) and is preferably formic acid. This reaction is carried out in the presence of an acidic catalyst, for example: an inorganic acid, such as hydrochloric acid, hydrobromic acid, nitric acid, sulfuric acid or perchloric acid; or a strong organic acid, such as trifluoroacetic acid or trifluoromethanesulfonic acid, of which sulfuric acid or trifluoromethanesulfonic acid are preferred. Suitable inert solvents include: ethers, such as diethyl ether, tetrahydrofuran or ethylene glycol dimethyl ether; ketones, such as acetone or methyl ethyl ketone; and halogenated hydrocarbons, such as methylene chloride or chloroform. Of these, the halogenated hydrocarbons are preferred. Alternatively, the reaction can be successfully carried out using an excess of the carboxylic acid, which then serves as both reagent and solvent.

In reacting the compound of formula (XLVIII) with a hydrogen halide, the hydrogen halide may be, for example, hydrochloric acid, hydrobromic acid or hydroiodic acid, of which hydrobromic acid is preferred. Suitable inert solvents for this reaction include: alcohols, such as methanol, ethanol or propanol; organic acids, such as acetic acid; water; an aqueous alcohol; or an aqueous organic acid, of which water or an aqueous organic acid are preferred.

The temperature at which both reactions may be carried out is usually from 0° C. to 50° C. and the time required for the reaction is normally from 1 hour to 10 hours.

Step (G11)

In this step, the ketonic oxygen atom at the 7-position of the bicyclooctane system is reduced to a hydroxy group. This is essentially the same reaction as is employed in step (A2) and may be carried out using the same reagents and reaction conditions.

Step (G12)

In this step, the 7-hydroxy group prepared in the previous step is protected: this protecting reaction is essentially the same as that described in step (A3) and may be carried out using the same reagents and reaction conditions.

Step (G13)

In this step, the group represented by $R^{71}$ in the compound of formula (LI) prepared as described in step (G12), is eliminated to produce the compound of formula (LII) having an endo double bond at the 2-position. When $R^{71}$ represents a halogen atom, this may be achieved by treating the compound of formula (LI) with a base. When $R^{71}$ represents a group of formula $R^{50}$.COO—, the process may be carried out as follows: the compound of formula (LI) is solvolysed; the resulting hydroxy derivative is reacted with a sulfonyl halide [for example, those described in step (G7) above] to convert it to the sulfonyl derivative; and this is then treated with a base.

Solvolysis of the compound of formula (LI) may be carried out as described in step (G6) above; reaction of the hydroxy derivative with a sulfonyl halide may be carried out as described in step (G7) above.

The base employed for either of the reactions to produce the compound of formula (LII) may be, for example: an organic amine, such as triethylamine, ethyldiisopropylamine, 1,5-diazobicyclo[4,3,0]non-5-ene or 1,8-diazobicyclo[5,4,0]undec-7-ene; alkali metal alkoxides, such as sodium methoxide, sodium ethoxide or potassium t-butoxide; alkali metal or alkaline earth metal hydrides, such as sodium hydride, potassium hydride or calcium hydride; alkali metal salts of organic carboxylic acids, such as sodium acetate, potassium acetate, sodium propionate, sodium benzoate or potassium benzoate; alkali metal phenoxides, such as sodium phenoxide, potassium phenoxide, sodium p-methoxyphenoxide, sodium thiophenoxide, potassium thiophenoxide, lithium selenophenoxide, sodium selenophenoxide, potassium selenophenoxide, sodium o-methylphenoxide or potassium p-methylphenoxide; alkali metal or alkaline earth metal hydroxides, such as sodium hydroxide, potassium hydroxide, calcium hydroxide or barium hydroxide; and alkali metal carbonates or bicarbonates, such as sodium carbonate, sodium bicarbonate, potassium carbonate or potassium bicarbonate. Of these, the alkali metal phenoxides (including the thiophenoxides and selenophenoxides) and alkali metal salts of organic carboxylic acids are preferred, the alkali metal selenophenoxides and alkali metal acetates being most preferred.

There is no particular limitation on the nature of the solvent employed for this reaction, provided that it has no adverse effect on the reaction. Suitable solvents include, for example: hydrocarbons, such as hexane, cyclohexane, benzene or toluene; halogenated hydrocarbons, such as methylene chloride, chloroform or 1,2-dichloroethane; ethers, such as diethyl ether, tetrahydrofuran, dioxane or ethylene glycol dimethyl ether; ketones, such as acetone or methyl ethyl ketone; alcohols, such as methanol, ethanol or propanol: amides, such as dimethylformamide or dimethylacetamide; and sulfoxides, such as dimethyl sulfoxide. Of these, alcohols and sulfoxides are preferred.

The reaction temperature is preferably from 0° C. to 100° C. and the time required for the reaction is normally from 15 minutes to 5 hours.

Step (G14)

In this step, the carboxy or alkoxycarbonyl group at the 6-position of the bicyclooctane ring system is reduced to a hydroxymethyl group in the compound of formula (LIII). This reaction is identical with that of step (F8) and may be carried out employing the same reagents and reaction conditions.

Step (G15)

In this step, the hydroxymethyl group prepared in the previous step is oxidized to a formyl group. This reaction is essentially the same as that described in step (A4) and may be carried out using the same reagents and reaction conditions.

PHARMACOLOGICAL ACTIVITY

The compounds of the invention have shown excellent thrombocyte agglutination inhibitory, coronary blood vessel dilatory and bronchodilatory activities. Of these activities, the results of a study of thrombocyte agglutination inhibition will be discussed in more detail below.

The inhibition of platelet aggregation was assessed by Born's turbidimeteric method [Nature, 194, 927–929 (1962)].

Blood was collected from either rabbit or human sources and mixed with one tenth of its volume of a 3.8% w/v sodium citrate solution, and the mixture was centrifuged, to prepare a platelet-rich plasma. Platelet aggregation was determined by the following means: 0.05 ml of a test liquid (containing, in various concentrations, the compound whose inhibitory effect was to be tested) was added to 1 ml of this platelet-rich plasma; two minutes after the addition, 0.2 ml of a liquid containing adenosine diphosphate at a concentration of 5 μM was added; the increase in light transmission at 600 nm was determined by means of a platelet aggregometer manufactured by Bryston Co. Limited. The inhibition of platelet aggregation was assessed by comparing the increase in the amount of light transmitted through the test sample-treated platelet-rich plasma with a control platelet-rich plasma which had been treated in the same way except that the test compound was omitted. The concentration required for a 50% inhibition was calculated and the results are shown in the following Table. The compounds of the invention are identified by the numbers assigned to them in the forgoing list, whilst the prior art compounds also tested and whose results are also given are identified by the following codes:

Compound A: $PGE_1$, which has the formula:

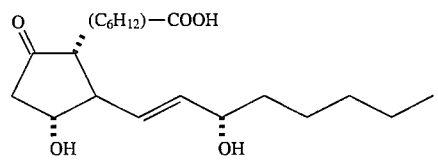

Compound B: carbacyclin, which has the formula:

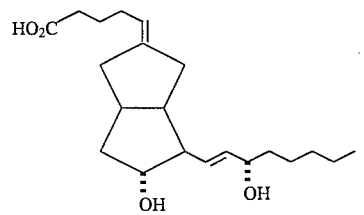

Compound C: 3-(4-carboxybutyl)-6μ-(3α-hydroxyoct-1-enyl)-7α-hydroxy-cis-bicyclo[3,3,0oct- 2-ene, which is the compound mentioned above and discussed in the lecture "Preparation of new prostacyclin-carbon analogs", and which has the formula:

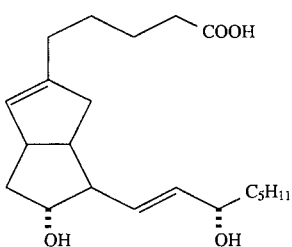

TABLE

| Test Compound | Concentration (ng/ml) for 50% inhibition | |
|---|---|---|
| | Rabbit blood | Human blood |
| 60 | 1.1 | 1.8 |
| 85 | 3.6 | 0.4 |
| 90 | 3.7 | 0.5 |
| 98 | 3.3 | 0.9 |
| 100 | (not tested) | 1.1 |
| 315 (2-ene isomer) | 3.5 | 0.4 |
| A | 36 | 9.3 |
| B | 36 | 13.3 |
| C | 5.9 | 3.6 |

As can be seen from the results in the above Table, the activity of the compounds of the invention is substantially better than that of the prior art compounds and, accordingly, the compounds of the invention are useful for the inhibition of platelet aggregation and can be used for the propylaxis and treatment of trombic diseases. The compounds may be administered orally or parenterally, for example as tablets, capsules, granules, powders, syrups or intravenous injections. The dose will depend upon the route of administration, as well as upon the symptoms, age and body weight of the patient, but the preferred dose for an adult human would normally be from 0.0001 mg to 1000 mg, more preferably from 0.01 mg to 100 mg, per day, which may be administered in a single dose or in divided doses.

The invention is further illustrated by the following Examples, which describe preparation of various compounds of the present invention. The preparation of starting materials for use in these Examples, except where the starting materials are otherwise well-known, is described in the following Preparations.

EXAMPLE 1

A mixture of 3-(4-carboxybuty! )-6β-(3α-hydroxy-4-methylnona-1,8-dienyl)-7α-hdroxy-cis-bicyclo[3,3,0]-oct-2(3)-ene 1(a) A mixture of 3-(5-benzyloxypentyl)-6β-(3-oxo-4-methylnona- 1,8-dienyl)-7α-(2-tetrahydropyranyloxy)-cis-bicyclo[3,3,0]oct-2(3)-ene 0.41 g of a 55% w/w suspension of sodium hydride in oil was washed with hexane; 60 ml of tetrahydrofuran and 2.70 g of dimethyl (2-oxo-3-methyl-7-octenyl)phosphonate were added to the washed suspension and the mixture was stirred for 30 minutes. 3.24 g of 3-(5-benzyloxypentyl)-6β-formyl-7α-( 2-tetrahydropyranyloxy)-cis-bicyclo[3,3,0]oct-2(3)-ene (prepared as described in Preparation 8) were then dissolved in 20 ml of tetrahydrofuran and the resulting solution was added to the reaction mixture, which was then stirred for 30 minutes at room temperature. The reaction mixture was then diluted with ice-water and extracted with ethyl acetate. The extract was washed with water and then dried over anhydrous sodium sulfate. The solvent was distilled off from the extract under reduced pressure. The remaining residue was subjected to column chromatography through 95.7 g of silica gel, and 3.74 g of the title compound as an oil were obtained from the fractions eluted with hexane containing from 10 to 20% by volume ethyl acetate.

Infrared Absorption Spectrum (liquid film)$v_{max}cm^{-1}$: 1624, 1670, 1696. Nuclear Magnetic Resonance Spectrum (CDCl$_3$) δ ppm: 1.09 (3H, doublet, J=7.2 Hz, —CH$_3$); 3.47 (2H, triplet, J=7.0 Hz, CH$_2$O-benzyl); 4.51 (2H, singlet, OCH$_2$-phenyl); 4.8–5.2 (2H, multipier, olefin Hx2); 5.30 (1H, broad singlet, olefin H); 6.26 (1H, doublet of doublets, J=15.0 Hz & 5.0 Hz, olefin H); 6.70–7.10 (1H, multipier, olefin H); 7.35 (SH, singlet, phenyl H).

1(b) A mixture of 3-(5-benzyloxypentyl)-6β-(3α-hydroxy-4-methylnona- 1,8-dienyl)-7α-(2-tetrahydropyranyloxy)-cis-bicyclo[3,3,0]oct-2(3)-ene and their 6β-(3β-hydroxy)isomers. The enone compound (3.70 g) obtained as described in step (a) above was dissolved in 25 ml of methanol, and this solution was added to 30 ml of a methanolic solution containing 3.1 g of cerium chloride heptahydrated, whilst cooling with ice. 393 mg of sodium borohydride were then added to the mixture, which was stirred for 30 minutes at a solution temperature of 5°–10° C. The reaction mixture was then poured into water, and the mixture was extracted with ethyl acetate. The extract was washed with a saturated aqueous solution of sodium chloride and dried over anhydrous sodium sulfate. The solvent was distilled off from the extract to yield 3.90 g of residue. On purifying the residue by silica gel column chromatography, 1.22 g of the 6β-(3β-hydroxy) isomer of the title compound and 2.03 g of the 6β-(3α-hydroxy) isomer of the title compound were obtained in the form of oils from the fractions eluted with hexane containing 25–30% and 20–25% by volume, respectively, of ethyl acetate and with low and high polarity, respectively.

6β-(3α-hydroxy)isomer:

Infrared Absorption Spectrum (liquid film)$v_{max}cm^{-1}$: 1024, 1120, 1454, 1642, 3460. Nuclear Magnetic Resonance Spectrum (CDCl$_3$) δ ppm: 0.83–0.97 (3H, multipier, —CH$_3$); 3.47 (2H, triplet, J=7.0 Hz, CH$_2$O-benzyl); 4.53 (2H, singlet, CH$_2$O-phenyl); 4.70 (1H, broad singlet, 2-H of tetrahydropyran); 4.83–5.20 (2H, multipier, olefin Hx2); 5.30 (1H, broad singlet, olefin H); 5.47–6.20 (3H, multipier, olefin Hx3); 7.37 (5H, singlet, phenyl H).

6β-(3β-hydroxy)isomer:

Infrared Absorption Spectrum (liquid film)$v_{max}cm^{-1}$: 1023, 1120, 1454, 1642, 3460. Nuclear Magnetic Resonance Spectrum (CDCl$_3$) δ ppm: 0.90 (3H, multipier, CH$_3$); 3.47 (2H, triplet, J=7 Hz, CH$_2$CH$_2$O-benzyl); 4.53 (2H, singlet, CH$_2$O-phenyl); 4.70 (1H, broad singlet, 2-H of tetrahydropyran); 4.83–5.20 (2H, multipier, olefin Hx2); 5.30 (1H, broad singlet, —CH=); 5.47–6.20 (3H, multipier, olefin Hx3).

1(c) A mixture of 3-(5-benzyloxypentyl)-6β-[3α-(2-tetrahydropyranyloxy)- 4-methylnona-1,8-dienyl]-7α-(2-tetrahydropyranyloxy)-cis-bicyclo[3,3,0]oct-2(3)-ene.

2.02 g of the 6β-(3α-hydroxy) isomer obtained as described in step (b) above were dissolved in 20 ml of methylene chloride, to which 0.62 ml of 2,3-dihydropyran and a catalytic amount of p-toluenesulfonic acid had been added, and the mixture was stirred for 1 hour at a solution temperature of 2° C. After completion of the reaction, the reaction product was neutralized with a 5% w/v aqueous solution of sodium bicarbonate. A saturated aqueous solution of sodium chloride was added and the mixture was extracted with ethyl acetate. The ethyl acetate extract was washed with a saturated aqueous solution of sodium chloride and dried over anhydrous sodium sulfate. The solvent was distilled off from the extract under reduced pressure to yield 3.90 g of residue. On purifying the residue by silica gel column chromatography, 2.09 g of the title product was obtained as an oil from the fractions eluted with hexane containing 10–14% by volume ethyl acetate.

Infrared Absorption Spectrum (liquid film)$v_{max}$cm$^{-1}$: 1018, 1120, 1198, 1450, 1638. Nuclear Magnetic Resonance Spectrum (CDCl$_3$) δ ppm: 0.80–1.03 (3H, multipier, —CH$_3$); 3.47 (2H, triplet, J=7.0 Hz, CH$_2$O-benzyl); 4.52 (2H, singlet, CH$_2$O-phenyl); 4.70 (2H, broad singlet, 2-H of tetrahydropyran×2); 4.83–6.20 (8H, multipier, olefin —H×8); 7.37 (5H, singlet, phenyl —H).

1(d) A mixture of 3-(5-hydroxypenyl)-6β-[3α-(2-tetrahydropyranyloxy)-4-methylnona- 1,8-dienyl]-7α-(2-tetrahydropyranyloxy)-cis-bicyclo[3,3,0]oct-2(3)-ene An excess of metallic sodium was added to a solution of 2.07 g of the benzylpyranyl compound obtained as described in step (c) above in 40 ml of liquid ammonia and 30 ml of tetrahydrofuran at a solution temperature of −70° C. and under a nitrogen atmosphere, whereupon the solution developed a dark blue color. The mixture was stirred for 30 minutes at −70° C., and then a large excess of ammonium chloride was added, and the mixture was returned to room temperature. Ammonia was distilled off from the mixture, and then water was added to the residue, which was extracted with diethyl ether. The extract was washed with water and dried over anhydrous sodium sulfate. The solvent was then distilled off from the extract under reduced pressure, to yield 2.00 g of a residue. On purifying the residue through silica gel column chromatography, 1.53 g of the title compound was obtained in the form of an oil from the fractions eluted with hexane containing 20–25% by volume of ethyl acetate.

Infrared Absorption Spectrum (liquid film)$v_{max}$cm$^{-1}$: 1642, 3450. Nuclear Magnetic Resonance Spectrum (CDCl$_3$) δ ppm: 0.80–1.01 (3H, multipier, —CH$_3$); 3.30–4.30 (8H, multipier); 4.67 (2H, broad singlet, 2-H of tetrahydropyran×2); 4.83–6.20 (6H, multipier, olefin -H×6).

1(e) A mixture of 3-(4-carboxybutyl)-6β-[3α-(2-tetrahydropyranyloxy)- 4-methylnona-1,8-dienyl]-7α-(2-tetrahydropyranyloxy)-cis-bicyclo[3,3,0]oct-2(3)-ene.

2.8 ml of Jones' reagent (prepared by diluting 26.7 g of chromic anhydride and 23 ml of concentrated sulfuric acid with water to a total volume of 100 ml) were added dropwise at a solution temperature of −25° C. to 175 ml of an acetone solution containing 1.51 g of the alcoholic compound obtained as described in step (d) above, and the mixture was stirred at the same temperature for one hour. Upon completion of the reaction, the solution was neutralized with a 5% w/v aqueous solution of sodium bicarbonate. Acetone was distilled off from the solution under reduced pressure. Water was added to the residue, and the solution was extracted with diethyl ether. The extract was washed with water and dried over anhydrous sodium sulfate. The solvent was then distilled off under reduced pressure, to give 1.63 g of a residue. This product was purified by silica gel column chromatography, yielding 1.30 g of the title compound in the form of an oil from the fractions eluted with hexane containing 20–25% by volume of ethyl acetate.

Infrared Absorption Spectrum (liquid film)$v_{max}$cm$^{-1}$: 1638, 1708, 1732. Nuclear Magnetic Resonance Spectrum (CDCl$_3$) δ ppm: 0.80–1.01 (3H, multipier, —CH$_3$); 4.67 (2H, broad singlet, 2-H of tetrahydropyran×2); 4.83–6.20 (6H, multipier, olefin —H×6); 7.70–8.60 (1H, broad singlet, COOH).

1(f) A mixture of 3-(4-carboxybutyl)-6β-(3α-hydroxy-4-methylnona-1,8-dienyl)- 7α-hydroxy-cis-bicyclo[3,3,0 oct-2(3)-ene.

28 mg of d-camphorsulfonic acid were added to a solution of 0.52 g of the tetrahydropyranyl compound obtained as described in step (e) above in 15.6 ml of acetone and 8 ml of water and the mixture was stirred for 2 hours at a solution temperature of 40°–45° C. Upon completion of the reaction, the reaction product was poured into water, which was then extracted with ethyl acetate. The extract was washed with water and dried over anhydrous sodium sulfate. The solvent was distilled off under reduced pressure, to yield 460 mg of a residue. On purifying the residue through silica gel column chromatography, 250 mg of the title product were obtained in the form of an oil from the fractions eluted with hexane containing 40–85% by volume of ethyl acetate.

Infrared Absorption Spectrum (liquid film)$v_{max}$cm$^{-1}$: 1640, 1708, 3340. Nuclear Magnetic Resonance Spectrum (CDCl$_3$) δ ppm: 0.90 (3H, multipier, CH$_3$); 3.30–4.10 (2H, multiplet); 4.80–6.10 (9H, multipier, olefin -H×6+OH×2+COOH). Mass Spectrum, m/e: 358 (M-18).

EXAMPLE 2

A mixture of
3-(4-carboxybutyl)-6β-[3α-hydroxy-5(R),9-dimethyldeca-1,8-dienyl]-7α-hydroxy-cis-bicyclo[3,3,0]oct-2(3)-ene.

2(a) A mixture of 3-(5-benzyloxypentyl)-6ε-[3-oxo-5(R),9-dimethyldeca- 1,8-dienyl]-7α-(2-tetrahydropyranyloxy)-cis-bicyclo[3,3,0]oct-2(3)-ene.

3.05 g of crude 3-(5-benzyloxypentyl)-6β-formyl-7α-(2-tetrahydropyranyloxy)-cis-bicyclo[ 3,3,0]oct-2(3)-ene (prepared as described in Preparation 8) and 3.55 g of dimethyl [2-oxo-4(R),8-dimethylnona-1,8-dienyl]-phosphonate phosphonate were reacted as described in Example 1(a), yielding 3.50 g of the title compound in the form of an oil.

Infrared Absorption Spectrum (liquid film)$v_{max}$cm$^{-1}$: 1625, 1670, 1695.

Nuclear Magnetic Resonance Spectrum (CDCl$_3$) δ ppm:

0.89 (3H, doublet, J=7 Hz, CH$_3$);

3.48 (2H, triplet, CH$_2$OCH$_2$-phenyl);

4.50 (2H, singlet, CH$_2$-phenyl);

4.8–5.4 (2H, multipier, =CH—×2);

6.18 (1H, doublet of doublets, J=16.3 Hz, =CH—);

6.5–7.2 (1H, multipier, =CH—);

7.29 (5H$_0$ singlet, phenyl H).

2(b) A mixture of 3-(5-benzyloxypentyl)-6β-[3α -hydroxy-5(R),9-dimethyldeca-1,8-dienyl]-7α-hydroxy-cis-bicyclo[ 3,3,0]oct-2(3)-ene and their 6β-(3β -hydroxy)isomers.

3.50 g of the ketone compound prepared as described in step (a) above were reacted as described in Example 1(b), to obtain the corresponding hydroxy compound. As this compound gave 3 spots on a thin layer chromatogram, it was dissolved, without purification, in 50 ml of acetic acid, and 30 ml of water and 20 ml of tetrahydrofuran (THF) were added; the mixture was then stirred for 2.5 hours at 50° C. In the meantime, 15 ml of water were added. Upon completion of the reaction, an aqueous solution of 40 g of sodium hydroxide was added to the reaction product to neutralize it, and the neutralized mixture was extracted with ethyl acetate. The extract was washed with an aqueous solution of sodium chloride and then dried over anhydrous sodium sulfate. The solvent was distilled off, and the resulting residue was purified by column chromatography through silica gel. 1.15 g of the 6β-(3β-hydroxy) isomer (showing 2 spots on a thin layer chromatogram) were obtained from the fractions eluted with hexane containing 20-25% v/v of ethyl acetate, while 1.54 g of the 6β-(3α-hydroxy) isomer (also showing 2 spots on a thin layer chromatogram) were obtained from the fractions eluted with hexane containing 30-50% v/v of ethyl acetate. Both isomers were in the form of an oil.

6β-(3β-hydroxy) isomer:

Infrared Absorption Spectrum (liquid film)$v_{max}$cm$^{-1}$: 3370.

Nuclear Magnetic Resonance Spectrum (CDCl$_3$) δ ppm:

0.90 (3H, doublet, CH$_3$);

1.60 (3H, singlet, CH$_3$);

1.68 (3H, singlet, CH$_3$);

3.45 (2H, triplet, —CH$_2$O—);

4.50 (2H, singlet, CH$_2$O—);

5.10 (1H, triplet, =CH—);

5.28 (1H, broad singlet, =CH—);

5.60 (2H, multipier, —CH=CH—).

6β-(3α-hydroxy) isomer:

Infrared Absorption Spectrum (liquid film)$v_{max}$cm$^{-1}$: 3360.

Nuclear Magnetic Resonance Spectrum (CDCl$_3$) δ ppm:

0.90 (3H, multipier, CH$_3$);

1.60 (3H, singlet, CH$_3$);

1.65 (3H, singlet, CH$_3$);

3.50 (2H, triplet. J=6 Hz. —CH$_2$O—);

4.50 (2H, singlet, —CH$_2$O—);

5.12 (1H, broad triplet. =CH—);

5.28 (1H, broad singlet, =CH—);

5.50 (2H, multipier, —CH=CH—).

2(c) A mixture of 3-(5-benzyloxypentyl)-6β-[3α-(2-tetrahydropyranyloxy)-5(R),9-dimethyldeca-1,8-dienyl] -7α(2-tetrahyhdopyranyloxy)-cis-bicyclo[3,3,0]oct-2(3)-ene. 1.50 g of the 6β-(3α-hydroxy) isomer prepared as described in step (b) above were reacted as described in Example 1(c), to give 2.10 g of the title compound in the form of an oil.

Infrared Absorption Spectrum (liquid film)$v_{max}$cm$^{-1}$: 1022, 1035.

Nuclear Magnetic Resonance Spectrum (CDCl$_3$) δ ppm:

0.90 (3H, multipier, CH$_3$);

3.46 (2H, triplet, —CH$_2$O—);

4.50 (2H, singlet, —CH$_2$O—);

4.70 (2H, broad singlet, 2–H of tetrahydropyranx2);

4.90–5.8 (4H, multipier, =CH—×4).

2(d) A mixture of 3-(5-hydroxypentyl)-6β-[3α-(2-tetrahydropyranyloxy)-5(R),9-dimethyldeca-1,8-dienyl] -7α-(2-tetrahydropyranyloxy)-cis-bicyclo[3,3,0]oct-2(3)-ene.

2.10 g of the benzyl compound prepared as described in step (c) above were reacted as described in Example 1(d), to give 1.46 g of the title compound in the form of an oil.

Infrared Absorption Spectrum (liquid film)$v_{max}$cm$^{-1}$: 3350.

Nuclear Magnetic Resonance Spectrum (CDCl$_3$) δ ppm:

0.92 (3H, multipier, CH$_3$);

2.63 (3H, singlet, CH$_3$);

2.69 (3H, singlet, CH$_3$);

3.64 (2H, triplet, —CH$_2$O—);

4.82 (2H, broad singlet, 2–H of tetrahydropyranx2);

5.0–5.8 (4H, multipier, —CH=×4).

2(e) A mixture of 3-(4-carboxybutyl)-6β-[3α-(2-tetrahydropyranyloxy)-5(R),9-dimethyldeca-1,8-dienyl] -7α-(2-tetrahydropyranyloxy)-cis-bicyclo[3,3,0]oct-2(3)-ene 1.20 g of the alcoholic compound prepared as described in step (d) above was reacted as described in Example 1(e), to give 737 mg of the title compound in the form of an oil.

Infrared Absorption Spectrum (liquid film) $v_{max}$cm$^{-1}$: 1735, 1710.

Nuclear Magnetic Resonance Spectrum (CDCl$_3$) δ ppm:

0.92 (3H, multipier, CH$_3$);

1.62 (3H, singlet, CH$_3$);

1.69 (3H, singlet, CH$_3$);

4.72 (2H, broad singlet, 2–H of tetrahydropyranx2);

5.0–5.8 (4H, multipier, =CH—×4).

2(f) A mixture of 3-(4-carboxybutyl)-6β-[3α-hydroxy-5(R),9-dimethyldeca-1,8-dienyl]-7α-hydroxy-cis-bicyclo[3,3,0]oct-2(3)-ene 730 mg of the pyranyl compound prepared as described in step (e) above were reacted as described in Example 1(f), to give 394 mg of the title compound as an oil.

Infrared Absorption Spectrum (liquid film)$v_{max}$cm$^{-1}$: 3350, 1710.

Nuclear Magnetic Resonance Spectrum (CDCl$_3$) δ ppm:

0.91 (3H, multipier, CH$_3$);

1.62 (3H, singlet, CH$_3$);

1.70 (3H, singlet. CH$_3$);

3.72 (1H, multipier, CHOH);

4.15 (1H, multipier, CHOH);

5.11 (1Ho triplet, =CH—);

5.34 (1H, broad singlet, =CH—);

5.50 (2H, multipier, —CH=CH—).

This compound could be readily converted into the corresponding methyl ester (infrared absorption spectrum $v_{max}$1725 cm$^{-1}$) by treatment with diazomethane.

EXAMPLE 3

A mixture of 3,-(5-hydroxypentyl);6β-[3α-hydroxy-5(R),9-dimethyldeca-1,8-dienyl]-7α-hydroxy-cis-bicyclo-[3,3,0]oct-2(3)-ene.

250 mg of 3-(5-hydroxypentyl)-6β-[3α-(2-tetrahydropyranyloxy)-5(R),9-dimethyldeca-1,8-dienyl] -7α-(2-tetrahydropyranyloxy)-cis-bicyclo[3,3,0]oct-2(3)-ene [prepared as described in Example 2(d)] were reacted as described in Example 1(f), to give 121 mg of the title compound as an oil. This compound showed 2 spots on a thin layer chromatogram.

Infrared Absorption Spectrum (liquid film) $v_{max}$cm$^{-1}$: 3370, 975.

Nuclear Magnetic Resonance Spectrum (CDCl$_3$) δ ppm:

0.91 (3H, doublet, CH$_3$);

1.59 (3H, singlet, CH$_3$);

1.66 (3H, singlet, CH$_3$);

5.02 (1H, triplet, =CH—);

5.19 (1H, broad singlet, =CH—);

5.40 (2H, multipier, —CH=CH—).

EXAMPLE 4

A mixture of 3-(4-carboxybutyl)-6β-(3α-hydroxy- 3-cyclopentyl-1-propenyl)-7α-hydroxy-cis-bicyclo-[3,3,0]-oct-2(3)-ene.

4(a) A mixture of 3-(5-benzyloxypentyl)-6β-(3-oxo-3-cyclopentyl-1-propenyl)-7α-(2-tetrahydropyranyloxy)-cis-bicyclo[3,3,0]oct-2(3)-ene.

0.41 g of a 55% w/w suspension of sodium hydride oil was washed with hexane, and then 60 ml of tetrahydrofuran and 2.39 g of dimethyl (2-oxo- 2-cyclopentylethyl)phosphonate were added, and the mixture was stirred for 30 minutes.

Meanwhile, 3.05 g of 3-(5-benzyloxypentyl)-6β -formyl-7α-(2-tetrahydropyranyloxy)-cis-bicyclo[3,3,0] -oct2(3)-ene (prepared as described in Preparation 8) were dissolved in 20 ml of tetrahydrofuran, and this solution was added to the above phosphonate solution: the mixture was stirred for 30 minutes at room temperature. The reaction product was then diluted in ice-water, and the mixture was extracted with ethyl acetate. The extract was washed with water and dried over anhydrous sodium sulfate. The solvent was distilled off under reduced pressure and the resulting residue was subjected to column chromatography with silica gel, to give 3.50 g of the title compound as an oil.

Infrared Absorption Spectrum (liquid film) $v_{max}cm^{-1}$: 1030, 1120, 1626, 1693.

Nuclear Magnetic Resonance Spectrum (CDCl$_3$) δ ppm:
3.48 (2H, triplet, J=6 Hz, —CH$_2$O—benzyl);
4.52 (2H, singlet, —OCH$_2$-phenyl);
5.30 (1H, broad singlet, olefin H);
6.23 (1H, multiplet, olefin H);
6.90 (1H, multipier, olefin H);
7.38 (5H, singlet, phenyl H).
Mass spectrum, m/e: 506 (M+), 422 (M-84).

4(b) A mixture of 3-(5-benzyloxypentyl)-6β-(3α-hydroxy-3-cyclopentyl-1-propenyl)-7α-(2 -tetrahydropyranyloxy)-cis-bicyclo[3,3,0]oct-2(3)-ene.

3.40 g of the enone compound prepared as described in step (a) above were reacted as described in Example 1(b), to give 1.91 g of the title compound and 1.07 g of its 6β-(3β-hydroxy) isomer, both in the form of oils.

Infrared Absorption Spectrum (liquid film); $v_{max}cm^{-1}$: 1025, 1075, 1120, 3450.

Nuclear Magnetic Resonance Spectrum (CDCl$_3$) δ ppm:
3.47 (2H, triplet, J=6 Hz, —CH$_2$O—benzyl);
4.52 (2H, singlet, —OCH$_2$-phenyl);
4.70 (1H, broad singlet, 2–H of tetrahydropyran);
5.28 (1H, broad singlet, olefin H);
5.65 (2H, multipier, olefin H×2);
7.36 (5H, singlet, phenyl H).
Mass spectrum, m/e: 406 (M-102).

4(c) A mixture of 3-(5-benzyloxypentyl)-6β-3α-(2 -tetrahydropyranyloxy)-3-cyclopentyl-1-propenyl]-7α-(2 -tetrahydropyranyloxy)-cis-bicyclo[3,3,0]oct-2(3)-ene.

1.85 g of the hydroxy compound prepared as described in step (b) above was reacted as described in Example 1(c), to give 2.18 g of the title compound as an oil.

Infrared Absorption Spectrum (liquid film)$v_{max}cm^{-1}$: 978, 1023, 1078, 1120.

Nuclear Magnetic Resonance Spectrum (CDCl$_3$) δ ppm:
3.46 (2H, triplet, J=6 Hz, —CH$_2$O—benzyl);
4.51 (2H, singlet, —OCH$_2$phenyl);
4.74 (2H, broad singlet, 2–H of tetrahydropyranx2);
5.27 (1H, broad singlet, olefin H);
5.62 (2H, multiplet, olefin H);
7.36 (5H, singlet, phenyl H).
Mass spectrum, m/e: 4.90 (M-102).

4(d) A mixture of 3-(5-hydroxypentyl)-6β-[3α-(2 -tetrahydropyranyloxy)-3-cyclopentyl-1-propenyl]-7α -(2-tetrahydropyranyloxy)-cis-bicyclo[3,3,0]oct-2(3)-ene.

2.12 g of the benzyl compound prepared as described in step (c) above were reacted as described in Example 1(d), to give 1.50 g of the title compound as an oil.

Infrared Absorption Spectrum (liquid film)$v_{max}cm^{-1}$: 970, 1020, 1075, 1120, 1130, 3430.

Nuclear Magnetic Resonance Spectrum (CDCl$_3$) δ ppm:
4.75 (2H, broad singlet, 2–H of tetrahydropyran×2);
5.30 (1H, broad singlet, olefin H);
5.65 (2H, multiplet, olefin H).
Mass spectrum, m/e: 400(M-102).

4(e) A mixture of 3-(4-carboxybutyl)-6β-[3α-(2 -tetrahydropyranyloxy)-3-cyclopentyl-1-propenyl]-7α-(2 -tetrahydropyranyloxy)-cis-bicyclo[3,3,0]oct-2(3)-ene.

1.36 g of the hydroxy compound prepared as described in step (d) above was reacted as described in Example 1(e), to give 0.7 g of the title compound as an oil.

Infrared Absorption Spectrum (liquid film) $v_{max}cm^{-1}$: 980, 1022, 1130, 1710, 1738, 3000–3200.

Nuclear Magnetic Resonance Spectrum (CDCl$_3$) δ ppm:
4.73 (2H, broad singlet, 2–H of tetrahydropyran×2);
5.30 (1H, broad singlet, olefin H);
5.60 (2H, multipier, olefin H).
Mass spectrum, m/e: 414 (M-102).

4(f) A mixture of 3-(4-carboxybutyl)-6β-(3α -hydroxy-3-cyclopentyl-1-propenyl)-7α-hydroxy-cis-bicyclo[3,3,0]oct-2(3)-ene 0.57 g of the dipyranyl compound prepared as described in step (e) above was treated as described in Example 1(f), and the resulting residue was recrystallized from a mixture of ethyl acetate and hexane, giving 0.17 g of the title compound as crystals melting at 104°–106.5° C.

Infrared Absorption Spectrum (KBr) $v_{max}cm^{-1}$: 970, 1080, 1235, 1710, 3350, 3480.

Nuclear Magnetic Resonance Spectrum (CDCl$_3$) δ ppm:
5.60–5.90 (2H, multipier, CHOH×2)
5.30 (1H, broad singlet, olefin H);
5.54 (2H, multipier, olefin H×2).
Mass spectrum, m/e: 330 (M-18), 312(M-36).

EXAMPLE 5

A mixture of 3-(5-hydroxypentyl)-6β-(3α -hydroxy-3-cyclotpentyl-1-propenyl)-7α-hydroxy-cis-biclyclo[3,3,0]oct-2(3)-ene.

0.30 g of 3-(5-hydroxypentyl)-6β-[3α -(2-tetrahydropyranyloxy)-3-cyclopentyl-1-propenyl]-7α -(2-tetrahydropyranyloxy)-cis-bicyclo[3,3,0]oct-2(3)-ene prepared as described in Example 4(d)] was treated as described in Example 1(f), and the resulting residue was recrystallized from a mixture of ethyl acetate and hexane, giving 0.13 g of the title compound as crystals melting at 108°–110° C.

Infrared Absorption Spectrum (KBr) $v_{max}cm^{-1}$: 1243, 1434, 3420.

Nuclear Magnetic Resonance Spectrum (CDCl$_3$) δ ppm:
3.55–3.85 (4H, multipier, CHOH×2 and 2×H at 5-pentyl);
5.30 (1H, broad singlet, olefin H);
5.54 (2H, multipier, olefin H×2).
Mass spectrum, m/e: 316 (M-18), 298(M-36).

EXAMPLE 6

A mixture of 3-(2-hydroxyethyl)-6β-[3α-(2 -tetrahydropyranyloxy)-5(R),9-dimethyldeca-1,8-dienyl] -7α-(2-tetrahydropyranyloxy)-cis-bicyclo[3,3,0]oct-2(3)-ene.

6(a) A mixture of 3-(methoxycarbonylmethyl)-6β-[3α-(2-tetrahydropyranyloxy)-5(R),9-dimethyldeca-1,8-dienyl]-7α-(2-tetrahydropyranyloxy)-cis-bicyclo[3,3,0] oct-2(3)-ene.

1.95 g of 3-methoxycarbonylmethylidene-6β-[3α-(2-tetrahydropyranyloxy)-5(R),9-dimethyldeca-1,8-dienyl]-7α-(2-tetrahydropyranyloxy)-cis-bicyclo-[3,3,0]octane (prepared as described in Japanese Patent Application Kokai No. 462/78) was dissolved in 5 ml of tetrahydrofuran. 10 ml of a tetrahydrofuran solution of diisopropylaminolithium (prepared from 935 mg of diisopropylamine, 5.43 ml of a 15% w/v butyllithium hexane solution and 1.6 ml of hexamethylphosphoric triamide) were then added at −60° C. to this solution. The mixture was allowed to react for one hour at the same temperature, and it was then poured into a saturated aqueous solution of ammonium chloride. The mixture was extracted with ethyl acetate. The extract was dried over anhydrous sodium sulfate, and the solvent was distilled off. The residue was then purified by column chromatography through silica gel, giving 1.30 g of the title compound as an oil from the fractions eluted with hexane containing 4–5% by volume of ethyl acetate.

Infrared Absorption Spectrum (liquid film) $v_{max}cm^{-1}$: 1737.

Nuclear Magnetic Resonance Spectrum (CDCl$_3$) δ ppm:
0.92 (3H, multipier, CH$_3$);
0.62 (3H, singlet, CH$_3$);
0.68 (3H, singlet, CH$_3$);
3.10 (2H, singlet, CH$_2$);
3.69 (3H, singlet, COOCH$_3$);
4.82 (2H, broad singlet, 2–H of tetrahydropyran×2);
5.12 (1H, triplet, =CH—);
5.3–5.8 (3H, multipier, =CH—, —CH=CH—).

6(b) A mixture of 3-(2-hydroxyethyl)-6β-[3α-(2-tetrahydropyranyloxy)-5.(R),9-dimethyldeca-1,8-dienyl]-7α-(2-tetrahydropyranyloxy)-cis-bicyclo[3,3,0]oct-2(3)-ene.

510 mg of the ester compound prepared as described in step (a) above were dissolved in 20 ml of diethyl ether. 500 mg of lithium aluminum hydride were then added to the solution, whilst cooling with ice. After 1 hour, 2 ml of a 4% w/v aqueous solution of sodium hydroxide were added, with stirring. The resulting precipitate was filtered off and the filtrate was condensed by evaporation under reduced pressure, leaving an oily residue. On purifying the residue by column chromatography using silica gel, 430 mg of the title compound were obtained, as an oil, from the fractions eluted with hexane containing 14–16% by volume of ethyl acetate.

Infrared Absorption Spectrum (liquid film) $v_{max}cm^{-1}$: 3350.

Nuclear Magnetic Resonance Spectrum (CDCl$_3$) δ ppm:
0.91 (3H, multipier, CH$_3$);
2.62 (3H, singlet, CH$_3$);
2.69 (3H, singlet, CH$_3$);
4.80 (2H, broad singlet, 2–H of tetrahydropyran×2);
5.0–5.8 (4H, multipier, =CH—×4).

EXAMPLE 7

3-(4-Carboxybutyl)-6β-(3α-hydroxy-3-cyclopentyl-1-propenyl)-7α-hydroxy-cis-bicyclo[3,3,0]oct-2-ene 7(a) 3-(5-Benzyloxypentyl)-6β-(3-oxo-3-cyclopentyl-1-propenyl)-7α-(2-tetrahydropyranyloxy)-cis-bicyclo-[3,3,0]oct-2-ene 74 mg of a 55% w/w suspension of sodium hydride in oil was washed with hexane, and then 10 ml of tetrahydrofuran and 418 mg of dimethyl (2-oxo-2-cyclopentylethyl)phosphonate were added, with stirring, to the washed suspension: stirring was then continued for 30 minutes. A solution of 469 mg of 3-(5-benzyloxypentyl)-6β-formyl-7α-(2-tetrahydropyranyloxy)-cis-bicyclo[3,3,0]oct-2-ene (prepared as described in Preparation 14) in 3 ml of tetrahydrofuran was then added to the resulting reaction mixture, and the mixture was stirred at room temperature for 1 hour. Upon completion of the reaction, the reaction mixture was added to ice-water and extracted with ethyl acetate. The extract was washed with water and dried over anhydrous sodium sulfate. The solvent was distilled off under reduced pressure, leaving a residue in an amount of 937 mg. This was purified by column chromatography through silica gel, to give 503 mg of the title compound as an oil from the fractions eluted with hexane containing 10–20% by volume of ethyl acetate.

Infrared Absorption Spectrum (liquid film) $v_{max}cm^{-1}$: 1120, 1625, 1665, 1690.

Nuclear Magnetic Resonance Spectrum (CDCl$_3$) δ ppm:
3.48 (2H, triplet, J=6.0 Hz, CH$_2$OCH$_2$-phenyl);
4.52 (2H, singlet, OCH$_2$-phenyl);
5.30 (1H, singlet, =CH—);
6.23 (1H, doublet of doublets, J=17.0 Hz & 5.0 Hz, =CH—);
6.90 (1H, multipier, =CH—);
7.38 (5H, singlet, phenyl).

7(b) 3-(5-Benzyloxypentyl)-6β-(3α-hydroxy-3-cyclopentyl-1-propenyl)-7α-(2-tetrahydropyranyloxy)-cis-bicyclo[3,3,0]oct-2-ene A solution of 484 mg of the enone compound prepared as described in step (a) above in 7 ml of methanol was added to a solution of 430 mg of cerium chloride heptahydrate in 4 ml of methanol, whilst cooling with ice. The reaction mixture was then cooled down to −20° C., whereupon 62 mg of sodium borohydride were added and the mixture was kept at the same temperature for 15 minutes, with stirring.

Upon completion of the reaction, the reaction mixture was added to water, and then the mixture was extracted with ethyl acetate. The extract was washed with a saturated aqueous solution of sodium chloride and dried over anhydrous sodium sulfate. Upon distilling the solvent off from this mixture under reduced pressure, 498 mg of a residue were obtained.

This residue was purified by column chromatography through silica gel. 262 mg of the 3β-hydroxy isomer of the title compound and 184 mg of the 3β hydroxy isomer were obtained in the form of oils from the fractions with higher and lower polarity, eluted with hexane containing 25–30% by volume or 20–25% by volume, respectively, of ethyl acetate.

3α-Hydroxy isomer

Infrared Absorption Spectrum (liquid film) $v_{max}cm^{-1}$: 1025, 1075, 1120, 3450.

Nuclear Magnetic Resonance Spectrum (CDCl$_3$) δ ppm:
3.47 (2H, triplet, J=6.0 Hz, CH$_2$CH$_2$OCH$_2$-phenyl);
4.52 (2H, singlet, OCH$_2$-phenyl);
4.70 (1H, broad singlet, 2–H of tetrahydropyran);
5.28 (1H, broad singlet, =CH—);
5.65 (2H, multipier, =CH—×2);
7.36 (SH, singlet, phenyl).

3β-Hydroxy isomer

Infrared Absorption Spectrum (liquid film) $v_{max}cm^{-1}$: 1025, 1074, 1120, 3450.

7(c) 3-(5-Benzyloxypentyl)-6β-[3α-(2-tetrahydropyranyloxy)-3-cyclopentyl-1-propenyl]-7α-(2-tetrahydropyranyloxy)-cis-bicyclo[3,3,0]oct-2-ene.

379 mg of the 3α-hydroxy isomer prepared as described in step (b) above were dissolved in 4 ml of methylene chloride, to which 0.1 ml of 2,3-dihydropyran and a catalytic amount of p-toluenesulfonic acid had been added, and the mixture was stirred for 30 minutes. On completion of the reaction, the reaction mixture was neutralized with a 5% w/v aqueous solution of sodium bicarbonate, and water was added to it. The mixture was extracted with ethyl acetate. The extract was washed with water and dried over anhydrous sodium sulfate. The solvent was distilled off under reduced pressure, to obtain 482 mg of a residue.

This product was purified by column chromatography through silica gel, to give 425 mg of the title compound as an oil from the fractions eluted with hexane containing 10–14% by volume of ethyl acetate.

Infrared Absorption Spectrum (liquid film) $v_{max}cm^{-1}$: 1025, 1080, 1120.

Nuclear Magnetic Resonance Spectrum (CDCl$_3$) δ ppm:

3.46 (2H, triplet, J=6.0 Hz, —CH$_2$OCH$_2$-phenyl);

4.51 (2H, singlet, OCH$_2$-phenyl);

4.74 (2H, broad singlet, 2–H of tetrahydropyran×2);

5.27 (1H, broad singlet, =CH—);

5.62 (2H, multipier, —CH=CH—);

7.36 (5H, singlet, phenyl).

7(d) 3-(5-Hydroxypentyl)-6β-[3α-(2-tetrahydropyranyloxy)-3-cyclopentyl-1-propenyl)-7α-(2-tetrahydropyranyloxy)-cis-bicyclo[3,3,0]oct-2-ene.

Under an atmosphere of nitrogen, an excess of metallic sodium was added to a solution of 415 mg of the benzyl ether compound prepared as described in step (c) above in 20 ml of liquid ammonia and 14 ml of tetrahydrofuran at a temperature of –70° C. in the reaction mixture, whereupon the mixture developed a dark blue color. The mixture was stirred at –70° C. for 30 minutes, and then a large excess of ammonium chloride was added to it. The reaction mixture was returned to room temperature, as a result of which ammonia distilled off. Water was added to the residue, and the mixture was extracted with diethyl ether. The extract was washed with water and dried over anhydrous sodium sulfate. The solvent was distilled off from the extract under reduced pressure, leaving a residue in a yield of 372 mg. This residue was purified by column chromatography through silica, giving 339 mg of the title compound as an oil from the fractions eluted with hexane containing 20–25% by volume of ethyl acetate.

Infrared Absorption Spectrum (liquid film) $v_{max}cm^{-1}$: 3430.

Nuclear Magnetic Spectrum (CDCl$_3$) δ ppm:

4.75 (2H, broad singlet, 2–H of tetrahydropyran×2);

5.30 (1H, broad singlet, =CH—);

5.65 (2H, multipier, =CH—×2).

7(e) 3-(4-Carboxybutyl)-6β-[3α-(2-tetrahydropyranyloxy)-3-cyclopentyl-1-propenyl]-7α-(2-tetrahydropyranyloxy)-cis-bicyclo[3,3,0]oct-2-ene.

0.6 ml of Jones' reagent [prepared as described in Example 1(e)] was dissolved in 10 ml of acetone, and the solution was cooled down to –25° C. A solution of 329 mg of the alcoholic compound prepared as described in step (d) above in 15 ml of acetone was added dropwise to the solution of Jones' reagent, and the mixture was stirred at the same temperature for 80 minutes. On completion of the reaction, isopropanol was added to the solution, the mixture was neutralized with a 5% w/v aqueous solution of sodium bicarbonate, and a saturated aqueous solution of sodium chloride was added. The mixture was extracted with diethyl ether. The extract was washed with water and dried over anhydrous sodium sulfate, and then the solvent wad distilled off under reduced pressure, leaving 342 mg of a residue.

This residue was purified by column chromatography through silica gel, to give 203 mg of the title compound as an oil from the fractions eluted with hexane containing 20–25% by volume of ethyl acetate.

Infrared Absorption Spectrum (liquid film) $v_{max}cm^{-1}$: 980, 1025, 1120, 1135, 1710, 1735, 3100.

Nuclear Magnetic Resonance Spectrum (CDCl$_3$) δ ppm:

4.73 (2H, broad singlet, 2–H of tetrahydropyran×2);

5.30 (1H, broad singlet, =CH—);

5.50 (2H, multiplet, —CH=CH—).

7(f) 3-(4-Carboxybutyl)-6β-(3α-hydroxy-3-cyclopentyl-1-propenyl)-7α-hydroxy-cis-bicyclo-[3,3,0]oct-2-ene.

20 mg of d-camphorsulfonic acid were added to a solution of 207 mg of the tetrahydropyranyl compound prepared as described in step (e) above in 8 ml of acetone and 3 ml of water, and the mixture was stirred for 2 hours at a solution temperature of 40°–45° C. Upon completion of the reaction, the reaction mixture was poured into water and the mixture was extracted with ethyl acetate. The extract was washed with water and dried over anhydrous sodium sulfate, and then the solvent was distilled off, leaving 180 mg of a residue.

This residue was purified by column chromatography through silica gel eluted with hexane containing 40–85% by volume of ethyl acetate and then recrystallized from a mixture of ethyl acetate and hexane, to give 75 mg of the title compound melting at 108°–110° C.

Infrared Absorption Spectrum (CHCl$_3$) $v_{max}cm^{-1}$: 975, 1710, 3300.

Nuclear Magnetic Resonance Spectrum (CDCl$_3$) δ ppm:

5.33 (1H, broad singlet, —CH=);

5.50 (5H, multipier, —CH=CH—, OH×2, COOH).

EXAMPLE 8

3-(4-Carboxybutyl)-6β-[3α-hydroxy-5(R),9-dimethyl-deca-1,8-dienyl]-7α-hydroxy-cis-bicyclo[3,3,0]oct-2-ene.

8(a) 3-(5-Benzyloxypentyl)-6β-(3-oxo-5(R),9-dimethyl-deca-1,8-dienyl)-7α-(2-tetrahydropyranyloxy)-cis-bicyclo[3,3,0]oct-2-ene.

2.91 g of crude 3-(5-benzyloxypentyl)-6β-formyl-7α-(2-tetrahydropyranyloxy)-cis-bicyclo[3,3,0]oct-2-ene (prepared as described in Preparation 14) and dimethyl (2-oxo-4,8-dimethylnona-1-enyl)phosphonate were reacted and the reaction mixture was treated as described in Example 7(a), giving 3.16 g of the title compound as an oil.

Infrared Absorption Spectrum (liquid film)$v_{max}cm^{-1}$ : 1625, 1665, 1690.

Nuclear Magnetic Resonance Spectrum (CDCl$_3$) δ ppm:

0.90 (3H, multipier, CH$_3$);

3.48 (2H, triplet, —CH$_2$O—);

4.50 (2H, singlet, —CH$_2$—);

4.8–5.4 (2H, multipier, =CH—×2);

6.18 (1H, doublet of doublets: J=16.5 Hz, =CH—);

6.5–7.2 (1H, multipier, =CH—).

(b) 3-(5-Benzyloxypentyl)-6β-[3α-hydroxy-5(R),9-dimethyldeca-1,8-dienyl]-7α-hydroxy-cis-bicyclo-[3,3,0]oct-2-ene and its 6β-(3β-hydroxy) isomer.

3.1 g of the ketone compound prepared as described in step (a) above was reacted and treated as described in Example 7(b) to yield the hydroxy compound, which was then dissolved in 45 ml of acetic acid. To this solution were added 25 ml of water and 17 ml of tetrahydrofuran, and the mixture was stirred for 2.5 hours at 50° C., during which time, 15 ml of water were added to the reaction mixture. Upon completion of the reaction, an aqueous solution of 36 g of sodium hydroxide was added for neutralization, and the resulting solution was extracted with ethyl acetate. The extract was washed with an aqueous solution of sodium chloride and then dried over anhydrous sodium sulfate. The residue obtained by distilling the solvent off from the extract was purified by column chromatography through silica gel, from which 1.01 g of the 6β-(3α-hydroxy) compound (which shows two spots on a thin layer chromatogram) could be obtained from the fractions eluted with hexane containing 20–25% by volume of ethyl acetate, while 1.31 g of the 6β-(3α-hydroxy) compound (which also shows two spots on a thin layer chromatogram) could be obtained from the fractions eluted with hexane containing 30–50% by volume of ethyl acetate.

6β-(3β-hydroxy) isomer

Infrared Absorption Spectrum (liquid film) $v_{max}cm^{-1}$: 3380.

Nuclear Magnetic Resonance Spectrum (CDCl$_3$) δ ppm;

0.91 (3H, singlet, CH$_3$);

1.60 (3H, singlet, CH$_3$);

1.68 (3H, singlet, CH$_3$);

3.45 (2H, triplet, —CH$_2$O—);

4.50 (2H, singlet, —CH$_2$—);

5.11 (1H, triplet, =CH—);

5.29 (1H, broad singlet, =CH—);

5.60 (2H, multipier, —CH=CH—);

6β(3α-hydroxy) isomer

Infrared Absorption Spectrum (liquid film)$v_{max}cm^{-1}$: 3360.

Nuclear Magnetic Resonance Spectrum (CDCl$_3$) δ ppm:

0.91 (3H, multipier, CH$_3$);

1.60 (3H, singlet, CH$_3$);

1.66 (3H, singlet, CH$_3$);

3.50 (2H, triplet. —CH$_2$—);

4.51 (2H, singlet, —CH$_2$—);

5.12 (1H, triplet, =CH—);

5.28 (1H, broad singlet, =CH—);

5.50 (2H, multipier, —CH=CH—).

8(c) 3-(5-Benzyloxypentyl)-6β-[3α-(2 -tetrahydropyranyloxy)-5(R),9-dimethyldeca-1,8-dienyl] -(2-tetrahydropyranyloxy)-cis-bicyclo[3,3,0]oct-2-ene 1.21 g of the 6β-(3β-hydroxy) isomer prepared as in step (b) above was treated as described in Example 7(c), and 1.71 g of the title compound was obtained as an oil.

Infrared Absorption Spectrum (liquid film) $v_{max}cm^{-1}$: 1022, 1035.

Nuclear Magnetic Resonance Spectrum (CDCl$_3$) δ ppm:

0.91 (3H, multipier, CH$_3$);

3.45 (2H, triplet, —CH$_2$—);

4.50 (2H, singlet, —CH$_2$—);

4.70 (2H, broad singlet, 2—H of tetrahydropyran×2);

4.90–5.80 (4H, multipier, =CH—×4).

8(d) 3-(5-Hydroxypentyl)-6β-[3α-(2 -tetrahydropyranyloxy)-5(R),9-dimethyldeca-1,8-dienyl] -7α-(2-tetrahydropyranyloxy)-cis-bicyclo[3,3,0]oct-2-ene.

1.62 g of the benzyl compound prepared as described in step (c) above was treated as described in Example 7(d), giving 1.06 g of the title compound as an oil.

Infrared Absorption Spectrum (liquid film)$v_{max}cm^{-1}$: 3350.

Nuclear Magnetic Resonance Spectrum (CDCl$_3$) δ ppm;

0.92 (3H, multipier, CH$_3$);

2.62 (3H, singlet, CH$_3$);

2.69 (3H, singlet, CH$_3$);

4.82 (2H, broad singlet, —OCHO—×2);

5.0–5.8 (4H, multipier, =CH—×4).

8(e) 3-(4-Carboxybutyl)-6β-[3α-(2 -tetrahydropyranyloxy)-5(R),9-dimethyldeca-1,8-dienyl] -7α-(2-tetrahydropyranyloxy)-cis-bicyclo[3,3,0]oct-2-ene 1.0 g of the alcoholic compound prepared as described in step (d) above was treated as described in Example 7(e), giving 521 mg of the title compound as an oil.

Infrared Absorption Spectrum (liquid film) $v_{max}cm^{-1}$: 1734, 1710.

Nuclear Magnetic Resonance Spectrum (CDCl$_3$) δ ppm:

0.92 (3H$_0$ multipier, CH$_3$);

1.62 (3H, singlet, CH$_3$);

1.69 (3H, singlet, CH$_3$);

4.72 (2H, broad singlet, 2—H of tetrahydropyran×2);

5.0–5.8 (4H, multipier, =CH—×4).

8(f) 3-(4-Carboxybutyl)-6β-[3α-hydroxy-5(R),9 -dimethyldeca-1,8-dienyl]-7α-hydroxy-cis-bicyclo-[ 3,3,0]oct-2-ene 505 mg of the dipyranyl compound prepared as described in step (e) above were reacted as described in Example 7(f), to obtain 190 mg of the title compound as an oil.

Infrared Absorption Spectrum (liquid film)$v_{max}cm^{-1}$ : 3350, 1710, 972.

Nuclear Magnetic Resonance Spectrum (CDCl$_3$) δ ppm:

0.91 (3H, doublet, CH$_3$);

1.62 (3H, singlet, CH$_3$);

1.69 (3H, singlet, CH$_3$);

3.72 (1H, multipier, CHOH);

4.15 (1H, multipier, CHOH);

5.11 (1H, triplet, =CH—);

5.34 (1H, broad singlet, =CH—);

5.50 (2H, multipier, —CH=CH—).

This compound could readily be converted into its corresponding methyl ester (infrared absorption spectrum: 1725 cm$^{-1}$) when treated with diazomethane.

EXAMPLE 9

3-(5-Hydroxypentyl)-6β-[3α-hydroxy-5(R),9 -dimethyldeca-1,8-dienyl]-7α-hydroxy-cis-bicyclo-[3,3,0]oct-2-ene 200 mg of 3-(5-hydroxypentyl)-6β-[3α-(2 -tetrahydropyranyloxy)-5(R),9-dimethyldeca-1,8-dienyl] -7α-(2-tetrahydropyranyloxy)-cis-bicyclo[3,3,0]oct-2-ene

[prepared as described in Example 8(d) were reacted as described in Example 7(f), to give 98 mg of the title compound as an oil.

Infrared Absorption Spectrum (CHCl$_3$) $v_{max}cm^{-1}$: 3370. 975.

Nuclear Magnetic Resonance Spectrum (CDCl$_3$) δ ppm:

0.91 (3H, doublet, CH$_3$);

1.59 (3H, singlet, CH$_3$);

1.66 (3H, singlet, CH$_3$);

5.02 (1H, triplet, =CH—);

5.19 (1H, broad singlet, =CH—);

5.40 (2H, multipier, —CH=CH—).

EXAMPLE 10

3-(4-Carboxybutyl)-6β-(3α-hydroxy-4-methylnona-1,8-dienyl)-7α-hydroxy-cis-bicyclo[3,3,0]oct-2-ene 10(a) 3-(5-Benzyloxypentyl)-6β-(3-oxo-4-methylnona-1,8-dienyl)-7α-(2-tetrahydropyranyloxy)-cis-bicyclo[3,3,0]oct-2-ene 540 mg of 3-(5-benzyloxypentyl)-6β-formyl-7α-(2-tetrahydropyranyloxy)-cis-bicyclo[3,3,0]oct-2-ene [prepared as described in Preparation 14 and dimethyl (2-oxo-3-methyl-7-octenyl)phosphonate were reacted as described in Example 7(a), to give 639 mg of the title compound as an oil.

Infrared Absorption Spectrum (liquid film) $v_{max}cm^{-1}$: 1034, 1078, 1120, 1624, 1666, 1692.

Nuclear Magnetic Resonance Spectrum (CDCl$_3$) δ ppm:
1.09 (3H, doublet, J=7.0 Hz, —CH$_3$);
3.47 (2H, triplet, J=6.0 Hz, —CH$_2$O—);
4.51 (2H, singlet, —OCH$_2$—);
4.60–6.10 (5H, multipier, =CH—×4, 2–H of tetrahydropyran);
5.29 (1H, broad singlet, =CH—);
6.25 (1H, doublet of doublets, J=17.0 & 6.0 Hz, =CH—);
6.90 (1H, multipier, =CH—);
7.35 (5H, singlet, phenyl)

10(b) 3-(5-Benzyloxypentyl)-6β-(3α-hydroxy-4-methylnona-1,8-dienyl)-7α-(2-tetrahydropyranyloxy)-cis-bicyclo[3,3,0]oct-2-ene 630 mg of the enone compound prepared as described in step (a) above were reacted as described in Example (b), to give 270 mg of the title compound as an oil.

Infrared Absorption Spectrum (liquid film) $v_{max}cm^{-1}$: 1020, 1072, 1118, 1640, 3450.

Nuclear Magnetic Resonance Spectrum (CDCl$_3$) δ ppm:
0.89 (3H, multipier, CH$_3$);
3.47 (2H, triplet, J=6.0 Hz, —CH$_2$O—);
4.51 (2H, singlet, —OCH$_2$—);
4.68 (1H, broad singlet, 2–H of tetrahydropyran);
4.77–6.10 (6H, multipier, =CH—×6);
7.37 (5H, singlet, phenyl).

10(c) 3-(5-Benzyloxypentyl)-6β-[3α-(2 tetrahydropyranyloxy)-4-methylnona-1,8-dienyl]-7α-(2-tetrahydropyranyloxy)-cis-bicyclo[3,3,0]oct-2-ene 336 mg of the 3α-hydroxy compound prepared as described in step (b) above were reacted as described in Example 7(c), to give 392 mg of the title compound as an oil.

Infrared Absorption Spectrum (liquid film) $v_{max}cm^{-1}$: 1020, 1120, 1640.

Nuclear Magnetic Resonance Spectrum (CDCl$_3$) δ ppm:
0.88 (3H, multiplet, CH$_3$);
3.47 (2H, triplet, J=6.0 Hz, —CH$_2$O—);
4.51 (2H, singlet, —OCH$_2$—);
4.6–6.2 (8H, =CH—×6, 2–H of tetrahydropyran×2);
7.37 (5H, singlet, phenyl).

10(d) 3-(5-Hydroxypentyl)-6β-[3α-(2-tetrahydropyranyloxy)-4-methylnona-1,8-dienyl]-7α-(2-tetrahydropyranyloxy)-cis-bicyclo[3,3,0]oct-2-ene 382 mg of the benzyl compound prepared as described in step (c) above were reacted as described in Example 7(d), to give 308 mg of the title compound as an oil.

Infrared Absorption Spectrum (liquid film) $v_{max}cm^{-1}$: 972, 1020, 1032, 1074, 1118, 1130, 1640, 3450.

Nuclear Magnetic Resonance Spectrum (CDCl$_3$) δ ppm:
0.88 (3H, multipier, CH$_3$);
4.73 (2H, broad singlet, 2–H of tetrahydropyran×2);
4.83–6.10 (6H, multipier, =CH—×6).

10(e) 3-(4-Carboxybutyl)-6β-[3α-(2-tetrahydropyranyloxy)-4-methylnona-1,8-dienyl]-7α-(2-tetrahydropyranyloxy)-cis-bicyclo[3,3,0]oct-2-ene 291 mg of the hydroxy compound prepared as described in step (d) above were reacted as described in Example 7(e), to give 222 mg of the title compound as an oil.

Infrared Absorption Spectrum (liquid film) $v_{max}cm^{-1}$: 980, 1022, 1038, 1080, 1120, 1138, 1642, 1712, 1740.

Nuclear Magnetic Resonance Spectrum (CDCl$_3$) δ ppm:
0.87 (3H, multipier, CH$_3$);
4.73 (2H, broad singlet, 2–H of tetrahydropyran×2);
3.83–6.07 (6H, multipier, =CH—×6).

10(f) 3-(4-Carboxybutyl)-6β-(3α-hydroxy-4-methylnona-1,8-dienyl)-7α-hydroxy-cis-bicyclo[3,3,0]oct-2-ene 212 mg of the dipyranyl compound prepared as described in step (e) above were reacted as described in Example 7(f), to give 91 mg of the title compound as an oil.

Infrared Absorption Spectrum (liquid film) $v_{max}cm^{-1}$: 1640, 1708, 3340.

Nuclear Magnetic Resonance Spectrum (CDCl$_3$) δ ppm:
0.90 (3H, multipier, CH$_3$);
3.50–4.10 (2H, multiplet, CHOH×2);
5.30 (1H, broad singlet, =CH—);
5.52 (2H, multipier, —CH=CH—);
4.4–6.1 (3H, multipier, —CH=CH$_2$).

EXAMPLE 11

3-(4-Carboxybutyl)-6β-(3α-hydroxy-3-cyclohexyl-1-propenyl)-7α-hydroxy-cis-bicyclo[3,3,0]oct-2-ene 11(a) 3-(5-Benzyloxypentyl)-6β-(3-oxo-3-cyclohexyl-1-propenyl)-7α-(2-tetrahydropyranyloxy)-cis-bicyclo[3,3,0]oct-2-ene 515 mg of 3-(5-benzyloxypentyl)-6β-formyl-7α-(2-tetrahydropyranyloxy)-cis-bicyclo[3,3,0]oct-2-ene (prepared as described in Preparation 14) and dimethyl (2-oxo-2-cyclohexylethyl)phosphonate were reacted as described in Example 7(a), to give 548 mg of the title compound as an oil.

Infrared Absorption Spectrum (liquid film) $v_{max}cm^{-1}$: 1622, 1666, 1692.

Nuclear Magnetic Resonance Spectrum (CDCl$_3$) δ ppm:
3.47 (2H, triplet, J=6.0 Hz, —CH$_2$O—);
4.51 (2H, singlet, —OCH$_2$—);
5.28 (1H, broad singlet, =CH—);
6.24 (1H, doublet of doublets, J=15.0 & 4.0 Hz, =CH—);
6.88 (1H, multipier, =CH—);
7.36 (5H, singlet, phenyl).

11(b) 3-(5-Benzyloxypentyl)-6β-(3α-hydroxy-3-cyclohexyl-1-propenyl)-7α-(2-tetrahydropyranyloxy)-cis-bicyclo[3,3,0]oct-2-ene 530 mg of the enone compound prepared as described in step (a) above were reacted as described in Example 7(b), to give 295 mg of the title compound as an oil, and 140 mg of its 3β-hydroxy isomer, also as an oil.

3α-Hydroxy isomer

Infrared Absorption Spectrum (liquid film) $v_{max}cm^{-1}$: 1022, 1076, 1120, 3450.

Nuclear Magnetic Resonance Spectrum (CDCl$_3$) δ ppm:
3.47 (2H, triplet, J=6.0 Hz, —CH$_2$O—);
4.51 (2H, singlet, —OCH$_2$—);
4.69 (1H, broad singlet, 2–H of tetrahydropyran);

5.27 (1H, broad singlet, =CH—);
5.61 (2H, multipier, —CH=CH—);
7.37 (5H, singlet, phenyl).

3β-Hydroxy isomer

Infrared Absorption Spectrum (liquid film) $v_{max}cm^{-1}$: 1022, 1077, 1120, 3450.

Nuclear Magnetic Resonance Spectrum (CDCl$_3$) δ ppm:
3.46 (2H, triplet, J=6 Hz, —CH$_2$O—);
4.50 (2H, singlet, —CH$_2$O—);
4.72 (1H, broad singlet, 2–H of tetrahydropyran);
5.29 (1H, broad singlet, =CH—);
5.63 (2H, multipier, —CH=CH—);
7.38 (5H, singlet, phenyl).

11(c) 3-(5-Benzyloxypentyl)-6β-[3α-(2 -tetrahydropyranyloxy)-3-cyclohexyl-1-propenyl]-7α-(2 -tetrahydropyranyloxy)-cis-bicyclo[3,3,0]oct-2-ene 445 mg of the 3α-hydroxy compound prepared as described in step (b) above were reacted as described in Example 7(c), to give 435 mg of the title compound as an oil.

Infrared Absorption Spectrum (liquid film) $v_{max}cm^{-1}$: 975, 1022, 1035.

Nuclear Magnetic Resonance Spectrum (CDCl$_3$) δ ppm:
3.47 (2H, triplet, J=6 Hz, —CH$_2$O—);
4.51 (2H, singlet, —CH$_2$O—);
4.75 (2H, broad singlet, 2–H of tetrahydropyran×2);
5.0–5.8 (3H, multipier, =CH—×3);
7.33 (5H, singlet, phenyl).

11(d) 3-(5-Hydroxypentyl)-6β-[3α-(2 -tetrahydropyranyloxy)-3-cyclohexyl-1-propenyl]-7α-(2 -tetrahydropyranyloxy)-cis-bicyclo[3,3,0]oct-2-ene 420 mg of the benzyl compound prepared as described in step (c) above were reacted as described in Example 7(d), to give 317 mg of the title compound as an oil.

Infrared Absorption Spectrum (liquid film) $v_{max}cm^{-1}$: 3450.

Nuclear Magnetic Resonance Spectrum (CDCl$_3$) δ ppm:
4.72 (2H, broad singlet, 2–H of tetrahydropyran×2);
5.1–5.8 (3H, multipier, =CH—×3);

11(e) 3-(4-Carboxybutyl)-6β-[3α-(2 -tetrahydropyranyloxy)-3-cyclohexyl-1-propenyl]-7α-(2 -tetrahydropyranyloxy)-cis-bicyclo[3,3,0]oct-2-ene 300 mg of the hydroxy compound prepared as described in step (d) above were reacted as described in Example 7(e), to give 211 mg of the title compound as an oil.

Infrared Absorption Spectrum (liquid film) $v_{max}cm^{-1}$: 1705, 1738.

Nuclear Magnetic Resonance Spectrum (CDCl$_3$) δ ppm:
4.73 (2H, broad singlet, 2–H of tetrahydropyran×2);
5.1–5.8 ( 3H, multipier, =CH—, —CH=CH— );

11(f) 3-(4-Carboxybutyl)-6β-(3α-hydroxy-3-cyclohexyl-1-propenyl)-7α-hydroxy-cis-bicyclo[ 3,3,0]oct-2-ene 195 mg of the dipyranyl compound prepared as described in step (e) above were reacted as described in Example 7(f), to give 94 mg of the title compound in the form of an oil. After leaving this compound in a refrigerator, crystals of the compound were obtained, melting at 77°–79° C.

Infrared Absorption Spectrum (CHCl$_3$) $v_{max}cm^{-1}$: 976, 1709, 3350.

Nuclear Magnetic Resonance Spectrum (CDCl$_3$) δ ppm:
5.34 (1H, broad singlet, =CH—);
5.50 (2H, multipier, —CH=CH—).

EXAMPLE 12

3-(4-Carboxybutyl)-6β-(3α-hydroxy-4,7-dimethylocta-1,6-dienyl)-7α-hydroxy-cis-bicyclo[3,3,0]oct-2-ene 12(a) 3-(5-Benzyloxypentyl)-6β-(3-oxo-4,7 -dimethylocta-1,6-dienyl)-7α-(2-tetrahydropyranyloxy)-cis-bicyclo[3,3,0]oct-2-ene 290 mg of crude 3-(5-benzyloxypentyl)-6β-formyl-7α-(2-tetrahydropyranyloxy)-cis-bicyclo[3,3,0] -oct-2-ene (prepared as described in Preparation 14) and dimethyl (2-oxo-3,6-dimethyloct-5-enyl)phosphonate were reacted as described in Example 7(a), to give 310 mg of the title compound as an oil.

Infrared Absorption Spectrum (liquid film) $v_{max}cm^{-1}$: 1624, 1665, 1692.

Nuclear Magnetic Resonance Spectrum (CDCl$_3$) δ ppm:
3.47 (2H, triplet, —CH$_2$O—);
4.50 (2H, singlet, —CH$_2$O—);
4.8–5.4 (2H, multipier, =CH—×2);
6.17 (1H, doublet of doublets, J=17 Hz & 5 Hz, =CH—);
6.5–7.2 (1H, multipier, =CH—).

12(b) 3-(5-Benzyloxypentyl)-6β-(3α-hydroxy-4,7 -dimethylocta-1,6-dienyl)-7α-(2-tetrahydydropyranyloxy)-cis-bicyclo[ 3,3,0]oct-2-ene 310 mg of the ketone compound prepared as described in step (a) above were reacted as described in Example 7(b), to give 157 mg of the title compound and 61 mg of its 3β-hydroxy isomer, both in the form of oils.

3α-Hydroxy isomer

Infrared Absorption Spectrum (liquid film) $v_{max}cm^{-1}$: 3450.

Nuclear Magnetic Resonance Spectrum (CDCl$_3$) δ ppm:
0.88 (3H, multipier, CH$_3$);
3.47 (2H, triplet, —CH$_2$O—);
4.50 (2H, singlet, —CH$_2$O—);
4.70 (1H, broad singlet, 2–H of tetrahydropyran);
5.0–5.6 (4H, multipier, =CH—×4);
7.37 (5H, singlet, phenyl).

12(c) 3-(5-Benzyloxypentyl)-6β-[3α-(2 -tetrahydropyranyloxy)-4,7-dimethylocta-1,6-dienyl]-7α -(2-tetrahydropyranyloxy)-cis-bicyclo[3,3,0]oct-2-ene 300 mg of the 3β-hydroxyl compound prepared as described in step (b) above were reacted as described in Example 7(c), to give 327 mg of the title compound as an oil.

Infrared Absorption Spectrum (liquid film) $v_{max}cm^{-1}$: 1020, 1120.

Nuclear Magnetic Resonance Spectrum (CDCl$_3$) δ ppm:
0.89 (3H, multipier, CH$_3$);
3.46 (2H, triplet, —CH$_2$O—);
4.51 (2H, singlet, —CH$_2$O—);
4.70 (2Ho broad singlet, 2–H of tetrahydropyran×2);
4.90–5.80 (4H, multiplet, =CH—×4)

12(d) 3-(5-Hydroxypentyl)-6β-[3α-(2 -tetrahydropyranyloxy)-4,7-dimethylocta-1,6-dienyl]-7α-(2 -tetrahydropyranyloxy)-cis-bicyclo[3,3,0]oct-2-ene 380 mg of the dipyranyl compound prepared as described in step (c) above were reacted as described in Example 7(d), to give 297 mg of the title compound as an oil.

Infrared Absorption Spectrum (liquid film) $v_{max}cm^{-1}$ : 3350.

Nuclear Magnetic Resonance Spectrum (CDCl$_3$) δ ppm:
0.91 (3H, multipier, CH$_3$);
2.61 (3H, singlet, CH$_3$);
2.69 (3H, singlet, CH$_3$);
4.80 (2H, broad singlet, 2–H of tetrahydropyran×2);
5.0–5.8 (4H, multipier, =CH—×2, —CH=CH— ).

12(e) 3-(4-Carboxybutyl)-6β-[3α-(2 -tetrahydropyranyloxy)-4,7-dimethylocta-1,6-dienyl] -7α-(2-tetrahydropyranyloxy)-cis-bicyclo[3,3,0]oct-2 -ene 556 mg of the hydroxy compound prepared as described in step (d) above were reacted as described in Example 7(e), to give 241 mg of the title compound as an oil.

Infrared Absorption Spectrum (liquid film) $\nu_{max}$cm$^{-1}$: 1734, 1709.

Nuclear Magnetic Resonance Spectrum (CDCl$_3$) δ ppm:
0.91 (3H, multipier, CH$_3$);
1.62 (3H, singlet, CH$_3$);
1.69 (3H, singlet, CH$_3$);
5.0–5.8 (4H, multipier, =CH—×20 —CH=CH— ).

12(f) 3-(4-Carboxybutyl)-6β-(3α-hydroxy-4,7-dimethylocta-1,6-dienyl)-7α-hydroxy-cis-bicyclo-[3,3,0]oct-2-ene.

231 mg of the dipyranyl compound prepared as described in step (e) above were reacted as described in Example 7(f), to give 99 mg of the title compound as an oil.

Infrared Absorption Spectrum (liquid film) $\nu_{max}$cm$^{-1}$: 972, 1709, 3350.

Nuclear Magnetic Resonance Spectrum (CDCl$_3$) δ ppm:
0.90 (3H, multipier, CH$_3$);
1.62 (3H, singlet, CH$_3$);
1.68 (3H, singlet, CH$_3$);
3.71 (1H, multipier, CHOH);
4.14 (1H, multipier, CHOH);
5.11 (1H, triplet, =CH—);
5.34 (1H, broad singlet, =CH—);
5.52 (2H, multipier, —CH=CH—).

EXAMPLE 13

A mixture of 3-(4-carboxybutyl)-6β-(3α-hydroxy-3-cyclohexyl-1-propenyl)-7α-hydroxy-cis-bicyclo[3,3,0]oct-2(3)-ene 13(a) A mixture of 3-(5-benzyloxypentyl)-6β-(3-oxo-3-cyclohexyl-1-propenyl)-7α-(2-tetrahydropyranyloxy)-cis-bicyclo[3,3,0]oct-2(3)-ene 2.92 g of 3-(5-benzyloxy-pentyl)-6β-formyl-7α -(2-tetrahydropyranyloxy)-cis-bicyclo[3,3,0]oct-2(3)-ene (prepared as described in Preparation 8 and dimethyl (2-oxo-2-cyclohexylethyl)- phosphonate were reacted as described in Example 1(a), to give 3.59 g of the title compound in the form of an oil.

Infrared Absorption Spectrum (liquid film) $\nu_{max}$cm$^{-1}$: 1622, 1664, 1692.

Nuclear Magnetic Resonance Spectrum (CDCl$_3$) δ ppm:
3.47 (2H, triplet, J=6.0 Hz, —CH$_2$O—);
4.51 (2H, singlet, —OCH$_2$—);
5.29 (1H, broad singlet, =CH—);
6.25 (1H, doublet of doublets, J=17.0 & 5.0 Hz, =CH—);
6.90 (1H, multipier, =CH—);
7.36 (5H, singlet, phenyl).

13(b) A mixture of 3-(5-benzyloxypentyl)-6β-(3α -hydroxy-3-cyclohexyl-1-propenyl)-7α-(2 -tetrahydropyranyloxy)-cis-bicyclo[3,3,0]oct-2(3)-ene 3.56 g of the enone compound prepared as described in step (a) above were reacted as described in Example 1(b), to give 1.65 g of the title compound in the form of an oil and 1.25 g of its 3β-hydroxy isomer, also as an oil.

3a-Hydroxy isomer

Infrared Absorption Spectrum (liquid film) $\nu_{max}$cm$^{-1}$: 1022, 1078, 1120, 3450.

Nuclear Magnetic Resonance Spectrum (CDCl$_3$) δ ppm:
3.45 (2H, triplet, J=8.0 Hz, —CH$_2$O— );
4.50 (2H, singlet, —OCH$_2$—);
4.67 (1H, broad singlet, 2–H of tetrahydropyran);
5.27 (1H, broad singlet, =CH—);
5.60 (2H, multipier, —CH=CH—);
7.33 (5H, singlet, phenyl).

3β-Hydroxy isomer

Infrared Absorption Spectrum (liquid film) $\nu_{max}$cm$^{-1}$: 1022, 1078, 1120, 3450.

Nuclear Magnetic Resonance Spectrum (CDCl$_3$) δ ppm;
3.46 (2H, triplet, —CH$_2$O—);
4.51 (2H, singlet, —CH$_2$O—);
4.67 (1H, broad singlet, 2–H of tetrahydropyran);
5.29 (1H, broad singlet, =CH—);
5.62 (2H, multipier, —CH=CH—);
7.34 (5H, singlet, phenyl).

13(c) A mixture of 3-(5-benzyloxypentyl)-6β-[3α-(2-tetrahydropyranyloxy)-3-cyclohexyl-1-propenyl)-7α-(2-tetrahydropyranyloxy)-cis-bicyclo[3,3,0]oct-2(3)-ene 1.63 g of the 3β-hydroxy compound prepared as described in step (b) above were reacted as described in Example 1(c), to give 1.89 g of the title compound in the form of an oil.

Infrared Absorption Spectrum (liquid film) $\nu_{max}$cm$^{-1}$: 1022, 1080, 1120.

Nuclear Magnetic Resonance Spectrum (CDCl$_3$) δ ppm:
3.47 (2H, triplet, J=6.0 Hz, —CH$_2$O—);
4.50 (2H, singlet, —OCH$_2$—);
4.70 (2H, broad singlet, 2–H of tetrahydropyran×2);
5.1–6.0 (3H, multipier, =CH—×3);
7.33 (5H, singlet, phenyl).

13(d) A mixture of 3-(5-hydroxypentyl)-6β-[3α-(2-tetrahydropyranyloxy)-3-cyclohexyl-1-propenyl]-7α-(2-tetrahydropyranyloxy)-cis-bicyclo[3,3,0]oct-2(3)-ene 1.88 g of the benzyl compound prepared as described in step (c) above were reacted as described in Example 1(d), to give 1.36 g of the title compound in the form of an oil.

Infrared Absorption Spectrum (liquid film) $\nu_{max}$cm$^{-1}$: 978, 1022, 1078, 1120, 1134, 3450.

Nuclear Magnetic Resonance Spectrum (CDCl$_3$) δ ppm:
4.70 (2H, broad singlet, 2–H of tetrahydropyran×2);
5.28 (1H, broad singlet, =CH—);
5.1–5.8 (2H, multiplet, —CH=CH—).

13(e) A mixture of 3-(4-carboxylbutyl)-6β-[3α-(2-tetrahydropyranyloxy)-3-cyclohexyl-1-propenyl]-7α-(2-tetrahydropyranyloxy)-cis-bicyclo[3,3,0]oct-2(3)-ene 1.34 g of the hydroxy compound prepared as described in step (d) above were reacted as described in Example 1(e), to give 1.16 g of the title compound in the form of an oil.

Infrared Absorption Spectrum (liquid film) $\nu_{max}$cm$^{-1}$: 978, 1020, 1078, 1120, 1134, 1705, 1738.

Nuclear Magnetic Resonance Spectrum (CDCl$_3$) δ ppm:
4.73 (2H, broad singlet, 2–H of tetrahydropyran×2);
5.30 (1H, broad singlet, =CH—);
5.10–5.80 (2H, multipier, —CH=CH—).

13(f) A mixture of 3-(4-carboxybutyl)-6β-(3α -hydroxy-3-cyclohexyl-1-propenyl)-7α-hydroxy-cis-bicyclo[3,3,0]oct-2(3)-ene 1.14 g of the dipyranyl compound prepared as described in step (e) above were reacted as described in Example 1(f), to give 0.46 g of the title compound in the form of an oil.

Infrared Absorption Spectrum (CHCl$_3$) $\nu_{max}$cm$^{-1}$: 1705, 3400.

Nuclear Magnetic Resonance Spectrum (CDCl$_3$) δ ppm:

3.50–3.95 (2H, multipier, CHOH×2);

5.30 (1H, broad singlet, =CH—);

5.50 (2H, multiplet, —CH=CH—).

EXAMPLE 14

3-(4-Carboxybutyl)-6β(3α-hydroxy-3-cyclopentyl-1-propenyl)-7α-hydroxy-cis-bicyclo[3,3,0]oct-2-ene (a) 3-(5-Benzyloxypentyl)-6β-(3-oxo-3-cyclopentyl-1-propenyl)-7α-(2-tetrahydropyranyloxy)-cis-bicyclo-[ 3,3,0]-oct-2-ene The procedure described in Example 1(a) was repeated, but using 74 mg of a 55% w/w suspension of sodium hydride in oil, 418 mg of dimethyl(2-oxo-2-cyclopentylethyl)phosphonate and a solution of 469 mg of 3-(5-benzyloxypentyl)-6β-formyl-7α-(2-tetrahydropyranyloxy)-cis-bicyclo[ 3,3,0] oct-2-ene (prepared as described in preparation 14) dissolved in 3 ml of tetrahydrofuran.

There were obtained 503 mg of the title compound as an oil.

Infrared Absorption Spectrum (liquid film) $v_{max}cm^{-1}$: 1120, 1625, 1665, 1690.

Nuclear Magnetic Resonance Spectrum (CDCl$_3$) δ ppm:

3.48 (2H, triplet, J=6.0 Hz, —CH$_2$O—benzyl);

4.52 (2H, singlet, OCH$_2$-phenyl);

5.30 (1H, singlet, =CH—);

6.23 (1H, doublet of doublets, J=17.0 & 5.0 Hz, =CH—);

6.90 (1Ho multiplet, =CH—);

7.38 (5H, singlet, phenyl).

(b) 3-(5-Benzyloxypentyl)-6β-(3α-hydroxy-3-cyclo-pentyl- 1-propenyl)-7α-(2-tetrahydropyranyloxy)-cis-bicyclo[3,3,0]oct-2-ene A solution of 484 mg of the enone compound obtained as described in step (a) above in 7 ml of methanol was added to a solution of 430 mg of cerium chloride heptahydrate in 4 ml of methanol, with ice cooling. The reaction mixture was cooled down to −20° C., and then 62 mg of sodium borohydride were added and the mixture was stirred for 15 minutes at the same temperature.

Upon completion of the reaction, the reaction mixture was poured into water and then extracted with ethyl acetate. The extract was washed with a saturated aqueous solution of sodium chloride and dried over anhydrous sodium sulphate. The solvent was then distilled off from the reaction product, giving 498 mg of a residue. This residue was purified by silica gel column chromatography, to give 262 mg of the title compound as an oil from the fraction with higher polarity, and 184 mg of the 3β-hydroxy isomer from the fraction with a lower polarity.

The infrared, nuclear magnetic resonance and mass spectra of the 3α-hydroxy isomer were essentially the same as those of the product of Example 4(b).

3β-Hydroxy isomer

Infrared Absorption Spectrum (liquid film) $v_{max}cm^{-1}$: 1025, 1074, 1120, 3450.

(c) 3-(5-Benzyloxypentyl)-6β-[3α-(2-tetrahydropyranyloxy)- 3-cyclopentyl-1-propenyl]-7α-(2-tetrahydropyranyloxy)-cis-bicyclo[ 3,3,0]oct-2-ene The procedure described in Example 1(c) was repeated, but using 379 mg of the 3α-hydroxy compound prepared as described in step (b) above. 425 mg of the title compound were obtained as an oil. The nuclear magnetic resonance spectrum of this product was essentially the same as reported for the product of Example 4(c).

Infrared Absorption Spectrum (liquid film) $v_{max}cm^{-1}$: 1025, 1080, 1120.

(d) 3-(5-Hydroxypentyl)-6β-[3α-(2-tetrahydropyranyloxy)-3-cyclopentyl-1-propenyl]-7α-(2-tetrahydropyranyloxy)-cis-bicyclo[3,3,0]oct-2-ene The procedure described in Example 1(d) was repeated, but using 415 mg of the benzyl ether produced as described in step (c) above. There were obtained 339 mg of the title compound. The nuclear magnetic resonance spectrum of this product was essentially the same as that of the product of Example 4(d).

Infrared Absorption Spectrum (liquid film) $v_{max}cm^{-1}$: 3430.

(e) 3-(4-Carboxybutyl)-6β-[3α-(2-tetrahydropyranyloxy)-3-cyclopentyl-1-propenyl]-7α-(2-tetrahydropyranyloxy)-cis-bicyclo[3,3,0]oct-2-ene 0.6 ml of Jones' reagent (prepared by diluting 26.7 g of chromic anhydride and 23 ml of concentrated sulphuric acid with water to a total volume of 100 ml) was dissolved in 10 ml of acetone, and the solution was cooled to −25° C. To this solution, was added dropwise a solution of 329 mg of the alcohol compound prepared as described in step (d) above in 15 ml of acetone, and the mixture was stirred for 80 minutes a the same temperature. Upon completion of the reaction, isopropanol was added, and the mixture was neutralized with a 5% w/v aqueous solution of sodium bicarbonate; a saturated aqueous solution of sodium chloride was then added. The mixture was extracted with diethyl ether, and the extract was washed with water and dried over anhydrous sodium sulphate. The solvent was distilled off from the mixture under reduced pressure, leaving 342 mg of residue. This residue was purified by silica gel column chromatography, giving 217 mg of the title compound as an oil. The nuclear magnetic resonance spectrum of this product was essentially the same as that of the product of Example 4(e).

Infrared Absorption Spectrum (liquid film) $v_{max}cm^{-1}$: 980, 1025, 1120, 1135, 1710, 1735, 3100.

(f) 3-(4-Carboxybutyl)-6β-(3α-hydroxy-3-cyclopentyl-1-propenyl)-7α-hydroxy-cis-bicyclo[3,3,0]oct-2-ene The procedure described in Example 1(f) was repeated, but using 207 mg of the tetrahydropyranyl compound prepared as described in step (e) above. After the silica gel column chromatography, the product was recrystallized from a mixture of ethyl acetate and hexane, giving 75 mg of the title compound as crystals melting at 108°–110° C.

Infrared Absorption Spectrum (CHCl$_3$) $v_{max}cm^{-1}$: 975, 1710, 3300.

Nuclear Magnetic Resonance Spectrum (CDCl$_3$) δ ppm:

5.33 (1H, broad singlet, —CH=);

5.50 (5H, multiplet, —CH=CH—, OH×2, COOH).

EXAMPLE 15

3-(4-Carboxybutyl)-6β-[3α-hydroxy-5(R),9-dimethyl-deca- 1,8-dienyl]-7α-hydroxy-cis-bicyclo[3,3,0]oct-2-ene (a) 3-(5-Benzyloxypentyl)-6β[3-oxo-5(R),9-dimethyl-deca- 1,8-dienyl]-7α-(2-tetrahydropyranyloxy)-cis-bicyclo-[3,3,0]oct-2-ene 2.91 g of the crude 3-(5-benzyloxypentyl)-6β -formyl-7α-(2-tetrahydropyranyloxy)-cis-bicyclo[3,3,0] -oct-2-ene (prepared as described in preparation 14) and 3.49 g of dimethyl [2—oxo-4(R),8-dimethylnon-1-enyl]phosphonate were reacted as described in Example 1(a), to give 3.16 g of the title compound as an oil.

Infrared Absorption Spectrum (liquid film) $v_{max}cm^{-1}$: 1625, 1665, 1690.

Nuclear Magnetic Resonance Spectrum (CDCl$_3$) δ ppm:

0.90 (3H, multipier, CH$_3$);

3.48 (2H, triplet, —CH$_2$O—);

4.50 (2H, singlet, —CH$_2$—);

4.8–5.4 (2H, multipier, =CH—×2);

6.18 (1H, doublet of doublets, J=16.5 Hz, =CH—);

6.5–7.2 (1H, multipier, =CH—).

(b) 3-(5-Benzyloxypentyl)-6β-[3α-hydroxy-5(R),9 -dimethyldeca-1,8-dienyl]-7α-hydroxy-cis-bicyclo[3,3,0] -oct-2-ene and its 6β-(3β-hydroxy)isomer The procedure described in Example 1(b) was repeated, but using 3.1 g of the ketone compound prepared as described in step (a) above. From the fractions eluted with hexane containing 20–25% by volume of ethyl acetate were obtained 1.01 g of the 6β-(3β-hydroxy) isomer as an oil (having 2 spots on a thin layer column chromatogram). From the fractions eluted with hexane containing 30–50% by volume of ethyl acetate were obtained 1.31 g of the 6β-(3α-hydroxy) isomer, also as an oil (having 2 spots on a thin layer chromatogram).

6β-(3β-hydroxy) isomer

Infrared Absorption Spectrum (liquid film) $v_{max}$cm$^{-1}$: 3380.

Nuclear Magnetic Resonance Spectrum (CDCl$_3$) δ ppm:

0.91 (3H, singlet, CH$_3$);

1.60 (3H, singlet, CH$_3$);

1.68 (3H, singlet, CH$_3$);

3.45 (2H, triplet, —CH$_2$O—);

4.50 (2H, singlet, —CH$_2$—);

5.11 (1H, triplet, =CH—);

5.29 (1H, broad singlet, =CH—);

5.60 (2H, multipier, —CH=CH—).

6β-(3α-hydroxy) isomer

Infrared Absorption Spectrum (liquid film) $v_{max}$cm$^{-1}$: 3360.

Nuclear Magnetic Resonance Spectrum (CDCl$_3$) δ ppm:

0.91 (3H, multipier, CH$_3$);

1.60 (3H, singlet, CH$_3$);

1.66 (3H, singlet, CH$_3$);

3.50 (2H, triplet, —CH$_2$—);

4.51 (2H, singlet, —CH$_2$—);

5.12 (1Ho triplet, =CH—);

5.28 (1Ho broad singlet, =CH—);

5.50 (2H, multipier, —CH=CH—).

(c) 3-(5-Benzyloxypentyl)-6β-[3α-(2-tetrahydropyranyloxy)-5(R),9-dimethyldeca-1,8-dienyl]-7α-(2 -tetrahydropyranyloxy)-cis-bicyclo[3,3,0]oct-2-ene 1.21 g of the 6β-(3α-hydroxy) isomer prepared as described in step (b) above was reacted as described in Example 1(c). to give 1.71 g of the title compound as an oil.

Infrared Absorption Spectrum (liquid film) $v_{max}$cm$^{-1}$: 1022. 1035.

Nuclear Magnetic Resonance Spectrum (CDCl$_3$) δ ppm:

0.91 (3H, multiplet, CH$_3$);

3.45 (2H, triplet, —CH$_2$—);

4.50 (2H, singlet, —CH$_2$—);

4.70 (2H, broad singlet, 2–H of tetrahydropyran×2);

4.90–5.8 (4H, multipier, =CH—×4).

(d) 3-(5-Hydroxypentyl)-6β-[3α-(2-tetrahydropyranyloxy-5(R),9-dimethyldeca-1,8-dienyl]-7α -(2-tetrahydropyranyloxy)-cis-bicyclo[3,3,0]oct-2-ene 1.62 g of the benzyl compound prepared as described in step (c) above was reacted as described in Example 1(d) to give 1.06 g of the title compound as an oil.

Infrared Absorption Spectrum (liquid film) $v_{max}$cm$^{-1}$: 3350.

Nuclear Magnetic Resonance Spectrum (CDCl$_3$) δ ppm:

0.92 (3H, multipier, CH$_3$);

2.62 (3H, singlet, CH$_3$);

2.69 (3H, singlet, CH$_3$);

4.82 (2H, broad singlet, 2–H of tetrahydropyran×2);

5.0–5.8 (4H, multipier, =CH—×4).

(e) 3-(4-Carboxybutyl)-6β-[3α-(2-tetrahydropyranyloxy)-5(R),9-dimethyldeca-1,8-dieneyl]-7α-(2-tetrahydropyranyloxy)-cis-bicyclo[ 3,3,0]oct-2-ene 1.0 g of the alcoholic compound prepared as described in step (d) above was reacted as described in Example 14(e), to give 521 mg of the title compound as an oil.

Infrared Absorption Spectrum (liquid film) $v_{max}$cm$^{-1}$: 1734, 1710.

Nuclear Magnetic Resonance Spectrum (CDCl$_3$) δ ppm:

0.92 (3Ho multipier, CH$_3$);

1.62 (3H, singlet, CH$_3$);

1.69 (3H, singlet, CH$_3$);

4.72 (2H, broad singlet, 2–H of tetrahydropyran×2);

5.0–5.8 (4H, multipier, =CH—×4).

(f) 3-(4-Carboxybutyl)-6β-[3α-hydroxy-5(R),9-dimethyl-1,8-decadienyl]-7α-hydroxy-cis-bicyclo[3,3,0]oct-2-ene 505 mg of the dipyranyl compound prepared as described in step (e) above were reacted as described in Example 14(f), to give 190 mg of the title compound in the form of an oil.

Infrared Absorption Spectrum (liquid film) $v_{max}$cm$^{-1}$: 3350, 1710, 972.

Nuclear Magnetic Resonance Spectrum (CDCl$_3$) δ ppm:

0.91 (3H, doublet, CH$_3$);

1.62 (3H, singlet, CH$_3$) ]

1.69 (3H, singlet, CH$_3$);

3.72 (1H, multipier, C$\underline{H}$OH);

4.15 (1H, multipier, C$\underline{H}$OH);

5.11 (1H, triplet, =C$\underline{H}$—);

5.34 (1H, broad singlet, =CH—);

5.50 (2H, multipier, —CH=CH—).

This compound could be readily converted into its methyl ester (infrared absorption spectrum $v_{max}$: 1725 cm$^{-1}$) by treatment with diazomethane.

EXAMPLE 16

3-(5-Hydroxypentyl)-6β-[3α-hydroxy-5(R),9-dimethlyldeca-1,8-dienyl]-7α-hydroxy-cis-bicyclo[3,3,0]oct-2-ene 200 mg of 3-(5-hydroxypentyl)-6β-[3α-(2 -tetrahydropyranyloxy)-5(R),9-dimethyldeca-1,8-dienyl] -7α-(2-tetrahydropyranyloxy)-cis-bicyclo[3,3,0]oct-2-ene prepared as described in Example 15(d) ] were reacted as described in Example 14(f), to give 98 mg of the title compound as an oil. The infrared and nuclear magnetic resonance spectra of this product were the same as those of the product of Example 3.

EXAMPLE 17

3-(4-Carboxybutyl)-6β-(3α-hydroxy-4-methylnona-1,8 -dienyl)-7α-hydroxy-cis-bicyclo[3,3,0]oct-2-ene 17(a) 3-(5-Benzyloxypentyl)-6β-(3-oxo-4-methylnona-1, 8-dienyl)-7α-(2-tetrahydropyranyloxly)-cis-bicyclo[ 3,3,0]oct-2-ene 540 mg of 3-(5-benzyloxypentyl)-6β-formyl-7α -(2-tetrahydropyranyloxy)-cis-bicyclo[3,3,0]oct-2-ene prepared as described in preparation 14) and 500 mg of dimethyl (2-oxo-3-methyl-7-octenyl)phosphonate were reacted as described in Example 1(a), to give 639 mg of the title compound as an oil.

Infrared Absorption Spectrum (liquid film) $v_{max}cm^{-1}$: 1034, 1078, 1120, 1624, 1666, 1692.

Nuclear Magnetic Resonance Spectrum (CDCl$_3$) δ ppm:
1.09 (3H, doublet, J=7.0 Hz, —CH$_3$ );
3.47 (2H, triplet, J=6.0 Hz, —CH$_2$ O— );
4.51 (2H, singlet, —OCH$_2$—);
4.60–6.10 (5H, multipier, =CH—×4, 2–H of tetrahydropyran);
5.29 (1H, broad singlet, =CH—);
6.25 (1H, doublet of doublets, J=17.0 & 6.0 Hz, =CH—);
6.90 (1H, multipier, =CH—);
7.35 (5H, singlet, phenyl).

17(b) 3-(5-Benzyloxypentyl)-6β-(3α-hydroxy-4-methylnona-1,8-dienyl)-7α-(2-tetrahydropyranyloxy)-cis-bicyclo[3,3,0]oct-2-ene.

630 mg of the enone compound prepared as described in step (a) above were reacted as described in Example 1(b), to give 270 mg of the title compound as an oil.

Infrared Absorption Spectrum (liquid film) $v_{max}cm^{-1}$: 1020, 1072, 1118, 1640, 3450.

Nuclear Magnetic Resonance Spectrum (CDCl$_3$) δ ppm:
0.89 (3H, multiplet, CH$_3$);
3.47 ( 2H, triplet, J=6.0 Hz, —CH$_2$O—);
4.51 (2H, singlet, —OCH$_2$—);
4.68 (1H, broad singlet, 2–H of tetrahydropyran);
4.77–6.10 (6H, multipier, =CH—×6);
7.37 (5H, singlet, phenyl).

17(c) 3-(5-Benzyloxypentyl)-6β-[3α-(2 -tetrahydropyranyloxy)-4-methylnona-1,8-dienyl]-7α-(2 -tetrahydropyranyloxy)-cis-bicyclo[3,3,0]oct-2-ene 336 mg of the 3β-hydroxy compound prepared as described in step (b) above were reacted as described in Example 1(c), to give 392 mg of the title compound as an oil.

Infrared Absorption Spectrum (liquid film) $v_{max}cm^{-1}$: 1020, 1120, 1640.

Nuclear Magnetic Resonance Spectrum (CDCl$_3$) δ ppm:
0.88 (3H, multipier, CH$_3$);
3.47 (2H, triplet, J=6.0 Hz, —CH$_2$O—);
4.51 (2H, singlet, —OCH$_2$—);
4.6–6.2 (8H, multipier, =CH—×6, 2–H of tetrahydropyran×2);
7.37 (5H, singlet, phenyl).

17(d) 3-(5-Hydroxypentyl)-6β-[3α-(2 -tetrahydropyranyloxy)-4-methylnona-1,8-dienyl]-7α-(2 -tetrahydropyranyloxy)-cis-bicyclo[3,3,0]oct-2-ene.

382 mg of the benzyl compound prepared as described in step (c) above were reacted as described in Example 1(d), to give 308 mg of the title compound as an oil.

Infrared Absorption Spectrum (liquid film) $v_{max}cm^{-1}$: 972, 1020, 1032, 1074, 1118, 1130, 1640, 3450.

Nuclear Magnetic Resonance Spectrum (CDCl$_3$) δ ppm:
0.88 (3H, multipier, CH$_3$);
4.73 (2H, broad singlet, 2–H of tetrahydropyran×2);
4.83–6.10 (6H, multipier, =CH—×6).

17(e) 3-(4-Carboxybutyl)-6β-[3α-(2 -tetrahydropyranyloxy)-4-methylnona-1,8-dienyl]-7α-(2 -tetrahydropyranyloxy)-cis-bicyclo[3,3,0]oct-2-ene 291 mg of the hydroxy compound prepared as described in step (d) above were reacted as described in Example 4(e), to give 222 mg of the title compound as an oil.

Infrared Absorption Spectrum (liquid film) $v_{max}cm^{-1}$ : 980, 1022, 1038, 1080, 1120, 1138, 1642, 1712, 1740.

Nuclear Magnetic Resonance Spectrum (CDCl$_3$) δ ppm:
0.87 (3H, multipier, CH$_3$);
4.73 (2H, broad singlet, 2–H of tetrahydropyran×2);
4.83–6.07 (6H, triplet, =CH—×6).

17(f) 3-(4-Carboxybutyl)-6β-(3α-hydroxy-4 -methylnona-1,8-dienyl)-7α-hydroxy-cis-bicyclo-[ 3,3,0]oct-2-ene 212 mg of the dipyranyl compound prepared as described in step (e) above were reacted as described in Example 14(f) 0 to give 91 mg of the title compound as an oil.

Infrared Absorption Spectrum (liquid film) $v_{max}cm^{-1}$: 1640, 1708, 3340.

Nuclear Magnetic Resonance Spectrum (CDCl$_3$) δ ppm:
0.90 (3H, multipier, CH$_3$);
3.50–4.10 (2H, multipier, CHOH×2);
5.30 (1H, broad singlet, =CH—);
5.52 (2H, multipier, —CH=CH—);
4.4–6.1 (3H, multipier, —CH=CH$_2$).

EXAMPLE 18

3-(4-Carboxybutyl)-6β-(3α-hydroxynona-1,8-dienyl)-7α-hydroxy-cis-bicyclo[3,3,0]oct-2-ene 18(a) 3-(5-Benzyloxypentyl)-6β-(3-oxonona-1,8 -dienyl)-7α-(2-tetrahydropyranyloxy)-cis-bicyclo-[ 3,3,0]oct-2-ene 300 mg of 3-(5-benzyloxypentyl)-6β-formyl-7α-(2-tetrahydropyranyloxy)-cis-bicyclo[3,3,0]oct-2 -ene prepared as described in preparation 14) and 310 mg of dimethyl (2-oxo-7-octenyl)phosphonate were reacted as described in Example 1(a), to give 317 mg of the title compound as an oil.

Infrared Absorption Spectrum (liquid film) $v_{max}cm^{-1}$ : 1624, 1666, 1692.

Nuclear Magnetic Resonance Spectrum (CDCl$_3$) δ ppm:
3.47 ( 2H, triplet, J=6.0 Hz, —CH$_2$O—);
4.51 (2H, singlet, —OCH$_2$—);
4.60–6.10 (5H, multipier, =CH—×4, 2–H of tetrahydropyran);
5.29 (1H, broad singlet, =CH—);
6.25 (1H, doublet of doublets, J=17.0 & 6.0 Hz, =CH—);
6.90 (1H, multipier, =CH—);
7.35 (5H, singlet, phenyl).

18(b) 3-(5-Benzyloxypenty1)-6β-(3α-hydroxynona-1,8-dienyl)-7α-(2-tetrahydropyranyloxy)-cis-bicyclo[ 3,3,0]oct-2-ene 300 mg of the enone compound prepared as described in step (a) above were reacted as described in Example 1(b), to give 141 mg of the title compound as an oil.

Infrared Absorption Spectrum (liquid film) $v_{max}cm^{-1}$: 1118, 1640, 3450.

Nuclear Magnetic Resonance Spectrum (CDCl$_3$) δ ppm:
3.47 (2H, triplet, J=6.0 Hz, —CH$_2$O—);
4.51 (2H, singlet, —OCH$_2$—);
4.68 (1H, broad singlet, 2–H of tetrahydropyran);
4.77–6.10 (6H, multipier, =CH—×6);
7.37 (5H, singlet, phenyl).

18(c) 3-(5-Benzyloxypentyl)-6β-[3α-(2 -tetrahydropyranyloxy)nona-1,8-dienyl]-7α-(2 -tetrahydropyranyloxy)-cis-bicyclo[3,3,0]oct-2-ene 330 mg of the 3α-hydroxy compound prepared following the procedure described in step (b) above were reacted as described in Example 1(c), to give 390 mg of the title compound as an oil.

Infrared Absorption Spectrum (liquid film) $v_{max}cm^{-1}$: 1640.

Nuclear Magnetic Resonance Spectrum (CDCl$_3$) δ ppm:

3.47 (2H, triplet, J=6 Hz, —CH$_2$O—);

4.51 (2H, singlet, —OCH$_2$—);

4.6–6.20 (8H, multipier, =CH—×6; 2–H of tetrahydropyran×2);

7.37 (5H, singlet, phenyl).

18(d) 3-(5-Hydroxypentyl)-6β-[3α-(2-tetrahydropyranyloxy)nona-1,8-dienyl]-7α-(2 -tetrahydropyranyloxy)-cis-bicyclo[3,3,0]oct-2-ene 380 mg of the benzyl compound prepared as described in step (c) above were reacted as described in Example 1(d), to give 300 mg of the title compound as an oil.

Infrared Absorption Spectrum (liquid film) $v_{max}cm^{-1}$: 973, 1640, 3450.

Nuclear Magnetic Resonance Spectrum (CDCl$_3$) δ ppm:

4.73 (2H, broad singlet, 2–H of tetrahydropyran);

4.83–6.10 (6H, multipier, =CH—×6).

18(e) 3-(4-Carboxybutyl)-6β-[3α-(2 -tetrahydropyranyloxy)nona-1,8-dienyl]-7α-(2 -tetrahydropyranyloxy)-cis-bicyclo[3,3,0]oct-2-ene 290 mg of the hydroxy compound prepared as described in step (d) above were reacted as described in Example 14(e), to give 220 mg of the title compound as an oil.

Infrared Absorption Spectrum (liquid film) $v_{max}cm^{-1}$: 980, 1642, 1712, 1740.

Nuclear Magnetic Resonance Spectrum (CDCl$_3$) δ ppm:

4.73 (2H, broad singlet, 2–H of tetrahydropyran×2);

3.83–6.07 (6H, multipier, =CH—×6).

18(f) 3-(4-Carboxybutyl)-6β-(3α-hydroxynona-1,8-dienyl)-7α-hydroxy-cis-bicyclo[3,3,0]oct-2-ene 202 mg of the dipyranyl compound prepared as described in step (e) above were reacted as described in Example 14(f), to give 90 mg of the title compound as an oil.

Infrared Absorption Spectrum (CHCl$_3$) $v_{max}cm^{-1}$: 1640, 1708, 3340.

Nuclear Magnetic Resonance Spectrum (CDCl$_3$) δ ppm:

3.50–4.10 (2H, multipier, CHOH×2);

5.30 (1H, broad singlet, =CH—);

5.52 (2H, multipier, —CH=CH—);

4.4–6.1 (3H, multipier, —CH=CH$_2$).

EXAMPLE 19

3-(4-Carboxybutyl)-6β-(3α-hydroxy-4-cyclopentyl-1 -butenyl)-7α-hydroxy-cis-bicyclo[3,3,0]oct-2-ene 19(a) 3-(5-Benzyloxypentyl)-6β-(3-oxo, 4-cyclopentyl-1-butenyl)-7α-(2-tetrahydropyranyloxy)bicyclo[3,3,0]oct-2-ene 60 mg of crude 3-(5-benzyloxypentyl)-6α -formyl-7α-(2-tetrahydropyranyloxy)-cis-bicyclo-[ 3,3,0]oct-2-ene (prepared as described in preparation and 408 mg of dimethyl (2-oxo-3-cyclopentylpropyl)- phosphonate were reacted as described in Example 1(a), to give 491 mg of the title compound as an oil.

Infrared Absorption Spectrum (liquid film) $v_{max}cm^{-1}$: 625, 1665, 1690.

Nuclear Magnetic Resonance Spectrum (CDCl$_3$) δ ppm:

3.48 (2H, triplet, J=6.0 Hz, —CH$_2$OCH$_2$-phenyl);

4.52 (2H, singlet, —OCH$_2$-phenyl);

5.30 (1H, singlet, =CH—);

6.23 (1H, doublet of doublets: J=17.0 & 5.0 Hz, =CH—);

6.90 (1H, multipier, =CH—);

7.38 (5H, singlet, phenyl).

19(b) 3-(5-Benzyloxypentyl)-6β-(3α-hydroxy-4-cyclopentyl-1-butenyl)-7a-(2-tetrahydropyranyloxy)-cis-bicyclo[3,3,0]oct-2-ene 480 mg of the enone compound prepared as described in step (a) above were reacted as described in Example 1(b), to give 498 mg of the title compound in crude form.

On purification of this compound by silica gel column chromatography, 260 mg of the title substance in the form of an oil and 173 mg of its 3β-hydroxy isomer were obtained from the fractions with higher and lower polarities, respectively, eluted with hexane containing 5–30% and 20–25% by volume of ethyl acetate, respectively.

3α-Hydroxy isomer

Infrared Absorption Spectrum (liquid film) $v_{max}cm^{-1}$: 3450.

Nuclear Magnetic Resonance Spectrum (CDCl$_3$) δ ppm:

3.47 (2H, triplet, J=6.0 Hz, CH$_2$OCH$_2$-phenyl);

4.52 (2H, singlet, —OCH$_2$-phenyl);

4.70 (1H, broad singlet, 2–H of tetrahydropyran);

5.28 (1H, broad singlet, =CH—);

5.65 (2H, multipier, =CH—×2);

7.36 (5H, singlet, phenyl).

3β-Hydroxy isomer

Infrared Absorption Spectrum (liquid film) $v_{max}cm^{-1}$ : 1120, 3450.

19(c) 3-(5-Benzyloxypentyl)-6β-[3α-(2 -tetrahydropyranyloxy)-4-cyclopentyl-1-butenyl]-7α-(2 -tetrahydropyranyloxy)-cis-bicyclo[3,3,0]-oct-2-ene 379 mg of the 3β-hydroxy compound prepared in the manner described in step (b) above were reacted as described in Example 1(c), to give 482 mg of the crude title compound. This was purified by silica gel column chromatography to give 405 mg of the title compound as an oil from the fractions eluted with hexane containing 0–14% by volume of ethyl acetate.

Infrared Absorption Spectrum (liquid film) $v_{max}cm^{-1}$: 1025, 1080. 1120.

Nuclear Magnetic Resonance Spectrum (CDCl$_3$) δ ppm;

3.46 (2H, triplet. J=6.0 Hz, —CH$_2$OCH$_2$-phenyl);

4.51 (2H, singlet, OCH$_2$-phenyl);

4.74 (2H, broad singlet, 2–H of tetrahydropyran×2);

5.27 (1H, broad singlet, =CH—);

5.62 (2H, multipier, —CH=CH—);

7.36 (5H, singlet, phenyl).

19(d) 3-(5-Hydroxypentyl)-6β-[3α-(2 -tetrahydropyranyloxy)-4-cyclopentyl-1-butenyl)-7α-(2 -tetrahydropyranyloxy)-cis-bicyclo[3,3,0]oct-2-ene 405 mg of the benzyl ether compound prepared as described in step (c) above were reacted as described in Example 1(d), to give a crude substance. This substance was purified by silica gel column chromatography, to give 325 mg of the title compound as an oil from the fractions eluted with hexane containing 20–25% by volume of ethyl acetate.

Infrared Absorption Spectrum (liquid film) $v_{max}cm^{-1}$: 3430.

Nuclear Magnetic Resonance Spectrum (CDCl$_3$) δ ppm:

4.75 (2H, broad singlet, 2–H of tetrahydropyran×2);

5.30 (1H, broad singlet, =CH—);

5.65 (2H, multiplet, =CH—×2).

19(e) 3-(4-Carboxybutyl)-6β-[3α-(2-tetrahydropyranyloxy)-4-cyclopentyl-1-butenyl]-7α-(2-tetrahydropyranyloxy)-cis-bicyclo[3,3,0]oct-2-ene 313 mg of the alcoholic compound prepared as described in step (d) above were reacted as described in Example 14(e), to give 342 mg of a crude substance. This substance was purified by silica gel column chromatography, to give 192 mg of the title compound as an oil from the fractions eluted with hexane containing 20–25% by volume of ethyl acetate.

Infrared Absorption Spectrum (liquid film) $\nu_{max}$cm$^{-1}$: 980, 1710, 1735, 3100.

Nuclear Magnetic Resonance Spectrum (CDCl$_3$) δ ppm:

4.73 (2H, broad singlet, 2–H of tetrahydropyran×2);

5.30 (1H, broad singlet, =CH—);

5.50 (2H, multiplet, —CH=CH—).

19(f) 3-(4-Carboxybutyl)-6β-(3α-hydroxy-4-cyclopentyl-1-butenyl)-7α-hydroxy-cis-bicyclo[3,3,0]oct-2-ene 200 mg of the tetrahydropyranyl compound prepared as described in step (e) above were reacted as described in Example 14(f), to give 180 mg of a crude substance. This substance was purified by silica gel column chromatography, to give 75 mg of the title compound as an oil from the fractions eluted with hexane containing 40–85% by volume of ethyl acetate.

Infrared Absorption Spectrum (CHCl$_3$) $\nu_{max}$cm$^{-1}$: 975, 1710, 3300.

Nuclear Magnetic Resonance Spectrum (CDCl$_3$) δ ppm:

5.33 (1H, broad singlet, —CH=);

5.50 (5H, multipier, —CH=CH—, OH×2, COOH)

EXAMPLE 20

3-(4-Carboxybutyl)-6β-(3α-hydroxy-4-methyloct-6-yn-1-enyl)-7α-hydroxy-cis-bicyclo[3,3,0]oct-2-ene 20(a) 3-(4-Methoxycarbonylbutyl)-6α-(3-oxo-4-methyloct-6-yn-1-enyl)-7α-(2-tetrahydropyranyloxy)-cis-bicyclo[3,3,0]oct-2-ene 180 mg of crude 3-(4-methoxycarbonylbutyl)-6α-formyl-7α-(2-tetrahydropyranyloxy)-cis-bicyclo-[3,3,0]oct-2-ene (prepared as described in preparation 36) and 163 mg of dimethyl (2-oxo-3-methylhept-5-ynyl)-phosphonate were reacted as described in Example 1(a), to give 175 mg of the title compound as an oil.

Infrared Absorption Spectrum (liquid film) $\nu_{max}$cm$^{-1}$: 1630, 1670, 1695, 1740, 2330.

Nuclear Magnetic Resonance Spectrum (CDCl$_3$) δ ppm:

1.28 (3H, doublet, J=6 Hz, CH$_3$);

1.73 (3H, triplet, CH$_3$);

3.64 (3H, singlet, CH$_3$);

4.58 (1H, broad singlet, 2–H of tetrahydropyran);.

5.25 (1H, broad singlet, =CH—);

5.95–7.20 (2H, multipier, —CH=CH—).

20(b) 3-(4-Methoxycarbonylbutyl)-6β-(3α-hydroxy-4-methyloct-6-yn-1-enyl)-7α-(2-tetrahydropyranyloxy)-cis-bicyclo[3,3,0]oct-2-ene 175 mg of the ketone compound prepared as described in step (a) above were reacted as described in Example 1(b), to give 50 mg of the 3β-hydroxy isomer of the title compound and 80 mg of the title compound as oils from the fractions with low and high polarity, respectively.

3α-Hydroxy isomer

Infrared Absorption Spectrum (liquid film) $\nu_{max}$cm$^{-1}$: 3460, 1741, 1022, 1033.

Nuclear Magnetic Resonance Spectrum (CDCl$_3$) δ ppm:

0.95 (3H, doublet, J=6 Hz, CH$_3$);

1.85 (3H, triplet, J=3 Hz, CH$_3$);

3.62 (3H, singlet, CH$_3$);

4.60 (1H, broad singlet, 2–H of tetrahydropyran);

5.22 (1H, broad singlet, =CH—);

5.52 (2H, multipier, —CH=CH—).

3β-Hydroxy isomer:

Infrared Absorption Spectrum (liquid film) $\nu_{max}$cm$^{-1}$: 3460, 1741, 1022, 1033.

Nuclear Magnetic Resonance Spectrum (CDCl$_3$) δ ppm:

0.97 (3H, multipier, CH$_3$);

1.78 (3H, triplet, J=3 Hz, CH$_3$);

3.68 (3H, singlet, CH$_3$);

4.67 (1H, broad singlet, 2–H of tetrahydropyran);

5.29 (1H, broad singlet, =CH—);

5.60 (2H, multipier, —CH=CH—).

20(c) 3-(4-Carboxybutyl)-6β-(3α-hydroxy-4-methyloct-6-yn-1-enyl)-7α-(2-tetrahydropyranyloxy)-cis-bicyclo[3,3,0]oct-2-ene A mixture of 75 mg of the ester compound prepared as described in step (b) above and 5 ml of a 5% w/v solution of potassium hydroxide in 30% v/v aqueous methanol was stirred at room temperature for 2.25 hours. Upon completion of the reaction, ice-water was added to the reaction mixture, which was then acidified slightly with 3.5% w/v hydrochloric acid and extracted with ethyl acetate. The extract was washed with a saturated aqueous solution of sodium chloride and dried over anhydrous sodium sulfate. On distilling the solvent off from the reaction mixture, 70 mg of the title compound were obtained as an oil.

Infrared Absorption Spectrum (liquid film) $\nu_{max}$cm$^{-1}$: 3430, 1730, 1716.

Nuclear Magnetic Resonance Spectrum (CDCl$_3$) δ ppm:

0.98 (3H, doublet, J=6 Hz, CH$_3$);

1.77 (3H, triplet, J=3 Hz, CH$_3$);

4.66 (1H, broad singlet, 2–H of tetrahydropyran;

5.26 (1H, broad singlet, =CH—);

5.58 (2H, multipier, —CH=CH—).

20(d) 3-(4-Carboxybutyl)-6β-(3α-hydroxy-4-methyloct-6-yn-1-enyl)-7α-hydroxy-cis-bicyclo-[3,3,0]oct-2-ene 70 mg of the carbonic acid prepared as described in step (c) above were reacted as described in Example 14(f), to give 50 mg of the title compound as an oil.

Infrared Absorption Spectrum (liquid film) $\nu_{max}$cm$^{-1}$: 3370, 1712, 975.

Nuclear Magnetic Resonance Spectrum (CDCl$_3$) δ ppm:

0.98 (3H, multipier, CH$_3$);

1.78 (3H, broad singlet, CH$_3$);

3.40–4.32 (2H, multipier, CHOH×2);

5.27 (1H, broad singlet, =CH—);

5.51 (2H, multipier, —CH=CH—).

EXAMPLE 21

A mixture of 3-[2-(carboxymethoxy)ethyl]-6β-[3α-hydroxy-5(R),9-dimethyldeca-1,8-dienyl]-7α-hydroxy-cis-bicyclo[3,3,0]oct-2(3)-ene 21(a) A mixture of 3-[2-(carboxymethoxy)ethyl]-6β-[3α-(2-tetrahydropyranyloxy)-5(R),9-dimethyldeca-1,8-dienyl]-7α-(2-tetrahydropyranyloxy)-cis-bicyclo[3,3,0]oct-2(3)-ene 105 mg of a mixture of 3-(2-hydroxyethyl)-6β-[3α-(2-tetrahydropyranyloxy)-5(R),9-dimethyldeca- 1,8-dienyl]-7α-(2-tetrahydropyranyloxy)-cis-bicyclo[ 3,3,0]oct-2(3)-ene (prepared as described in Example 6) were dissolved in a mixture of 1.5 ml of dimethyl sulfoxide and 1.5 ml of dimethylformamide. To the solution were added 96 mg of a 55% w/w suspension of sodium hydride in oil, and the mixture was then stirred at room temperature for 30 minutes. 596 mg of lithium chloroacetate were added, and the mixture was stirred for 22 hours. The reaction mixture was then poured into ice-water, acidified with acetic acid and extracted with ethyl acetate. The extract was washed with an aqueous solution of sodium chloride and then with water and dried over anhydrous sodium sulfate. The solvent was distilled off and the resulting residue was purified by thin layer chromatography (plate: 2 mm thick, 20 cm.×cm.:silica gel). The developing solvent was hexane containing a small amount of a 1:1 by volume mixture of acetic acid and ethyl acetate.

38 mg of the starting material were recovered from the fractions having a lower polarity. 28 mg of the title compound were obtained as an oil from the fractions having a higher polarity.

Infrared Absorption Spectrum (liquid film) $v_{max}cm^{-1}$: 1720, 1750.

Nuclear Magnetic Resonance Spectrum (CDCl$_3$) δ ppm;

0.92 (3H, multipier, CH$_3$);

3.63 (2H, triplet, J=7 Hz, —CH$_2$O—);

4.07 (2H, singlet, —OCH$_2$—);

4.68 (2H, broad singlet, 2–H of tetrahydropyran×2);

5.07 (1H, broad triplet, J=6 Hz, =CH—);

5.2–5.8 (3H, multipier, —HC=×3).

21(b) 3-[2-(Carboxymethoxy)ethyl]-6β-[3α -hydroxy-5(R),9-dimethyldeca-1,8-dienyl]-7α-hydroxy-cis-bicyclo[ 3,3,0]oct,2(3)-ene To a solution of 200 mg of the mixture of 3-[2 -(carboxymethoxy)ethyl]-6β-[3α-(2-tetrahydropyranyloxy)-5(R),9-dimethyldeca-1,8-dienyl]-7α-(2 -tetrahydropyranyloxy)-cis-bicyclo[3,3,0]oct-2(3)-ene, prepared as described in step (a) above in 6 ml of acetone were added 20 mg of camphorsulfonic acid. Water was added to the mixture until the mixture became cloudy. The mixture was then stirred at 50° C. for 3.5 hours, and then diluted with an aqueous solution of sodium chloride and extracted with ethyl acetate. The extract was washed with an aqueous solution of sodium chloride and dried over anhydrous sodium sulfate. The solvent was distilled off and the residue was purified by column chromatography through 5 g of silica gel. There were obtained 137 mg of a mixture of the oily oct-2-ene and oct-3-ene compounds from the fractions eluted with ethyl acetate and hexane in volume ratios gradually increasing from 20:80 to 100:0.

Infrared Absorption Spectrum (liquid film) $v_{max}cm^{-1}$: 975, 1735, 3360.

Nuclear Magnetic Resonance Spectrum (CDCl$_3$) δ ppm:

0.92 (3H, doublet, J=6 Hz, CH$_3$);

1.61 (3H, singlet, CH$_3$);

1.69 (3H, singlet, CH$_3$);

3.4–4.5 (2H, multipier, CHOH×2);

3.77 (2H, triplet, J=6 Hz, —CH$_2$—);

4.08 (2H, singlet, —CH$_2$—);

5.11 (1H, triplet, J=6 Hz, =CH—);

5.39 (1H, broad singlet, =CH—);

5.53 (2H, multipier, —CH=CH—).

This mixture was purified by high-pressure liquid chromatography and the pure oct-2-ene and oct-3-ene compounds were obtained separately. The column used was an octadecyl-chemical bond type silica gel column and the solvent was a 45:55 by volume mixture of 0.05M aqueous phosphoric acid and acetonitrile.

oct-2-ene compound

Infrared Absorption Spectrum (CHCl$_3$) $v_{max}cm^{-1}$: 1735, 3370, 973.

Nuclear Magnetic Resonance Spectrum (CDCl$_3$) δ ppm;

0.92 (3H, doublet, J=6 Hz, CH$_3$);

1.61 (3H, singlet, CH$_3$);

1.69 (3H, singlet, CH$_3$);

3.4–4.5 (2H, multipier, CHOH×2);

3.77 (2H, triplet, J=6 Hz, —CH$_2$O—);

4.08 (2H, singlet, —CH$_2$O—);

5.11 (1H, triplet, J=6 Hz, =CH—);

5.39 (1H, singlet, =CH—);

5.53 (2H, multipier, —CH=CH—).

oct-3-ene compound

Infrared Absorption Spectrum (CHCl$_3$) $v_{max}cm^{-1}$: 1735, 3370, 973.

Nuclear Magnetic Resonance Spectrum (CDCl$_3$) δ ppm:

0.92 (3H, doublet, J=6 Hz, CH$_3$);

1.61 (3H, singlet, CH$_3$);

1.69 (3H, singlet, CH$_3$);

3.4–4.5 (2H, multipier, CHOH×2);

3.77 (2H, triplet, J=6 Hz, —CH$_2$O—);

4.08 (2H, singlet, —CH$_2$O—);

5.11 (1H, triplet, J=6 Hz, =CH—);

5.39 (1H, singlet, =CH—);

5.53 (2H, multipier, —CH=CH—).

EXAMPLE 22

A mixture of 3-[2—(carboxymethoxy)ethyl]-6β -(3α-hydroxyoct-1-enyl)-7α-hydroxy-cis-bicyclo[ 3,3,0]oct-2(3)-ene 22(a) A mixture of 3-[2-(carboxymethoxy)ethyl] -6β-[3α-(2-tetrahydropyranyloxy)oct-1-enyl]-7α-(2 -tetrahydropyranyloxy)-cis-bicyclo[3,3,0]oct-2(3)-ene The procedure described in Example 21(a) was repeated, but using 110 mg of a mixture of 3-(2-hydroxyethyl)-6β-[3α-(2-tetrahydropyranyloxy)oct- 1-enyl]-7α-(2-tetrahydropyranyloxy)-cis-bicyclo[3,3,0] -oct-2(3)-ene (prepared as described in preparation 37), to obtain 31 mg of the title compound as an oil.

Infrared Absorption Spectrum (liquid film) $v_{max}cm^{-1}$: 1720, 1750.

Nuclear Magnetic Resonance Spectrum (CDCl$_3$) δ ppm:

0.90 (3H, triplet, CH$_3$);

3.62 (2H, triplet, J=7 Hz, —CH$_2$O—);

4.07 (2H, singlet, —CH$_2$O—);

4.67 (2H, broad singlet, 2–H of tetrahydropyran×2);

5.2–5.8 (3H, multipier, =CH—×3).

22(b) A mixture of 3-[2-(carboxymethoxy)ethyl- 6β-(3α-hydroxyoct-1-enyl)-7α-hydroxy-cis-bicyclo[ 3,3,0]oct-2(3)-ene The procedure described in Example 21(b) was repeated, but using 152 mg of a mixture of 3-[2—(carboxymethoxy)ethyl]-6β-[3α-(2 -tetrahydropyranyloxy)oct-1-enyl]-7α-(2 -tetrahydropyranyloxy)-cis-bicyclo[3,3,0]oct-2(3)-ene, prepared as described in step (a) above, to give 95 mg of the title compound as an oil.

Infrared Absorption Spectrum (liquid film) $v_{max}$cm$^{-1}$: 973, 1733, 3360.

Nuclear Magnetic Resonance Spectrum (CDCl$_3$) δ ppm:
0.90 (3H, triplet, CH$_3$);
3.75 (2H, triplet, J=6 Hz, —CH$_2$O—);
4.08 (2H, singlet, —CH$_2$O—);
5.41 (1H, broad singlet, =CH—);
5.53 (2H, multipier, —CH=CH—).

EXAMPLE 23

A mixture of 3-[2-(carboxymethoxy)ethyl]-6β -(3α-hydroxy-4-methyloct-1-enyl)-7α-hydroxy-cis-bicyclo[ 3,3,0] oct-2(3)-ene The procedure described in Example 21(a) and 21(b) was repeated, but using 162 mg of a mixture of 3-(2-hydroxyethyl)-6β-[3α-(2-tetrahydropyranyloxy)-4 -methyloct-1-enyl]-7α-(2-tetrahydropyranyloxy)-cis-bicyclo[ 3,3,0]oct-2(3)-ene, prepared as described in preparation 38, to give 36 mg of the title compound as an oil.

Infrared Absorption Spectrum (liquid film) $v_{max}$cm$^{-1}$ : 1730, 3360, 974.

EXAMPLE 24

A mixture of 3-[2-(carboxymethoxy)ethyl]-6β -(3α-hydroxy-5-methylnon-1-enyl)-7α-hydroxy-cis-bicyclo[ 3,3,0] oct-2(3)-ene The procedure described in Example 21(a) and 21(b) was repeated, but using 105 mg of a mixture of 3-(2-hydroxyethyl)-6β-[3α-(2-tetrahydropyranyloxy)-5 -methylnon-1-enyl]-7α-(2-tetrahydropyranyloxy)-cis-bicyclo[3,3,0]oct-2(3)-ene, prepared as described in preparation 39, to give 23 mg of the title compound as an oil.

Infrared Absorption Spectrum (CHCl$_3$) $v_{max}$cm$^{-1}$: 972, 1730, 3350.

EXAMPLE 25

A mixture of 3-(2-hydroxyethyl)-6β-[3α-(2 -tetrahydropyranyloxy)-4-methylnona-1,8-dienyl]-7α-(2 -tetrahydropyranyloxy)-cis-bicyclo[3,3,0] oct-2(3)-ene The procedure described in Example 6(a) and 6(b) was repeated, but using 512 mg of 3-methoxycarbonylmethylidene-6β-[3α-(2-tetrahydropyranyloxy)-4-methylnona-1,8-dienyl]-7α-(2-tetrahydropyranyloxy)-cis-bicyclo[ 3,3,0] octane, to give 196 mg of the title compound as an oil.

Infrared Absorption Spectrum (liquid film) $v_{max}$cm$^{-1}$: 3350, 1032, 1022, 974.

EXAMPLE 26

A mixture of 3-[2-(carboxymethoxy)ethyl]-6β -(3α-hydroxy-4-methylnona-1,8-dienyl)-7α-hydroxy-cis-bicyclo[ 3,3,0]oct-2(3)-ene 26(a) A mixture of 3-[2-(carboxymethoxy)ethyl]-6β -[3α-(2-tetrahydropyranyloxy)-4-methylnona- 1,8-dienyl] -7α-(2-tetrahydropyranyloxy)-cis-bicyclo[3,3,0]oct- 2(3)-ene The procedure described in Example 21(a) was repeated, but using 430 mg of a mixture of 3-(2 -hydroxyethyl)-6β-[3α-(2-tetrahydropyranyloxy)-4 -methylnona-1,8-dienyl]-7α-(2-tetrahydropyranyloxy)-cis-bicyclo[3,3.01oct-2(3)-ene, prepared as described in Example 25° to give 102 mg of the title compound as an oil.

Infrared Absorption Spectrum (liquid film) $v_{max}$cm$^{-1}$: 1640, 1720, 1745.

Nuclear Magnetic Resonance Spectrum (CDCl$_3$) δ ppm:
0.91 (3H, multipier, CH$_3$);
3.62 (2H, triplet, —CH$_2$O—);
4.07 (2H, singlet, —CH$_2$O—);
4.70 (2H, broad singlet, 2–H of tetrahydropyran);
4.82–6.20 (6H, multipier, —CH=CH—, CH=CH$_2$, =CH—).

26(b) A mixture of 3-[2-(carboxymethoxy)ethyl]-6β -(3α-hydroxy-4-methylnona-1,8-dienyl)-7α-hydroxy-cis-bicyclo[ 3,3,0]oct-2(3)-ene The procedure described in Example 21(b) was repeated, but using 100 mg of a mixture of 3-[2-(carboxymethoxy)ethyl]-6β-[3α-(2 -tetrahydropyranyloxy)-4-methylnona-1, 8-dienyl]-7α-(2 -tetrahydropyranyloxy)-cis-bicyclo[3,3,0] oct-2(3)-ene, prepared as described in step (a) above, to give 59 mg of the title compound as an oil.

Infrared Absorption Spectrum (liquid film) $v_{max}$cm$^{-1}$ : 973, 1638, 1735, 3370.

Nuclear Magnetic Resonance Spectrum (CDCl$_3$) δ ppm:
0.90 (3H, multipier, CH$_3$);
3.76 (2H, triplet, —CH$_2$O—);
4.08 (2H, singlet, —CH$_2$O—);
3.4–4.3 (2H, multipier, CHOH×2);
5.32 (1H, broad singlet, =CH—);
5.53 (2H, multipier, —CH=CH—) =
4.3–6.2 (3H, multipier, —CH=CH$_2$).

This compound was treated with diazomethane to give the corresponding methyl ester.

Infrared Absorption Spectrum (liquid film) $v_{max}$cm$^{-1}$: 973, 1638. 1740, 3380.

EXAMPLE 27

A mixture of 3-(2-hydroxyethyl)-6β-[3α-(2 -tetrahydropyranyloxy)-4,7-dimethylocta-1,6-dienyl]-7α -(2-tetrahydropyranyloxy)-cis-bicyclo[3,3,0]oct-2(3)-ene The procedure described in Example 6(a) and 6(b) was repeated, but using 457 mg of 3-methoxycarbonylmethylidene- 6β-[3α-(2-tetrahydropyranyloxy)-4,7 -dimethylocta-1,6-dienyl]-7α-(2-tetrahydropyranyloxy)-cis-bicyclo[ 3,3,0]octane, to give 159 mg of the title compound as an oil.

Infrared Absorption Spectrum (liquid film) $v_{max}$cm$^{-1}$ : 3350, 1032, 1022, 974.

EXAMPLE 28

A mixture of 3-[2-(carboxymethoxy)ethyl] -6β-(3α-hydroxy-4,7-dimethylocta-1,6-dienyl)-7α -hydroxy-cis-bicyclo[3,3,0]oct-2(3)-ene 28(a) A mixture of 3-[2—(carboxymethoxy)ethyl]-6β -[3α-(2-tetrahydropyranyloxy)-4,7-dimethylocta-1,6 -dienyl]-7α-(2-tetrahydropyranyloxy)-cis-bicyclo[ 3,3.01oct-2(3)-ene The procedure described in Example 21(a) was repeated, but using 150 mg of a mixture of 3-(2-hydroxyethyl)-6β- [3α-(2-tetrahydropyranyloxy)-4,7-dimethylocta-1,6-dienyl] -7α-(2 -tetrahydropyranyloxy)-cis-bicyclo[3,3,0]-2(3)-ene, prepared as described in Example 27, to give 53 mg of the title compound as an oil.

Infrared Absorption Spectrum (liquid film) $v_{max}$cm$^{-1}$ : 1720, 1750.

Nuclear Magnetic Resonance Spectrum (CDCl$_3$) δ ppm:

0.90 (3H, multipier, CH$_3$);

3.45 (2H, triplet, —CH$_2$O—);

4.51 (2H, singlet, —CH$_2$O—);

4.70 (2H, broad singlet, 2-H of tetrahydropyran×2);

5.0–5.8 (4H, multipier, =CH—×2, —CH=CH— ).

28(b) A mixture of 3-[2-(carboxymethoxy)ethyl]-6β -(3α-hydroxy-4,7-dimethylocta-1,6-dienyl)-7α-hydroxy-cis-bicyclo[3,3,0]oct-2(3)-ene The procedure described in Example 21(b) was repeated, but using 124 mg of a mixture of 3-[2-(carboxymethoxy)ethyl]-6β-[3α-(2 -tetrahydropyranyloxy)-4,7-dimethylocta-1,6-dienyl]-7α -(2-tetrahydropyranyloxy)-cis-bicyclo[3,3,0]oct-2(3)-ene, prepared as described in step (a) above, to give 75 mg of the title compound as an oil.

Infrared Absorption Spectrum (liquid film) $v_{max}$cm$^{-1}$ : 971, 1707, 3350.

Nuclear Magnetic Resonance Spectrum (CDCl$_3$) δ ppm:

0.90 (3H, multiplet, CH$_3$);

3.75 (2H, triplet, —CH$_2$O—);

4.09 (2H, singlet, —CH$_2$O—);

3.4–4.4 (2H, multipier, CHOH×2);

5.11 (1H, triplet, =CH—);

5.38 (1H, broad singlet, =CH—);

5.53 (2H, multipier, —CH=CH—).

EXAMPLE 29

A mixture of 3-(2-hydroxyethyl)-6β-[3α-(2 -tetrahydropyranyloxy)-9-methyldeca-1,8-dienyl]-7α-(2 -tetrahydropyranyloxy)-cis-bicyclo[3,3,0]oct-2(3)-ene The procedure described in Example 6(a) and 6(b) was repeated, but using 941 mg of 3-methoxycarbonylmethylidene- 6β-[3α-(2-tetrahydropyranyloxy)-9-methyldeca-1, 8-dienyl]-7α-(2-tetrahydropyranyloxy)-cis-bicyclo[3,3,0]octane, to give 387 mg of the title compound as an oil.

Infrared Absorption Spectrum (liquid film) $v_{max}$cm$^{-1}$ : 3350, 1032, 1022, 973.

EXAMPLE 30

A mixture of 3-[2-(carboxymethoxy)etyl]-6β -(3α-hydroxy-9-methyldeca-1,8-dienyl)-7α-hydroxy-cis-bicyclo[3, 3,0]oct-2(3)-ene The procedure described in Example 21(a) and 21(b) was repeated, but using 150 mg of 3-(2-hydroxyethyl)-6β-[3α-(2-tetrahydropyranyloxy)-9 -methyldeca-1,8-dienyl]-7α-(2-tetrahydropyranyloxy)-cis-bicyclo[3,3,0]oct-2(3)-ene, prepared as described in Example 29, to give 39 mg of the title compound as an oil.

Infrared Absorption Spectrum (liquid film)$v_{max}$cm$^{-1}$: 974, 1735, 3350.

EXAMPLE 31

A mixture of 3-(2-hydroxyethyl)-6β-[3α-(2-tetrahydropyranyloxy)-4-methyloct-1-en-6 -ynyl]-7α-(2-tetrahydropyranyloxy)-cis-bicyclo[3,3,0]oct-2(3)-ene The procedure described in Example 6(a) and 6(b) was repeated, but using 543 mg of 3-methoxycarbonylmethylidene-6β-[3α-(2-tetrahydropyranyloxy)-4 -methyloct-1-en-6-ynyl]-7α-(2-tetrahydropyranyloxy)-cis-bicyclo-[3,3,0]octane, to give 210 mg of the title compound as an oil.

Infrared Absorption Spectrum (liquid film)$v_{max}$cm$^{-1}$: 3350, 1032, 1022, 974.

EXAMPLE 32

A mixture of 3-[2-(carboxymethoxy)ethyl]-6β-(3α-hydroxy-4-methyloct-1-en-6 -ynyl )-7α-hydroxy-cis-bicyclo[3,3,0]oct-2(3)-ene 32(a) A mixture of 3-[2-(carboxymethoxy)ethyl]-6β-[3α-(2-tetrahydropyranyloxy)-4 -methyloct-1-en-6-ynyl]-7α-(2-tetrahydropyranyloxy)-cis-bicyclo[3,3,0]oct-2(3)-ene The procedure described in Example 21(a) was repeated, but using 103 mg of a mixture of 3-(2 -hydroxyethyl)-6β-[3α-(2-tetrahydropyranyloxy)-4-methyloct-1-en-6-ynyl]-7α-(2 -tetrahydropyranyloxy)-cis-bicyclo[3,3,0oct-2(3)-ene, prepared as described in Example 31, to give 41 mg of the title compound as an oil.

Infrared Absorption Spectrum (liquid film)$v_{max}$cm$^{-1}$: 1718, 1750.

Nuclear Magnetic Resonance Spectrum (CDCl$_3$)δppm:

0.95 (3H, multiplet, CH$_3$);

1.79 (3H, triplet, J=1.5 Hz, CH$_3$);

3.61 (2H, triplet, J=7 Hz, —CH$_2$O—);

4.06 (2H, singlet, —CH$_2$)—);

4.67 (2H, broad singlet, 2-H of tetrahydropyran×2);

5.2–5.8 (3H, multiplet, =CH—, —CH=CH—).

32(b) A mixture of 3-[2-(carboxymethoxy)ethyl]-6β-(3α-hydroxy-4-methyloct-1 -en-6-ynyl)-7α-hydroxy-cis-bicyclo[3,3,0]oct-2(3)-ene The procedure described in Example 21(b) was repeated, but using 100 mg of a mixture of 3-[2-(carboxymethoxy)ethyl]-6β-[3α-(2 -tetrahydropyranyloxy)-4-methyloct-1-en-6-ynyl]-7α-(2-tetrahydropyranyloxy)-cis-bicyclo[3,3,0 ]oct-2(3)-ene, prepared as described in step (a) above, to give 59 mg of the title compound as an oil.

Infrared Absorption Spectrum (liquid film)$v_{max}$cm$^{-1}$: 974, 1735, 3360.

Nuclear Magnetic Resonance Spectrum (CDCl$_3$) δppm:

0.95 (3H, multiplet, CH$_3$);

1.78 (3H, triplet, J=1.5 Hz, CH$_3$);

3.4–4.5 (2H, multiplet, CHOH×2);

3.76 (2H, triplet J=6 Hz, —CH$_2$O—);

4.08 (2H, singlet, —CH$_2$O—);

5.39 (1H, broad singlet, =CH—);

5.54 (2H, multiplet, —CH=CH—).

EXAMPLE 35

A mixture of 3-(2-hydroxyethyl)-6β-[3α-(2-tetrahydropyranyloxy)-3-cyclohexyl-1 -propenyl]-7α-(2-tetrahydropyranyloxy)-cis-bicyclo[3,3,0]oct-2(3)-ene The procedure described in Example 6(a) and 6(b) was repeated, but using 871 mg of 3-methoxycarbonylmethylidene-6β-[3α-(2-tetrahydropyranyloxy)-3 -cyclohexyl-1- propenyl]-7α-(2-tetrahydropyranyloxy)-cis-bicyclo-[3,3,0] octane, to give 387 mg of the title compound as an oil.

Infrared Absorption Spectrum (liquid film)$v_{max}$cm$^{-1}$: 3350, 1032, 1022, 974.

EXAMPLE 36

A mixture of
3-[2-(carboxymethoxy)ethyl]-6β-(3α-hydroxy-3-cyclohexyl-1-propenyl)-7
α-hydroxy-cis-bicyclo[3,3,0]oct-2(3)-ene

36(a) A mixture of
3-[2-(carboxymethoxy)ethyl]-6β-[3α-(2-tetrahydropyranyloxy)-3
-cyclohexyl-1-propenyl]-7α-(2-tetrahydropyranyloxy)-cis-bicyclo[3,3,0]oct-2(3)-ene The procedure described in Example 21(a) was repeated, but using 273 mg of a mixture of 3-(2-hydroxyethyl)-6β-[3α-(2 -tetrahydropyranyloxy)-3-cyclohexyl-1-propenyl]-7α-(2-tetrahydropyranyloxy)-cis-bicyclo[3,3,0] oct-2(3)-ene, prepared as described in Example 35, to give 79 mg of the title compound as an oil.

Infrared Absorption Spectrum (liquid film)$v_{max}$cm$^{-1}$: 1720, 1747.

Nuclear Magnetic Resonance Spectrum (CDCl$_3$) δppm:
3.64 (2 H, triplet, —CH$_2$O—);
4.06 (2 H, singlet, —CH$_2$O—);
4.70 (2 H, broad singlet, 2-H of tetrahydropyranx2);
5.2–5.8 (3 H, multiplet, —CH=CH—, =CH—).

36(b) A mixture of
3-[2-(carboxymethoxy)ethyl]-6β-(3α-hydroxy-3-cyclohexyl-1
-propenyl)-7α-hydroxy-cis-bicyclo[3,3,0]oct-2(3)-ene The procedure described in Example 21(b) was repeated, but using 312 mg of a mixture of 3-[2-(carboxymethoxy)ethyl]-6β-[3α-(2 -tetrahydro-pyranyloxy)-3-cyclohexyl-1-propenyl]-7α-(2-tetrahydropyranyloxy)-cis-bicyclo[3,3,0 ]oct-2(3)-ene, prepared as described in step (a) above, to give 136 mg of the title compound.

Infrared Absorption Spectrum (CHCl$_3$)$v_{max}$cm$^{-1}$: 972, 1735, 3350.

Nuclear Magnetic Resonance Spectrum (CDCl$_3$) δppm:
3.76 (2 H, triplet, —CH$_2$O—);
4.08 (2 H, singlet, —CH$_2$O—);
3.4–4.3 (2 H, multiplet, CHOHx2);
5.38 (1 H, broad singlet, =CH—);
5.52 (2 H, multiplet, —CH=CH—).

EXAMPLE 37

A mixture of
3-[2-(carboxymethylthio)ethyl]-6β-(3α-hydroxy-5(R),9-dimethyldeca-1,8
-dienyl)-7α-hydroxy-cis-bicyclo[3,3,0]oct-2(3)-ene

37(a) A mixture of
3-(2-methanesulfonyloxyethyl)-6β-[3α- (2-tetrahydropyranyloxy)-5
(R),9-dimethyldeca-1,8-dienyl]-7α-(2-tetrahydropyranyloxy)-cis-bicyclo[3,3,0]-oct-2(3)-ene To a solution of 294 mg of a mixture of 3-(2-hydroxyethyl)-6β-[3α-(2 -tetrahydropyranyloxy)-5-(R),9-dimethyldeca-1,8-dienyl]-7α-(2 -tetrahydro-pyranyloxy)-cis-bicyclo [3,3,0]oct-2(3)-ene (prepared as described in Example 6) in 10 ml of methylene chloride were added 87 mg of triethylamine. 97 mg of methanesulfonyl chloride were then added to the resulting mixture, with ice-cooling, and the mixture was cooled with ice for 2 hours. After completion of the reaction, the mixture was diluted with ethyl acetate, washed successively with an aqueous solution of sodium chloride, an aqueous solution of acetic acid, a dilute aqueous solution of sodium bicarbonate and an aqueous solution of sodium chloride, and dried over anhydrous sodium sulfate. The solvent was distilled off, yielding mg of the title compound as an oil.

Nuclear Magnetic Resonance Spectrum (CDCl$_3$) δppm:
0.93 (3 H, multiplet, CH$_3$);
2.92 (3 H, singlet, CH$_3$);
4.70 (2 H, multiplet, 2-H of tetrahydropyranx2);
5.05 (1 H, triplet, J=6 Hz, =CH—);
5.2–5.8 (3H, =CH—x3).

37(b) A mixture of
3-[2-(carboxymethylthio)ethyl]-6β-[3α-(2-tetrahydropyranyloxy)-5
(R),9-dimethyl-deca-1,8-dienyl]-7α-(2-tetrahydropyranyloxy)-cis-bicyclo[3,3,0]oct-2 (3)-ene 400 mg of a 55% w/w suspension of sodium hydride in oil were washed with hexane, and then 15 ml of dimethyl sulfoxide and 400 mg of thioglycolic acid were added thereto. The mixture was stirred at room temperature until bubbles almost ceased. To the mixture were added 303 mg of a mixture of 3-(2-methanesulfonyloxyethyl)-6β-[3α-(2-tetrahydropyranyloxy)-5 (R),9-dimethyldeca-1,8-dienyl]-7α-(2-tetrahydropyranyloxy)-cis-bicyclo[3,3,0]oct-2(3)-ene, prepared as described in step (a) above. The resulting mixture was stirred at room temperature for 1 hour, poured into ice-water, acidified with acetic acid and extracted with ethyl acetate. The extract was washed with an aqueous solution of sodium chloride, and dried over anhydrous sodium sulfate. The solvent was distilled off and the resulting residue was purified by thin layer chromatography on a 2 mm thick plate of silica gel, developed with a 1:1 by volume mixture of hexane and ethyl acetate containing 0.25% v/v acetic acid, to give 187 mg of the title compound as an oil.

Infrared Absorption Spectrum (liquid film)$v_{max}$cm$^{-1}$: 1725, 1710.

Nuclear Magnetic Resonance Spectrum (CDCl$_3$) δppm:
0.90 (3 H, multiplet, CH$_3$);
3.20 (2 H, singlet, —SCH$_2$—);
4.65 (2 H, broad singlet, 2-H of tetrahydropyranx2);
5.01 (1 H, triplet, J=6 Hz, CH$_3$);
5.2–5.7 (3 H, multiplet, =CH—x3).

37(c) A mixture of
3-[2-(carboxymethylthio)ethyl]-6β-[3α-hydroxy-5(R),9
-dimethyldeca-1,8-dienyl]-7α-hydroxy-cis-bicyclo[3,3,0]oct-2(3)-ene 180 mg of a mixture of 3-[2-(carboxymethyl-thio)ethyl] -6β-[3α-(2 -tetrahydropyranyloxy)-5(R),9-dimethyldeca-1, 8-dienyl]-7α-(2-tetrahydropyranyloxy)-cis-bicyclo[3,3,0 ]oct-2(3)-ene, prepared as described in step (b) above, were treated by the same procedure as described in Example 21(b), and the resulting residue was purified by silica gel column chromatography. 120 mg of a mixture of the oct-2-ene and the oct-3-ene isomers were obtained as an oil from the fractions eluted with a mixture of ethyl acetate and hexane in volume ratios gradually increasing from 30:70 to 100:0.

The mixture of the oct-2-ene and the oct-3-ene isomers

Infrared Absorption Spectrum (liquid film)$v_{max}$cm$^{-1}$:
975, 1705, 3350.
Nuclear Magnetic Resonance Spectrum (CDCl$_3$) δppm:
0.94 (3 H, doublet, J=6 Hz, CH$_3$);
1.62 (3 H, singlet, CH$_3$);
1.70 (3 H, singlet, CH$_3$);
3.22 (2 H, singlet, —CH$_2$—);
3.4–4.5 (2 H, broad, CHOHx2);
5.08 (1 H, broad triplet, J=6 Hz, =CH—);
5.36 (1 H, broad singlet, =CH—);
5.60 (2 H, multiplet, —CH=CH—).

This mixture was purified by high-pressure liquid chromatography to give the pure oct-2-ene and oct-3-ene compounds, respectively (column: octadecyl chemical bond type silica gel, solvent: a 45:55 by volume mixture of aqueous 0.05M phosphoric acid solution and acetonitrile).

oct-2-ene compound

Infrared Absorption Spectrum (CHCl$_3$)$v_{max}$cm$^{-1}$:
974, 1705, 3350.
Nuclear Magnetic Resonance Spectrum (CDCl$_3$) δppm:
0.94 (3 H, doublet, J=6 Hz, —CH$_3$);
1.62 (3 H, singlet, CH$_3$);
1.70 (3 H, singlet, CH$_3$);
3.22 (2 H, singlet, —CH$_2$S—);
3.4–4.5 (2 H, broad, CHOHx2);
5.08 (1 H, triplet, J=6 Hz, =CH—);
5.36 (1 H, broad singlet, =CH—);
5.60 (2 H, multiplet, —CH=CH—).

oct-3-ene compound

Infrared Absorption Spectrum (CHCl$_3$)$v_{max}$cm$^{-1}$:
974, 1705, 3350.
Nuclear Magnetic Resonance Spectrum (CDCl$_3$) δppm:
0.94 (3 H, doublet, J=6 Hz, CH$_3$);
1.62 (3 H, singlet, CH$_3$);
1.70 (3 H, singlet, CH$_3$);
3.22 (2 H, singlet, —CH$_2$S—);
3.4–4.5 (2 H, broad, CHOHx2);
5.08 (1 H, triplet, J=6 Hz, =CH—);
5.36 (1 H, broad singlet, =CH—);
5.60 (2 H, multiplet, —CH=CH—).

EXAMPLE 38

A mixture of
3-[2-(carboxymethylthio)ethyl]-6β-(3α-hydroxy-3-cyclohexyl-1-propenyl)-7
α-hydroxy-cis-bicyclo[3,3,0]oct-2(3)-ene The procedure described in Example 37(b) and 37(c) was repeated, but using 237 mg of a mixture of 3-(2-methanesulfonyloxyethyl)-6β-[3α-(2 -tetrahydropyranyloxy)-3-cyclohexyl-1-propenyl]-7α-(2-tetrahydropyranyloxy)-cis-bicyclo[3,3,0 ]oct-2(3)-ene [prepared from the product of Example 35, following essentially the same procedure as described in Example 37(a)], to give 102 mg of the title compound.

Infrared Absorption Spectrum (CHCl$_3$) $v_{max}$cm$^{-1}$:
975, 1707, 3350.

EXAMPLE 39

A mixture of
3-(4-methoxycarbonyl-3-butenyl)-6β-[3α-hydroxy-5(R), 9-dimethyldeca-1,8-dienyl]-7α-hydroxy-cis-bicyclo[3,3,0]oct-2(3)-ene (a) A mixture of
3-(4-phenylseleno-4-methoxycarbonyl-butyl)-6β-[3α-(2-tetrahydropyranyloxy)-5 (R),
9-dimethyldeca-1,8-dienyl]-7α-(2-tetrahydropyranyloxy)-cis-bicyclo[3,3,0]oct-2(3)-ene To a diisopropylaminolithium solution (prepared from a solution of 0.84 g of diisopropylamine in 14 ml of tetrahydrofuran and 3.07 ml of a 15% w/v hexane solution of butyllithium) was added dropwise at −70° C. a solution of 1.4 g of a mixture of 3-(4-methoxycarbonylbutyl)-6β-[3α-(2-tetrahydropyranyloxy)-5 (R),9-dimethyldeca-1.8-dienyl] -7α-(2-tetrahydropyranyloxy)-cis-bicyclo[3,3,0]oct-2(3 )-ene [which is the methyl ester prepared as described in Example 2(e)] in 6 ml of tetrahydrofuran. The mixture was stirred at the same temperature for 20 minutes, and then a solution of 1.61 g of diphenyldiselenide in 5 ml of tetrahydrofuran was added thereto at −78° C. The mixture was stirred at room temperature for 1 hour. The reaction mixture was then diluted with a saturated aqueous solution of ammonium chloride and then extracted with ethyl acetate. The extract was washed with an aqueous solution of sodium chloride and dried over anhydrous sodium sulfate. The solvent was distilled off and the residue was purified by silica gel column chromatography. 1.74 g of the title compound was obtained as an oil from the fractions eluted with hexane containing 10–20% by volume of ethyl acetate.

Infrared Absorption Spectrum (liquid film) $v_{max}$cm$^{-1}$:
1580, 1735.
Nuclear Magnetic Resonance Spectrum (CDCl$_3$) δppm:
0.91 (3 H, multiplet, CH$_3$);
2.61 (3 H, singlet, CH$_3$);
2.66 (3 H, singlet, CH$_3$);
3.62 (3 H, singlet, CH$_3$);
4.70 (2 H, broad singlet, 2-H of tetrahydropyranx2);
5.0–5.8 (4 H, multiplet, =CH—x4);
7.30 (3 H, multiplet, aromatic protons):
7.59 (2 H, multiplet, aromatic protons).

(b) A mixture of
3-(4-methoxycarbonyl-3-butenyl)-6β-[3α-(2-tetrahydropyranyloxy)-5
(R),9-dimethyldeca-1,8-dienyl]-7α-(2-tetrahydropyranyloxy)-cis-bicyclo[3,3,0]oct-2(3)-ene To 6 ml of an ethyl acetate solution containing 0.70 g of a mixture of 3-(4-phenylseleno-4-methoxy-carbonylbutyl)-6β-[3α-(2 -tetrahydropyranyloxy)-5(R),9-dimethyldeca-1, 8-dienyl]-7α-(2-tetrahydropyranyloxy)-cis-bicyclo[3,3,0 ]-oct-2(3)-ene, prepared as described in step (a) above, were added dropwise successively at 20° C. 4 ml of methanol and 0.85 ml of 30% hydrogen peroxide, and then the mixture was stirred at room temperature for 40 minutes. After completion of the reaction, the reaction mixture was diluted with 100 ml of ethyl acetate, washed successively with a saturated aqueous solution of sodium bicarbonate and an aqueous solution of sodium chloride, and dried over anhydrous sodium sulfate. The solvent was distilled off and the resulting residue was purified by silica gel column chromatography. 338 mg of the title compound were obtained as an oil from the fractions eluted with hexane containing 5–10% by volume of ethyl acetate.

Infrared Absorption Spectrum (liquid film) $v_{max}cm^{-1}$: 1655, 1730.

Nuclear Magnetic Resonance Spectrum (CDCl$_3$) δppm:

0.89 (3 H, multiplet, CH$_3$);

3.69 (3 H, singlet, CH$_3$);

4.67 (2 H, broad singlet, 2-H of tetrahydropyranx2);

4.85–5.90 (5 H, multiplet, =CH—x5)

6.87 (1 H, doublet of triplets, J=15 & 7 Hz, =CH—)

(c) A mixture of
3-(4-methoxycarbonyl3-butenyl)-6β-(3α-hydroxy-
5(R),9 -dimethyldeca-1,8-dienyl]-7α-hydroxy-cis-
bicyclo[3,3,0]oct-2(3)-ene A mixture of 400 mg of a mixture of 3-(4-methoxycarbonyl-3-butenyl)-6β-[3α-(2 -tetrahydropyranyloxy)-5(R),9-dimethyldeca-1,8-dienyl]-7α-(2-tetrahydropyranyloxy)-cis-bicyclo[3,3,0 ]oct-2(3)-ene [prepared as described in step (b) above], 6 ml of acetic acid, 4 ml of water and 1 ml of tetrahydrofuran was stirred at 60° C. for 1 hour. After completion of the reaction, the reaction mixture was diluted with water and extracted with ethyl acetate. The extract was washed successively with a saturated aqueous solution of sodium bicarbonate and an aqueous solution of sodium chloride, and dried over anhydrous sodium sulfate. The solvent was distilled off and the resulting residue was purified by silica gel column chromatography. 230 mg of the title compound were obtained as an oil from the fractions eluted with hexane containing 40%–60% by volume of ethyl acetate.

Infrared Absorption Spectrum (liquid film) $v_{max}cm^{-1}$: 1650, 1725, 3355.

Nuclear Magnetic Resonance Spectrum (CDCl$_3$) δppm:

0.93 (3 H, doublet, J=6 Hz, CH$_3$ );

1.62 (3 H, singlet, CH$_3$);

1.68 (3 H, singlet, CH$_3$);

3.70 (3 H, singlet, CH$_3$);

4.90–5.90 (5 H, multiplet, =CH—x5);

6.88 (1 H, doublet of triplets, J=15 & 7 Hz, =CH—).

EXAMPLE 40

A mixture of
3-[2-(2-hydroxyethoxy)ethyl]-6β-[3α-hydroxy-5(R),9
-dimethyldeca-1,8-dienyl]-7α-hydroxy-cis-
bicyclo[3,3,0]oct-2(3)-ene (a) A mixture of
3-[2-(2-hydroxyethoxy)ethyl]-6β-(2-
tetrahydropyranyloxy-5(R),9
-dimethyldeca-1,8-dienyl]-7α-(2-tetrahydropyranyloxy]-
cis-bicyclo-[3,3,0]oct-2(3)-ene 310 mg of 3-[2-(carboxymethoxy)ethyl]-6β-[3α-(2-tetrahydropyranyloxy)-5(R),9 -dimethyldeca-1,8-dienyl]-7α-(2-tetrahydropyranyloxy)-cis-bicyclo-[3,3,0]oct-2(3)-ene, prepared as described in Example 21(a), were reacted with an excess of diazomethane in diethyl ether at room temperature for 30 minutes to give 321 mg of the corresponding methyl ester [Infrared Absorption Spectrum (liquid film) $v_{max}cm^{-1}$: 1720].

250 mg of this ester were dissolved in 10 ml of diethyl ether, and 250 mg of lithium aluminum hydride were added to the resulting solution. The mixture was stirred at room temperature for 30 minutes. After completion of the reaction, the reaction mixture was diluted with 1 ml of a 4% w/v aqueous solution of sodium hydroxide. The resulting precipitate was filtered off and the filtrate was concentrated by evaporation under reduced pressure. The resulting residue was purified by column chromatography through silica gel, eluted with hexane containing 20–30% v/v of ethyl acetate, to afford 187 mg of the title compound as an oil.

Infrared Absorption Spectrum (liquid film)$v_{max}cm^{-1}$: 3410, 1120, 1076, 1022.

(b) A mixture of
3-[2-(2-hydroxyethoxy)ethyl]-6β-[3α-hydroxy-5(R),9
-dimethyldeca-1,8-dienyl]-7α-hydroxy-cis-
bicyclo[3,3,0]oct-2(3)-ene 180 mg of the hydroxy compound prepared as described in step (a) above were dissolved in 5 ml of a 5:3:1 by volume mixture of acetic acid, water and tetrahydrofuran. The solution was maintained at 40° C. for 3 hours. After completion of the reaction, the reaction mixture was diluted with a saturated aqueous solution of sodium chloride, and extracted with ethyl acetate. The extract was washed with water and dried over anhydrous sodium sulfate. The solvent was distilled off and the resulting residue was purified by column chromatography through silica gel, eluted with hexane containing 30–60% v/v ethyl acetate, to give 91 mg of the title compound as an oil.

Infrared Absorption Spectrum (liquid film)$v_{max}cm^{-1}$: 3350, 971.

EXAMPLE 41

A mixture of
3-[2-(formylmethoxy)ethyl]-6β-[3α-hydroxy-5(R),9-
dimethyldeca-1,8
-dienyl]-7α-hydroxy-cis-bicyclo[3,3,0]oct-2(3)-ene 171 mg of 3-[2-(2-hydroxyethoxy)ethyl]-6β-[3α-(2-tetrahydropyranyloxy)-5 (R),9-dimethyldeca-1,8-dienyl]-7α-(2-tetrahydropyranyloxy)-cis-bicyclo-[3,3,0]oct-2(3)-ene [prepared as described in Example 40(a)] were dissolved in 50 ml of methylene chloride. 2.5 g of a pyridine—chromic anhydride complex (Collin's reagent) were added to the resulting solution, with ice-cooling, and the mixture was then stirred for 30 minutes. After completion of the reaction, the reaction mixture was diluted with an excess of diethyl ether and washed with a saturated aqueous solution of sodium chloride. The organic layer was separated and dried over anhydrous sodium sulfate, and the solvent was distilled off to obtain 161 mg of a mixture of 3-[2-(formylmethoxy)ethyl]-6β-[3α-(2-tetrahydropyranyloxy)-5(R),9 -dimethyldeca-1,8-dienyl]-7α-(2-tetrahydropyranyloxy)-cis-bicyclo [3,3,0]oct-2(3)-ene [Infrared Absorption Spectrum (liquid film)$v_{max}cm^{-1}$: 2720, 1710].

This formyl compound was subjected to a reaction to remove the protecting group following the same procedure as described in Example 40(b), to afford 75 mg of the title compound.

Infrared Absorption Spectrum (liquid film)$v_{max}$cm$^{-1}$: 2710, 1710.

PREPARATION 1

3-(4-Carboxybutylidene)-7,7-ethylenedioxy-cis-bicyclo-[3,3,0]octane

An ylide solution was prepared from 440 g of triphenyl (4-carboxybutyl)phosphonium bromide and sodium dimsyl (prepared from 75.0 g of a 55% w/w suspension of sodium hydride in oil and 3 liters of dimethyl sulfoxide) in dimethyl sulfoxide. To this were added dropwise 36.0 g of 7.7-ethylenedioxy-3-oxo-cis-bicyclo[3,3.0]octane in 400 ml of dimethyl sulfoxide, and the mixture was left standing at room temperature for 48 hours under an atmosphere of nitrogen. Upon completion of the reaction, the reaction product was neutralized with acetic acid, and the mixture was poured into a saturated aqueous solution of sodium chloride. The mixture was extracted with ethyl acetate, and the extract was washed with a saturated aqueous solution of sodium chloride and then dried over anhydrous sodium sulfate. The solvent was distilled off under reduced pressure, giving 164.3 g of residue. On purifying the residue by column chromatography through silica gel, 49.10 g of the title compound was obtained in the form of an oil, from the fractions eluted with hexane containing 30–40% by volume of ethyl acetate.

Infrared Absorption Spectrum (liquid film)$v_{max}$cm$^{-1}$: 1710.
Nuclear Magnetic Resonance Spectrum (CDCl$_3$) δppm:
3.88 (4 H, singlet, OCH$_2$CH$_2$O);
5.23 (1 H, triplet, J=6.0 Hz, olefin H)
10.36 (1 H, singlet, COOH).
Mass spectrum, m/e: 266 (M$^+$).

PREPARATION 2

3-(5-Hydroxypentylidene)-7,7-ethylenedioxy-cis-bicyclo-[3,3,0]octane 49.10 g of 3-(4-carboxybutylidene)-7,7-ethylenedioxy-cis-bicyclo[3,3,0 ]octane (prepared as described in Preparation 1) in 150 ml of tetrahydrofuran were added dropwise to a suspension of 10.50 g of lithium aluminum hydride in 675 ml of tetrahydrofuran, whilst cooling with ice. The mixture was then heated under reflux for 80 minutes. Upon completion of the reaction, 42 ml of a 4% w/v aqueous solution of sodium hydroxide were added, and the mixture was stirred at room temperature. The resulting precipitate was removed by filtration, and the filtrate was condensed by evaporation under reduced pressure, giving 46.90 g of a residue. On purifying the residue by silica gel column chromatography, 40.10 g of the title compound were obtained as an oil, from the fractions eluted with hexane containing 20–30% by volume of ethyl acetate.

Infrared Absorption Spectrum (liquid film)$v_{max}$cm$^{-1}$: 3320, 1430, 1330, 1110.
Nuclear Magnetic Resonance Spectrum (CDCl$_3$) δppm:
3.81 (4 H, singlet, OCH$_2$CH$_2$O);
5.14 (1 H, triplet, J=6.0 Hz, olefin H).
Mass spectrum, m/e: 252 (M$^+$).

PREPARATION 3

3,(5-Benzyloxypentylidene)-7,7-ethylenedioxy-cis-bicyclo-[3,3,0]octane 10.0 g of 3-(5-hydroxypentylidene)-7,7-ethylenedioxy-cis-bicyclo[3,3,0]octane (prepared as described in Preparation 2) in 20 ml of dimethylformamide were added dropwise to 2.60 g of a 55% w/w suspension of sodium hydride in oil, suspended in 35 ml of dimethylformamide, whilst cooling with ice and stirring, and the mixture was then stirred for 30 minutes at room temperature. 7.1 ml of benzyl bromide were then added dropwise to the reaction mixture at room temperature, and the mixture was stirred for 30 minutes. Upon completion of the reaction, the reaction mixture was poured into ice-water and extracted with diethyl ether. The extract was washed with water and dried over anhydrous sodium sulfate. The solvent was distilled off from the extract, giving 22.0 g of a residue. On purifying the residue by silica gel column chromatography, 12.30 g of the title compound were obtained as an oil from the fractions eluted with hexane containing 2–5% by volume of ethyl acetate.

Infrared Absorption Spectrum (liquid film)$v_{max}$cm$^{-1}$: 1455, 1330, 1110.
Nuclear Magnetic Resonance Spectrum (CDCl$_3$) δppm;
3.47 (2 H, triplet, J=6.0 Hz, CH$_2$O-benzyl);
3.88 (4 H, singlet, OCH$_2$CH$_2$O);
4.48 (2 H, singlet, OCH$_2$-phenyl);
5.20 (1 H, triplet, J=6.0 Hz, olefin H);
7.35 (5H, singlet, phenyl H).

PREPARATION 4

3-(5-Benzyloxypentyl)-7,7-ethylenedioxy-cis-bicyclo-[3,3,0]oct-2-ene 1.50 g of p-toluenesulfonic acid and 2.9 ml of ethylene glycol were added to 17.8 g of 3-(5-benzyloxy-pentylidene)-7,7-ethylenedioxy-cis-bicyclo[3,3,0 ]octane (prepared as described in Preparation 3) in 300 ml of benzene, and the mixture was heated, with stirring, for 2.5 hours whilst removing water as an azeotropic mixture. Upon completion of the reaction, the reaction mixture was washed with water and dried over anhydrous sodium sulfate. The solvent was distilled off from the reaction mixture under reduced pressure, to give 18.20 g of the title compound as an oil. This mixture was used for the subsequent reaction of Preparation 5 without purification.

Infrared Absorption Spectrum (liquid film)$v_{max}$cm$^{-1}$: 1445, 1320, 1100, 1020.
Nuclear Magnetic Resonance Spectrum (CDCl$_3$) δppm:
3.42 (2 H, triplet, J=6.0 Hz, CH$_2$O-benzyl)
3.84 (4 H, singlet, OCH$_2$CH$_2$O);
4.44 (2 H, singlet, OCH$_2$-phenyl);
5.15 (1 H, broad singlet, olefin H);
7.28 (5 H, singlet, phenyl H)
Mass spectrum, m/e: 342 (M$^+$).

PREPARATION 5

3-(5-Benzyloxypentyl)-7-oxo-cis-bicyclo[3,3,0]-oct-2-ene 6.65 g of 3-(5-benzyloxypentyl)-7,7-ethylenedioxy-cis-bicyclo[3,3,0]oct-2-ene (prepared as described in Preparation 4 or 10) were added to a mixture of 120 ml of acetone, 45 ml of water and 1.0 ml of concentrated hydrochloric acid, and the mixture was stirred for 2 hours at room temperature. After completion of the reaction, sodium bicarbonate was added to the reaction mixture for neutralization, and acetone was distilled off under reduced pressure. A saturated aqueous solution of sodium chloride was added to the residue, and then the mixture was extracted with ethyl acetate. The extract was washed with a saturated aqueous solution of sodium chloride, and dried over anhydrous sodium sulfate. The solvent was distilled off from the extract under reduced pressure, giving 6.00 g of residue. On purifying this residues by silica gel column chromatography, 5.33 g of the title compound were obtained from the fractions eluted with hexane containing 7–10% by volume of ethyl acetate.

Infrared Absorption Spectrum (liquid film)$v_{max}cm^{-1}$: 1725.

Nuclear Magnetic Resonance Spectrum ($CDCl_3$) δppm:

3.42 (2 H, triplet, J=6.0 Hz, $CH_2CH_2OCH_2$-phenyl);

4.43 (2 H, singlet, $OCH_2$-phenyl);

5.14 (1 H, broad singlet, olefin H);

7.24 (SH, singlet, phenyl, H).

Mass spectrum, m/e: 298 ($M^+$).

PREPARATION 6

A mixture of
3-(5-benzyloxypentyl)-6βcarboxy-7α-hydroxy-cis-bicyclo[3,3,0]oct-2 -ene and
3-(5-benzyloxy-pentyl)-6β-carboxy-7α-hydroxy-cis-bicyclo[3,3,0]oct-3-ene 9.60 g of 2,6-di-t-butyl-p-cresol were added to 1.91 g of a 55% w/w suspension of sodium hydride in oil, suspended in 170 ml of 1,2-dimethoxyethane, and the mixture was vigorously stirred for 1 hour at a mixture temperature of 40° C. The mixture was then cooled down to 30° C. and stirred at the same temperature while blowing carbon dioxide gas through it. After cooling the suspension down to a temperature of 10° C., a solution of 4.32 g of 7-(5-benzyloxypentyl)-3-oxo-cis-bicyclo[3,3,0]- oct-2-ene (prepared as described in Preparation 5) in 20 ml of 1,2-dimethoxyethane was added dropwise, and the mixture was stirred for 2 hours at a temperature of 10° C. A solution of 820 mg of sodium borohydride in 40 ml of t-butanol and 13 ml of water was then added dropwise and the mixture was stirred for 1 hour at a mixture temperature of 10° C. Upon completion of the reaction, the reaction mixture was poured into water and washed with hexane. The water layer was acidified with 10% w/v hydrochloric acid and extracted with ethyl acetate. The extract was washed with a saturated aqueous solution of sodium chloride, and dried over anhydrous sodium sulfate. The solvent was distilled off from the mixture under reduced pressure, to give 5.42 g of a residue. On purifying this residue by silica gel column chromatography, 4.28 g of the title compound were obtained as an oil from the fractions eluted with hexane containing 25–30% by volume of ethyl acetate.

Infrared Absorption Spectrum (liquid film)$v_{max}cm^{-1}$: 3350, 1710.

Nuclear Magnetic Resonance Spectrum ($CDCl_3$) δppm:

3.49 (2 H, triplet, J=6.0 Hz, $CH_2CH_2O$-benzyl);

4.52 (2 H, singlet, $CH_2OCH_2$-phenyl);

7.08 (2 H, singlet, OH, COOH);

7.37 (5 H, singlet, phenyl H).

Mass spectrum, m/e: 344 ($M^+$).

PREPARATION 7

A mixture of
3-(5-benzyloxypentyl)-6β-hydroxymethyl-7α-(2-tetrahydropyranyloxy)-cis-bicyclo[3,3,0]oct-2(3)-ene 4.28 g of 3-(5-benzyloxypentyl)-6β-carboxy-7α-hydroxy-cis-bicyclo[3,3,0]oct-2 (3)-ene (prepared as described in Preparation 6) were dissolved in 10 ml of methylene chloride, and then 3.4 ml of dihydropyran and a catalytic amount of pyridine hydrochloride were added, and the mixture was stirred at room temperature for 2 hours. The mixture was then added, with ice cooling, to a solution of 500 mg of lithium aluminum hydride in 300 ml of tetrahydrofuran, and the mixture was stirred for 1 hour at a temperature of 18° C. Upon completion of the reaction, 2 ml of a 4% w/v aqueous solution of sodium hydroxide were added to the mixture, and the mixture was stirred at room temperature. The white precipitate generated was removed by filtration, and the filtrate was condensed by evaporation under reduced pressure, giving 7.60 g of a residue. On purifying the residue by silica gel column chromatography, 4.840 g of the title compound were obtained as an oil from the fraction eluted with hexane containing 20% by volume of ethyl acetate.

Infrared Absorption Spectrum (liquid film)$v_{max}cm^{-1}$: 3430, 1455, 1120.

Nuclear Magnetic Resonance Spectrum ($CDCl_3$) δppm:

3.47 (2 H, triplet, J=6.0 Hz, $CH_2O$-benzyl);

4.53 (2 H, singlet, $OCH_2$-phenyl);

5.30 (1 H, broad singlet, olefin H);

7.37 (5 H, singlet, phenyl H).

Mass spectrum m/e: 414 ($M^+$).

PREPARATION 8

A mixture of
3-(5-benzyloxypentyl)-6β-formyl-7α-(2-tetrahydropyranyloxy)-cis-bicyclo[3,3,01 oct-2(3)-ene Triethylamine (13.5 ml) was added to a solution of 4.82 g of 3-(5-benzyloxypentyl)-6β-hydroxymethyl-7α-(2 -tetrahydropyranyloxy)-cis-bicyclo[3,3,0]oct-2(3)-ene (prepared as described in Preparation 7) in 42 ml of dimethyl sulfoxide, and then a solution of 4.720 g of pyridine-sulfuric anhydride complex in 22 ml of dimethyl sulfoxide was added. The mixture was stirred for 30 minutes at room temperature. Upon completion of the reaction, the reaction mixture was poured into a saturated aqueous solution of sodium chloride, and then extracted with ethyl acetate. The extract was washed with water and dried over anhydrous sodium sulphate, and then the solvent was distilled off under reduced pressure, giving 4.96 g of the title compound in the form of an oil.

This substance can be used for subsequent reactions without purification.

Infrared Absorption Spectrum (liquid film)$v_{max}cm^{-1}$: 1725.

Nuclear Magnetic Resonance Spectrum ($CDCl_3$) δppm:

4.45 (2 H, singlet, $OCH_2$-phenyl);

5.23 (1 H, broad singlet, olefin H);

7.26 (5 H, singlet, phenyl H)

9.68 (1 H, triplet, J=4.0 Hz, CHO).

PREPARATION 9

3-(5-Benzyloxypentyl)-7,7-ethylenedioxy-3-hydroxy-cis-bicyclo[3,3,0]octane

A solution of 501 mg of 7,7-ethylenedioxy-3-oxo-cis-bicyclo[3,3,0]octane in 5 ml of diethyl ether was added dropwise at room temperature to 5-benzyloxy-pentamethylene-magnesium bromide, which had been prepared in 5 ml of diethyl ether from 1.00 g of 5-benzyloxypentyl bromide and 100 mg of metallic magnesium at room temperature. The 5-benzyloxypentyl bromide, in turn, had been prepared from pentamethylene bromide and benzyl alcohol according to the method of A. W. Burgstabler et al. [J. Org. Chem. 42, 566 (1977)]. The mixture was stirred for 1.5 hours at room temperature. Upon completion of the reaction, an aqueous solution of ammonium chloride was added to the reaction mixture, which was then extracted with diethyl ether. The extract was washed with water and dried over anhydrous sodium sulfate. The solvent was distilled off under reduced pressure, giving 1.47 of residue. On purifying the residues by silica gel column chromatography, 556 mg of the title compound were obtained as an oil from the fractions eluted with hexane containing 25–30% by volume of ethyl acetate.

Infrared Absorption Spectrum (liquid film)$v_{max}$cm$^{-1}$:
3480, 1470, 1330, 1110.
Nuclear Magnetic Resonance Spectrum (CDCl$_3$) δppm:
3.47 (2 H, triplet, J=6.0 Hz, CH$_2$O-benzyl);
3.91 (4 H, singlet, OCH$_2$CH$_2$O);
4.52 (2 H, singlet, OCH$_2$-phenyl);
7.36 (5 H, singlet, phenyl H).
Mass spectrum m/e: 360 (M$^+$), 342 (M-18).

PREPARATION 10

3-(5-Benzyloxypentyl)-7,7-ethylenedioxy-cis-bicyclo-[3.3,0]oct-2-ene

Ethylene glycol (0.05 ml) and 10 mg of p-toluenesulfonic acid were added to a solution of 209 mg of 3-(5-benzyloxypentyl)-7,7-ethylenedioxy-3-hydroxy-cis-bicyclo[3,3,0]octane (prepared as described in Preparation 9) in 2 ml of benzene, and the mixture was heated, with stirring, for 3.5 hours, whilst removing water as an azeotropic mixture. Upon completion of the reaction, the reaction mixture was neutralized with a 5% w/v aqueous solution of sodium bicarbonate. The reaction mixture was then washed with water and dried over anhydrous sodium sulfate. The solvent was distilled off from the reaction mixture under reduced pressure, giving 193 mg of a residue. This residue was purified by silica gel column chromatography and 142 mg of the title compound were obtained as an oil from the fractions eluted with hexane containing 2–5% by volume of ethyl acetate. The product had the same properties as that of Preparation 4.

PREPARATION 11

3-(5-Hydroxypentyl)-7,7-ethylenedioxy-cis-bicyclo[3,3,0]-oct-2-ene 1.20 g of 3-(5-benzyloxypentyl)-7,7-ethylenedioxy-cis-bicyclo[3,3,0]oct-2-ene (prepared as described in Preparation 10) was subjected to reaction as described in Example 1(d), to give 0.67 g of the title compound as an oil.

Infrared Absorption Spectrum (liquid film)$v_{max}$cm$^{-1}$:
3350.
Nuclear Magnetic Resonance Spectrum (CDCl$_3$) δppm:
3.85 (4 H, singlet, OCH$_2$CH$_2$O);
5.15 (1 H, broad singlet =CH—).

When treated with a 3:7 by volume mixture of 10% w/v hydrochloric acid and acetone, this compound could be converted into the corresponding ketone (infrared absorption spectrum: 3350, 1725 cm$^{-1}$).

PREPARATION 12

3-(4-Methoxycarbonylbutyl)7,7-ethylenedioxy-cis-bicyclo-[3,3,0]oct-2-ene

A solution of 1.56 g of 3-(5-hydroxypentyl)-7,7-ethylenedioxy-cis-bicyclo[3,3,0]oct-2-ene (prepared as described in Preparation 11) in 45 ml of acetone was prepared. To this were added 4 ml of Jones' reagent dropwise at –20° to 10° C. Upon completion of the reaction, the mixture was neutralized with a 5% w/v aqueous solution of sodium bicarbonate. The mixture was then acidified with acetic acid and extracted with ethyl acetate. The extract was dried over anhydrous sodium sulfate. The solvent was distilled off from the mixture, and the resulting residue (the corresponding carbonic acid: infrared absorption spectrum 1705 cm$^{-1}$) was esterified with diazomethane. The product was puried by column chromatography through 30 g of silica gel, to give the title compound as an oil from the fractions eluted with hexane containing 20–30% by volume of ethyl acetate.

Infrared Absorption Spectrum (liquid film)$v_{max}$cm$^{-1}$:
1725.
Nuclear Magnetic Resonance Spectrum (CDCl$_3$) δppm:
3.63 (3 H, singlet, COOCH$_3$);
3.84 (4 H, singlet, OCH$_2$CH$_2$O);
5.15 (1 H, broad singlet, =CH—).

This ester could be converted into corresponding amides by heating with a primary or secondary amine.

PREPARATION 13

3-(3-Benzyloxypropyl)-7,7-ethylenedioxy-cis-bicyclo-[3,3,0]oct-2-ene 5 g of 3-oxo-7,7-ethylenedioxo-cis-bicyclo-[3,3,0]octane and 1.2 molar equivalents of 3-benzyloxypropylmagnesium bromide were reacted following the procedure described in Preparations 9 and 10, to give 3.1 g of the title compound as an oil.

Infrared Absorption Spectrum (liquid film)$v_{max}$cm$^{-1}$:
1445.
Nuclear Magnetic Resonance Spectrum (CDCl$_3$) δppm;
3.41 (2 H, triplet, CH$_2$OCH$_2$-phenyl);
3.84 (4 H, singlet, OCH$_2$CH$_2$O);
4.45 (1 H, singlet, CH$_2$-phenyl);
5.14 (1 H, broad singlet, =CH—).

PREPARATION 14

3-(5-Benzyloxypentyl)-6β-formyl-7α-(2-tetrahydropyranyloxy)-cis-bicyclo[3,3,0]oct-2 -ene 7.1 ml of triethylamine were added to a solution of 1.06 g of 3-(5-benzyloxypentyl)-6β-hydroxymethyl-7α-(2-tetrahydropyranyloxy)-cis-bicyclo[3,3,0]oct-2-ene in 8 ml of dimethyl sulfoxide. While vigorously stirring the reaction mixture, a solution of 2.04 g of a complex of pyridine with sulfuric anhydride in 7 ml of dimethyl sulfoxide was added to the reaction mixture at room temperature. The mixture was subsequently stirred for 30 minutes. After completion of the reaction, the reaction mixture was poured into a saturated aqueous solution of sodium chloride and then extracted with ethyl acetate. The extract was then washed with water and dried over anhydrous sodium sulfate. Upon distilling the solvent off under reduced pressure, 1.03 g of the title compound could be obtained in the form of an oil.

This substance was used for the subsequent reaction without purification.

Its infrared absorption spectrum and nuclear magnetic resonance spectrum were essentially identical to those of the product of Preparation 8.

PREPARATION 15

A mixture of 3-(4-methoxycarbonylbutyl)-6β-formyl-7α-(2-tetrahydropyranyloxy)-cis-bicyclo[3,3,0]oct-2(3)-ene 165 mg of a mixture of 3-(4-methoxycarbonylbutyl)-6β-hydroxymethyl-7α-(2 -tetrahydropyranyloxy)-cis-bicyclo[3,3,0]oct-2(3)-ene were reacted as described in Preparation 8, to give 163 mg of the crude title compound as an oil.

Infrared Absorption Spectrum (liquid film)$v_{max}cm^{-1}$:
2700, 1735, 1030, 1020.

PREPARATION 16

3α-(5-Benzyloxypentyl)-7,7-ethylenedioxy-2β, 3β-epoxy-cis-bicyclo[3,3,0]octane 22.5 g of 3-(5-benzyloxypentyl)-7,7-ethylenedioxy-cis-bicyclo[3,3,0]oct-2-ene (prepared as described in Preparation 10) were dissolved in 200 ml of chloroform, and 14.7 g of m-chloroperbenzoic acid were added; the mixture was stirred for 2.5 hours, with ice-cooling. Upon completion of the reaction, the reaction product was washed with a 5% w/v aqueous solution of sodium bicarbonate and then with water, and dried over anhydrous sodium sulfate. The solvent was distilled off from the reaction product, leaving 24.1 g of a residue. This was purified by silica gel column chromatography, to give 16.2 g of the title compound as an oil from the fractions eluted with hexane containing from 8 to 14% by volume of ethyl acetate.

Infrared Absorption Spectrum (liquid film)$v_{max}cm^{-1}$:
1030, 1105, 1205, 1325, 1430, 1455.
Nuclear Magnetic Resonance Spectrum (CDCl$_3$) δppm:
3.40 (2 H, triplet; J=6.0 Hz, CH$_2$OCH$_2$-phenyl);
3.84 (4 H, singlet, OCH$_2$CH$_2$O);
4.44 (2 H, singlet, OCH$_2$-phenyl);
7.27 (5 H, singlet, phenyl).
Mass spectrum, m/e: 358 (M$^+$), 340 (M-18)

PREPARATION 17

3β-(5 -Benzyloxypentyl)-7,7-ethylenedioxy-cis-bicyclo-[3,3,0]- octan-2-one 7.10 g of 3α-(5-benzyloxypentyl)-7,7-ethylenedioxy-2β, 3β-epoxy-cis-bicyclo[3,3,0]octane (prepared as described in Preparation 16) were dissolved in 140 ml of toluene, and then 2.7 ml of boron trifluoride ether complex were added, with ice-cooling, and the mixture was stirred for 5 minutes. Upon completion of the reaction, triethylamine was added to the reaction mixture to adjust it to an alkaline pH, and then water was added. The mixture was extracted with toluene. The extract was washed with water, and dried over anhydrous sodium sulfate. The solvent was distilled off from the reaction mixture under reduced pressure, leaving 7.15 g of residue. The residue was purified by silica gel column chromatography, to give 3.90 g of the title compound as an oil from the fractions eluted with hexane containing 6–10% by volume of ethyl acetate.

Infrared Absorption Spectrum (liquid film)$v_{max}cm^{-1}$:
1020, 1105, 1730.
Nuclear Magnetic Resonance Spectrum (CDCl$_3$) δppm:
3.45 (2 H, triplet; J=6.0 Hz, CH$_2$OCH$_2$-phenyl);
3.87 (4 H, singlet, OCH$_2$CH$_2$O);
4.50 (2 H, singlet, OCH$_2$-phenyl);
7.33 (5 H, singlet, phenyl)
Mass spectrum m/e: 358 (M$^+$)

PREPARATION 18

3β-(5-Benzyloxypentyl)-7,7,-ethylenedioxy-2α-hydroxy-cis-bicyclo[3,3,0]octane 3.90 g of 3β-(5-benzyloxypentyl)-7,7-ethylenedioxy-cis-bicyclo[3,3,0]octan-2-one (prepared as described in Preparation 17) were dissolved in 78 ml of ethanol, and 412 mg of sodium borohydride were added to the solution, whilst ice-cooling. The mixture was stirred for 30 minutes. Upon completion of the reaction, the reaction product was poured into a saturated aqueous solution of sodium chloride, and the mixture was extracted with ethyl acetate. The extract was washed with water, and dried over anhydrous sodium sulfate. The solvent was distilled off under reduced pressure, leaving 3.92 g of residue. This residue was purified by silica gel column chromatography, to give 3.74 g of the title compound as an oil from the fractions eluted with hexane containing from 20 to 40% by volume of ethyl acetate.

Infrared Absorption Spectrum (liquid film)$v_{max}cm^{-1}$:
1030, 1105, 1330, 3460.
Nuclear Magnetic Resonance Spectrum (CDCl$_3$) δppm:
3.42 (2 H, triplet; J=6.0 Hz, CH$_2$OCH$_2$-phenyl);
3.84 (4 H, singlet, OCH$_2$CH$_2$);
4.47 (2 H, singlet, OCH$_2$-phenyl);
7.33 (5 H, singlet, phenyl).
Mass spectrum, m/e: 360 (M$^+$), 342 (M-18)

PREPARATION 19

3α-(5-Benzyloxypentyl)-2α-hydroxy-7-oxo-cis-bicyclo-[3,3,0]-octane 41.0 g of 3β-(5-benzyloxypentyl)-7,7-ethylenedioxy-2α-hydroxy-cis-bicyclo[3,3,0]octane (prepared as described in Preparation 18) were dissolved in 510 ml of acetone and 255 ml of water, and 75 ml of concentrated hydrochloric acid were added to the solution at room temperature. The mixture was stirred for 1 hour. Upon completion of the reaction, the reaction product was poured into a saturated aqueous solution of sodium chloride and extracted with ethyl acetate. The extract was washed with water and dried over anhydrous sodium sulfate. The solvent was distilled off from the reaction mixture under reduced pressure, leaving 36.1 g of residue, which was purified by silica gel column chromatography, to give 27.0 g of the title compound as an oil from the fractions eluted with hexane containing from 20 to 40% by volume of ethyl acetate.

Infrared Absorption Spectrum (liquid film)$v_{max}$cm$^{-1}$:
1100, 1725, 3450.

Nuclear Magnetic Resonance Spectrum (CDCl$_3$) δppm:
3.42 (2 H, triplet; J=6.0 Hz, CH$_2$OCH$_2$-phenyl);
3.77 [1 H, triplet, J=6.0 Hz, —CH$_2$(OH)—];
4.51 (2 H, singlet, OCH$_2$-phenyl);
7.33 (5 H, singlet, phenyl).
Mass spectrum m/e: 316 (M$^+$), 298 (M-18)

PREPARATION 20

3β-(5-Benzyloxypentyl),2β-formyloxy-7-oxobicyclo-[3,3,0]-octane 26.0 g of 3β-(5-benzyloxypentyl)-2α-hydroxy-7-oxo-cis-bicyclo[3,3,0]octane (prepared as described in Preparation 19) were dissolved in 1 liter of tetrahydrofuran, and then 43.1 g of triphenylphosphine, 6.2 ml of formic acid and 25.3 ml of diethyl azodicarboxylate were added, and the mixture was stirred for 1 hour. Upon completion of the reaction, water was added to the reaction product, and the mixture was extracted with ethyl acetate. The extract was washed with water and dried over anhydrous sodium sulfate. The solvent was distilled off from the reaction product under reduced pressure, and the resulting residue was dissolved in benzene, and hexane was added to the solution. The precipitated triphenylphosphine oxide was removed by filtration. The filtrate was condensed under reduced pressure, and 62.9 g of residue was obtained. This residue was purified by silica gel column chromatography, to give 16.7 g of the title compound as an oil from the fractions eluted with hexane containing from 12 to 20% by volume of ethyl acetate.

Infrared Absorption Spectrum (liquid film)$v_{max}$cm$^{-1}$:
1105, 1180, 1720, 1740.

Nuclear Magnetic Resonance Spectrum (CDCl$_3$) δppm:
3.45 (2 H, triplet, J=6.0 Hz, CH$_2$OCH$_2$-phenyl);
4.50 (2 H, singlet, OCH$_2$-phenyl);
5.07 [1 H, doublet, J=4.5 Hz, —CH(OCHO)];
7.35 (5 H, singlet, phenyl);
8.08 (1 H, singlet, —OCHO);
Mass spectrum, m/e:344 (M$^+$), 298 (M-46)

PREPARATION 21

3β,(5-Benzyloxypentyl)-2β-hydroxy-7-oxo-cis-bicyclo[3,3,0]-octane 16.6 g of 3β-(5-benzyloxypentyl)-2β-formyloxy-7-oxo-cis-bicyclo[3,3,0]octane (prepared as described in Preparation 20) were dissolved in 170 ml of methanol, and 5 g of anhydrous potassium carbonate were added. The mixture was stirred for 30 minutes at room temperature. Upon completion of the reaction, a saturated aqueous solution of sodium chloride was added to the reaction product, which was extracted with ethyl acetate. The extract was washed with a saturated aqueous solution of sodium chloride and dried over anhydrous sodium sulfate. The solvent was distilled off from the reaction product under reduced pressure, leaving 13.0 g of residue. This residue was purified by silica gel column chromatography, to give 12.1 g of the title compound as an oil from the fractions eluted with hexane containing from 30 to 50% by volume of ethyl acetate.

Infrared Absorption Spectrum (liquid film)$v_{max}$cm$^{-1}$:
1100, 1735, 3460.

Nuclear Magnetic Resonance Spectrum (CDCl$_3$) δppm:
3.38 (2 H, triplet, J=6.0 Hz, CH$_2$OCH$_2$-phenyl);
4.41 (2 H, singlet, OCH$_2$-phenyl);
7.20 (5 H, singlet, phenyl).
Mass spectrum, m/e: 316 (M$^+$)

PREPARATION 22

3β-(5-Benzyloxypentyl)-2β-hydroxy-7-oxo-cis-bicyclo[3,3,0]-octane

22(a)
3β-(5-Benzyloxypentyl)-2α-p-toluenesulfonyloxy-7,7-ethylenedioxy-cis-bicyclo[3,3,0octane 500 mg of 3β-(5-benzyloxypentyl)-7,7-ethylenedioxy-2α-hydroxy-cis-bicyclo[3,3,0]octane (prepared as described in Preparation 18) were dissolved in 5 ml of pyridine, and then 610 mg of p-toluenesulfonyl chloride and 40 mg of 4-(dimethylamino)pyridine were added. The mixture was stirred for 24 hours at room temperature, and then the reaction product was poured into ice-water and extracted with diethyl ether. The extract was washed with water and dried over anhydrous sodium sulfate. The solvent was distilled off from the extract under reduced pressure, leaving 789 mg of residue. This residue was recrystallized from a mixture of ethyl acetate and hexane, to give 388 mg of the title compound as crystals melting at 70°–72° C.

Nuclear Magnetic Resonance Spectrum (CDCl$_3$) δppm;
2.42 (3 H, singlet, CH$_3$);
3.43 (2 H, triplet. J=6.0 Hz, CH$_2$CH$_2$O);
3.86 (4 H, singlet, OCH$_2$CH$_2$O);
4.50 (2 H, singlet, OCH$_2$-phenyl);
7.33 (7 H, multiplet, Aromatic hydrogen);
7.83 (2 H, doublet, J=8.0 Hz, Aromatic Hydrogen)

22(b)
3β-(5-Benzyloxypentyl)-2β-hydroxy-7,7-ethylenedioxy-cis-bicyclo[3,3,0]octane 210 mg of 18-Crown-6 and 101 mg of the toluenesulfonate prepared as described in step (a) above were added to 2 ml of a suspension of 60 mg of pulverized potassium superoxide in dimethyl sulfoxide, and the mixture was vigorously stirred for 1 hour at room temperature under a stream of nitrogen gas. Upon completion of the reaction, a saturated aqueous solution of sodium chloride was added to the reaction product, and the mixture was extracted with ethyl acetate. The extract was washed with a saturated aqueous solution of sodium chloride, an aqueous solution of potassium iodide, an aqueous solution of sodium thiosulfate, and a saturated aqueous solution of sodium chloride, in that order, and then dried over anhydrous sodium sulfate. The solvent was distilled off from the extract under reduced pressure, leaving 71 mg of residue. This residue was purified by silica gel column chromatography, to give 54 mg of the title compound as an oil from the fractions eluted with hexane containing from 30 to 50% by volume of ethyl acetate.

Infrared Absorption Spectrum (liquid film)$v_{max}$cm$^{-1}$:
3460, 1455, 1330, 1100.

22(c) 3β-(5-Benzyloxypentyl)-2β-hydroxy-7-oxo-cis-bicyclo[3,3,0]octane 1 ml of 10% w/v hydrochloric acid was added to 1 ml of an acetone solution of 54 mg of the ketal compound prepared as described in step (b) above, and the mixture was stirred for 10 minutes at room temperature. Upon completion of the reaction, a saturated aqueous solution of sodium chloride was added to the reaction product, and the mixture was extracted with ethyl acetate. The extract was washed with a saturated aqueous solution of sodium chloride, and dried over anhydrous sodium sulfate. The solvent was distilled off from the extract under reduced pressure, leaving 46 mg of residue. This residue was purified by silica gel column chromatography, to give 40 mg of the title compound as an oil from the fractions eluted with hexane containing from 30 to 50% by volume of ethyl acetate. This product had the same properties as the product of Preparation 21.

PREPARATION 23

3β-(5-Benzyloxypentyl)-2β-methanesulfonyloxy-7-oxo-cis-bicyclo[3,3,0]octane 12.1 g of 3β-(5-benzyloxypentyl)-2β-hydroxy-7-oxo-cis-bicyclo[3,3,0]octane (prepared as described in Preparation 21 or 22) were dissolved in 250 ml of methylene chloride, and then 8.0 ml of triethylamine and 3.6 ml of methanesulfonyl chloride were added, with stirring and ice-cooling, and the mixture was stirred for 30 minutes.

Upon completion of the reaction, the reaction product was washed with water, 10% w/v hydrochloric acid, a 5% w/v aqueous solution of sodium bicarbonate and water, in that order, and then dried over anhydrous sodium sulfate. The solvent was distilled off from the extract under reduced pressure, giving 14.9 g of the title compound as an oil.

This substance could be used in the subsequent reaction without purification.

Infrared Absorption Spectrum (liquid film)$v_{max}$cm$^{-1}$:
915, 1175, 1350, 1740.
Nuclear Magnetic Resonance Spectrum (CDCl$_3$) δppm:
2.93 (3 H, singlet, SO$_2$CH$_3$);
3.40 (2 H, triplet, J=6.0 Hz, CH$_2$OCH$_2$-phenyl);
4.43 (2 H, singlet, OCH$_2$-phenyl);
4.72 [1 H, doublet, J=3.0 Hz, —CH(OSO$_2$CH$_3$)];
7.23 (5 H, singlet, phenyl).
Mass spectrum, m/e: 394 (M$^+$), 298 (M—CH$_3$SO$_3$H).

PREPARATION 24

3β-(5-Benzyloxypentyl)-7-oxotricyclo[3,3,0,0$^{2,8}$]octane 15 ml of 1,8-diazabicyclo[5,4,0]undecene-7 were added to 14.9 g of 3β-(5-benzyloxypentyl)-2β-methanesulfonyloxy-7-oxo-cis-bicyclo[3,3,0]octane (prepared as described in Preparation 23), and the mixture was stirred for 20 minutes at 50°–55° C.

Upon completion of the reaction, water was added to the reaction product, which was then extracted with diethyl ether. The extract was washed with 10% w/v hydrochloric acid and water and dried over anhydrous sodium sulfate. The solvent was distilled off from the extract, leaving 11.4 g of residue. This residue was purified by silica gel column chromatography, to give 9.28 g of the title compound as an oil from the fractions eluted with hexane containing from 7 to 10% by volume of ethyl acetate.

Infrared Absorption Spectrum (liquid film)$v_{max}$cm$^{-1}$:
1100, 1450, 1715.
Nuclear Magnetic Resonance Spectrum (CDCl$_3$) δppm:
3.43 (2 H, triplet, J=6.0 Hz, CH$_2$OCH$_2$-phenyl);
4.46 (2 H, singlet, OCH$_2$-phenyl);
7.30 (5 H, singlet, phenyl).
Mass spectrum, m/e: 298 (M$^+$).

PREPARATION 25

3β-(5-Benzyloxypentyl)-2β-bromo-7-oxo-cis-bicyclo[3,3,0]octane 198 mg of 3β-(5-benzyloxypentyl)-2α-hydroxy-7-oxo-cis-bicyclo[3,3,0]octane (prepared as described in Preparation 19) were dissolved in 4 ml of diethyl ether, and then 630 mg of carbon tetrabromide and 480 mg of triphenylphosphine were added and the mixture was stirred at room temperature for 1 hour. Water was then added to the reaction product, and the mixture was extracted with ethyl acetate. The extract was washed with water and dried over anhydrous sodium sulfate. The solvent was distilled off from the extract under reduced pressure, leaving 1.09 g of residue, which was purified by silica gel column chromatography, to give 65 mg of the title compound as an oil from the fractions eluted with hexane containing from 4 to 6% by volume of ethyl acetate.

Infrared Absorption Spectrum (liquid film)$v_{max}$cm$^{-1}$:
1100, 1165, 1455, 1735.
Nuclear Magnetic Resonance Spectrum (CDCl$_3$) δppm:
3.43 (2 H, triplet, J=6.0 Hz, CH$_2$OCH$_2$-phenyl);
4.23 (1 H, broad singlet, CH-Br);
4.43 (2 H, singlet, OCH$_2$-phenyl);
7.25 (5 H, singlet, phenyl).
Mass spectrum, m/e: 378 (M$^+$).

PREPARATION 26

3β-(5-Benzyloxypentyl)-7-oxotricyclo[3,3,0,0$^{2,8}$]-octane 0.5 ml of 1,8-diazabicyclo[5,4,0]undec-7-ene was added to 50 mg of 3β-(5-benzyloxypentyl)-2β-bromo-7-oxo-cis-bicyclo[3,3,0]octane (prepared as described in Preparation 25), and the mixture was stirred for 10 minutes at 50°–55° C.

Upon completion of the reaction, water was added to the reaction product, and the mixture was extracted with diethyl ether. The extract was washed with 10% w/v hydrochloric acid and then with water and dried over anhydrous sodium sulfate. The solvent was distilled off from the extract under reduced pressure, and the resulting residue was purified by silica gel column chromatography, to give 33 mg of the title compound as an oil from the fractions, eluted with hexane containing from 7 to 10% by volume of ethyl acetate. The product had the same properties as the product of Preparation 24.

PREPARATION 27

3β-(5-Benzyloxypentyl)-6β-methoxycarbonyl-7-oxotricyclo[3,3,0,0$^{2,8}$]octane 80 ml of 1,4-dioxane and 40 ml of dimethyl carbonate were added to 2.63 g of a 55% w/w suspension of sodium hydride in oil, under a stream of nitrogen gas, and the mixture was then heated to a temperature of 90° C. under the same gas stream. 30 ml of a 1,4-dioxane solution containing 2.63 g of 3β-(5-benzyloxypentyl)-7-oxotricyclo-[3,3,0,0$^{2.8}$] octane (prepared as described in Preparation 24 or 26) were then added dropwise, with stirring, over about one hour to the reaction mixture, and the mixture was then stirred for 2.5 hours at the same temperature.

Upon completion of the reaction, the reaction product was cooled with ice and neutralized with acetic acid. A saturated aqueous solution of sodium chloride was then added and the resulting mixture was extracted with ethyl acetate. The extract was washed with a saturated aqueous solution of sodium chloride and dried over anhydrous sodium sulfate. The solvent was distilled off from the extract under reduced pressure, leaving 3.88 g of residue. This residue was purified by silica gel column chromatography, to give 2.83 g of the title compound as an oil from the fractions eluted with hexane containing from 15 to 20% by volume of ethyl acetate.

Infrared Absorption Spectrum (liquid film)$v_{max}$cm$^{-1}$:
1100, 1155, 1720, 1740.
Nuclear Magnetic Resonance Spectrum δppm:
3.43 (2 H, triplet, J=6.0 Hz, CH$_2$OCH$_2$-phenyl);
3.70 (3 H, singlet, COOCH$_3$);
4.48 (2 H, singlet, OCH$_2$-phenyl);
7.33 (5 H, singlet, phenyl);
Mass spectrum, m/e: 356 (M$^+$).

PREPARATION 28

3β-(5-Benzyloxypentyl)-2β-formyloxy-6β-methoxy-carbonyl-7-oxo-cis-bicyclo[3,3,0]octane 7.00 g of 3β-(5-benzyloxypentyl)-6β-methoxy-carbonyl-7-oxotricyclo[3,3,0,0$^{2.8}$]octane (prepared as described in Preparation 27) were dissolved in 140 ml of formic acid, and then 28 ml of concentrated sulfuric acid were added, with ice-cooling. The mixture was then returned to room temperature and was stirred for 2 hours. The reaction product was poured into ice-water in which 10 g of sodium bicarbonate had been dissolved. The mixture was extracted with ethyl acetate, and the extract was washed with water and dried over anhydrous sodium sulfate. The solvent was distilled off from the extract, leaving 7.67 g of residue. This residue was purified by silica gel column chromatography, to give 4.56 g of the title compound as an oil from the fraction eluted with hexane containing 5% by volume of ethyl acetate.

In this process, 2.49 g of the tricyclo compound used as starting raw material were also recovered.

Infrared Absorption Spectrum (liquid film)$v_{max}$cm$^{-1}$:
1180, 1450, 1625, 1665, 1720.
Nuclear Magnetic Resonance Spectrum (CDCl$_3$) δppm:
3.45 (3 H, triplet, J=6.0 Hz, CH$_2$OCH$_2$-phenyl);
3.77 (3 H, singlet, COOCH$_3$);
4.50 (2 H, singlet, OCH$_2$-phenyl);
4.98 [1 H, doublet, J=3.0 Hz, —CH(OCHO)—];
7.33 (5 H, singlet, phenyl);
8.10 (1 H, singlet, CHO);
Mass spectrum, m/e: 402 (M$^+$), 356 (M-46)

PREPARATION 29

3β-(5-Benzyloxypentyl)-2β-formyloxy-7α-hydroxy,6β-methoxycarbonyl-cis-bicyclo[3,3,0 ]octane 4.90 g of 3β-(5-benzyloxypentyl)-2β-formyloxy-6β-methoxycarbonyl-7 -oxo-cis-bicyclo[3,3,0]octane (prepared as described in Preparation 28) were dissolved in 200 ml of ethanol, and the solution was cooled to −40° C. With constant stirring, 0.69 g of sodium borohydride was added, and the mixture was stirred for 30 minutes at the same temperature.

Upon completion of the reaction, acetic acid was added to the mixture to decompose the excess of sodium borohydride. A saturated aqueous solution of sodium chloride was then added to the reaction product, which was extracted with ethyl acetate. The extract was washed with a saturated aqueous solution of sodium chloride and dried over anhydrous sodium sulfate. The solvent was distilled off from the extract, leaving 5.04 g of residue. This residue was purified by silica gel column chromatography, to give 4.08 g of the title compound as an oil from the fractions eluted with hexane containing from 20 to 30% by volume of ethyl acetate.

Infrared Absorption Spectrum (liquid film)$v_{max}$cm$^{-1}$:
1100, 1170, 1720, 3440.
Nuclear Magnetic Resonance Spectrum (CDCl$_3$) δppm:
3.40 (2 H, triplet, J=6.0 Hz, CH$_2$OCH$_2$-phenyl);
3.70 (3 H, singlet, —COOCH$_3$);
4.44 (2 H, singlet, —OCH$_2$-phenyl);
4.88 (1 H, doublet, J=3.0 Hz, —CH(OCHO)—);
7.22 (5 H, singlet, phenyl);
7.90 (1 H, singlet, —OCHO);
Mass spectrum, m/e: 404 (M$^+$), 358 (M-46).

PREPARATION 30

3β-(5-Benzyloxypentyl)-2β-formyloxy-6β-methoxy-carbonyl-7α-(2 -tetrahydropyranyloxy)-cis-bicyclo-[3,3,0]octane 3.98 g of 3β-(5-benzyloxypentyl)-2β-formyloxy-7α-hydroxy-6 β-methoxycarbonyl-cis-bicyclo[3,3,0]octant (prepared as described in Preparation 29) were dissolved in 80 ml of methylene chloride, and then 1.35 ml of 2,3-dihydropyran and 50 mg of p-toluenesulfonic acid were added, and the mixture was stirred for 40 minutes.

Upon completion of the reaction, a 5% w/v aqueous solution of sodium bicarbonate was added for neutralization. Water was added to the mixture, which was then extracted with ethyl acetate. The extract was washed with water and dried over anhydrous sodium sulfate. The solvent was distilled off from the extract under reduced pressure, leaving 5.25 g of residue. This residue was purified by silica gel column chromatography, to give 4.57 g of the title compound as an oil from the fractions eluted with hexane containing from 6 to 10% by volume of ethyl acetate.

Infrared Absorption Spectrum (liquid film)$v_{max}$cm$^{-1}$:
1040, 1125, 1180, 1725.
Nuclear Magnetic Resonance Spectrum (CDCl$_3$) δppm:
3.40 (2 H, triplet, J=6.0 Hz, —C$_2$OCH$_2$-phenyl);
3.67 (3 H, singlet, —COOCH$_3$);
4.43 (2 H, singlet, —OCH$_2$-phenyl);
4.56 (1 H, broad singlet, 2-H of tetrahydropyran);
4.90 [1 H, doublet, J=3.0 Hz, —CH(OCHO)—];
7.23 (5 H, singlet, phenyl);
7.91 (1 H, singlet, —OCHO),
Mass spectrum, m/e: 488 (M$^+$).

PREPARATION 31

3β-(5-Benzyloxypentyl)-2β-hydroxy-6β-methoxycarbonyl-7α-(2-tetrahydropyranyloxy)-cis-bicyclo-[3,3,0]octane 4.57 g of 3β-(5-benzyloxypentyl)-2β-formyloxy-6β-methoxycarbonyl-7α-(2 -tetrahydropyranyloxy)-cis-bicyclo[3,3,0]octane (prepared as described in Preparation 30) were dissolved in 100 ml of methanol, and 1.0 g of anhydrous potassium carbonate was added thereto at room temperature; the mixture was stirred for 30 minutes.

Upon completion of the reaction, the reaction product was poured into water and extracted with ethyl acetate. The extract was washed with a saturated aqueous solution of sodium chloride and dried over anhydrous sodium sulfate. The solvent was distilled off from the extract under reduced pressure, leaving 4.31 g of residue. This residue was purified by silica gel column chromatography, to give 4.18 g of the title compound as an oil from the fractions eluted with hexane containing from 20 to 30% by volume of ethyl acetate.

Infrared Absorption Spectrum (liquid film)$v_{max}$cm$^{-1}$:
1125, 1730, 3475.
Nuclear Magnetic Resonance Spectrum (CDCl$_3$) δppm:
3.43 (2 H, triplet; J=6.0 Hz, CH$_2$OCH$_2$-phenyl);
3.67 (3 H, singlet, —COOCH$_3$);
4.45 (2 H, singlet, —OCH$_2$-phenyl);
4.57 (1 H, broad singlet, 2-H of tetrahydropyran);
7.25 (5 H, singlet, phenyl).
Mass spectrum, m/e: 460 (M$^+$), 442 (M-18).

PREPARATION 32

3β-(5-Benzyloxypentyl)-2β-methanesulfonyloxy-6β-methoxycarbonyl-7α-(tetrahydropyranyloxy)-cis-bicyclo[3,3,0]octane 4.08 g of 3β-(5-benzyloxypentyl)-2β-hydroxy-6β-methoxycarbonyl-7α-(2 -tetrahydropyranyloxy)-cis-bicyclo[3,3,0]octane (prepared as described in Preparation 31) were dissolved in 80 ml of methylene chloride, and then 20 ml of triethylamine and 0.8 ml of methanesulfonyl chloride were added, with stirring and ice-cooling, and the mixture was stirred for 30 minutes.

Upon completion of the reaction, the reaction product was washed with water, 10% w/v hydrochloric acid, a 5% w/v aqueous solution of sodium bicarbonate and water, in that order, and dried over anhydrous sodium sulfate. The solvent was distilled off from the extract under reduced pressure, yielding 4.78 g of the title compound as an oil.

This product could be used in the subsequent reaction without purification.

Infrared Absorption Spectrum (liquid film)$v_{max}$cm$^{-1}$:
920, 1175, 1355, 1735.
Nuclear Magnetic Resonance Spectrum (CDCl$_3$) δppm:
2.90 (3 H, singlet, CH$_3$SO$_3$—);
3.42 (2 H, triplet, J=6.0 Hz, CH$_2$OCH$_2$-phenyl);
3.66 (3 H, singlet, —COOCH$_3$);
4.44 (2 H, singlet, —OCH$_2$-phenyl);
4.53 (1 H, broad singlet, 2-H of tetrahydropyran);
4.65 [1 H, doublet, J=3.0 Hz, —CH(OSO$_2$CH$_3$)—];
7.23 (5 H, singlet, phenyl).

PREPARATION 33

3-(5-Benzyloxypentyl)-6β-methoxycarbonyl-7α-(2-tetrahydropyranyloxy)-cis-bicyclo[3,3,0 ]oct-2-ene To 4.58 g of 3β-(5-benzyloxypentyl)-2β-methane-sulfonyloxy-6β-methoxycarbonyl-7α-(2 tetrahydropyranyloxy)-cis-bicyclo[3,3,0]octane (prepared as described in Preparation 32) dissolved in 45 ml of ethanol was added sodium selenophenoxide [prepared in 25 ml of ethanol from 1.45 g of diphenyldiselenide and 0.69 g of sodium borohydride] at room temperature under a stream of nitrogen gas, and the mixture was stirred for 1 hour at a mixture temperature of 70°–75° C.

Upon completion of the reaction, the reaction product was cooled with ice and neutralized with acetic acid. The reaction product was then poured into a saturated aqueous solution of sodium chloride and extracted with ethyl acetate. The extract was washed with a saturated aqueous solution of sodium chloride and dried over anhydrous sodium sulfate. The solvent was distilled off from the extract under reduced pressure, leaving 5.13 g of residue. This residue was purified by silica gel column chromatography, to give 2.63 g of the title compound as an oil from the fractions eluted with hexane containing from 4 to 6% by volume of ethyl acetate.

Infrared Absorption Spectrum (liquid film)$v_{max}$cm$^{-1}$:
1030, 1040, 1080, 1125, 1735.
Nuclear Magnetic Resonance Spectrum (CDCl$_3$) δppm:
3.43 (2 H, triplet, J=6.0 Hz, CH$_2$OCH$_2$-phenyl);
3.69 (3 H, singlet, COOCH$_3$);
4.48 (2 H, singlet, OCH$_2$-phenyl);
4.62 (1 H, broad singlet, 2-H of tetrahydropyran);
5.24 (1 H, broad singlet, —CH—CH=C—);
7.33 (5 H, singlet, phenyl);
Mass spectrum, m/e: 442 (M$^+$), 358 (M-84)

PREPARATION 34

3(Benzyloxypentyl)-6β-hydroxymethyl-7α-(2-tetrahydropyranyloxy)-cis-bicyclo[3,3,0]oct-2-ene.

A solution of 2.63 g of 3-(5-benzyloxypentyl)-6β-methoxycarbonyl-7α-(2 -tetrahydropyranyloxy)-cis-bicyclo[3,3,0]oct-2-ene (prepared as described in Preparation 33) in 20 ml of tetrahydrofuran was added, with ice-cooling, to a tetrahydrofuran suspension of 0.44 g of lithium aluminum hydride, and the mixture was stirred for 30 minutes.

Upon completion of the reaction, 1.8 ml of a 4% w/v aqueous solution of sodium hydroxide was added to the mixture, and the mixture was stirred at room temperature. The resulting white precipitate was removed by filtration, and the filtrate was condensed by evaporation under reduced pressure, leaving 2.60 g of residue.

This residue was purified by silica gel column chromatography, to give 2.22 g of the title compound as an oil from the fractions eluted with hexane containing from 10 to 20% by volume of ethyl acetate.

Infrared Absorption Spectrum (liquid film)$v_{max}$cm$^{-1}$:
1120, 1455, 3430.
Nuclear Magnetic Resonance Spectrum (CDCl$_3$) δppm:
3.47 (2 H, triplet, J=6.0 Hz, CH$_2$OCH$_2$-phenyl);
4.53 (2 H, singlet, OCH$_2$-phenyl);
5.30 (1 H, broad singlet, —CH—CH=C—);

7.37 (5 H, singlet, phenyl).
Mass spectrum, m/e: 414 (M+), 396 (M-18).

PREPARATION 35

3-(5-Acetoxypentyl)-6β-hydroxymethyl-7α-(2-tetrahydropyranyloxy)-cis-bicyclo[3,3,0 ]oct-2-ene 500 mg of 3-(5-benzyloxypentyl)-6β-hydroxymethyl-7α-(2 -tetrahydropyranyloxy)-cis-bicyclo[3,3,0]oct-2-ene prepared as described in Preparation 34 were reacted as described in Example 1(d), to give 350 mg of the corresponding diol compound [infrared absorption spectrum (liquid film) $v_{max}cm^{-1}$; 3400, 1034, 1022] in the form of an oil. This diol compound was dissolved in 2 ml of pyridine, and then 0.4 ml of acetic anhydride was added, with ice cooling, and the mixture was left standing for 40 minutes.

Upon completion of the reaction, water was added to the reaction product to decompose the excess reagents, and the reaction mixture was extracted with ethyl acetate. The extract was washed with dilute hydrochloric acid, a dilute aqueous solution of sodium bicarbonate and a saturated aqueous solution of sodium chloride, in that order, and then dried over anhydrous sodium sulfate. The solvent was distilled off from the extract under reduced pressure. The resulting residue was purified by silica gel column chromatography, to give 124 mg of the title compound as an oil from the fractions eluted with hexane containing from 20 to 30% by volume of ethyl acetate.

Infrared Absorption Spectrum (liquid film)$v_{max}cm^{-1}$:
1740, 3450.
Nuclear Magnetic Resonance Spectrum (CDCl$_3$) δppm:
2.04 (3 H, singlet, COCH$_3$);
4.6–4.8 (1 H, broad singlet, 2-H of tetrahydropyran);
5.26 (1 H, singlet, =CH—).

PREPARATION 36

3-(4-Methoxycarbonylbutyl)-6β-formyl-7α-(2-tetrahydropyranyloxy)-cis-bicyclo[3,3,0 ]oct-2-ene 300 mg of 3-(4-methoxycarbonylbutyl)-6β-hydroxymethyl7α-(2 -tetrahydropyranyloxy)-cis-bicyclo[3,3,0]oct-2-ene were reacted as described in Preparation 14, to give 291 mg of the title compound as an oil.

Infrared Absorption Spectrum (liquid film)$v_{max}cm^{-1}$:
2705, 1735, 1030, 1021.

PREPARATION 37

A mixture of 3-(2-hydroxyethyl)-6β-[3α-(2-tetrahydropyranyloxy)oct-1-enyl]-7 α-(2-tetrahydropyranyloxy)-cis-bicyclo[3,3,0]oct-2(3)-ene The procedure described in Example 6(a) and 6(b) was repeated, but using 520 mg of 3-methoxycarbonyl-methylidene-6β-[3α-(2-tetrahydropyranyloxy)oct-1 -enyl]-7α-(2-tetrahydropyranyloxy)-cis-bicyclo[3,3,0]-octane, to give 194 mg of the title compound as an oil.

Infrared Absorption Spectrum (liquid film)$v_{max}cm^{-1}$:
3350, 1032, 1022, 974.

PREPARATION 38

A mixture of 3-(2-hydroxyethyl)-6β-[3α-(2-tetrahydropyranyloxy)-4-methyloct-1 -enyl]-7α-(2-tetrahydropyranyloxy)-cis-bicyclo[3,3,0]oct-2(3)-ene The procedure described in Example 6(a) and 6(b) was repeated, but using 712 mg of 3-methoxycarbonyl-methylidene-6β-[3α-(2-tetrahydropyranyloxy)-4 -methyloct-1-enyl]-7α-(2-tetrahydropyranyloxy)-cis-bicyclo[3,3,0]octane, to give 287 mg of the title compound as an oil.

Infrared Absorption Spectrum (liquid film)$v_{max}cm^{-1}$:
3350, 1032, 1022, 974.

PREPARATION 39

A mixture of 3-(2-hydroxyethyl)-6β-[3α-(2-tetrahydropyranyloxy)-5-methylnon-1 -enyl]-7α-(2-tetrahydropyranyloxy)-cis-bicyclo[3,3,0]oct-2(3)-ene The procedure described in Example 6(a) and 6(b) was repeated, but using 712 mg of 3-methoxycarbonylmethylidene-6β-[3α-(2 -tetrahydropyranyloxy)-5-methylnon-1-enyl]-7α-(2-tetrahydropyranyloxy)-cis-bicyclo[3,3,0]-octane, to give 286 mg of the title compound as an oil.

Infrared Absorption Spectrum (liquid film)$v_{max}cm^{-1}$:
3350, 1032, 1022, 974.

PREPARATION 40

3-(5-Benzyloxypentyl)-6β-ethoxycarbonyl-7-oxo-cis-bicyclo[3,3,0]oct-2-ene and its oct-3-ene isomer To 5 ml of dioxane and 200 mg of a suspension of 55% w/w sodium hydride in mineral oil was added 1 ml of diethyl carbonate, and the mixture was heated, with stirring, at an external temperature of 90° C. To the mixture was then added dropwise a solution of 150 ml of 3-(5-benzyloxypentyl)-7-oxo-cis-bicyclo[3,3,0]oct-2-ene (prepared as described in Preparation 5) in 3 ml of dioxane. During this addition, a catalytic amount of ethanol was also added. The mixture was stirred for 1 hour at 0° C., after which it was poured into ice-water, acidified with acetic acid and then extracted with ethyl acetate. The extract was washed with a saturated aqueous solution of sodium chloride and dried over anhydrous sodium sulfate. The solvent was evaporated off under reduced pressure, and the resulting residue was purified by silica gel column chromatography. 72 mg of the oct-2-ene isomer of the title compound and 57 mg of the oct-3-ene isomer were obtained from the fractions eluted with hexane containing 3% by volume of ethyl acetate and 5% by volume of ethyl acetate, respectively.

Oct-2-ene isomer

Infrared Absorption Spectrum (liquid film)$v_{max}cm^{-1}$:
698, 735, 1620, 1657, 1725, 1753.

Oct-3-ene isomer

Infrared Absorption Spectrum (liquid film)$v_{max}cm^{-1}$:
698, 735, 1620, 1658, 1723, 1751.

PREPARATION 41

3-(5-Benzyloxypentyl)-6β-ethoxycarbonyl-7α-hydroxy-cis-bicyclo[3,3,0]oct-2-ene

To a solution of 62 mg of 3-(5-benzyloxypentyl)-6β-ethoxycarbonyl-7-oxo-cis-bicyclo[3,3,0 ]oct-2-ene (prepared as described in Preparation 40) in 3 ml of ethanol were added 50 mg of sodium borohydride at a temperature between −40° and −20° C. The mixture was stirred for 45 minutes at the same temperature, after which it was diluted with acetic acid, further diluted with a saturated aqueous solution of sodium chloride at room temperature and extracted with ethyl acetate. The extract was washed with water and dried over anhydrous sodium sulfate. The solvent was evaporated off under reduced pressure, and the resulting residue was purified by silica gel column chromatography. 48 mg of the title compound were obtained in the form of an oil from the fractions eluted with hexane containing from 9 to 10% by volume of ethyl acetate.

Infrared Absorption Spectrum (liquid film)$v_{max}cm^{-1}$:
697, 735, 1300, 1728, 3450.

Nuclear Magnetic Resonance Spectrum (CDCl$_3$) δppm;
3.45 (2 H, triplet);
4.50 (2 H, singlet);
5.29 (1 H, broad singlet);
7.36 (5 H, singlet).

PREPARATION 42

3-(5-Benzyloxypentyl)-6β-hydroxymethyl-7α-(2-tetrahydropyranyloxy)-cis-bicyclo[3,3,0 ]oct-2-ene The procedure described in Preparation 7 was repeated, but using 25 mg of 3-(5-benzyloxypentyl)-6β-ethoxycarbonyl-7α-hydroxy-cis-bicyclo[3,3,0 ]oct-2-ene (prepared as described in Preparation 41). There were obtained 24 mg of the title compound in the form of an oil.

Infrared Absorption Spectrum (liquid film)$v_{max}cm^{-1}$:
1120, 1455, 3430.

Nuclear Magnetic Resonance Spectrum (CDCl$_3$) δppm:
3.47 (2 H, triplet);
4.53 (2 H, singlet);
5.30 (1 H, broad singlet);
7.37 (5 H, singlet).

PREPARATION 43

3-(2-Hydroxyethyl)-7,7-ethylenedioxy-cis-bicyclo-[3,3,0]oct-2-ene

The procedure described in Example 6 was repeated, but using 15.0 g of 3-methoxycarbonylmethylidene-7,7-ethylenedioxy-cis-bicyclo[3,3,0]octane. 12.4 g of the title compound were obtained in the form of an oil.

Infrared Absorption Spectrum (liquid film)$v_{max}cm^{-1}$:
722, 795, 950, 985, 1045, 1110, 1330, 1432, 1480, 2900, 3450.

PREPARATION 44

3-[2-(Dimethyl-t-butylsilyloxy)ethyl]-7-oxo-cis-bicyclo-[3,3,0oct-2-ene

44(a)
3-(2-Hydroxyethyl)-7-oxo-cis-bicyclo[3,3,0]oct-2-ene 3.00 g of 3-(2-hydroxyethyl)-7,7-ethylenedioxy-cis-bicyclo[3,3,0]oct-2-ene (prepared as described in Preparation 43) were dissolved in a mixture of 30 ml of acetone and 12 ml of water, and 0.5 ml of concentrated hydrochloric acid was added to the solution. The mixture was stirred for 1 hour at room temperature, after which it was diluted with a saturated aqueous solution of sodium chloride, and extracted with ethyl acetate. The extract was washed with a saturated aqueous solution of sodium chloride and dried over anhydrous sodium sulfate. The solvent was removed by evaporation under reduced pressure, and the resulting residue (2.61 g) was purified by silica gel column chromatography. 1.97 g of the title compound was obtained in the form of an oil from the fractions eluted with hexane containing from 35 to 45% by volume of ethyl acetate.

Infrared Absorption Spectrum (liquid film)$v_{max}cm^{-1}$:
1047, 1400, 1740, 2850, 2900, 3430.

44(b)
3-[2-(Dimethyl-t-butylsilyloxy)ethyl]-7-oxo-cis-bicyclo[3,3,0]oct-2-ene 2.58 g of t-butyldimethylsilyl chloride, 1.17 g of imidazole and 0.20 g of 4-dimethylaminopyridine were added to a solution of 1.90 g of the hydroxyethyl compound prepared as described in step (a) above, and the solution was stirred for 30 minutes at room temperature. After completion of the reaction, the reaction mixture was poured into a saturated aqueous solution of sodium chloride and extracted with ethyl acetate. The extract was washed with a saturated aqueous solution of sodium chloride and dried over anhydrous sodium sulfate. The solvent was removed by evaporation under reduced pressure, and the resulting residue (5.80 g) was purified by silica gel column chromatography. 3.02 g of the title compound were obtained in the form of an oil from the fractions eluted with hexane containing from 2 to 5% by volume of ethyl acetate.

Infrared Absorption Spectrum (liquid film)$v_{max}cm^{-1}$:
775, 839, 1100, 1257, 1745, 2860, 2900, 2940, 2970.

PREPARATION 45

3-[2-(Dimethyl-t-butylsilyloxy)ethyl]-6β-ethoxycarbonyl-7α-(2-tetrahydropyranyloxy)-cis-bicyclo[3,3,0]oct-2-ene

45(a) 3-[2-(Dimethyl-t-butylsilyloxy)ethyl]-6β-ethoxycarbonyl-7-oxo-cis-bicyclo[3,3,0 ]oct-2-ene and its oct-3-ene isomer The procedure described in Preparation 27 was repeated, but using diethyl carbonate in place of dimethyl carbonate and using 157 mg of 3-[2-(dimethyl-t-butylsilyloxy)ethyl]-7-oxo-cis-bicyclo-[3,3,0 ]oct-2-ene. 57 mg of the oct-2-ene isomer of the title compound [infrared absorption spectrum (liquid film)$v_{max}cm^{-1}$: 1662 1730 1757] and 49 mg of its oct-3-ene isomer [infrared absorption spectrum (liquid film)$v_{max}cm^{-1}$: 1662, 1728, 1757] were obtained, both in the form of oils.

45(b) 3-[2-(Dimethyl-t-butylsilyloxy)ethyl]-6β-ethoxycarbonyl-7α-(2-tetrahydropyranyloxy)-cis-bicyclo-[3,3,0]oct-2-ene 108 mg of the oct-2-ene isomer prepared following the procedure described in step (a) above were reacted as described in Preparations 29 and 30. 110 mg of the title compound were obtained in the form of an oil.

Infrared Absorption Spectrum (liquid film)$v_{max}cm^{-1}$:
777, 838, 975, 1023, 1039, 1110, 1258, 1730.

PREPARATION 46

3-[2-(Dimethyl-t-butylsilyloxy)ethyl]-6β-hydroxymethyl-7α-(2-tetrahydropyranyloxy)-cis-bicyclo[3,3,0]oct-2-ene 0.9 ml of a solution of 20% w/v diisobutylaluminum hydride in toluene was added at −70° C. to a solution of 115 mg of 3-[2-(dimethyl-t-butylsilyloxy)ethyl]-6β-ethoxycarbonyl-7α-(2-tetrahydropyranyloxy)-cis-bicyclo[3,3,0]oct-2-ene (prepared as described in Preparation 45) in 15 ml of methylene chloride. The mixture was stirred for 2.5 hours at the same temperature, after which it was diluted with acetic acid and a saturated aqueous solution of sodium chloride, and extracted with ethyl acetate. The extract was washed with a saturated aqueous solution of sodium chloride and dried over anhydrous sodium sulfate. The solvent was removed by evaporation under reduced pressure, and the resulting residue was purified by silica gel column chromatography. 86 mg of the title compound were obtained in the form of an oil from the fractions eluted with hexane containing from 10 to 20% by volume of ethyl acetate.

Infrared Absorption Spectrum (liquid film)$v_{max}cm^{-1}$:
780, 840, 982, 1024, 1040, 1100, 1260, 3470.

PREPARATION 47

3-[2-(Dimethyl-t-butylsilyloxy)ethyl]-6β-formyl-7α-(2-tetrahydropyranyloxy)-cis-bicyclo[3,3,0]oct-2-ene The procedure described in Preparation 8 was repeated, but using 80 mg of 3-[2-(dimethyl-t-butylsilyloxy)ethyl]-6β-hydroxymethyl-7α-(2-tetrahydropyranyloxy)-cis-bicyclo[3,3,0]oct-2-ene (prepared as described in Preparation 46), to give 94 mg of the title compound as an oil.

Infrared Absorption Spectrum (liquid film)$v_{max}cm^{-1}$:
781, 842, 1104, 1262, 1730, 2740.

PREPARATION 48

3-[2-(Carboxymethoxy)ethyl]-7,7-ethylenedioxy-cis-bicyclo-[3,3,0]oct-2-ene

The procedure described in Example 21(a) was repeated, but using 10.0 g of 3-(2-hydroxyethyl)-7,7-ethylenedioxy-cis-bicyclo[3,3,0]oct-2-ene (prepared as described in Preparation 43), to give 5.48 g of the title compound as an oil.

Infrared Absorption Spectrum (liquid film)$v_{max}cm^{-1}$:
1135, 1200, 1240, 1400, 1430, 1735, 2900, 2940, 3150.

PREPARATION 49

7,7-Ethylenedioxy-3-[2-(2-hydroxyethoxy)ethyl]-cis-bicyclo[3,3,0]oct-2-ene

To a solution of 3.00 g of 3-[2-(carboxymethoxy)ethyl]-7,7,-ethylenedioxy-cis-bicyclo[3,3,0]oct-2-ene (prepared as described in Preparation 48) in 10 ml of diethyl ether was added an excess of diazomethane in diethyl ether, and the solution was stirred for 30 minutes at room temperature. The solvent was evaporated off under reduced pressure, and the resulting residue was dissolved in 10 ml of diethyl ether. To the solution was added a suspension of 1.0 g of lithium aluminum hydride in 50 ml of diethyl ether, with ice-cooling, and the mixture was then stirred for 30 minutes at room temperature. To the mixture was added 4 ml of a 4% w/v aqueous solution of sodium hydroxide, and the mixture was stirred for 3 hours at room temperature. A white precipitate was removed by filtration, and then the filtrate was evaporated to dryness under reduced pressure. The resulting residue was purified by silica gel column chromatography, using hexane containing from 30 to 40% by volume of ethyl acetate as the eluent, to afford 1.82 g of the title compound as an oil.

Infrared Absorption Spectrum (liquid film)$v_{max}cm^{-1}$:
1048, 1080, 1110, 1325, 2900, 2950, 3440.

PREPARATION 50

3-{2-[2-(Dimethyl-t-butylsilyloxy)ethoxy]ethyl}-6β-methoxycarbonyl-7-oxo-cis-bicyclo[3,3,0]oct-2-ene and its oct-3-ene isomer 2.2 g of 7,7-ethylenedioxy-3-[2-(2-hydroxyethoxy)-ethyl]-cis-bicyclo[3,3,0]oct-2-ene (prepared as described in Preparation 49) was reacted following the procedures described in Preparation 44(a) and 44(b), and then the product thereof was treated as described in Preparation 27. There were obtained 1.06 g of the oct-2-ene isomer of the title compound and 0.96 g of its oct-3-ene isomer, both in the form of oils.

Oct-2-ene isomer

Infrared Absorption Spectrum (liquid film)$v_{max}cm^{-1}$:
778, 837, 1105, 1140, 1232, 1253, 1623, 16620 1732, 1759, 2860, 2940, 2970.

Oct-3-ene isomer

Infrared Absorption Spectrum (liquid film)$v_{max}cm^{-1}$:
778, 838. 1104, 1140, 1238, 1255, 1623, 1665, 1730, 1756, 2860, 2940, 2970.

PREPARATION 51

3-{2-[2-(Dimethyl-t-butylsilyloxy)ethoxy]ethyl}-6β-ethoxycarbonyl-7-oxo-cis-bicyclo[3,3,0]oct-2-ene and its oct-3-ene isomer 0.48 g of 7,7-ethylenedioxy-3-[2-(2-hydroxyethoxy)-ethyl]-cis-bicyclo[3,3,0]oct-2-ene (prepared as described in Preparation 49) was reacted following the procedures described in Preparation 44(a) and 44(b), and then the product thereof was treated as described in Preparation 27, except that diethyl carbonate was used in place of dimethyl carbonate. There were obtained 144 mg of the oct-2-ene isomer of the title compound and 114 mg of its oct-3-ene isomer, both in the form of oils.

Oct-2-ene isomer

Infrared Absorption Spectrum (liquid film)$v_{max}cm^{-1}$:
780, 838, 1107, 1143, 1232, 1255, 1623, 1662, 1730, 1757, 2860, 2940, 2960.

Oct-3-ene isomer

Infrared Absorption Spectrum (liquid film)$v_{max}cm^{-1}$:
778, 835, 1104, 1140, 1236, 1255, 1621, 1662, 1727, 1754, 2860, 2940, 2960.

PREPARATION 52

3-{2-[2-(Dimethyl-t-butylsilyloxy)ethoxy]ethyl}-6β-ethoxycarbonyl-7α-(2-tetrahydropyranyloxy)-cis-bicyclo-[3,3,0]oct-2-ene 130 mg of 3-{2-[2-(dimethyl-t-butylsilyloxy)-ethoxy]ethyl}-6β-ethoxycarbonyl-7 -oxo-cis-bicyclo-[3,3,0]oct-2-ene (prepared as described in Preparation 51) were treated by the procedure described in Preparation 29, and then the product thereof was treated by the procedure described in Preparation 30, to give 128 mg of the title compound in the form of an oil.

Infrared Absorption Spectrum (liquid film)$\nu_{max}$cm$^{-1}$:
779, 839, 978, 1022, 1039, 1123, 1260, 1732, 2950.

PREPARATION 53

3-{2-[2-(Dimethyl-t-butylsilyloxy)ethoxy]ethyl}-6β-formyl-7α-(2-tetrahydropyranyloxy)-cis-bicyclo[3,3,0]-oct-2-ene 128 mg of 3-{2-[2-(dimethyl-t-butylsilyloxy)-ethoxy]ethyl}-6β-ethoxycarbonyl-7α-(2 -tetrahydropyranyloxy)-cis-bicyclo[3,3,0]oct-2-ene (prepared as described in Preparation 52) were treated by the procedure described in Preparation 46, and then the product thereof was treated by the procedure described in Preparation 8, to give 110 mg of the title compound in the form of an oil.

Infrared Absorption Spectrum (liquid film)$\nu_{max}$cm$^{-1}$:
779, 835, 975, 1022, 1035, 1200, 1255, 1360, 1722, 2.720, 2860, 2930.

PREPARATION 54

3-[2-(2-Hydroxyethoxy)ethyl]-6β-methoxycarbonyl-7α-(2 -tetrahydropyranyloxy)-cis-bicyclo[3,3,0]oct-2-ene

54(a)
3-{2-[2-dimethyl-t-butylsilyloxy)ethoxy]-ethyl}-6β-methoxycarbonyl-7α-(2-tetrahydropyranyloxy)-cis-bicyclo[3,3,0]oct-2-ene 1.13 g of 3-{2-[2-(dimethyl-t-butylsilyloxy)-ethoxy]ethyl}-6β -methoxycarbonyl-7-oxo-cis-bicyclo-[3,3,0]oct-2-ene (prepared as described in Preparation 50) was treated by the procedure described in Preparation 29, and then the product thereof was treated by the procedure described in Preparation 30, to give 1.22 g of the title compound in the form of an oil.

Infrared Absorption Spectrum (liquid film)$\nu_{max}$cm$^{-1}$:
778, 836, 1023, 1036, 1120, 1137, 1198, 1252, 1737, 2860, 2950.

54(b)
3-[2-(2-Hydroxyethoxy)ethyl]-6β-methoxy-carbonyl-7α-(2-tetrahydropyranyloxy)-cis-bicyclo-[3,3,0]oct-2-ene To a solution of 600 mg of the silyl derivative obtained as described in step (a) above in 20 ml of tetrahydrofuran was added 2.6 ml of a 1 molar solution of tetrabutylammonium fluoride in tetrahydrofuran at room temperature. The mixture was stirred for 30 minutes at the same temperature, after which it was diluted with a saturated aqueous solution of sodium chloride, and extracted with ethyl acetate. The extract was washed with a saturated aqueous solution of sodium chloride and dried over anhydrous sodium sulfate. The solvent was evaporated off under reduced pressure, and the resulting residue was purified by silica gel column chromatography, using hexane containing from 30 to 40% by volume of ethyl acetate as the eluent, to give 448 mg of the title compound as an oil.

Infrared Absorption Spectrum (liquid film)$\nu_{max}$cm$^{-1}$:
755, 973. 1025, 1036, 1067, 1120, 1200, 1438, 1735, 2860, 2945, 3450.

PREPARATION 55

3-[2-(Methoxycarbonylmethoxy)ethyl]-6β-hydroxymethyl-7α-(2-tetrahydropyranyloxy)-cis-bicyclo[3,3,0]oct-2-ene

55(a)
3-[2-(Carboxymethoxy)ethyl]-6β-methoxycarbonyl-7α-(2-tetrahydropyranyloxy)-cis-bicyclo[3,3,0]oct-2-ene 470 mg of 3-[2-(2-hydroxyethoxy)ethyl]-6β-methoxycarbonyl-7α-(2 -tetrahydropyranyloxy)-cis-bicyclo-[3,3,0]oct-2-ene (prepared as described in Preparation 54) were treated according to the procedure described in Example 2(e), to give 173 mg of the title compound as an oil.

Infrared Absorption Spectrum (liquid film)$\nu_{max}$cm$^{-1}$:
755, 973, 1023, 1064, 1135, 1200, 1438, 1730, 2940, 3150.

55(b)
3-[2-(Methoxycarbonylmethoxy)ethyl]-6β-hydroxymethyl-7α-(2-tetrahydropyranyloxy)-cis-bicyclo-[3,3,0]oct-2-ene To a solution of 170 mg of the carboxy derivative obtained as described in step (a) above in 5 ml of tetrahydrofuran were added 200 mg of lithium borohydride. The mixture was stirred for 20 hours at room temperature, after which it was diluted with acetic acid and a saturated aqueous solution of sodium chloride, and extracted with diethyl ether. The extract was washed with a saturated aqueous solution of sodium chloride and dried over anhydrous sodium sulfate. The solvent was removed by evaporation under reduced pressure, and the resulting residue was diluted with 5 ml of diethyl ether. An excess of diazomethane in diethyl ether was then added to the solution. The solution was stirred for 30 minutes at room temperature, after which it was evaporated to dryness under reduced pressure, and the resulting residue was purified by silica gel column chromatography, using hexane containing from 20 to 30% by volume of ethyl acetate as the eluent, to afford 28 mg of the title compound as an oil.

Infrared Absorption Spectrum (liquid film)$\nu_{max}$cm$^{-1}$:
980, 1025, 1035, 1088, 1137, 1212, 1443, 1757, 2880, 2950, 3470.

PREPARATION 56

3-[2-(Methoxycarbonylmethoxy)ethyl]-6β-formyl-7α-(2-tetrahydropyranyloxy)-cis-bicyclo[3,3,0]oct-2-ene 26 mg of 3-[2-(methoxycarbonylmethoxy)ethyl]-6β-hydroxymethyl-7α-(2 -tetrahydropyranyloxy)-cis-bicyclo-[3,3,0]oct-2-ene (prepared as described in Preparation 55) were treated according to the procedure described in Preparation 8, to give 26 mg of the title compound in the form of an oil.

Infrared Absorption Spectrum (liquid film)$\nu_{max}$cm$^{-1}$:

978, 1030, 1042, 1083, 1140, 1210, 1445, 1725, 1760, 2960.

PREPARATION 57

3-(2-Benzoyloxyethyl)-6β-hydroxymethyl-7α-hydroxy-cis-bicyclo[3,3,0]oct-2-ene

57(a)
3-(2-hydroxyethyl)-6β-(2-tetrahydropyranyloxymethyl)-7α-(2-tetrahydropyranyloxy)-cis-bicyclo-[3,3,0]oct-2-ene 3.96 g of 3-[2-(dimethyl-t-butylsilyloxy)ethyl]-6β-hydroxymethyl-7α-(2 -tetrahydropyranyloxy)-cis-bicyclo[3,3,0]oct-2-ene (prepared as described in Preparation 46) were first treated according to the procedure described in Preparation 30, to protect the free hydroxy group by conversion to a tetrahydropyranyloxy group, and then the product thereof was treated according to the procedure described in Preparation 54(b), to give 2.11 g of the title compound as an oil.

57(b)
3-(2-Benzoyloxyethyl)-6β-(2-tetrahydropyranyloxymethyl)-7α-(2-tetrahydropyranyloxy)-cis-bicyclo-[3,3,0]oct-2-ene 2.11 g of the hydroxyethyl derivative obtained as described in step (a) above were dissolved in 15 ml of pyridine, and 1.15 g of benzoyl chloride was added to the solution. The solution was stirred at room temperature for 4 hours, after which it was diluted with water and extracted with ethyl acetate. The extract was washed with a saturated aqueous solution of sodium chloride, cooled 3% w/v hydrochloric acid, an aqueous solution of sodium bicarbonate and a saturated aqueous solution of sodium chloride, in that order, and dried over anhydrous sodium sulfate. The solvent was evaporated off under reduced pressure, and the resulting residue was purified by silica gel column chromatography, using hexane containing 5% by volume of ethyl acetate as the eluent, to afford 2.21 g of the title compound as an oil.

57(c)
3-(2-Benzoyloxyethyl)-6β-hydroxymethyl-7α-hydroxy-cis-bicyclo[3,3,0]oct-2-ene 2.21 g of the benzoyloxyethyl derivative obtained as described in step (b) above were dissolved in 52 ml of methanol, and 13 ml of water and 1.3 g of p-toluenesulfonic acid were added to the solution. The solution was stirred at 30°–35° C. for 1.5 hours, after which it was diluted with 100 ml of water and extracted with ethyl acetate. The extract was washed with water and dried over anhydrous sodium sulfate. The solvent was removed by evaporation under reduced pressure, and the resulting residue was washed with cyclohexane, to afford 2.8 g of the title compound as a powder.

Infrared Absorption Spectrum (KBr)$v_{max}$cm$^{-1}$:
1080, 1120, 1280, 1715, 3220.
Nuclear Magnetic Resonance Spectrum (CDCl$_3$) δppm:
4.43 (2 H, triplet);
5.46 (1 H, singlet);
7.48 (3 H, multiplet);
8.05 (2 H, multiplet).

PREPARATION 58

3-(2-Benzoyloxyethyl)-6β-hydroxymethyl-7α-(2-tetrahydropyranyloxy)-cis-bicyclo[3,3,0] oct-2-ene

58(a) 3-(2-Benzoyloxyethyl)-6β-(2,2,2-trichloroacetoxymethyl)-7α -hydroxy-cis-bicyclo-[3,3,0]oct-2-ene To a solution of 3.0 g of 3-(2-benzoyloxyethyl)-6β-hydroxymethyl-7α-hydroxy-cis-bicyclo[3,3,0 ]oct-2-ene (prepared as described in Preparation 57) in 60 ml of benzene was added dropwise a solution of 1.16 ml of trichloroacetyl chloride in 30 ml of benzene, with ice-cooling. The solution was stirred at the same temperature for 20 minutes, after which it was diluted with ice-water and extracted with ethyl acetate. The extract was washed with water and dried over anhydrous sodium sulfate. The solvent was removed by evaporation under reduced pressure, and the resulting residue (4.9 g) was purified by silica gel column chromatography, using hexane containing 20% by volume of ethyl acetate as the eluent, to afford 3.05 g of the title compound as an oil.

58(b) 3-(2-Benzoyloxyethyl)-6β-(2,2,2-trichloroacetoxymethyl)-7α-(2 -tetrahydropyranyloxy)-cis-bicyclo-[3,3,0]oct-2-ene 3.6 g of the title compound were prepared from 3.05 g of the 7α-hydroxy compound obtained as described in step (a) above by following essentially the procedure described in Preparation 30.

58(c)
3-(2-Benzoyloxyethyl)-6β-hydroxymethyl-7α-(2 -tetrahydropyranyloxy)-cis-bicyclo[3,3,0]oct-2-ene 3.6 g of the 6β-(2,2,2-trichloroacetoxymethyl) compound prepared as described in step (b) above were dissolved in 70 ml of methanol. 5 ml of a saturated aqueous solution of sodium bicarbonate were then added, and the mixture was stirred at 30°–40° C. for 2 hours. The mixture was then diluted with a saturated aqueous solution of sodium chloride and extracted with ethyl acetate. The extract was washed with water and dried over anhydrous sodium sulfate. The solvent was removed by evaporation under reduced pressure, and the resulting residue was purified by silica gel column chromatography, using hexane containing 20% by volume of ethyl acetate as the eluent, to afford 2.59 g of the title compound as an oil.

Infrared Absorption Spectrum (liquid film)$v_{max}$cm$^{-1}$:
970, 1020, 1070, 1110, 1270, 1600, 1715, 3420.

PREPARATION 59

3-(2-Benzoyloxyethyl)-6β-formyl-7α-(2-tetrahydropyranyloxy)-cis-bicyclo[3,3,0]oct-2-ene The procedure described in Preparation 8 was repeated, but using 2.50 g of 3-(2-benzoyloxy-ethyl)-6β-hydroxymethyl-7α-(2 -tetrahydropyranyloxy)-cis-bicyclo[3,3,0]oct-2-ene (prepared as described in Preparation 58). There were obtained 2.34 g of the title compound as an oil.

Infrared Absorption Spectrum (liquid film)$v_{max}$cm$^{-1}$:
715, 975, 1030, 1120, 1280, 1720, 2720.
Nuclear Magnetic Resonance Spectrum (CDCl$_3$) δppm:
4.64 (1 H, singlet);
5.46 (1 H, singlet);

9.78 (1 H, doublet).

We claim:

1. The compound designated 3-(4-Carboxybutyl)-6β-(3α-hydroxy-4-methylnona-1,8-dienyl)-7 α-hydroxy-cis-bicyclo[3,3,0]oct-2-ene.

2. The compound designated 3-(4-Carboxybutyl)-6β-(3α-hydroxy-4-methyloct-1-en-6-ynyl)-7α -hydroxy-cis-bicyclo[3,3,0]oct-2-ene.

3. A method of treating a mammal for the treatment or prophylaxis of thrombosis comprising administering to the mammal an effective amount of the compound of claim 1.

4. A pharmaceutical composition comprising an effective amount for the treatment of thrombosis, of a compound of claim 1 in a pharmaceutically acceptable carrier or diluent.

5. A method of treating a mammal for the treatment or prophylaxis of thrombosis comprising administering to the mammal an effective amount of the compound of claim 2.

6. A pharmaceutical composition comprising an effective amount for the treatment of thrombosis, of a compound of claim 2 in a pharmaceutically acceptable carrier or diluent.

* * * * *